(12) United States Patent
Li et al.

(10) Patent No.: US 10,793,576 B2
(45) Date of Patent: Oct. 6, 2020

(54) COMPOUND USED AS BRUTON'S TYROSINE KINASE INHIBITOR AND PREPARATION METHOD AND APPLICATION THEREOF

(71) Applicants: Chengdu Brilliant Pharmaceutical Co., LTD., Chengdu (CN); Chengdu Highbred Pharmaceutical Co., LTD., Chengdu (CN)

(72) Inventors: Yingfu Li, Chengdu (CN); Haoxi Huang, Chengdu (CN); Guanfeng Liu, Chengdu (CN); Tonghui Chen, Chengdu (CN); Junfeng Ren, Chengdu (CN); Zhonghai Su, Chengdu (CN)

(73) Assignees: CHENGDU BRILLIANT PHARMACEUTICAL CO., LTD., Chengdu, Sichuan (CN); CHENGDU HIGHBRED PHARMACEUTICAL CO., LTD., Chengdu, Sichuan (CN)

(*) Notice: Subject to any disclaimer, the term of this patent is extended or adjusted under 35 U.S.C. 154(b) by 0 days.

(21) Appl. No.: 16/468,658

(22) PCT Filed: Feb. 20, 2017

(86) PCT No.: PCT/CN2017/074108
§ 371 (c)(1),
(2) Date: Jun. 11, 2019

(87) PCT Pub. No.: WO2018/133151
PCT Pub. Date: Jul. 26, 2018

(65) Prior Publication Data
US 2019/0315758 A1 Oct. 17, 2019

(30) Foreign Application Priority Data
Jan. 20, 2017 (CN) .......................... 2017 1 0044771

(51) Int. Cl.
*C07D 487/04* (2006.01)
*A61P 35/00* (2006.01)
*C07D 519/00* (2006.01)

(52) U.S. Cl.
CPC ............ *C07D 487/04* (2013.01); *A61P 35/00* (2018.01); *C07D 519/00* (2013.01)

(58) Field of Classification Search
CPC .................. C07D 487/04; C07D 519/00; A61K 31/4985; A61K 31/5383
See application file for complete search history.

(56) References Cited

U.S. PATENT DOCUMENTS

| | | | |
|---|---|---|---|
| 9,790,226 B2 | 10/2017 | Barf et al. | |
| 9,804,509 B2 | 10/2017 | Sengers et al. | |
| 2014/0275014 A1 | 9/2014 | Bosanac et al. | |

FOREIGN PATENT DOCUMENTS

| | | |
|---|---|---|
| CN | 103889987 | 6/2014 |
| CN | 105732638 | 7/2016 |
| CN | 105913859 | 8/2016 |
| JP | 2016513675 | 5/2016 |
| WO | WO-2009/143051 | 11/2009 |
| WO | WO-2013/113097 | 8/2013 |
| WO | WO 2015/132799 | * 9/2015 |
| WO | WO-2015/132799 | 9/2015 |
| WO | WO-2015/181633 | 12/2015 |
| WO | WO-2016/109216 | 7/2016 |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-101 O, 1995.*
Johnson et al., Relationships between drug activity in NCI preclinical in vitro and in vivo models and early clinical trials, British Journal of Cancer, 84(10):1424-1431, 2001.*
Gura et al., Systems for identifying new drugs are often faulty, Science, 278:1041-1042, 1997.*
Ten Hacken et al., Microenvironment dependency in Chronic Lymphocytic Leukemia: The basis for new targeted therapies, 11 pages, Pharmacology & Therapeutics 144, (2014) pp. 338-348.*
Douglas, Jr., Introduction to Viral Diseases, Cecil Textbook of Medicine, 20th Edition, vol. 2, pp. 1739-1747, 1996.*

(Continued)

*Primary Examiner* — Deepak R Rao
(74) *Attorney, Agent, or Firm* — Sheppard Mullin Richter & Hampton LLP

(57) ABSTRACT

The present invention provides a compound having a structure shown in formula (I) or an isomer, pharmaceutically acceptable solvate, or salt thereof. The compound is used as a Bruton's tyrosine kinase inhibitor, and has a higher inhibitory activity against BTK and less adverse effects.

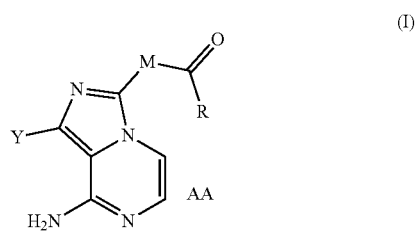

(I)

13 Claims, No Drawings

(56) References Cited

OTHER PUBLICATIONS

Bosseray et al., PubMed Abstract (Pathol Biol (Paris) 50(8):483-92), 2002.*
Off, PubMed Abstract (J Gene Med. 3(6):517-28), 2001.*
Razonable et al., PubMed Abstract (Herpes 10(3):60-5), 2003.*
Office Action for CN Appln. No. 201710044771.4 dated Feb. 9, 2018, 8 pages.
Office Action for CN Appln. No. 201710044771.4 dated Jun. 8, 2018, 8 pages.
Office Action for TW Appln. No. 106144341 dated Dec. 7, 2018, 4 pages.
Search Report for TW Appln. No. 106144341 dated Dec. 7, 2018, 1 page.
Search Report for CN Appln. No. 201710044771.4 dated Jan. 23, 2018, 2 pages.
Extended European Search Report for European Application No. 17893058.2 dated Jun. 18, 2020. (7 pages).

* cited by examiner

COMPOUND USED AS BRUTON'S TYROSINE KINASE INHIBITOR AND PREPARATION METHOD AND APPLICATION THEREOF

This application claims priority to Chinese patent application No. 201710044771.4 filed on Jan. 20, 2017 entitled "COMPOUND USED AS BRUTON'S TYROSINE KINASE INHIBITOR AND PREPARATION METHOD AND APPLICATION THEREOF", the disclosure of which is incorporated herein by reference in its entirety.

TECHNICAL FIELD

The present invention relates to the technical field of medicinal chemistry, in particular to a compound used as Bruton's tyrosine kinase inhibitor and preparation method and application thereof.

BACKGROUND ART

Ever since ibrutinib was reported to have a good therapeutic effect on a variety of B-cell lymphomas in the conference of American Society of Hematology in 2012, it has been realized that BTK, as a member of the non-receptor protein tyrosine kinase family, is a key signal enzyme expressed in all hematopoietic cell types except T lymphocytes and natural killer cells, plays a crucial role in the B cell signaling pathway and is closely related to the development, differentiation, signaling and survival of B lymphocyte. The important role of BTK in the B cell receptor (BCR) signaling pathway makes it a hot target for the treatment of B cell malignancies.

Although, in the treatment of chronic lymphocytic leukemia (CLL), mantle cell lymphoma (MCL) and Waldenström macroglobulinemia, ibrutinib has improved the survival time of certain malignancies, and avoids a variety of side effects caused by traditional chemotherapy, during clinical administration, there are still problems such as easy to be metabolized, low bioavailability (only 7%-23%), large clinical dosage (560 mg daily with 4 tablets per time), long course of treatment (28 days for one course of treatment, sometimes, several courses of treatment are required) and very strong drug resistance developed within a short time after administration and other problems.

In addition, the most common side effects of ibrutinib are bleeding, infection, cytopenia, atrial fibrillation, second primary malignant tumor, tumor lysis syndrome, embryo or fetal toxicity, etc. The incidence of the above bleeding event (such as subdural hematoma, gastrointestinal bleeding, hematuria and post-program bleeding) is 6%, and the bleeding mechanism is still unclear; the probability of infection of at least grade 3 is 14%-26%; grade 3 or 4 cytopenia comprising neutropenia (19%-29%), thrombocytopenia (5%-17%) and anemia (0%-9%) may occur; the incidence of atrial fibrillation and atrial flutter is 6%-9%, especially for a patient with heart disease, acute infection, or a history of atrial fibrillation; the incidence of other malignant tumors is 5%-14%, such as non-skin cancer (1%-3%), the most common one is non-melanoma skin cancer (4%-11%); patients treated with ibrutinib are presented with tumor lysis syndrome.

Therefore, it is necessary to further develop new BTK inhibitors that can increase patients' compliance while maintaining high efficiency, high safety and minimizing adverse reactions.

SUMMARY OF THE INVENTION

In view of the above, the technical problem to be solved by the present invention is to provide a compound used as Bruton's tyrosine kinase inhibitor and preparation method and application thereof. Comparing the prepared compound with ibrutinib already on the market, some Bruton's tyrosine kinase inhibitor compounds disclosed in this invention have better activities and higher cardiac safeties, especially in terms of pharmacokinetics, there are obvious advantages in parameters such as blood concentration, exposure, half-life and oral bioavailability after oral administration in animals. Bruton's tyrosine kinase inhibitor compounds disclosed in this application have broad clinical application prospects.

Definitions and General Terms

The "substitution" in the present invention means that one or more hydrogen atoms in the given structure are substituted by substituents. When more than one position in the given structural formula can be substituted by substituents, the substituents can be the same or different. The above substituents can optionally be substituted by one or more of the same or different secondary substituents. The secondary substituents described therein can be, but are not limited to, fluorine, chlorine, bromine, iodine, cyano, nitro, alkyl, haloalkyl, heteroalkyl, alkenyl, alkynyl, hydroxy, mercapto, amino, amido, alkylaminoacyl, aryl, heteroaryl and the like. The heteroalkyl can be, but not limited to, hydroxyalkyl, alkoxyalkyl, aminoalkyl, alkylaminoalkyl, cyanoalkyl, alkoxy, alkylthio and the like.

The "N-containing spirocyclic group" in the present invention means that two rings share one carbon atom, wherein two rings are independently carbocyclic or heterocyclic, and at least one of them is an N-containing heterocyclic ring. The carbocyclic and heterocyclic rings can be independently substituted, wherein the substituent can be, but is not limited to, fluorine, chlorine, bromine, iodine, cyano, nitro, alkyl, haloalkyl, heteroalkyl, alkenyl, alkynyl, hydroxy, mercapto, amino, amido, alkylaminoacyl, aryl, heteroaryl, and the like. The heteroalkyl can be, but is not limited to, hydroxyalkyl, alkoxyalkyl, aminoalkyl, alkylaminoalkyl, cyanoalkyl, alkoxy, alkylthio and the like.

The "N-containing bridged-ring group" in the present invention means a bicyclic or polycyclic heterocyclic compound with two or more shared carbon atoms. The heterocyclic compound can be substituted, wherein the substituent can be, but is not limited to, fluorine, chlorine, bromine, iodine, cyano, nitro, alkyl, haloalkyl, heteroalkyl, alkenyl, alkyne, hydroxy, mercapto, amino, amido, alkylaminoacyl, aryl, heteroaryl and the like. The heteroalkyl can be, but is not limited to, hydroxyalkyl, alkoxyalkyl, aminoalkyl, alkylaminoalkyl, cyanoalkyl, alkoxy, alkylthio and the like.

As described in the present invention, a substituent is attached to the ring via a chemical bond to form a ring system (as shown in the following figure), indicating that the substituent can substitute at any substitutable position on the ring. For example, formula a indicates that $R_1$ can substitute any substitutable position on the spirocyclic group, i.e., any of positions 1 to 7, as shown in formula b.

formula a

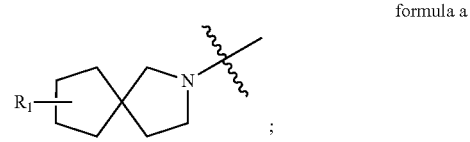

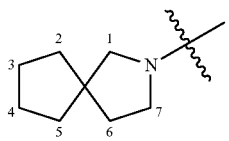

formula b

The bridge atom is attached to the ring via a chemical bond to form a ring system (as shown in the following figure), indicating that the bridge atom can be attached to any C atom or heteroatom that can be attached on the ring. For example, formula c indicates that the bridge atom E can be attached to any C atom or heteroatom which can attach the bridge atom on the six-membered ring, i.e., any of positions 1-3. When X or Q is N or C, the bridge atom E can also attach to X or Q, as shown in formula d.

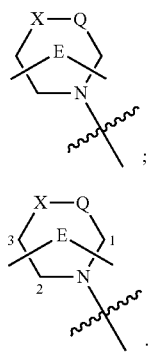

formula c formula d

The chemical bond is directly attached to the ring and interrupted by a bend line (as shown in formula e), indicating that the chemical bond is attached to a substituent and can be located at any substitutable position. For example, formula e indicates that the substituent can be at any of positions 1-3, and when X or Q is N or C, the substituent can be attached to X or Q.

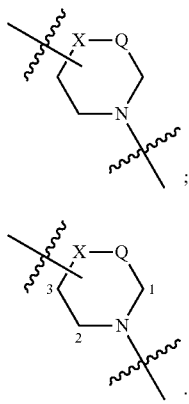

formula e formula f

The "isomer" in the present invention means that the structural formulas described in the present invention comprise all isomeric forms thereof (such as enantiomer, diastereomer, and geometric isomer (or conformational isomer)): for example, the R or S configuration containing an asymmetric center, the (Z) or (E) isomer of a double bond, and the conformational isomer of (Z) or (E). Thus, individual stereochemical isomers of the compounds of the present invention, or mixtures of enantiomers, diastereomers or geometric isomers (or conformational isomers) thereof are all within the scope of the present invention.

The "pharmaceutically acceptable salt" in the present invention means an organic acid salt and an inorganic acid salt of the compound of the present invention. The pharmaceutically acceptable acids capable of forming salts thereof comprise, but are not limited to, hydrochloric acid, sulfuric acid, phosphoric acid, hydrobromic acid, nitric acid, benzenesulfonic acid, p-toluenesulfonic acid, citric acid, L-proline, butyric acid, glycolic acid, acetic acid, hexanoic acid, nonylic acid, propionic acid, malic acid, aspartic acid, malonic acid, succinic acid, tartaric acid, ethionic acid, methanesulfonic acid, fumaric acid, benzoic acid, lactic acid, butanedisulfonic acid, adipic acid, α-ketoglutaric acid, lactobionic acid, maleic acid, 1,5-naphthalenedisulfonic acid, salicylic acid, acetylsalicylic acid, 2-naphthalenesulfonic acid, benzene acetic acid, nicotinic acid, 1-hydroxy-2-naphthoic acid, camphoric acid, 2-hydroxyethanesulfonic acid, mandelic acid, picric acid, cinnamic acid or oxalic acid, etc.

The "solvate" in the present invention refers to an associated matter formed by one or more solvent molecules with a compound of the present invention. Solvent-forming solvents comprise, but are not limited to, water, isopropanol, ethanol, methanol, acetone, acetonitrile, tetrahydrofuran, isopropyl ether, dichloromethane, dimethyl sulfoxide, ethyl acetate, acetic acid, aminoethanol.

Compound

The compound provided by the present invention, and pharmaceutical formulations thereof, have potential uses for the treatment of diseases or conditions modulated by Bruton's tyrosine kinases, particularly BTK receptors. The compound has the structure shown in formula (I) or an isomer thereof, a pharmaceutically acceptable solvate or salt:

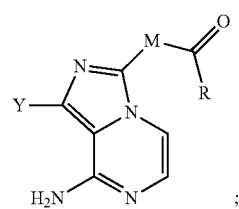

formula (I)

wherein, Y is selected from substituted or unsubstituted aryls or heteroaryls;

R is selected from substituted or unsubstituted alkenyls or alkynyls;

M is selected from substituted or unsubstituted N-containing spirocyclic group or N-containing bridged-ring group, and the N atom is attached to a carbonyl group;

or M is selected from the group shown in formula (II), A is a substituted or unsubstituted spirocyclic group or bridged-ring group, and the amino group is attached to a carbonyl group;

formula (II)

Wherein, M is preferably a substituted or unsubstituted C5-15 N-containing spirocyclic group or N-containing bridged-ring group, more preferably a substituted or unsubstituted C5-12 N-containing spirocyclic group or N-containing bridged-ring group, further preferably a substituted or unsubstituted C5-C8 N-containing spirocyclic group or N-containing bridged-ring group.

In certain specific embodiments of the present invention, the M is selected from any one of the following groups:

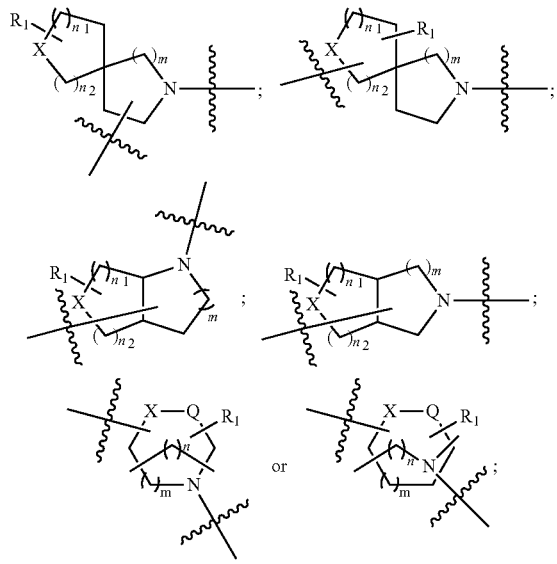

wherein, $n_1$, $n_2$, m are independently 0, 1 or 2;
n is 1, 2 or 3;
X, Q are independently selected from $CR_2R_3$, N—$R_4$, O, S or $S(O)_2$;
$R_1$, $R_2$, $R_3$ and $R_4$ are independently selected from H, substituted or unsubstituted C1-10 alkyls, substituted or unsubstituted C1-10 heteroalkyls, C1-10 carbonyls, substituted or unsubstituted C3-10 cycloalkyls, substituted or unsubstituted C3-10 heterocycloalkyls. Preferably, $R_1$, $R_2$, $R_3$ and $R_4$ are independently selected from H, substituted or unsubstituted C1-8 alkyls, substituted or unsubstituted C1-8 heteroalkyls, C1-8 carbonyls, substituted or unsubstituted C3-8 cycloalkyls, substituted or unsubstituted C3-8 heterocycloalkyls.

Further, $R_1$, $R_2$, $R_3$ and $R_4$ are independently selected from H, substituted or unsubstituted C1-3 alkyls, substituted or unsubstituted C1-3 heteroalkyls, C1-3 carbonyls, substituted or unsubstituted C3-6 cycloalkyls, substituted or unsubstituted C3-6 heterocycloalkyls. More preferably, $R_1$, $R_2$, $R_3$ and $R_4$ are independently selected from H, fluorine, chlorine, bromine, iodine, hydroxy, mercapto, cyano, amino, methyl, ethyl, trifluoromethyl, acetyl, isopropyl, trifluoroacetyl, isobutyl, cyclopropyl, epoxybutyl.

The above $R_1$, $R_2$, $R_3$, $R_4$ can also be substituted by a secondary substituent which can be, but is not limited to, fluorine, chlorine, bromine, iodine, cyano, nitro, alkyl, haloalkyl, heteroalkyl, alkenyl, alkynyl, hydroxy, mercapto, amino, amido, alkylaminoacyl, aryl, heteroaryl, and the like. The heteroalkyl can be, but is not limited to, hydroxyalkyl, alkoxyalkyl, aminoalkyl, alkylaminoalkyl, cyanoalkyl, alkoxyl, alkylthiol, and the like.

In still other specific embodiments of the present invention, the M is selected from the following groups:

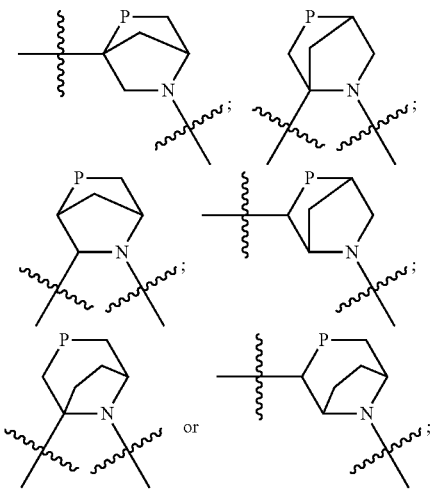

wherein, P is selected from $CR_5R_6$, N—$R_7$ or O;
$R_7$ is a substituted or unsubstituted C1-8 alkyl, substituted or unsubstituted C1-8 heteroalkyl, substituted or unsubstituted C3-8 cycloalkyl, substituted or unsubstituted C3-8 heterocycloalkyl, or

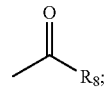

Preferably, $R_7$ is a substituted or unsubstituted C1-6 alkyl, substituted or unsubstituted C1-6 heteroalkyl, substituted or unsubstituted C3-6 cycloalkyl, substituted or unsubstituted C3-6 heterocycloalkyl, or

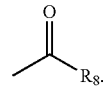

More preferably, $R_7$ is H, cyano, methyl, ethyl, isopropyl, acetyl, trifluoroacetyl, cyclopropyl or epoxybutyl.

$R_5$, $R_6$ and $R_8$ are independently selected from substituted or unsubstituted C1-8 alkyls, or substituted or unsubstituted C1-8 heteroalkyls, substituted or unsubstituted C3-8 cycloalkyls, substituted or unsubstituted C3-8 heterocycloalkyls;

Preferably, $R_5$, $R_6$ and $R_8$ are independently selected from substituted or unsubstituted C1-6 alkyls, or substituted or unsubstituted C1-6 heteroalkyls, substituted or unsubstituted C3-6 cycloalkyls, substituted or unsubstituted C3-6 heterocycloalkyls. More preferably, $R_5$, $R_6$ and $R_8$ are independently selected from H, fluorine, chlorine, bromine, iodine, hydroxy, mercapto, amino, methyl, ethyl, trifluoromethyl, acetyl, isopropyl, trifluoroacetyl, isobutyl, cyclopropyl or epoxybutyl.

The above $R_5$, $R_6$, $R_7$, $R_8$ can also be substituted by a secondary substituent which can be, but is not limited to, fluorine, chlorine, bromine, iodine, cyano, nitro, alkyl, haloalkyl, heteroalkyl, alkenyl, alkynyl, hydroxy, mercapto, amino, amido, alkylaminoacyl, aryl, heteroaryl, and the like. The heteroalkyl can be, but is not limited to, hydroxyalkyl, alkoxyalkyl, aminoalkyl, alkylaminoalkyl, cyanoalkyl, alkoxy, alkylthiol and the like.

In still other specific embodiments of the present invention, the M is selected from the following specific groups:

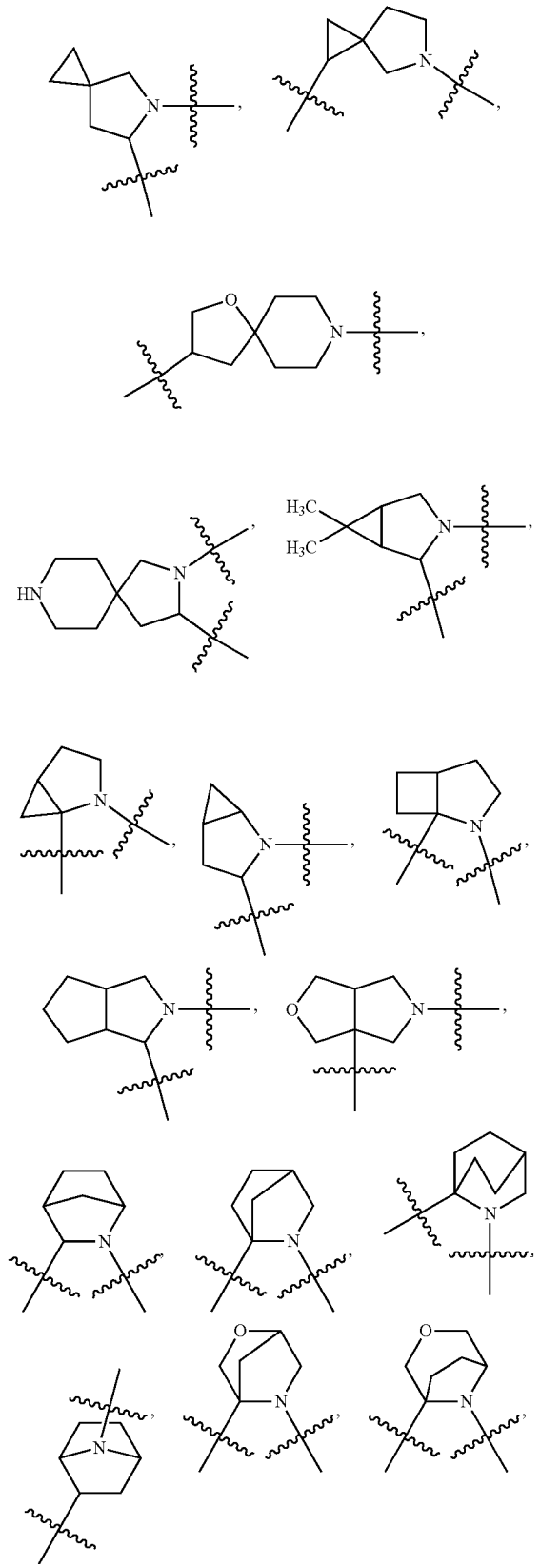

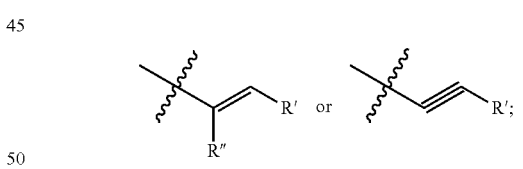

The R is a substituted or unsubstituted alkenyl or alkynyl. The following groups are preferred:

wherein, R' is H, a substituted or unsubstituted C1-8 alkyl, substituted or unsubstituted C1-8 heteroalkyl, substituted or unsubstituted C1-8 cycloalkyl or substituted or unsubstituted C1-8 heterocycloalkyl;

Preferably, R' is H, substituted or unsubstituted C1-6 alkyl, substituted or unsubstituted C1-6 heteroalkyl, substituted or unsubstituted C1-6 cycloalkyl or substituted or unsubstituted C1-6 heterocycloalkyl;

More preferably, R' is H, methyl, ethyl, N,N-dimethylaminomethyl, N-methyl-N-cyclopropylmethyl, methoxymethyl, ethoxymethyl, trifluoromethoxymethyl, N,N-dicyclopropylmethyl or N-methyl-N-ethylmethyl.

R" is H, nitro, fluorine, chlorine, bromine, iodine or cyano.

The Y is a substituted or unsubstituted aryl or heteroaryl, preferably a substituted or unsubstituted C5-10 aryl or heteroaryl, more preferably a substituted or unsubstituted C6-8 aryl or heteroaryl group.

When the Y is a substituted phenyl, the substituent of the phenyl is selected from substituted or unsubstituted amidos, substituted or unsubstituted alkyls, substituted or unsubstituted ether groups.

In certain specific embodiments of the present invention, the Y is selected from the following groups:

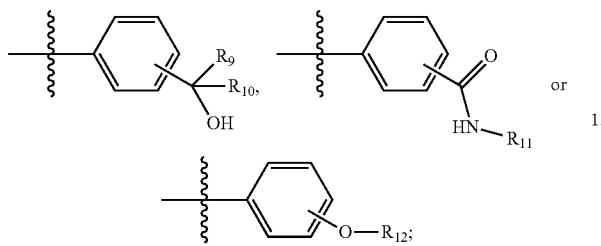

The substituent can be in the ortho, meta or para position.

Wherein, $R_9$ is a trifluoromethyl or methyl;

$R_{10}$, $R_{11}$ and $R_{12}$ are independently selected from substituted or unsubstituted aryls or heteroaryls.

Preferably, $R_{10}$, $R_{11}$ and $R_{12}$ are independently selected from substituted or unsubstituted C5-10 aryls or heteroaryls, more preferably, $R_{10}$, $R_{11}$ and $R_{12}$ are independently selected from substituted or unsubstituted C5-8 aryls or heteroaryls.

In certain specific embodiments of the present invention, the $R_{10}$, $R_{11}$ and $R_{12}$ are independently selected from substituted or unsubstituted phenyls, pyridyls, piperidinyls, piperazinyls or pyrimidinyls;

The substituent of the above groups is selected from nitro, hydroxy, mercapto, fluorine, chlorine, bromine, iodine, cyano, substituted or unsubstituted C1-10 alkyls, substituted or unsubstituted C1-10 heteroalkyls, substituted or unsubstituted C3-10 cycloalkyls, substituted or unsubstituted C3-10 heterocycloalkyls.

The A is a substituted or unsubstituted spirocyclic group or bridged-ring group, preferably a substituted or unsubstituted C6-15 spirocyclic group or bridged-ring group. In certain specific embodiments of the present invention, the A is adamantyl.

In certain specific embodiments of the present invention, the Y is a substituted or unsubstituted 2-aminopyridylbenzamido, M is a C5-10 spirocyclic group or bridged-ring group, and R is vinyl or propynyl. In certain specific embodiments of the present invention, H on the pyridyl of Y can optionally be substituted with fluorine, chlorine, bromine, iodine, methyl or trifluoromethyl and the substitution can be an ortho substitution, meta substitution or para substitution.

In still other specific embodiments of the present invention, the Y is a diphenylethanol, M is a C5-10 spirocyclic group or bridged-ring group, and R is vinyl or propynyl;

In still other specific embodiments of the present invention, the Y is a diphenyl ether group, M is a C5-10 spirocyclic group or bridged-ring group, and R is vinyl or propynyl;

In still other specific embodiments of the present invention, the Y is 2-aminopyridylbenzamido, M is a C5-10 bridged-ring group, and R is vinyl;

In still other specific embodiments of the present invention, the Y is diphenylethanol, M is a C5-10 bridged-ring group, and R is vinyl;

In still other specific embodiments of the present invention, the Y is a diphenyl ether group, M is a C5-10 bridged-ring group, and R is vinyl;

In still other specific embodiments of the present invention, the Y is trifluoromethyl substituted 2-aminopyridylbenzamido, M is a C5-10 bridged-ring group, and R is vinyl.

In certain specific embodiments of the present invention, the compound has any of the following structures or a stereoisomer or cis-trans isomer thereof:

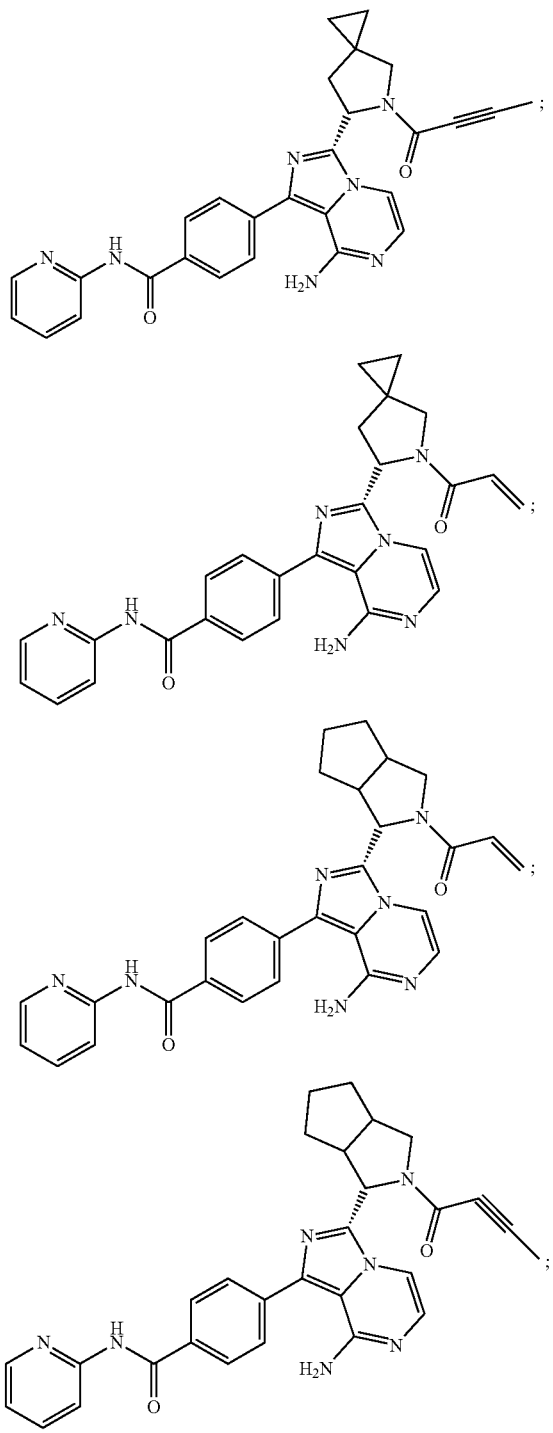

11
-continued
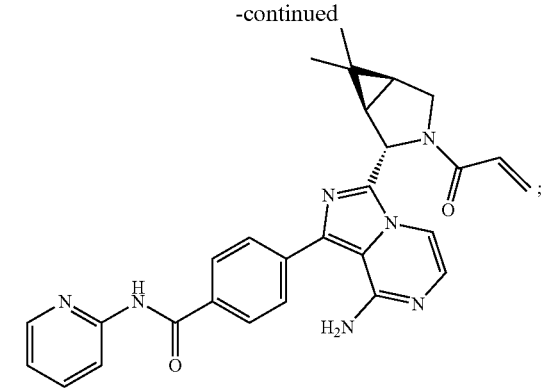
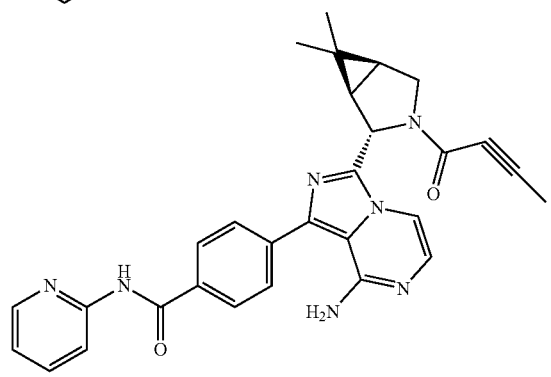
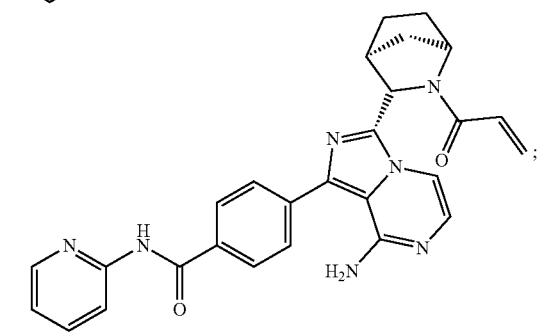
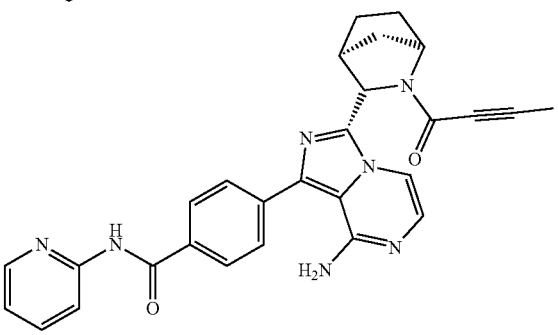
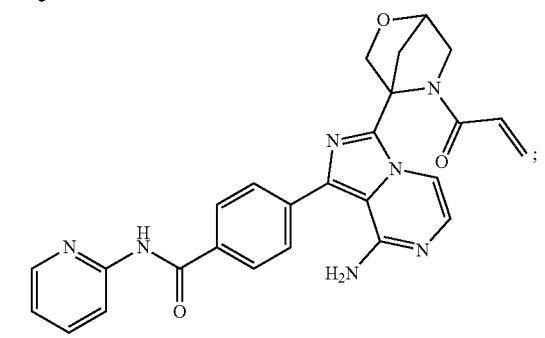
12
-continued
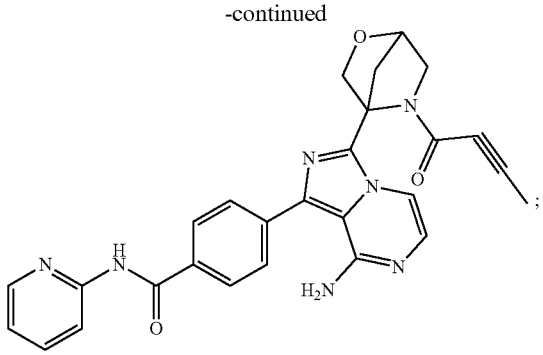
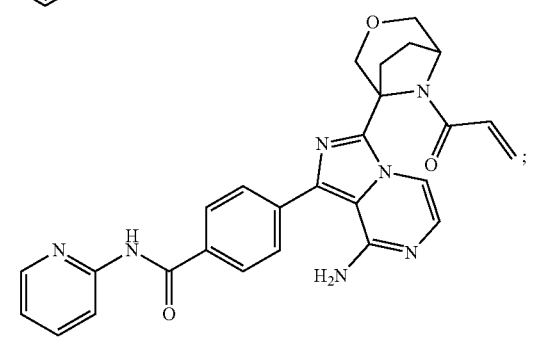
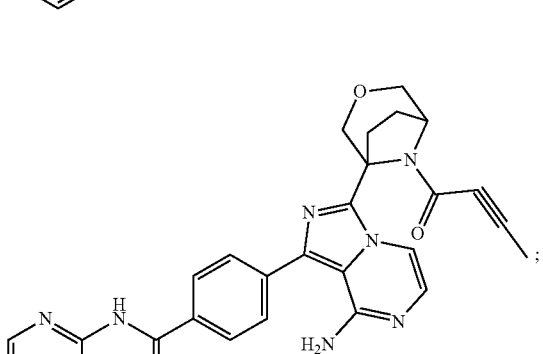
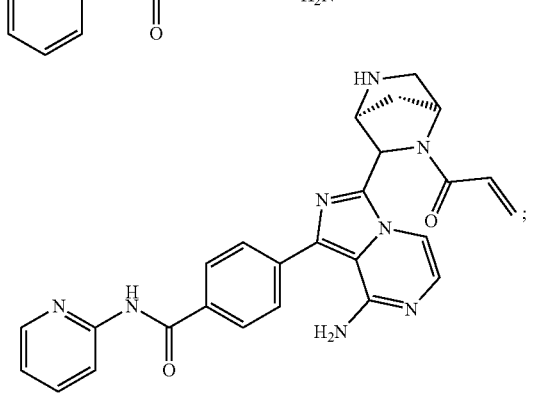
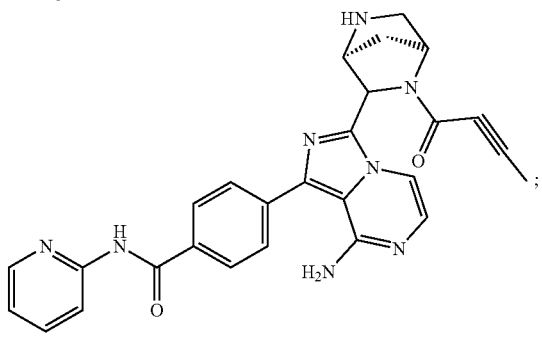

13 | 14
-continued | -continued
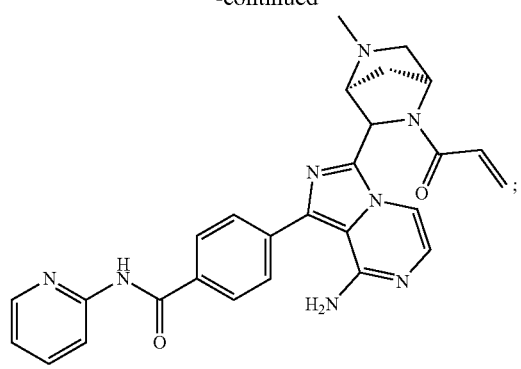
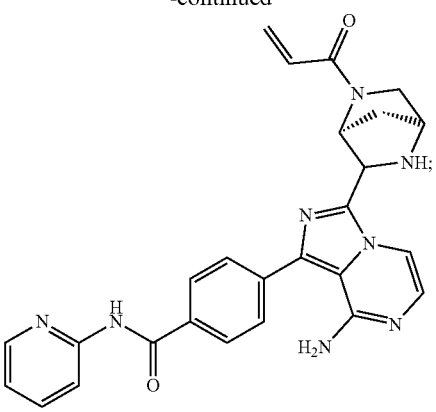
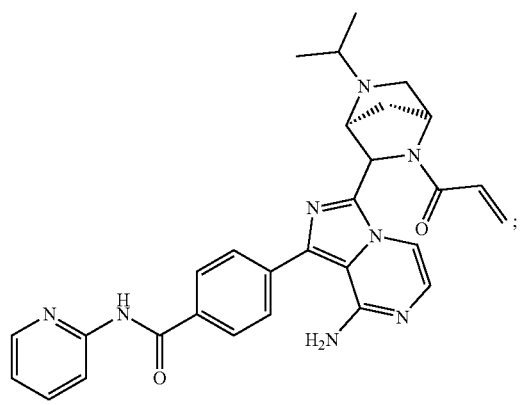
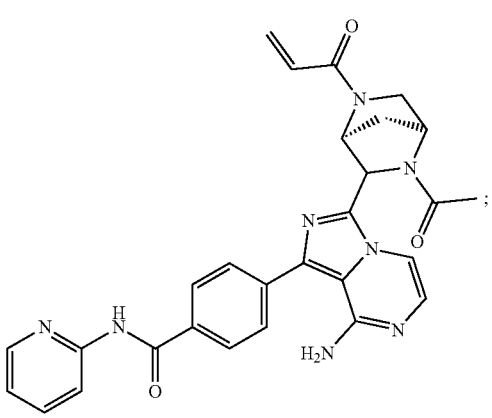
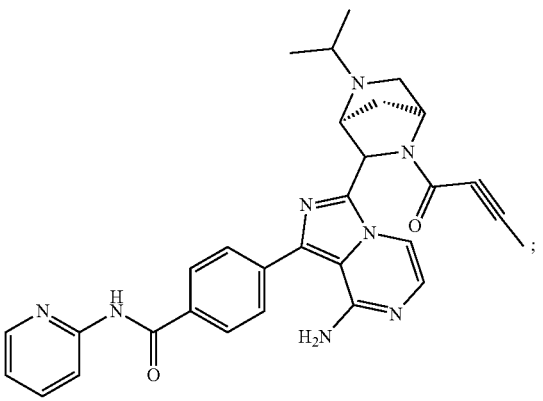
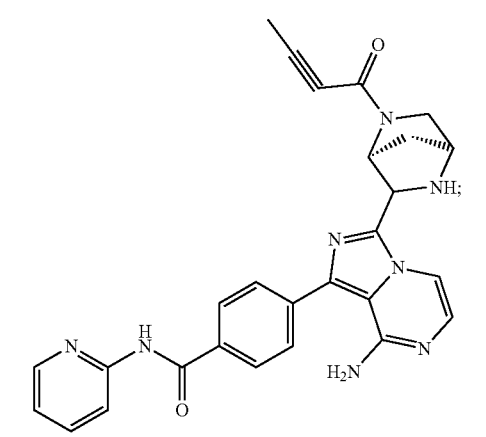
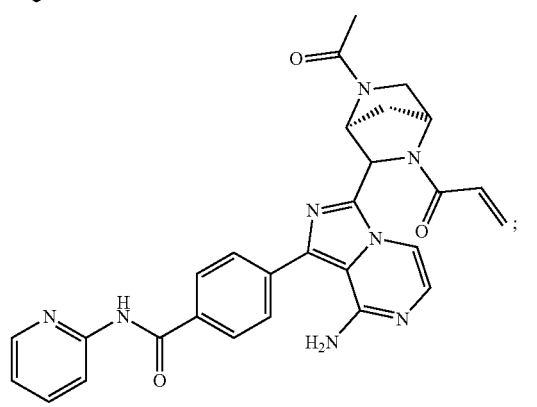
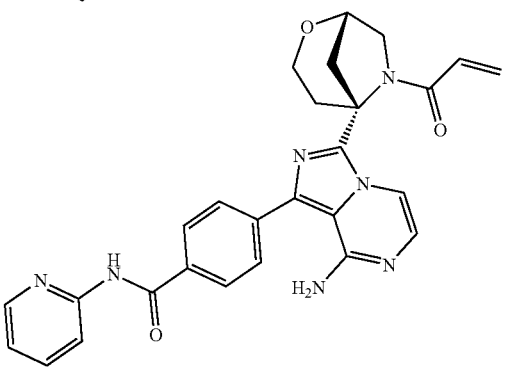

-continued

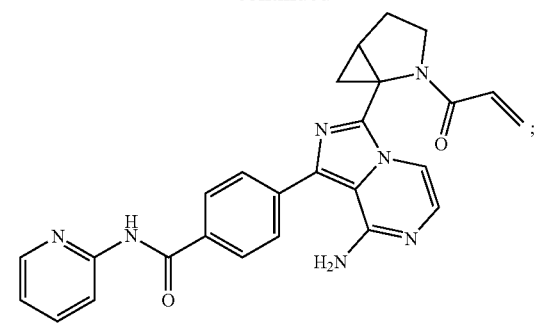
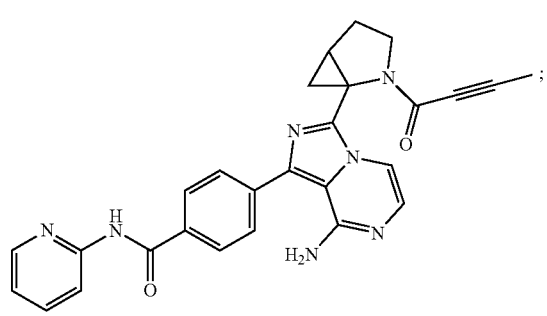
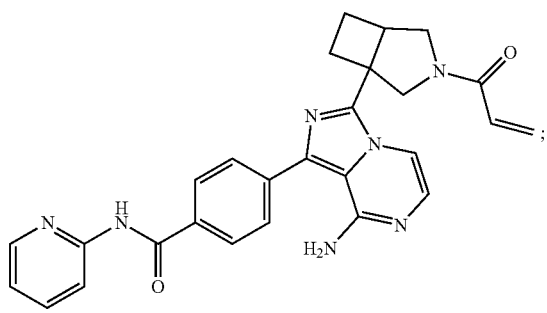
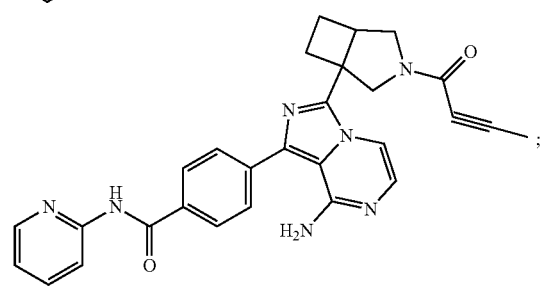
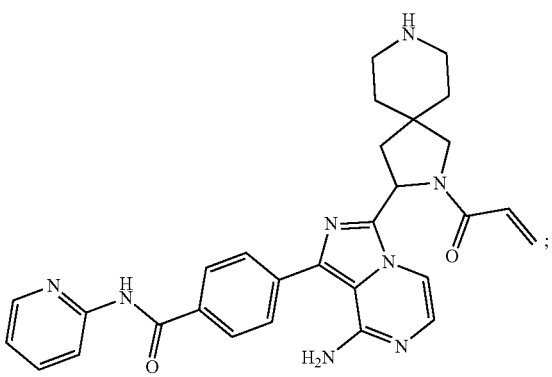
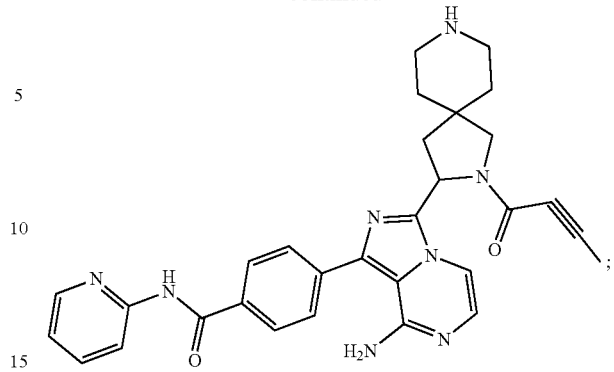
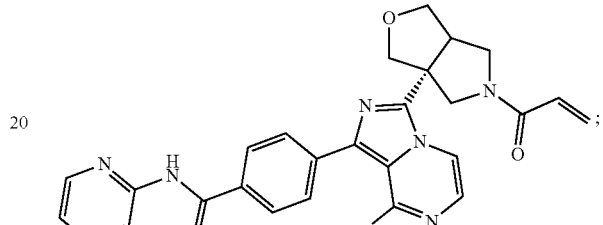
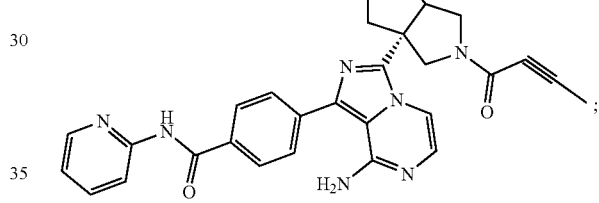
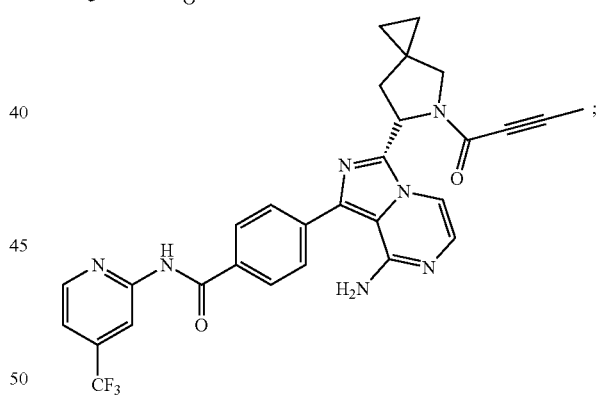
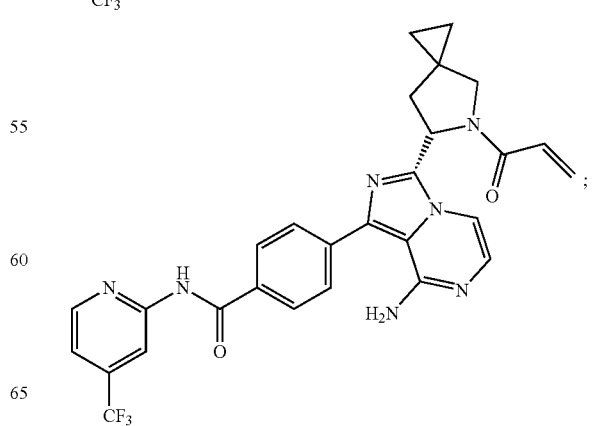

-continued
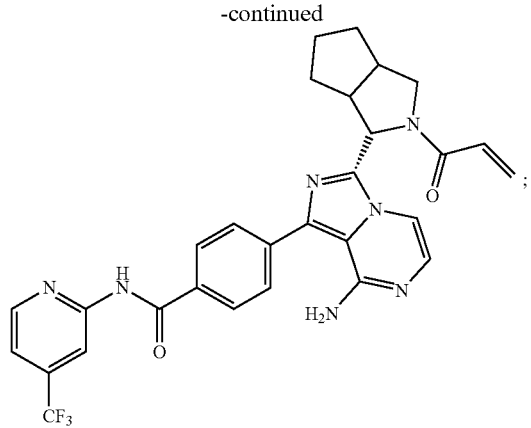
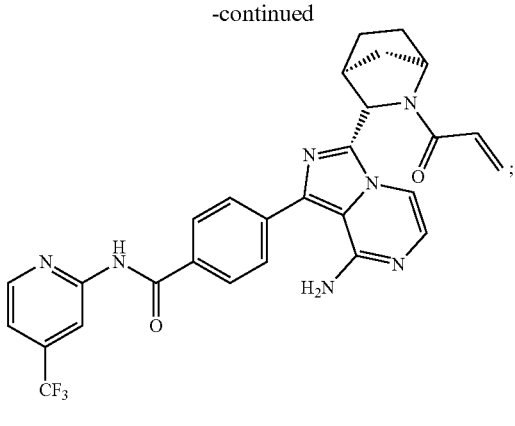
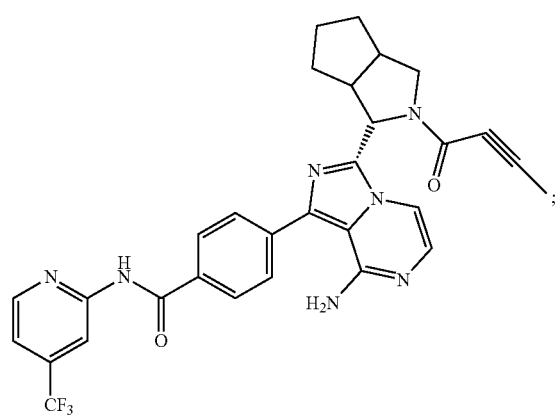
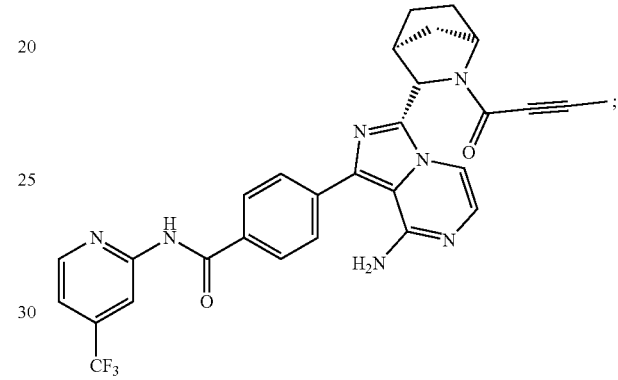
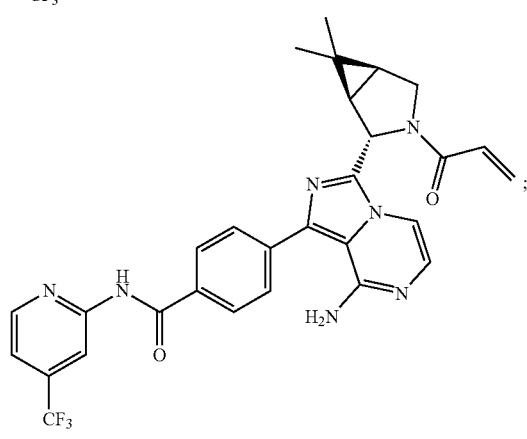
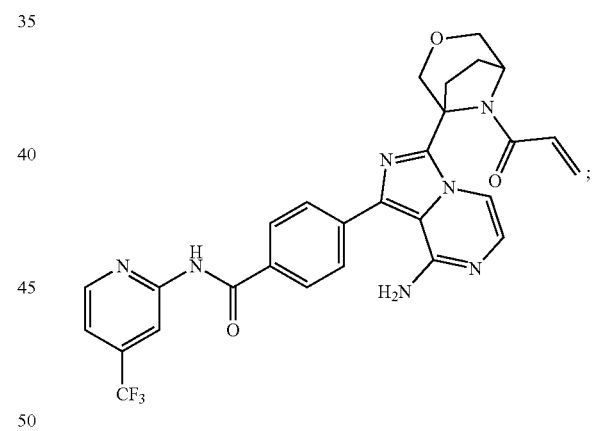
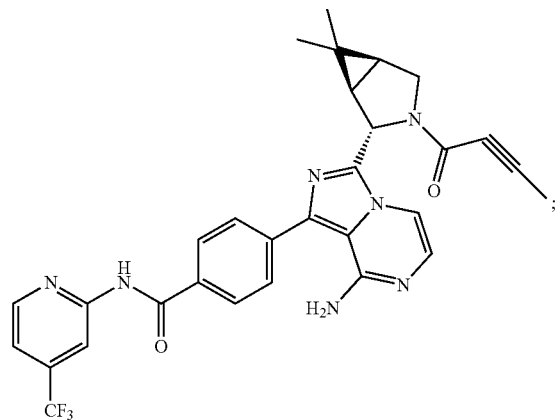
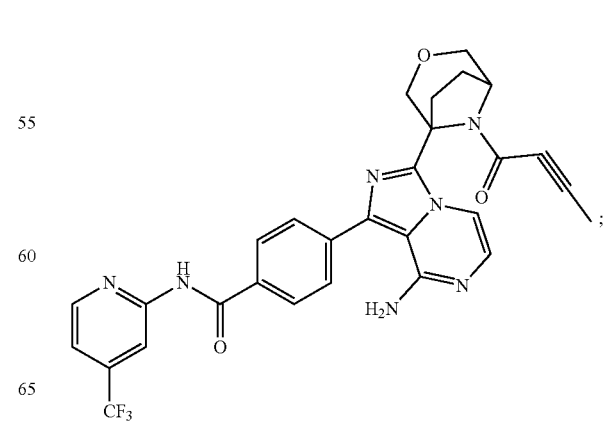

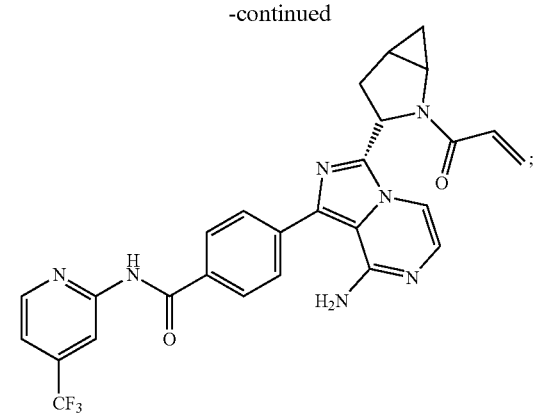
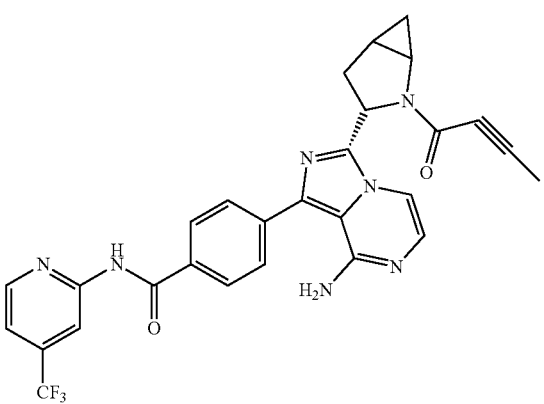
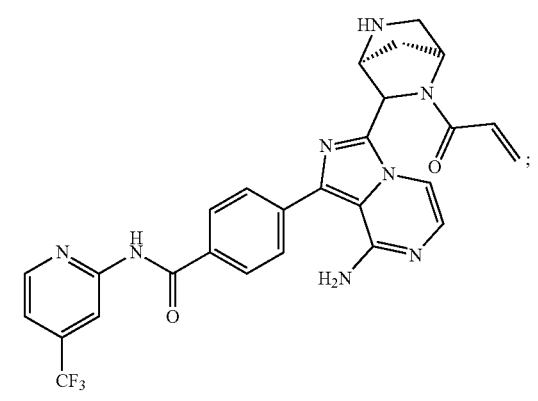
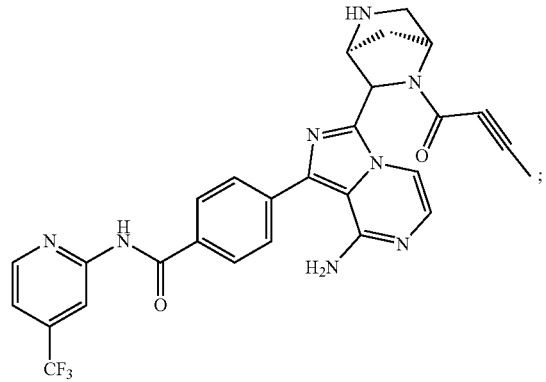
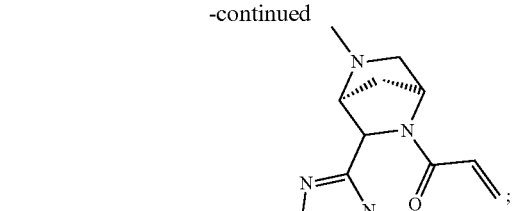
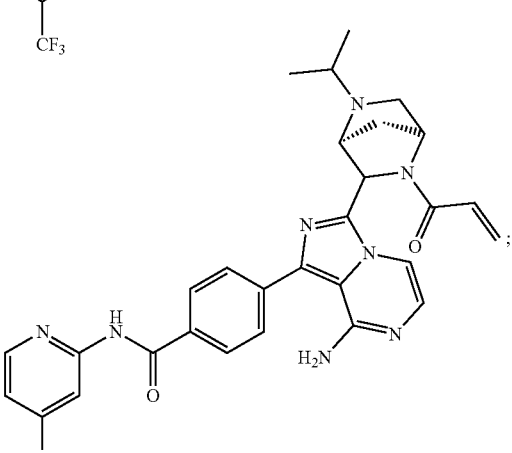
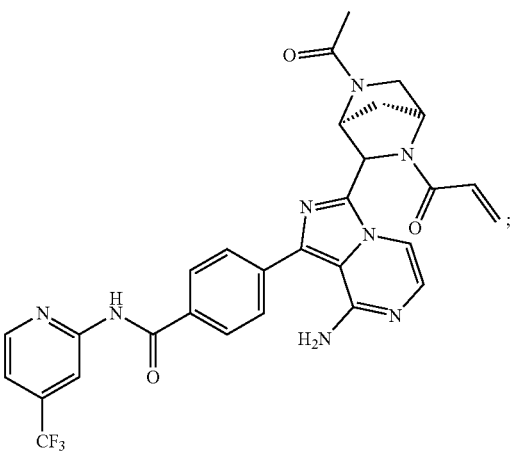
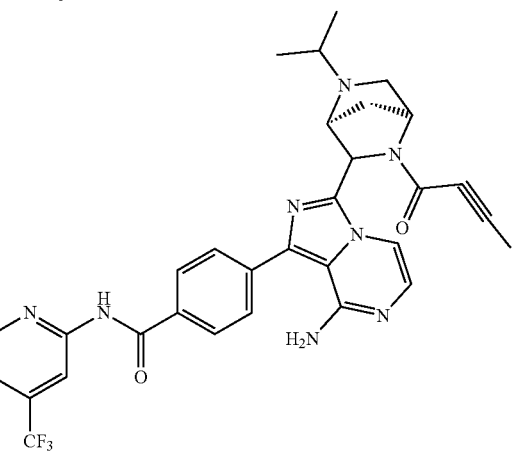

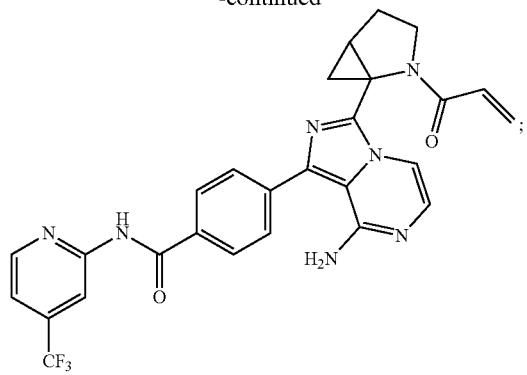
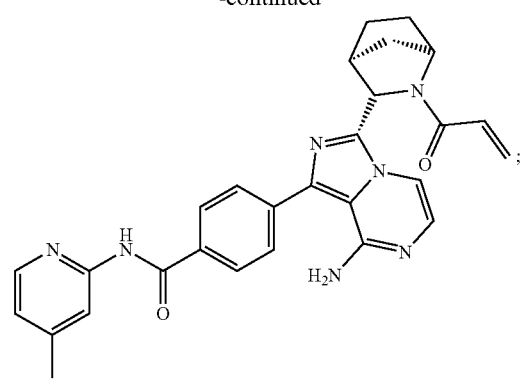
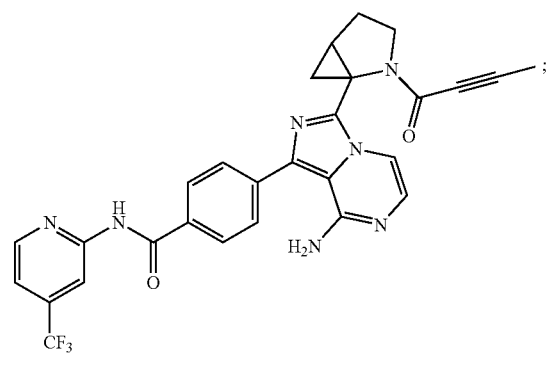
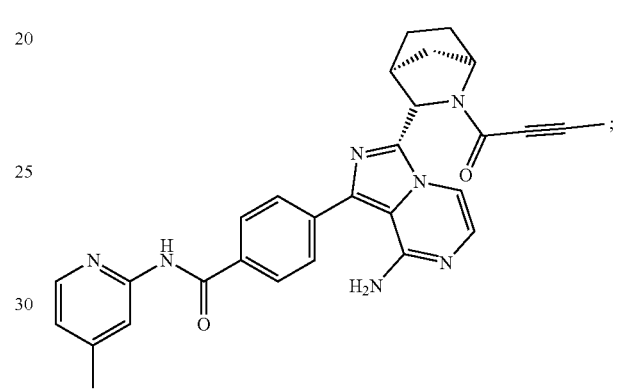
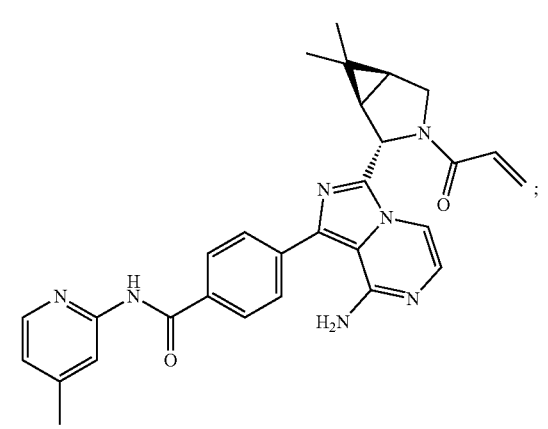
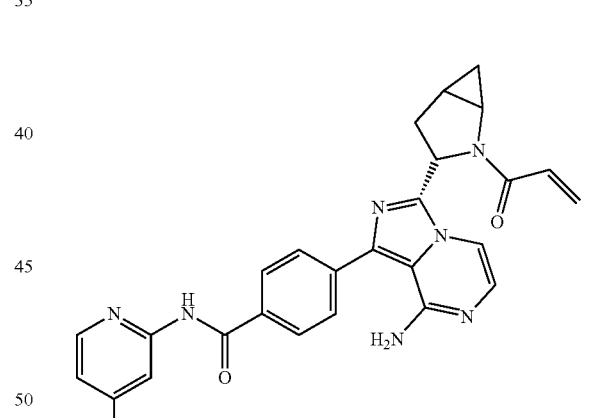
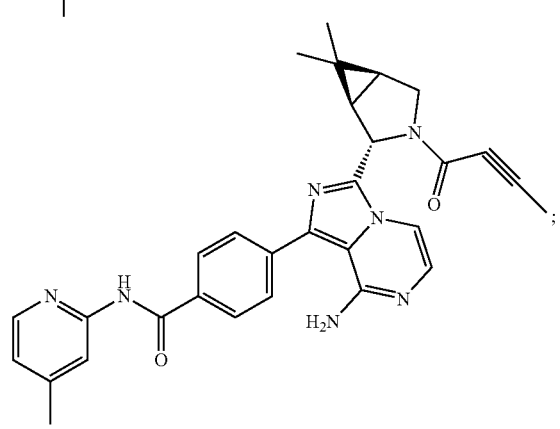
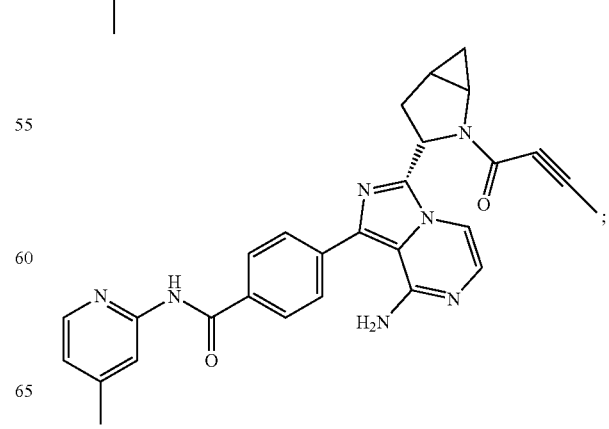

-continued
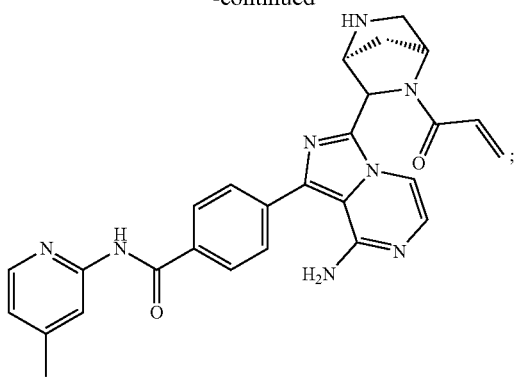
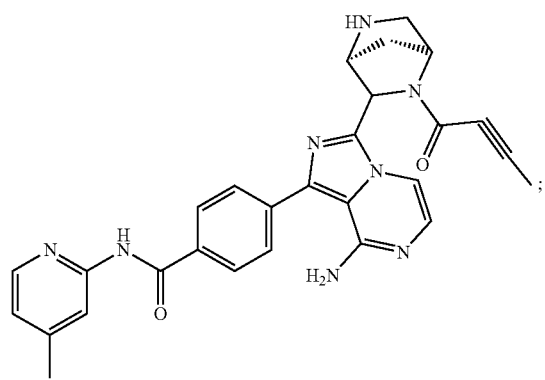
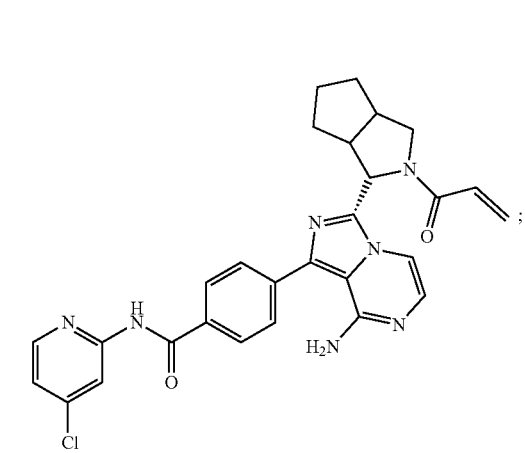
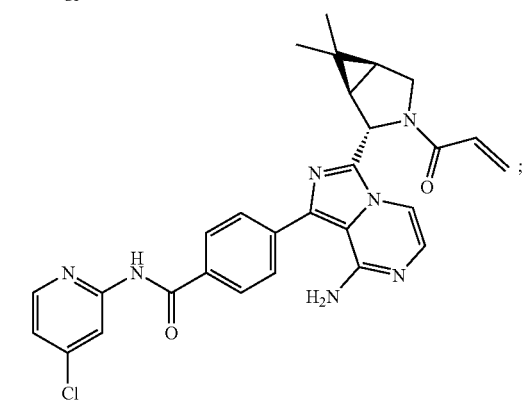
-continued
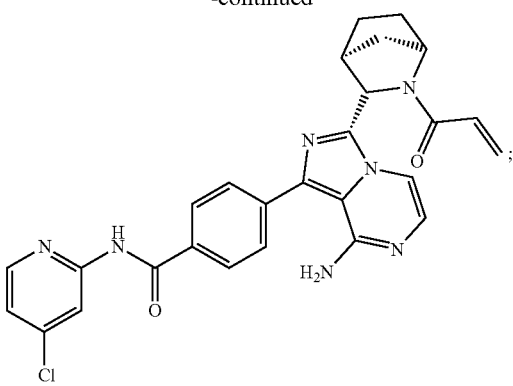
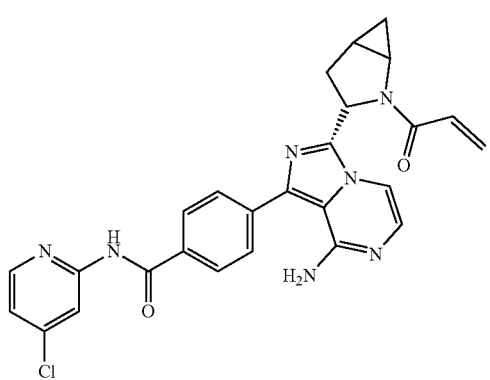
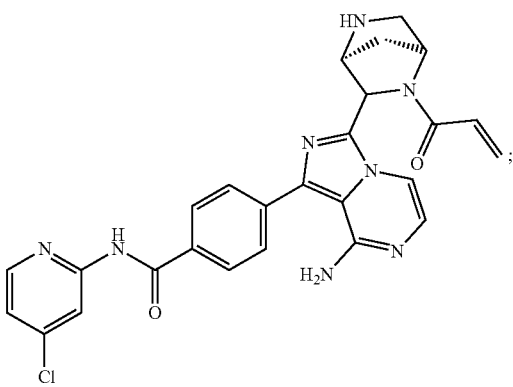
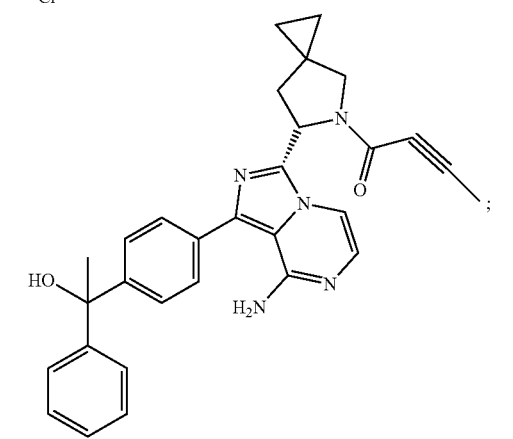

-continued
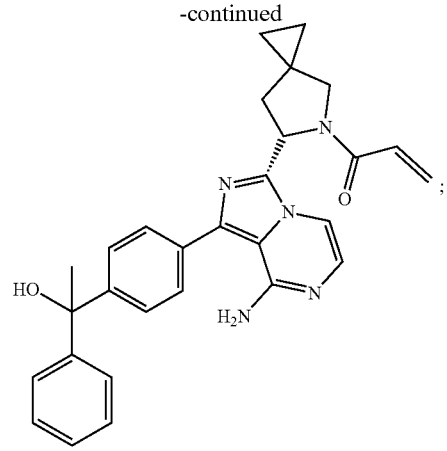
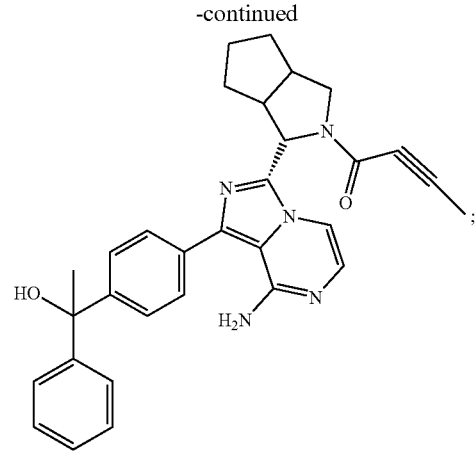
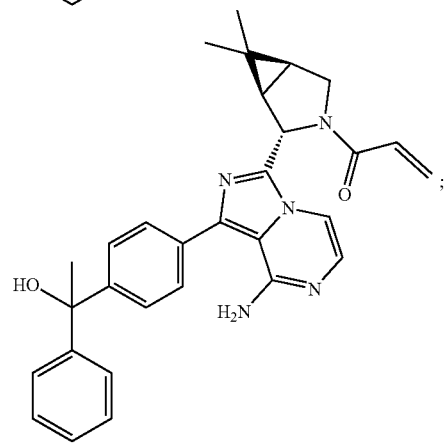
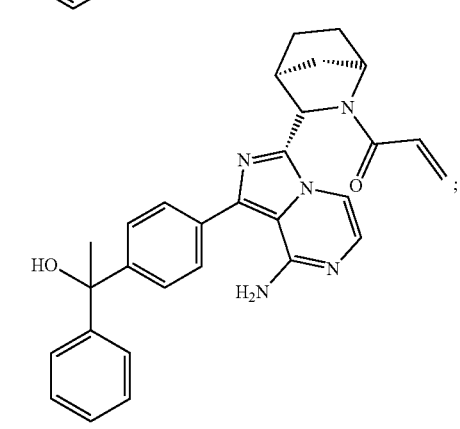
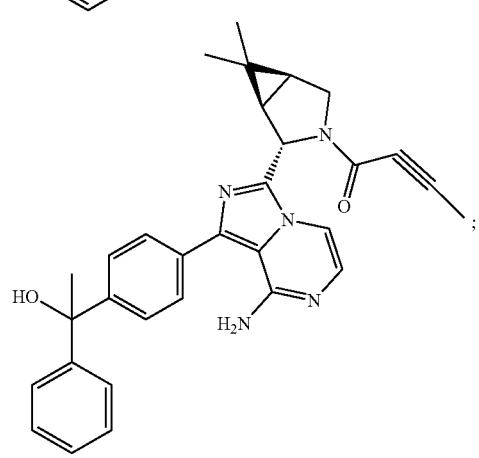
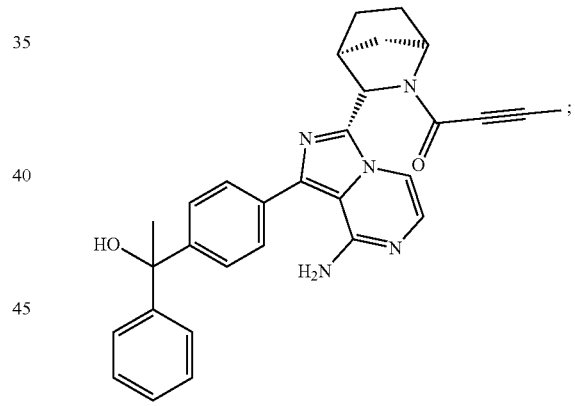
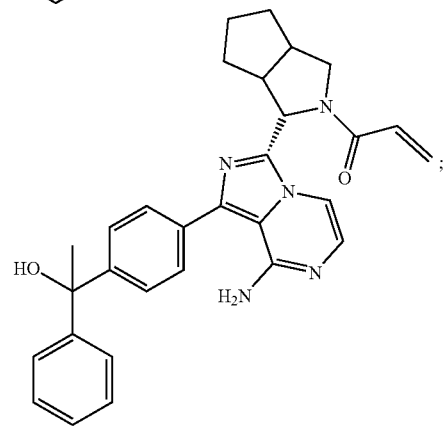
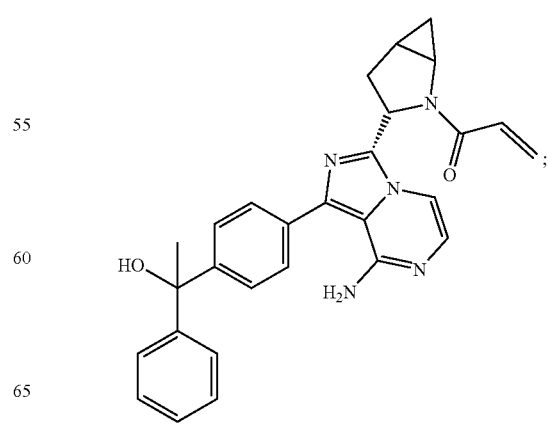

29
-continued
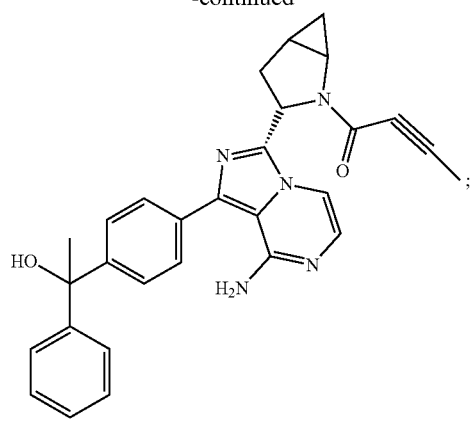;
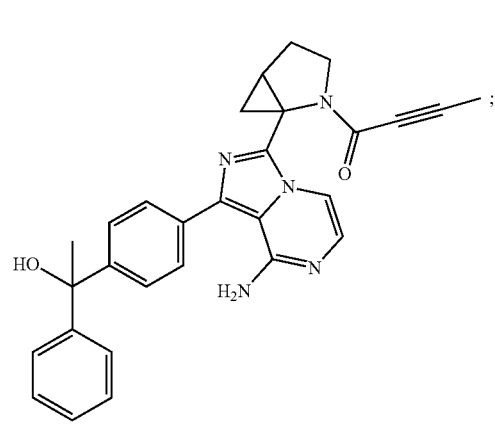 [SMILES: CC#CC(=O)N1CCC2CC21c1nc(-c2ccc(C(C)(O)c3ccccc3)cc2)c2c(N)nccn12];
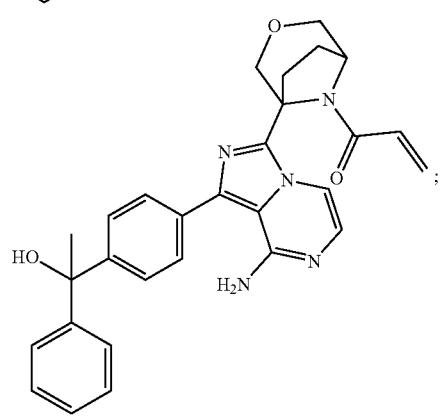;
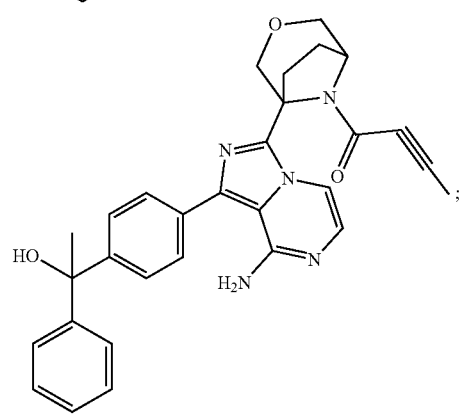;
30
-continued
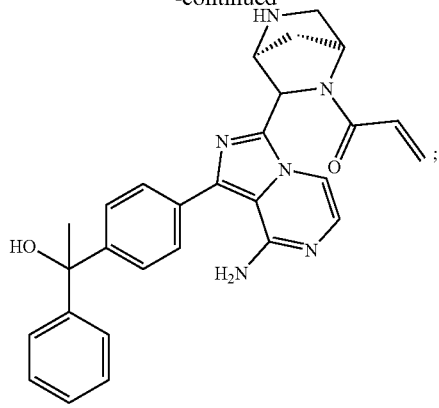;
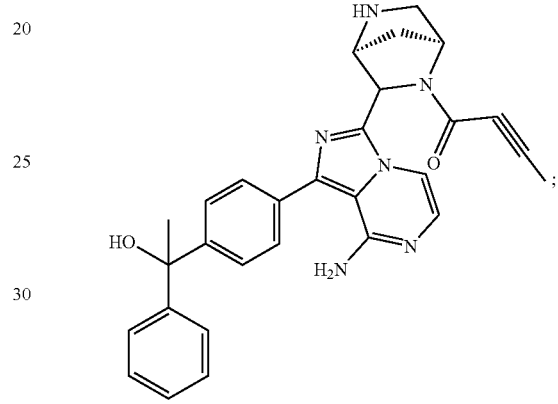;
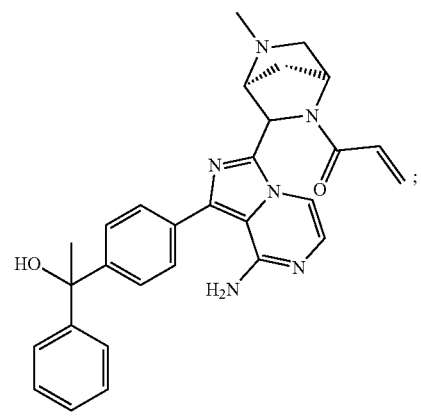;
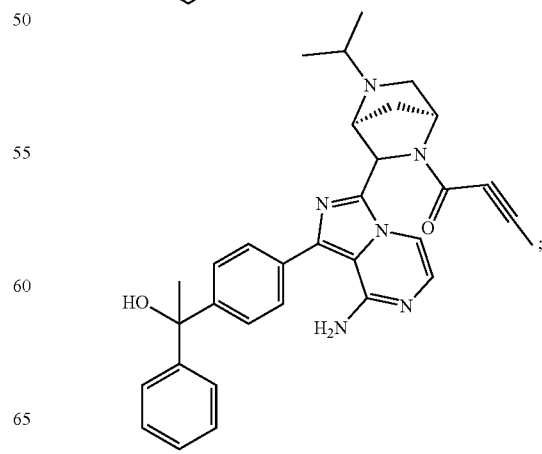;

31
-continued
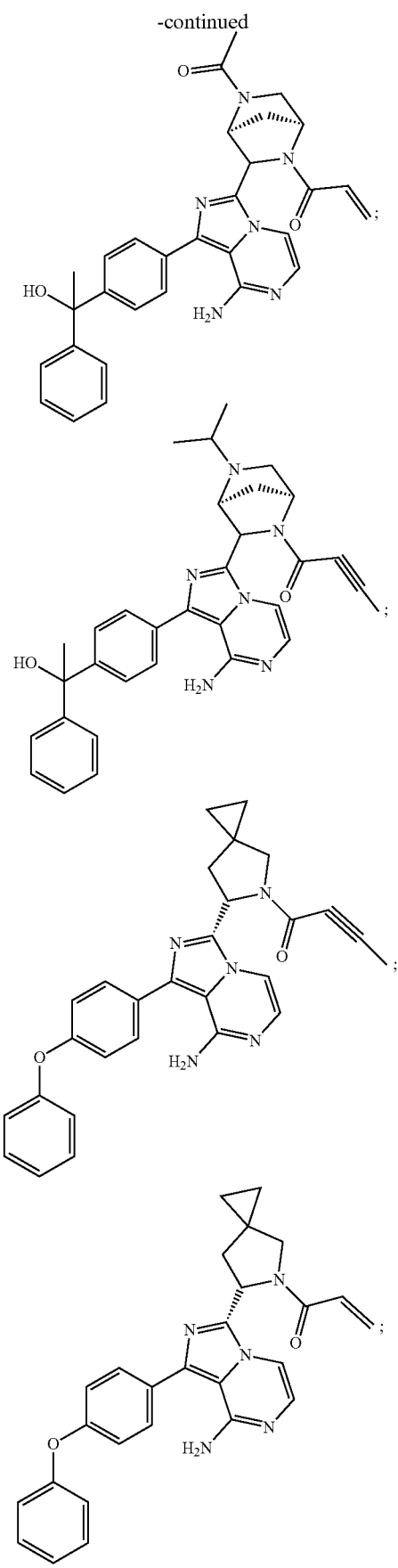
32
-continued
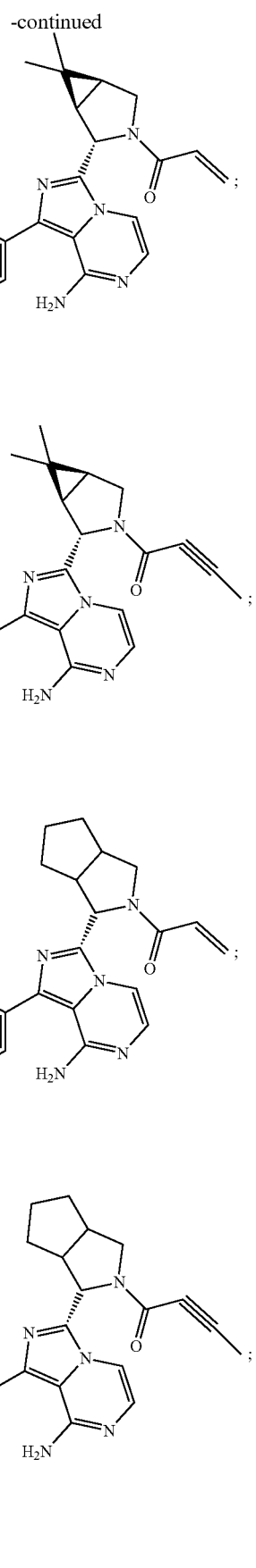

33
-continued
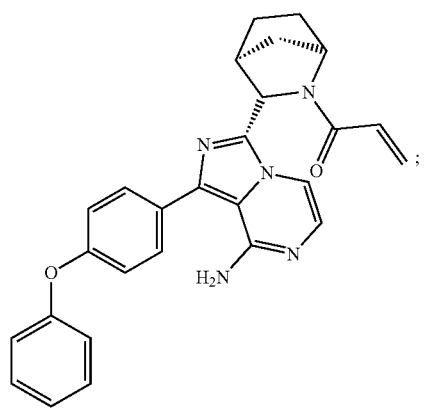
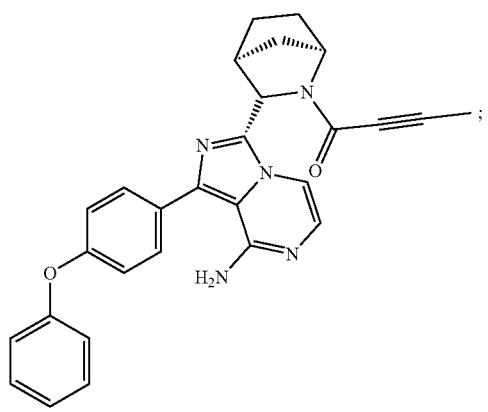
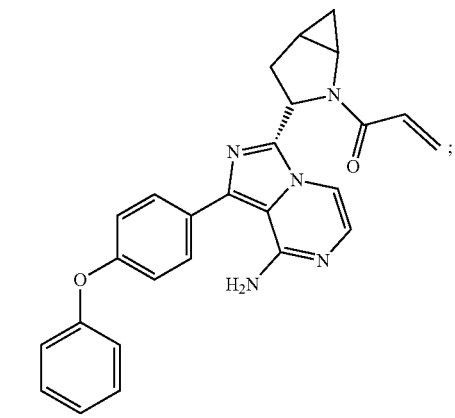
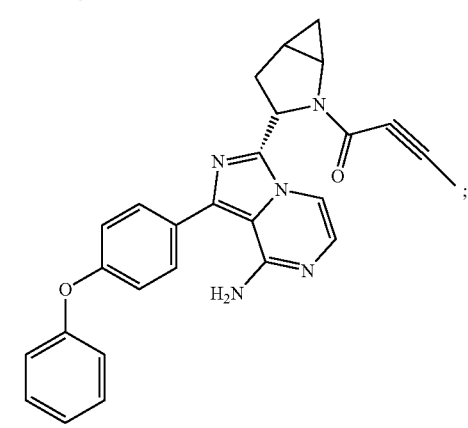
34
-continued
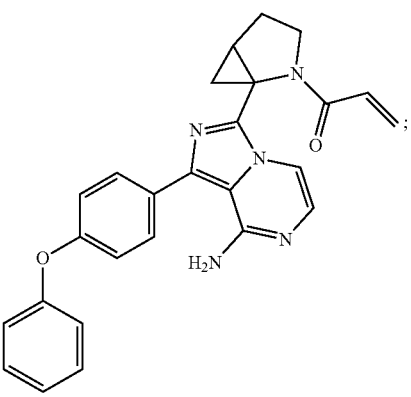
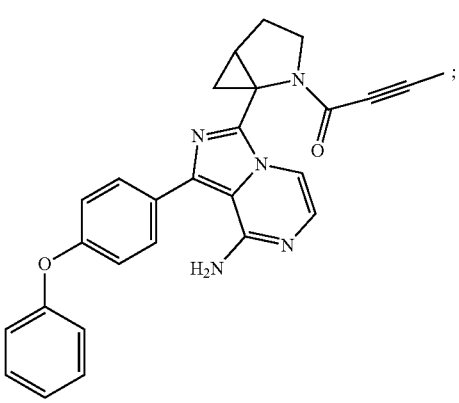
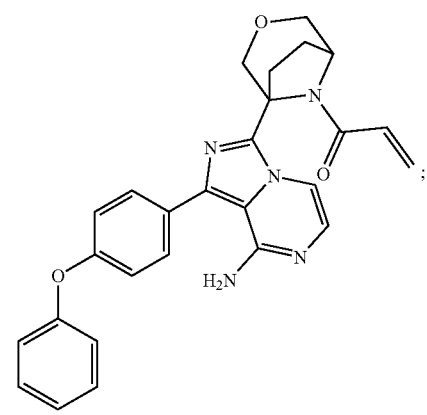
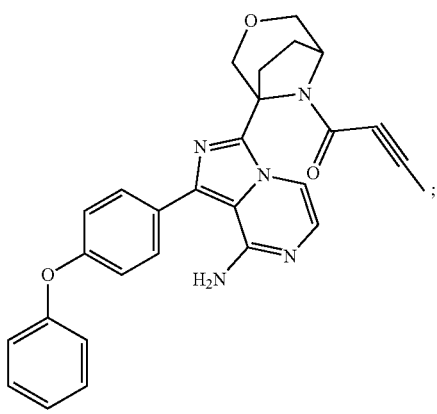

35
-continued
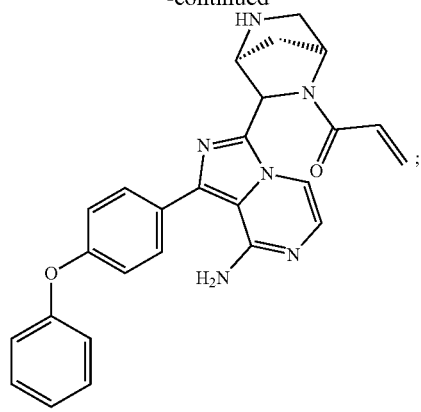
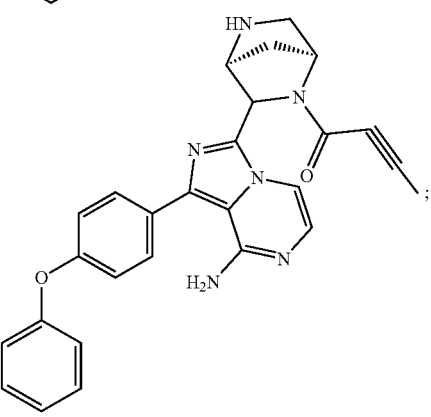
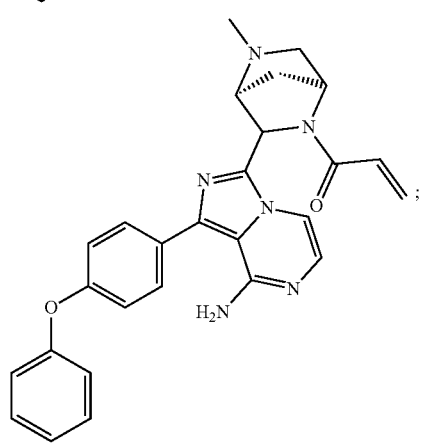
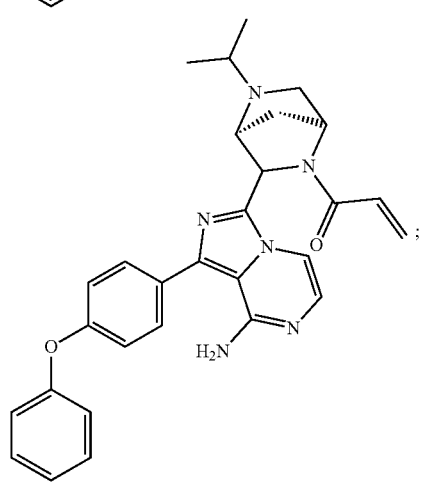
36
-continued
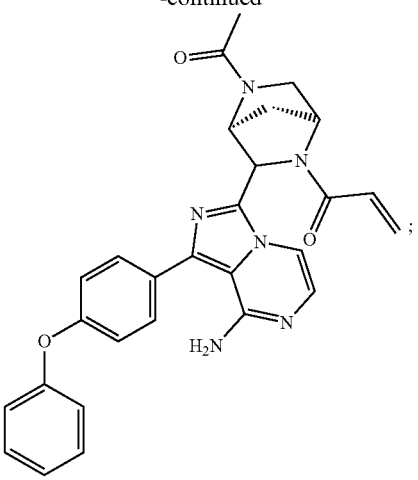
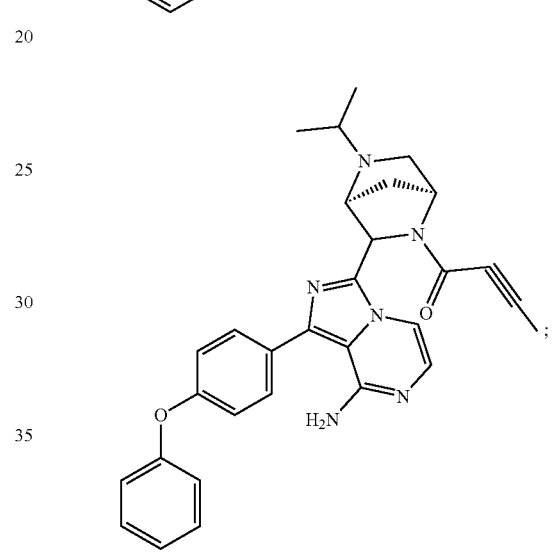
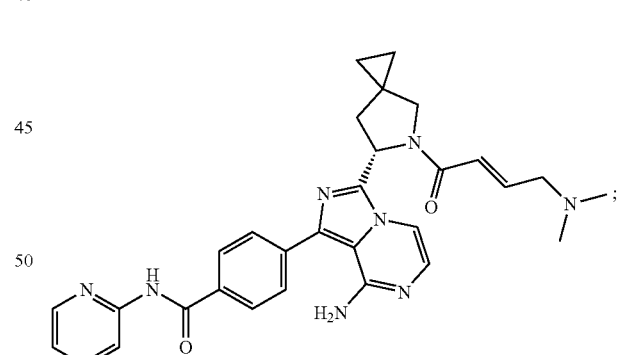
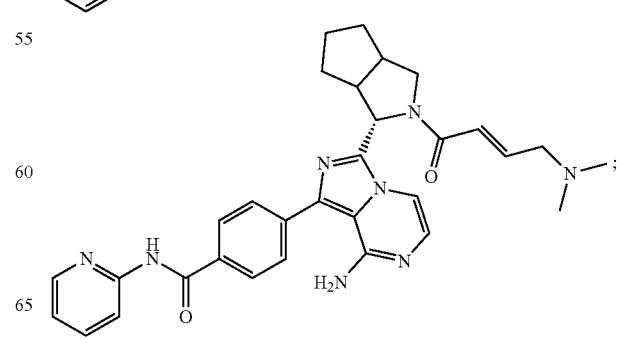

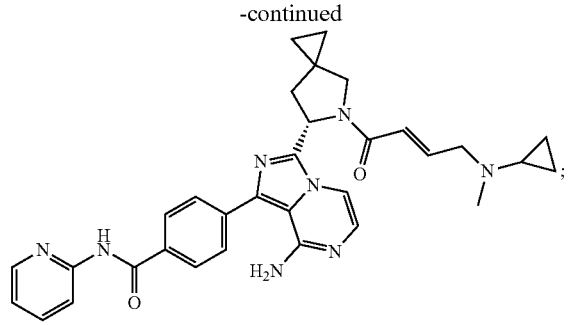
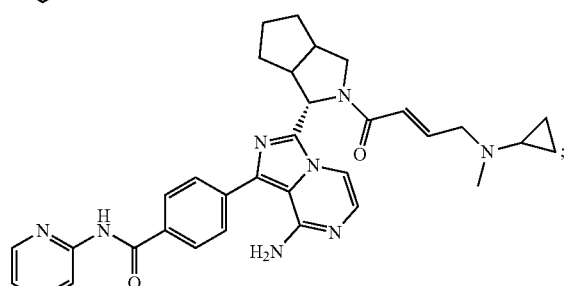
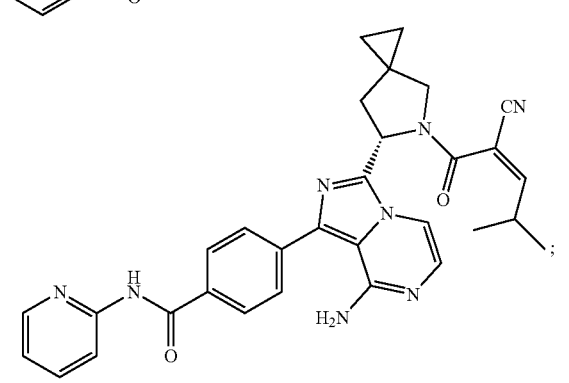
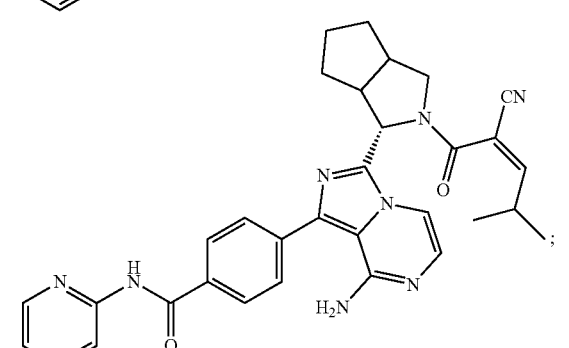
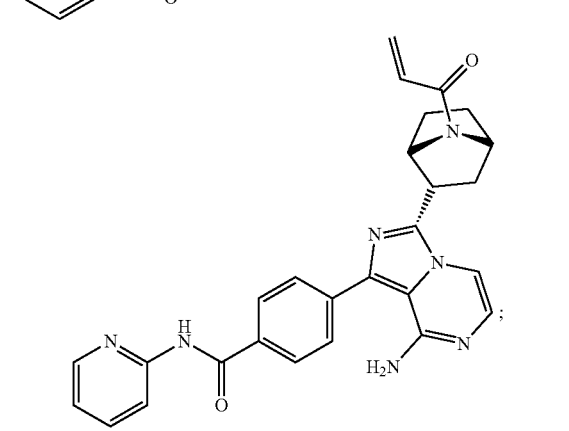
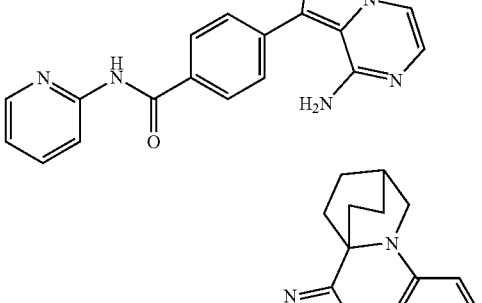
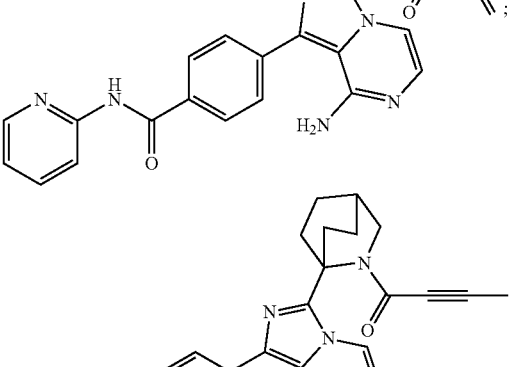
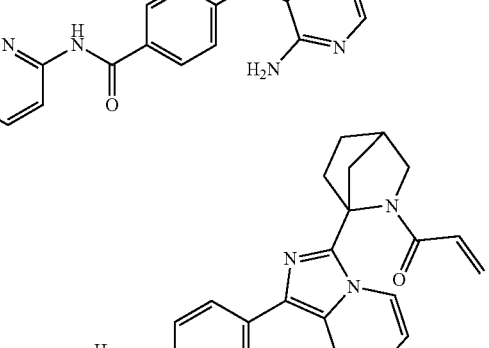
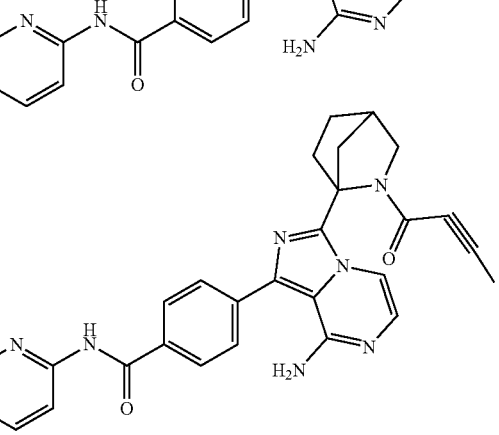

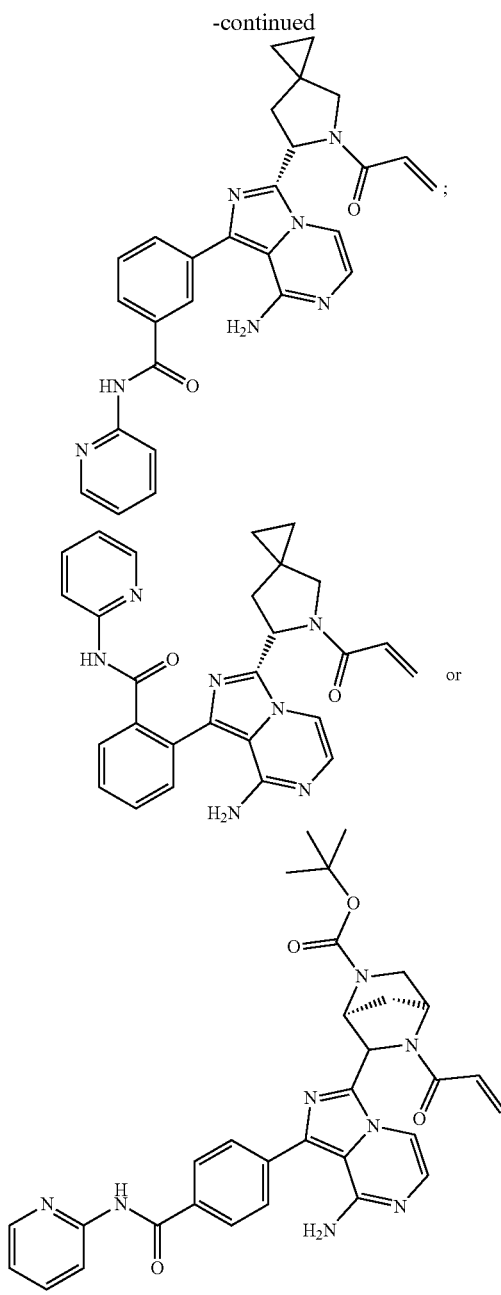

The present invention also provides a preparation method of the above compound, comprising the following steps:
1) using 2-chloropyrazine as a raw material, under the action of a basic compound, preparing (3-chloropyrazin-2-yl)methanol;
2) preparing (3-chloropyrazin-2-yl)methylamine by gabriel synthesis from (3-chloropyrazin-2-yl)methanol;
3) reacting the (3-chloropyrazin-2-yl)methylamine with a spirocyclic carboxylic acid or a bridged-ring carboxylic acid shown in formula (II) to prepare an amide compound;
4) subjecting the amide compound to a ring-closure reaction under the action of phosphorus oxychloride, and then obtaining a compound shown in formula (IV) by NBS bromination;
5) subjecting the compound shown in above formula (IV) to an amination reaction under the action of alcohol and ammonia water;
6) subjecting the product obtained by the above amination reaction and the boronic acid shown in formula (V-1) or the boronic acid ester shown in formula (V-2) to a Suzuki coupling reaction to obtain a compound shown in formula (VI);
7) subjecting the compound shown in formula (VI) above and a substituted or unsubstituted 2-butynoic acid to a condensation reaction under the action of a condensing agent, to obtain a compound of formula (I-1);
alternatively, reacting the compound shown in formula (VI) above with 3-chloropropionyl chloride or acryloyl chloride under the action of a base by direct condensation or direct condensation followed by olefination by eliminating hydrogen chloride, to obtain the compound shown in formula (I-2);
alternatively, reacting the compound shown in formula (VI) above with the olefinic acid derivative shown in formula (VII) under the action of a condensing agent, to obtain a compound of the formula (I-3) or the formula (I-4), R" is H or fluorine, chlorine, bromine, iodine, respectively;
alternatively, reacting the compound shown in formula (VI) above and cyanoacetic acid or nitroacetic acid under the action of a condensing agent to obtain an amide compound, and then subjecting to Knoevenagel reaction with the aldehyde compound shown in formula (VIII) to obtain a compound shown in formula (I-4); R" is nitro or cyano;

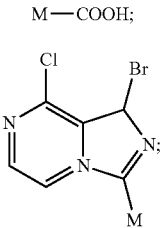

(III)

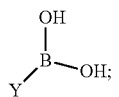

(IV)

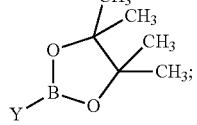

(V-1)

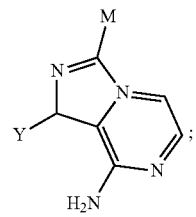

(V-2)

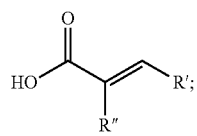

(VI)

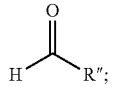

(VII)

(VIII)

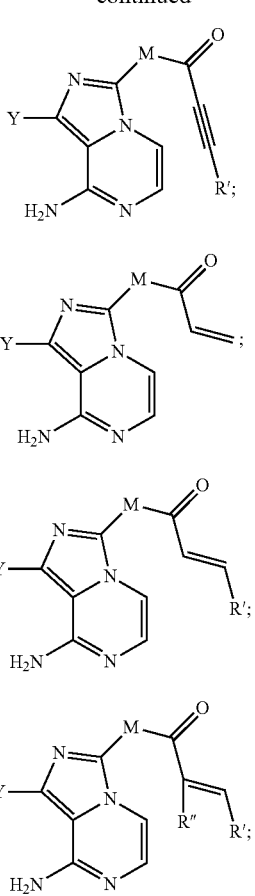

The ranges of the above Y, M, and R' are the same as above, and will not be repeated here.

The present invention also provides a pharmaceutical composition comprising the above compound or a salt thereof or a compound prepared by the above preparation method or a salt thereof, and a pharmaceutically acceptable carrier, excipient, diluent, adjuvant, vehicle or combinations thereof.

The present invention also provides a use of the above compound or the compound prepared by the above preparation method or the above pharmaceutical composition in the preparation of a medicament for treating or alleviating a BTK-mediated disease.

In certain specific embodiments of the present invention, the BTK-mediated disease is selected from the group consisting of immune, autoimmune, inflammatory diseases, allergies, infectious diseases, proliferative conditions and cancerous diseases and combinations thereof.

In still other specific embodiments of the present invention, the BTK-mediated disease is selected from the group consisting of rheumatoid arthritis, infectious arthritis, teratogenic arthritis, gouty arthritis, spondylitis, pancreatitis, chronic bronchitis, acute bronchitis, allergic bronchitis, toxic bronchitis, pediatric asthma, allergic alveolitis, allergic or non-allergic rhinitis, chronic nasosinusitis, cystic fibrosis or mucous viscous disease, cough, emphysema, interstitial lung disease, alveolitis, nasal polyps, pulmonary edema, pneumonia of various causes, lupus erythematosus, systemic scleroderma, sarcoidosis, subtypes of diffuse large B-cell lymphoma, mantle cell lymphoma (MCL), chronic lymphocytic lymphoma, extranodal marginal zone B-cell lymphoma, B-cell chronic lymphocytic leukemia (CLL), B-cell prolymphocytic leukemia, mature B-cell acute lymphoblastic leukemia, 17p-deletion chronic lymphocytic leukemia, Waldenstrom macroglobulinemia, lymphoplasmacytic lymphoma, splenic marginal zone lymphoma, plasma cell myeloma, plasmacytoma, intranodal marginal zone B-cell lymphoma, mantle cell lymphoma, intravascular large B-cell lymphoma and primary effusion lymphoma and combinations thereof.

The above compound or composition of the present invention can be used alone or in combination with other drugs when applied to the preparation of a medicament for treating or alleviating a BTK-mediated disease.

Compared with the prior art, the present invention provides a compound having the structure of formula (I), or an isomer, a pharmaceutically acceptable solvate thereof, or a salt thereof, for use as Bruton's tyrosine kinase inhibitor, which has a relatively high inhibitory activity against BTK, while having a small adverse effect.

DETAILED DESCRIPTION OF THE INVENTION

In order to further illustrate the present invention, the compound used as Bruton's tyrosine kinase inhibitor provided by the present invention and the preparation method and application thereof are described in detail below with reference to the examples.

The following abbreviations have the following meanings:
DMF represents N,N-dimethylformamide;
NBS represents N-bromosuccinimide;
DCM represents dichloromethane;
TEA represents triethylamine;
THF represents tetrahydrofuran;
TFA represents trifluoroacetic acid;
EA represents ethyl acetate;
PE represents petroleum ether;
MeOH represents methanol;
EtOH represents ethanol;
Et2O represents diethyl ether;
DIEA represents N,N-diisopropylethylamine;
HBTU represents benzotriazole-N,N,N',N'-tetramethylurea hexafluorophosphate;
TLC represents thin layer chromatography;
KOAc represents potassium acetate;
X-phos represents 2-dicyclohexylphosphino-2,4,6-triisopropylbiphenyl;
Pd2(dba)3 represents tris(dibenzylideneacetone)dipalladium;
Pd(pph3)4 represents triphenylphosphine palladium;
n-BuLi represents tert-butyllithium;
EDCI represents 1-(3-dimethylaminopropyl)-3-ethylcarbodiimide hydrochloride;
DIPEA represents N,N-diisopropylethylamine;
2-BuOH represents isobutanol;
STAB represents sodium triacetoxyborohydride;
DMSO represents dimethyl sulfoxide;
FAM represents carboxyfluorescein;
ATP represents adenosine triphosphate;
MEM represents minimum essential medium;
FBS represents fetal bovine serum;
IMDM represents Iscove's Modified Dulbecco's Media;
PS represents Penicillin-Streptomycin Solution;
RPMI 1640 medium represents Roswell Park Memorial Institute 1640 culture medium;

HEPES represents 4-(2-hydroxyethyl)-1-piperazine ethanesulfonic acid;
EGTA represents ethylene glycol diethyl ether diamine tetraacetic acid;
Na-ATP represents adenosine triphosphate sodium.
Example 1: Preparation of (S)-4-(8-amino-3-(5-(but-2-ynoyl)-5-azaspiro[2.4]heptan-6-yl)imidazo[1,5-a]pyrazin-1-yl)-N-(pyridin-2-yl)benzamide
The synthesis steps are as follows:
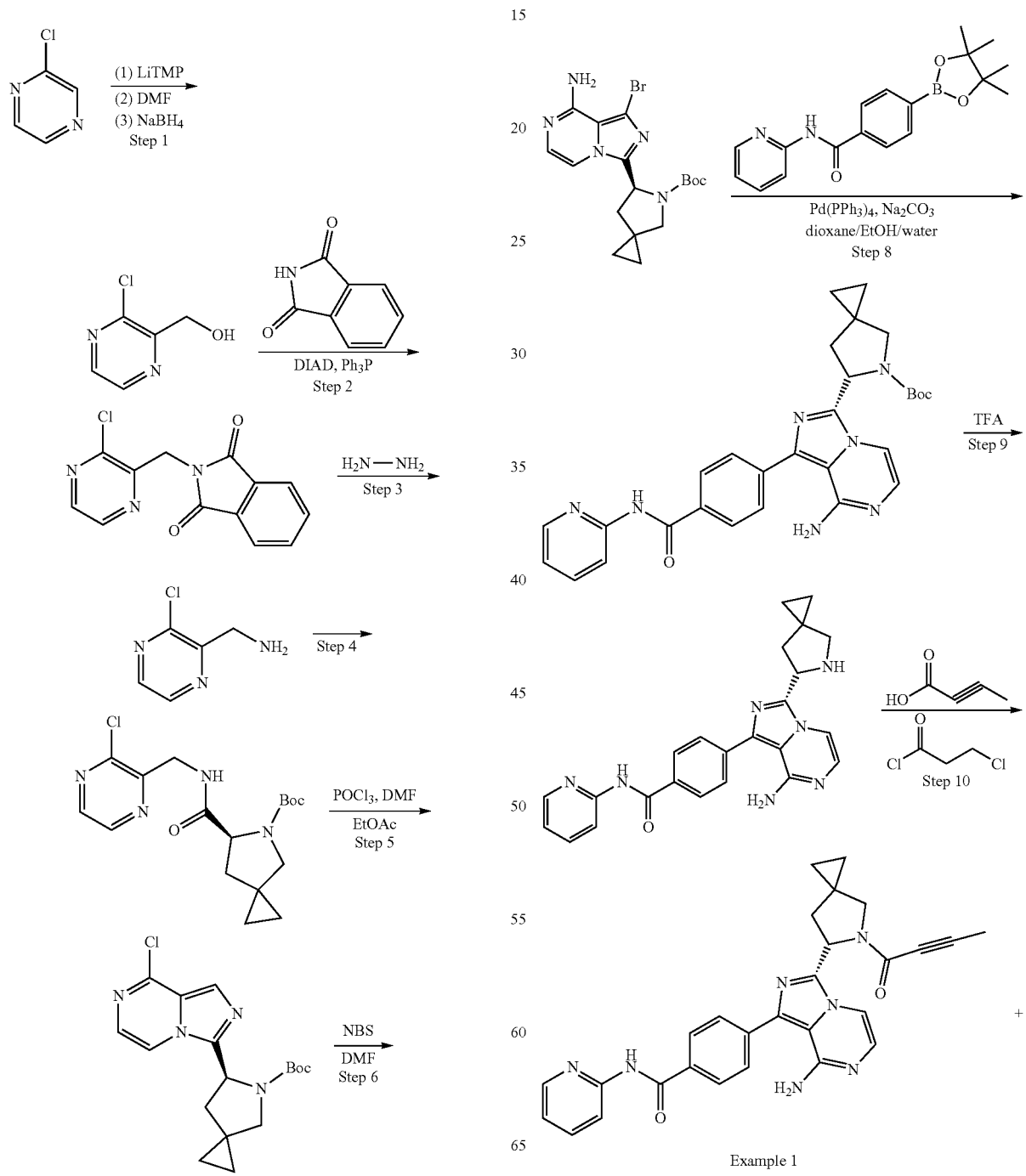

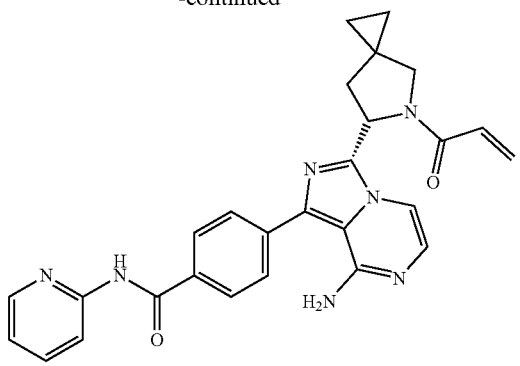

Example 2

Step 1: Preparation of (3-chloropyrazin-2-yl)methanol

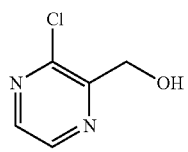

Under the protection of nitrogen, to a solution of 2,2,6,6-tetramethylpiperidine (72.8 g, 516.3 mmol) in 500 mL of dry THF, n-BuLi (346 mL, 553.7 mmol, 1.6 mol/L THF) was slowly added dropwise at −78° C., after the addition, the reaction mixture was naturally warmed to 0° C. and the reaction was stirred for 20 minutes, then the reaction mixture was cooled to −78° C., and a solution of 2-chloropyrazine (50 g, 436.3 mmol) in THF (100 mL) was added dropwise to the reaction mixture within 30 minutes. The colour of the reaction mixture changed from light yellow to dark brown, and the reaction was stirred at −78° C. for 10 minutes. DMF (84 ml, 1092 mmol) was dissolved in THF (50 mL) and the resulting solution was added dropwise to the reaction mixture within 10 minutes and the temperature of the reaction system was controlled within the range from −70° C. to −78° C. A reaction was conducted while being stirred at −78° C. for 2 hours. Then, MeOH (800 mL) was added to the reaction mixture, and after the addition, NaBH$_4$ (33 g, 868 mmol) was added in portions to the reaction mixture. After the addition, the reaction mixture was naturally warmed to room temperature and stirred for 2 hours. After TLC showed that the raw materials reacted completely, the reaction mixture was quenched with saturated NH$_4$Cl, extracted with DCM (1 L×3) for three times. The organic phase was washed with water, thoroughly dried with anhydrous Na$_2$SO$_4$, evaporated under vacuum and then purified by silica gel column (PE/EA=100/1-5/1) to obtain 60 g of target compound which was a yellow oily substance.

Step 2: Preparation of 2-((3-chloropyrazin-2-yl)methyl)isoindoline-1,3-dione

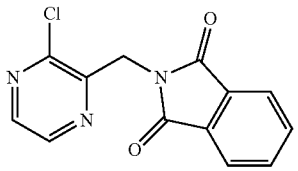 [SMILES: O=C1c2ccccc2C(=O)N1Cc1nccnc1Cl]

Under the protection of nitrogen, to a solution of (3-chloropyrazin-2-yl)methanol (60 g, 414.9 mmol), triphenylphosphine (130.4 g, 497.9 mmol) and phthalimide (73.2 g, 497.9 mmol) in 500 mL of THF, DIAD (100.6 g, 497.9 mmol) was slowly added dropwise at −5° C. After the addition, the reaction mixture was stirred at 20° C. for 3 hours. After TLC showed that the reaction was completed, water was added to the reaction mixture. The resulting mixture was then extracted with EA (1 L×3), the organic phase was thoroughly dried with anhydrous Na$_2$SO$_4$, evaporated under vacuum and then purified by rapid chromatography (PE/EA=30/1) to obtain 90.8 g of target compound which was a white solid.

Step 3: Preparation of (3-chloropyrazin-2-yl)methylamine

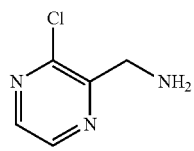

Under the protection of nitrogen, to a mixed solution of 2-((3-chloropyrazin-2-yl)methyl)isoindoline-1,3-dione (90 g, 328.5 mmol) in DCM/MeOH (800 mL/400 mL), hydrazine hydrate (41.1 g, 821.5 mmol) was added; the reaction mixture was stirred at room temperature overnight, a large amount of white solid was formed in the reaction system and the reaction system was subjected to suction filtration. The filter cake was washed with ethyl acetate and the filtrate was concentrated and then the resulting mixture was subjected to suction filtration again. The filter cake was washed with ethyl acetate and the filtrate was thoroughly dried with anhydrous Na$_2$SO$_4$, and the resulting mixture was evaporated under vacuum to obtain 38.2 g of target compound which was a yellow oily substance.

Step 4: Preparation of (S)-tert-butyl 6-(((3-chloropyrazin-2-yl)methyl)carbamoyl)-5-azaspiro[2.4]heptane-5-carboxylate

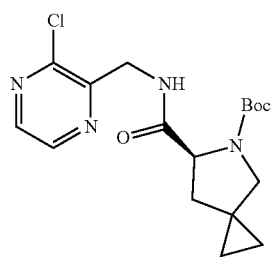 [SMILES: CC(C)(C)OC(=O)N1CC2(CC2)C[C@H]1C(=O)NCc1nccnc1Cl]

Under the protection of nitrogen, to a solution of (3-chloropyrazin-2-yl)methylamine (2.86 g, 20 mmol), (S)-5-tert-butoxycarbonyl-5-azaspiro[2.4]heptane-6-carboxylic acid (4.82 g, 20 mmol), HOBt (3.51 g, 26 mmol) and TEA (3.64 g, 36 mmol) in 30 mL DMF (0° C.), EDCI (4.97 g, 26 mmol) was added in portions. The reaction mixture was stirred at room temperature overnight. After TLC showed the raw materials reacted completely, the reaction was quenched with water and extracted with EA (50 mL×3). The organic phase was backwashed with saturated brine, thoroughly dried with anhydrous $Na_2SO_4$, evaporated under vacuum and then purified by column chromatography (PE/EA=5/1-3/1) to obtain 6.4 g of the target compound which was a yellow solid.

Step 5: Preparation of (S)-tert-butyl 6-(8-chloroimidazo[1,5-a]pyrazin-3-yl)-5-azaspiro[2.4]heptane-5-carboxylate

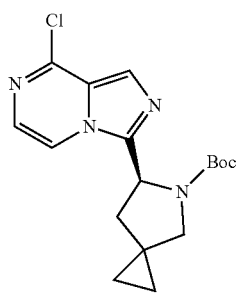 [SMILES: CC(C)(C)OC(=O)N1CC2(CC2)C[C@H]1c1ncc2c(Cl)nccn12]

In an ice salt bath, to a mixed solution of (S)-6-(((3-chloropyrazin-2-yl)methyl)carbamoyl)-5-azaspiro[2.4]heptane-5-carboxylic acid tert-butyl ester (6.3 g, 17.18 mmol) in DMF/EA (7.5 mL/50 mL), $POCl_3$ (12.6 mL, 103.08 mmol) was slowly added dropwise. After the addition, the reaction mixture was stirred at room temperature for 2 hours. After TLC showed that raw materials reacted completely, the reaction solution was slowly added to a solution of $Na_2CO_3$ (6 mol/L), pH was maintained to be more than 8 and the organic phase was separated. The aqueous phase was extracted with EA (20 mL×3), and the organic phase was pooled and thoroughly dried with anhydrous $Na_2SO_4$, evaporated under vacuum and then purified by column chromatography (PE/EA=3/1) to obtain 5.52 g of the target compound which was a white solid.

Step 6: Preparation of (S)-tert-butyl 6-(1-bromo-8-chloroimidazo[1,5-a]pyrazin3-yl)-5-azaspiro[2.4]heptane-5-carboxylate

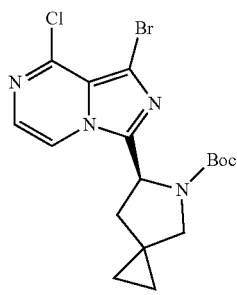 [SMILES: CC(C)(C)OC(=O)N1CC2(CC2)C[C@H]1c1nc(Br)c2c(Cl)nccn12]

In an ice salt bath, to a solution of (S)-tert-butyl 6-(8-chloroimidazo[1,5-a]pyrazin-3-yl)-5-azaspiro[2.4]heptane-5-carboxylate (5.5 g, 15.77 mmol) in 50 mL of DMF, NBS (2.95 g, 16.56 mmol) was added in portions. The reaction mixture was stirred for 1 hour in an ice salt bath. After TLC showed that raw materials reacted completely, the reaction solution was slowly added to $NaHCO_3$ (1 mol/L) solution to be quenched, extracted with EA (20 mL×3). The organic phase was washed with saturated NaCl, thoroughly dried with $Na_2SO_4$, vacuum evaporated and then purified by column chromatography (PE/EA=5/1) to obtain 6.07 g of the target compound which was a red brown solid.

Step 7: Preparation of (S)-tert-butyl 6-(8-amino-1-bromoimidazo[1,5-a]pyrazin-3-yl)-5-azaspiro[2.4]heptane-5-carboxylate

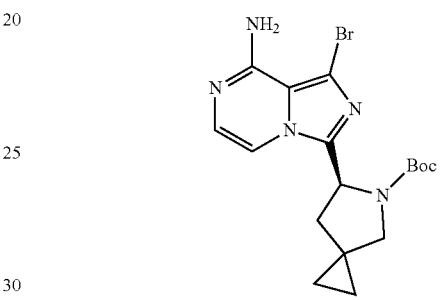

At room temperature, to a high pressure reactor containing (S)-tert-butyl 6-(1-bromo-8-chloroimidazo[1,5-a]pyrazin3-yl)-5-azaspiro[2.4]heptane-5-carboxylate (5.5 g, 12.86 mmol), 15 mL of 2-BuOH and 30 mL of aqueous ammonia were added, and the reaction mixture was stirred at 90° C. for 15 hours. After TLC showed the raw materials reacted completely, the reaction mixture was concentrated under vacuum to give a solid crude product. The crude product was pulped with EA/PE (5/1) to obtain 3.94 g of pure target compound which was a light yellow solid.

Step 8: Preparation of (S)-tert-butyl 6-(8-amino-1-(4-(pyridin-2-ylcarbamoyl)phenyl)imidazo [1,5-a]pyrazin-3-yl)-5-azaspiro[2.4]heptane-5-carboxylate

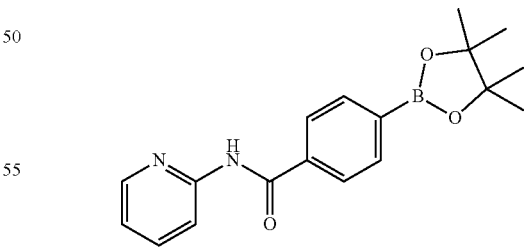

Under the protection of nitrogen, to a solution of 2-aminopyridine (5 g, 53.19 mmol) and 4-(4,4,5,5-tetramethyl-1,3,2-dioxaborolan-2-yl) benzoic acid (13.20 g, 53.19 mmol), DIPEA (13.72 g, 106.38 mmol) in 50 mL DMF (0° C.), HBTU (26.21 g, 69.15 mmol) was added in portions. The reaction mixture reacted under stirring at room temperature overnight. After TLC showed the raw materials reacted completely, the reaction mixture was quenched with water, and extracted with EA (30 mL×3). The organic phase was backwashed with saturated brine, thoroughly dried with anhydrous Na₂SO₄, evaporated under vacuum and then purified by column chromatography (PE/EA=20/1) to obtain 13.1 g of the target compound which was an off-white solid.

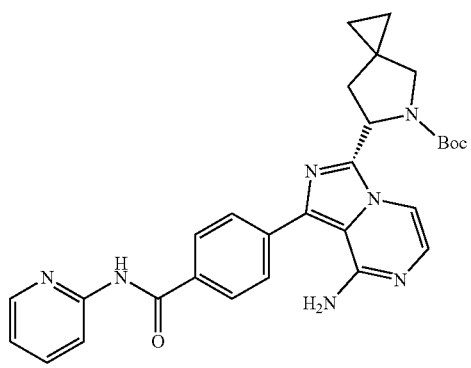

Under the protection of nitrogen, to a mixed solution of (S)-tert-butyl 6-(1-bromo-8-chloroimidazo[1,5-a] pyrazin3-yl)-5-azaspiro[2.4]heptane-5-carboxylate (3.5 g, 8.57 mmol), N-(pyridin-2-yl)-4-(4,4,5,5-tetramethyl-1,3,2-dioxaborolan-2-yl)benzamide (3.33 g, 10.28 mmol), Na₂CO₃ (1.82 g, 17.14 mmol) in dioxane/EtOH/water (36 mL/12 mL/12 mL), Pd(PPh₃)₄ (496.89 mg, 0.43 mmol) was added. The reaction mixture reacted under stirring at 90° C. overnight. After TLC showed the raw materials reacted completely, the reaction mixture was quenched with water, and extracted with EA (40 mL×3). The organic phase was backwashed with saturated brine, thoroughly dried with anhydrous Na₂SO₄, evaporated under vacuum and then purified by column chromatography (DCM/MeOH=60/1) to obtain 2.71 g of the target compound which was a light yellow solid.

Step 9: Preparation of (S)-4-(8-amino-3-(5-azaspiro [2.4]heptan-6-yl)imidazo [1,5-a]pyrazin-1-yl)-N-(pyridin-2-yl) benzamide

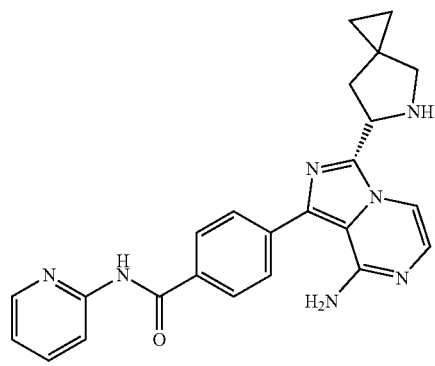

To a solution of (S)-tert-butyl 6-(8-amino-1-(4-(pyridin-2-ylcarbamoyl)phenyl)imidazo [1,5-a]pyrazin-3-yl)-5-azaspiro[2.4]heptane-5-carboxylate (2.71 g, 5.16 mmol) in DCM (20 mL), TFA (3 mL) was added. The reaction mixture reacted under stirring at room temperature overnight. After TLC showed the raw materials reacted completely, the reaction system was concentrated and pH was adjusted to 8 with Na₂CO₃ (3 mol/L). The reaction mixture was extracted with DCM/MeOH (10/1). The organic phase was dried with anhydrous Na₂SO₄, evaporated under vacuum and then purified by column chromatography (DCM/MeOH=60/1-10/1) to obtain 1.98 g of the target compound which was a white solid.

Step 10: Preparation of a (S)-4-(8-amino-3-(5-(but-2-ynoyl)-5-azaspiro[2.4]heptan-6-yl)imidazo[1,5-a] pyrazin-1-yl)-N-(pyridin-2-yl)benzamide

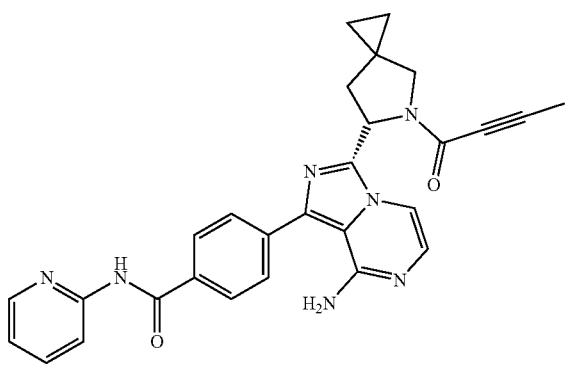

Under the protection of nitrogen, to a solution of (S)-4-(8-amino-3-(5-azaspiro[2.4]heptan-6-yl)imidazo[1,5-a] pyrazine-1-yl)-N-(pyridin-2-yl) benzamide (90 mg, 0.212 mmol), 2-butynoic acid (19.6 mg, 0.233 mmol), DIPEA (82 mg, 0.636 mmol) in DMF (3 mL), HBTU (96.4 mg, 0.254 mmol) was added. The reaction mixture reacted under stirring at room temperature for 1 hour. After TLC showed the raw materials reacted completely, the reaction system was quenched with water and extracted with EA (10 mL×3). The organic phase was backwashed with saturated brine, dried with anhydrous Na₂SO₄, evaporated under and then purified by preparative silica gel plate (DCM/MeOH=20/1) to obtain 55 mg of the target compound which was a yellow solid.

The structure of the product was characterized by nuclear magnetic resonance and mass spectrometry and the results were as follows:

$^1$H NMR (400 MHz, d$_6$-DMSO) δ 0.58-0.77 (4H, m), 1.58 (1H, s), 1.99 (2H, s), 2.24-2.33 (2H, m), 3.51 (0.4H, d, J=16.4 Hz), 3.61 (0.4H, d, J=11.6 Hz), 3.61 (0.6H, d, J=10.8 Hz), 3.84 (0.6H, d, J=10.8 Hz), 5.56-5.59 (0.6H, m), 5.79-5.82 (0.4H, m), 6.14-6.20 (2H, m), 7.11-7.20 (2H, m), 7.73-7.79 (2.6H, m), 7.84-7.89 (1.4H, m), 8.16 (2H, dd, J=8.4 Hz, 2.8 Hz), 8.23 (1H, d, J=8.4 Hz), 8.41 (1H, dd, J=4.8 Hz, 1.2 Hz), 10.85 (1H, s).

EM (calculated value): 491.2; MS(ESI) m/e (M+1H)+: 492.2.

It can be seen that the compound prepared by the present application has the same structure as the compound in the above reaction scheme.

Example 2: Preparation of (S)-4-(3-(5-acryloyl-5-azaspiro[2.4]heptan-6-yl)-8-aminoimidazo[1,5-a]pyrazin-1-yl)-N-(pyridin-2-yl)benzamide

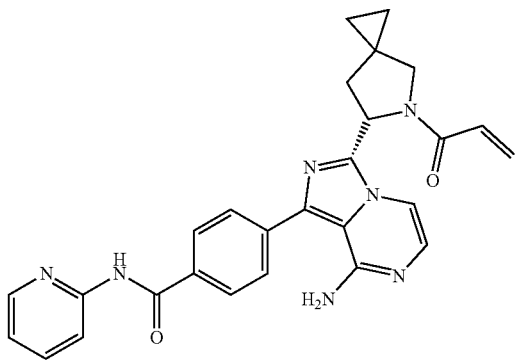

Under the protection of nitrogen, to a solution of (S)-4-(8-amino-3-(5-azaspiro[2.4]heptan-6-yl)imidazo[1,5-a]pyrazine-1-yl)-N-(pyridin-2-yl) benzamide (120 mg, 0.28 mmol), TEA (113.12 mg, 1.12 mmol) in DCM (10 mL), 3-chloropropionyl chloride (35.6 mg, 0.28 mmol) was added dropwise at 0° C. The reaction mixture reacted under stirring at room temperature overnight. After TLC showed the raw materials reacted completely, the reaction system was quenched with water and extracted with EA (10 mL×3). The organic phase was dried with anhydrous $Na_2SO_4$, evaporated under vacuum and then purified by preparative silica gel plate (DCM/MeOH=15/1) to obtain 40 mg of the target compound which was a yellow solid.

The structure of the product was characterized by nuclear magnetic resonance and mass spectrometry and the results were as follows:

$^1$H NMR (400 MHz, $d_6$-DMSO) δ 0.56-0.76 (4H, m), 2.24-2.26 (1.5H, m), 3.61-3.66 (1.5H, m), 3.87 (1H, d, J=10.4 Hz), 5.60-5.68 (2H, m), 6.05-6.20 (3H, m), 6.55 (1H, dd, J=16.8 Hz, 10.4 Hz), 7.11-7.20 (2H, m), 7.66-7.74 (2H, m), 7.83-7.88 (2H, m), 8.15 (2H, d, J=8.4 Hz), 8.22 (1H, d, J=8.4 Hz), 8.41 (1H, d, J=3.6 Hz), 10.84 (1H, s).

EM (calculated value): 479.2; MS(ESI) m/e (M+1H)+: 480.2.

It can be seen that the compound prepared by the present application has the same structure as the compound above reaction scheme.

Examples 3-21

Using the following compounds as raw materials, the following compounds were prepared by the preparation method of Example 1 or Example 2. The structures and nuclear magnetic characterization data of the compounds are shown in Table 1. Table 1 shows the structures and a summary of structural analysis data of the compounds prepared in Examples 3 to 21 of the present application.

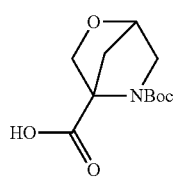

is prepared according to the literature Tetrahedron Letters 57 (2016) 599-602;

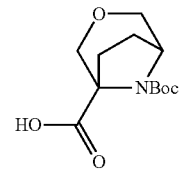

is prepared according to the literature Tetrahedron Letters 57 (2016) 599-602;

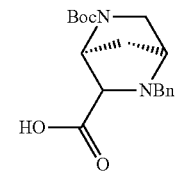

is prepared according to the literature Bioorganic & Medicinal Chemistry Letters 14 (2004) 6107-6111;

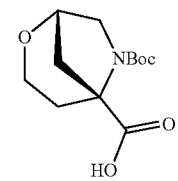

is prepared according to patent WO2014/140081A1;

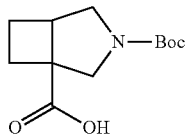

is prepared according to patent WO2011/35332;

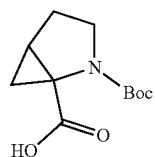 [SMILES: CC(C)(C)OC(=O)N1CCC2CC21C(=O)O]

is prepared according to the literature Journal of Organic Chemistry; vol. 59; nb. 2; (1994); p. 276-277;

Other key intermediate fragments are directly purchased or custom synthesized.

TABLE 1

Structures and structural analysis data of the compounds prepared in Examples 3-21

| Examples | Structures | Analysis data |
|---|---|---|
| 3 | 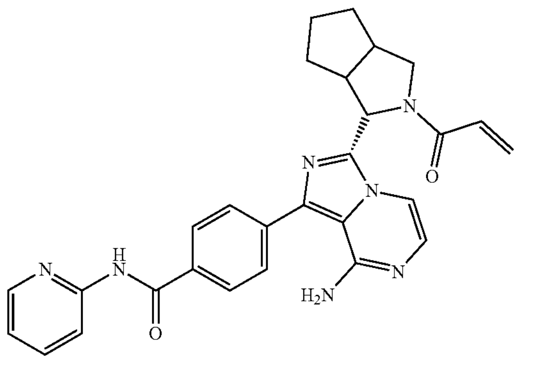 | $^1$H NMR (400 MHz, d$_6$-DMSO) δ 1.45-1.61 (3H, m), 1.76-1.80 (1H, m), 1.85-2.01 (2H, m), 2.67-2.69 (1H, m), 2.90-2.92 (1H, m), 3.62-3.66 (1H, m), 3.90-4.00 (1H, m), 5.45 (1H, d, J = 2.0 Hz), 5.67-5.70 (1H, m), 6.08-6.13 (3H, m), 6.76 (1H, dd, J = 16.8 Hz, 10.4 Hz), 7.13 (1H, d, J = 5.2 Hz), 7.18 (1H, dd, J = 6.8 Hz, 5.2 Hz), 7.70-7.74 (2H, m), 7.84-7.91 (2H, m), 8.15 (2H, d, J = 8.4 Hz), 8.22 (1H, d, J = 8.4 Hz), 8.41 (1H, d, J = 4.0 Hz), 10.84 (1H, s). EM (calculated value): 439.2; MS(ESI) m/e (M + 1H)$^+$: 440.2 |
| 4 | 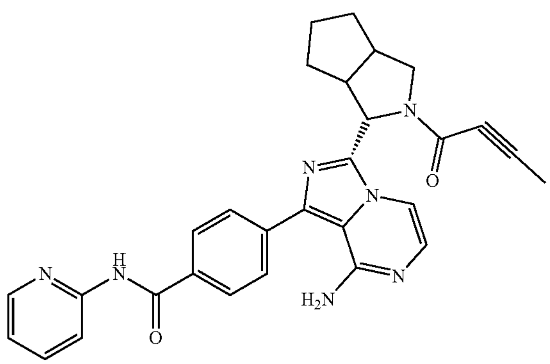 | $^1$H NMR (400 MHz, d$_6$-DMSO) δ 1.50-1.60 (3H, m), 1.76-1.80 (2H, m), 1.85-2.09 (4H, m), 2.73 (0.35H, brs), 2.97 (0.65H, brs), 3.48-3.51 (0.35H, m), 3.70-3.74 (0.65H, m), 3.79-3.84 (0.35H, m), 3.90-3.95 (0.65H, m), 5.41 (0.65H, d, J = 2.8 Hz), 5.52 (0.35H, d, J = 2.8 Hz), 6.19-6.22 (2H, m), 7.12-7.20 (2H, m), 7.75 (2H, dd, J = 8.0 Hz, 4.8 Hz), 7.83-7.90 (2H, m), 8.17 (2H, d, J = 8.4 Hz), 8.23 (1H, d, J = 8.4 Hz), 8.41 (1H, dd, J = 4.4 Hz, 0.8 Hz), 10.85 (1H, s). EM (calculated value): 505.2; MS(ESI) m/e (M + 1H)$^+$: 506.2 |
| 5 | 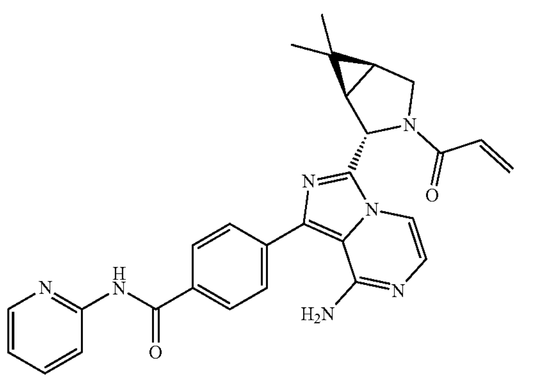 [SMILES: C=CC(=O)N1C[C@H]2[C@@H]([C@H]1c1nc(-c3ccc(C(=O)Nc4ccccn4)cc3)c3c(N)nccn13)C2(C)C] | $^1$H NMR (400 MHz, d$_6$-DMSO) δ 1.00-1.05 (6H, m), 1.49-1.55 (1H, m), 1.63-1.65 (0.3H, m), 1.74-1.77 (0.7H, m), 3.70-3.73 (0.3H, m), 3.77-3.80 (0.7H, m), 3.85-3.90 (0.3H, m), 4.04-4.08 (0.7H, m), 5.40 (0.7H, s), 5.51-5.53 (0.3H, m), 5.60 (0.3H, s), 5.66-5.69 (0.7H, m) 6.03-6.23 (3H, m), 6.38 (0.3H, dd, J = 16.8 Hz, 10.4 Hz), 6.57 (0.7H, dd, J = 16.8 Hz, 10.4 Hz), 7.13-7.20 (2H, m), 7.71-7.79 (2H, m), 7.84-7.92 (2H, m), 8.15 (2H, d, J = 8.4 Hz), 8.22 (1H, d, J = 8.4 Hz), 8.37-8.41 (1H, m), 10.85 (1H, s). EM (calculated value): 493.2; MS(ESI) m/e (M + 1H)$^+$: 494.2 |
| 6 | 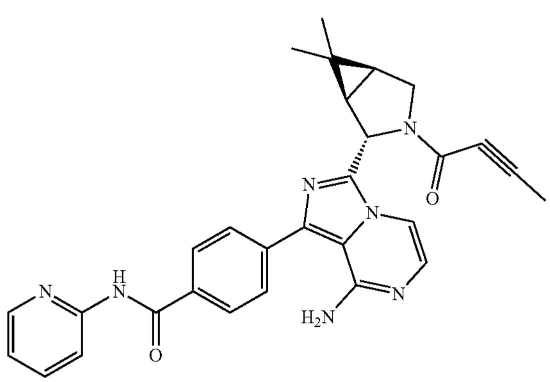 [SMILES: CC#CC(=O)N1C[C@H]2[C@@H]([C@H]1c1nc(-c3ccc(C(=O)Nc4ccccn4)cc3)c3c(N)nccn13)C2(C)C] | $^1$H NMR (400 MHz, d6-DMSO) δ 1.05 (6H, s), 1.49-1.53 (1H, m), 1.67-1.71 (1H, m), 1.74 (1.2H, s), 2.02 (1.7H, s), 3.63 (0.45H, d, J = 12.4 Hz), 3.78 (0.45H, dd, J = 12.4 Hz, 5.2 Hz), 3.85 (0.55H, d, J = 11.2 Hz), 3.78 (0.55H, dd, J = 11.2 Hz, 5.2 Hz), 5.36 (0.55H, s), 5.56 (0.45H, s), 6.13-6.21 (2H, m), 7.13-7.20 (2H, m), 7.72-7.76 (2H, m), 7.84-7.89 (1.55H, m), 7.96 (0.45H, d, J = 5.2 Hz), 8.16 (2H, d, J = 8.4 Hz), 8.23 (1H, d, J = 8.4 Hz), 8.41 (1H, d, J = 3.6 Hz), 10.86 (1H, s). EM (calculated value): 505.2; MS(ESI) m/e (M + 1H)+: 506.2 |

TABLE 1-continued

Structures and structural analysis data of the compounds prepared in Examples 3-21

| Examples | Structures | Analysis data |
|---|---|---|
| 7 | 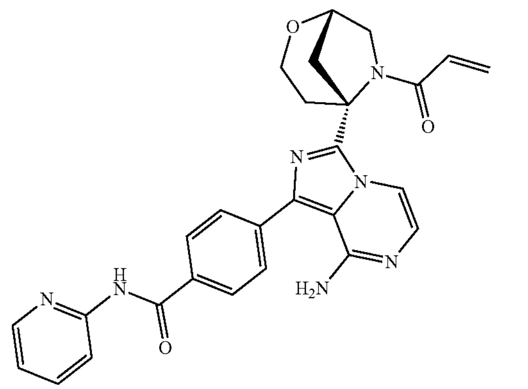 [SMILES: C=CC(=O)N1C[C@@H]2C[C@]1(c1nc(-c3ccc(C(=O)Nc4ccccn4)cc3)c3c(N)nccn13)CCO2] | ¹H NMR (400 MHz, d₆-DMSO) δ 1.79-1.85 (1H, m), 1.97-2.06 (2H, m), 2.31-2.34 (1H, m), 3.28-3.33 (2H, m), 3.96-4.07 (3H, m), 5.64-5.68 (1H, m), 6.06-6.19 (3H, m), 6.75 (1H, dd, J = 16.8 Hz, 10.4 Hz), 7.13 (1H, d, J = 5.2 Hz), 7.16-7.19(1H, m), 7.70 (2H, dd, J = 8.4 Hz, 4.0 Hz), 7.84-7.87 (1H, m), 7.90 (1H, d, J = 5.2 Hz), 8.15 (2H, d, J = 8.4 Hz), 8.24 (1H, d, J = 8.4 Hz), 8.39-8.41 (1H, m), 10.83 (1H, s)<br>EM (calculated value): 495.2; MS(ESI) m/e (M + 1H)⁺: 496.2 |
| 8 | 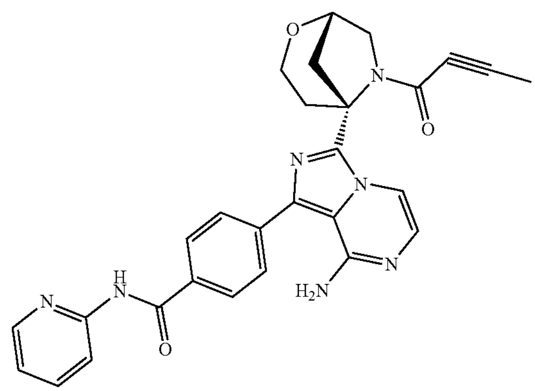 [SMILES: CC#CC(=O)N1C[C@@H]2C[C@]1(c1nc(-c3ccc(C(=O)Nc4ccccn4)cc3)c3c(N)nccn13)CCO2] | ¹H NMR (400 MHz, d₆-DMSO) δ 1.54 (1H, s), 1.78-1.85 (1H, m), 1.97-2.04 (4H, m), 2.33-2.35 (1H, m), 3.28-3.30 (2H, m), 3.96-4.07 (3H, m), 6.06-6.19 (2H, m), 7.15 (1H, d, J = 5.2 Hz), 7.16-7.20 (1H, m), 7.71 (2H, dd, J = 8.4 Hz, 4.0 Hz), 7.84-7.87 (1H, m), 7.88 (1H, d, J = 5.2 Hz), 8.14 (2H, d, J = 8.4 Hz), 8.25 (1H, d, J = 8.4 Hz), 8.39-8.41 (1H, m), 10.88 (1H, brs).<br>EM(calculated value): 507.2; MS(ESI) m/e (M + 1H)⁺: 508.2 |
| 9 | 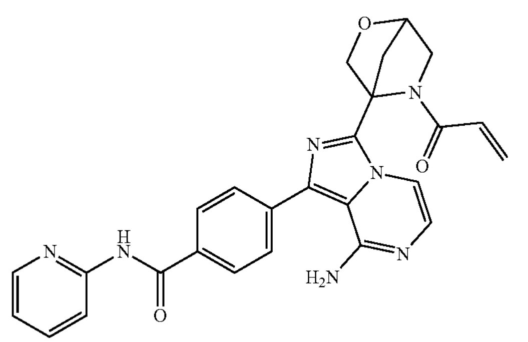 [SMILES: C=CC(=O)N1CC2CC1(c1nc(-c3ccc(C(=O)Nc4ccccn4)cc3)c3c(N)nccn13)CO2] | ¹H NMR (400 MHz, d6-DMSO) δ 2.37-2.40 (2H, m), 3.98-4.03 (2H, m), 4.43-4.45 (1H, m), 4.76-4.81 (2H, m), 5.65-5.69 (1H, m), 6.06-6.15 (3H, m), 6.72-6.74 (1H, m), 7.11-7.20 (2H, m), 7.73-7.89 (4H, m), 8.18 (2H, dd, J = 8.4 Hz, 2.8 Hz), 8.22 (1H, d, J = 8.4 Hz), 8.41 (1H, dd, J = 4.8 Hz, 1.2 Hz), 10.79 (1H, s).<br>EM(calculated value): 481.2; MS(ESI) m/e (M + 1H)+: 482.2 |
| 10 | 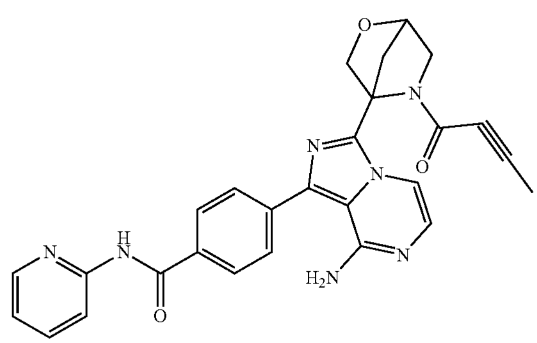 [SMILES: CC#CC(=O)N1CC2CC1(c1nc(-c3ccc(C(=O)Nc4ccccn4)cc3)c3c(N)nccn13)CO2] | ¹H NMR (400 MHz, d6-DMSO) δ 1.52 (1H, s), 2.02 (2H, s), 2.37-2.41 (2H, m), 3.98-4.11 (2H, m), 4.43-4.45 (1H, m), 4.77-4.80 (2H, m), 6.10-6.19 (2H, m), 7.11-7.20 (2H, m), 7.73-7.86 (4H, m), 8.18 (2H, dd, J = 8.4 Hz, 2.8 Hz), 8.22 (1H, d, J = 8.4 Hz), 8.45 (1H, dd, J = 4.8 Hz, 1.2 Hz), 10.83 (1H, s).<br>EM(calculated value): 493.2; MS(ESI) m/e (M + 1H)+: 494.2 |

TABLE 1-continued

Structures and structural analysis data of the compounds prepared in Examples 3-21

| Examples | Structures | Analysis data |
|---|---|---|
| 11 | 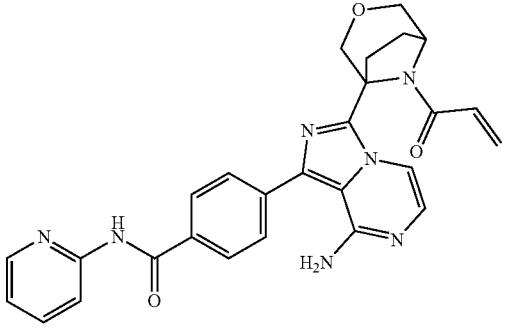 [SMILES: C=CC(=O)N1C2CCC1(c1nc(-c3ccc(C(=O)Nc4ccccn4)cc3)c3c(N)nccn13)COC2] | $^1$H NMR (400 MHz, d6-DMSO) δ 1.74-1.76 (1H, m), 1.92-2.09 (3H, m), 3.39-3.63 (4H, m), 3.98-4.03 (1H, m), 5.65-5.68 (1H, m), 6.06-6.20 (3H, m), 6.71-6.74 (1H, m), 7.13-7.20 (2H, m), 7.73-7.88 (4H, m), 8.18 (2H, dd, J = 8.4 Hz, 2.8 Hz), 8.20 (1H, d, J = 8.4 Hz), 8.43 (1H, dd, J = 4.8 Hz, 1.2 Hz), 10.59 (1H, s). EM(calculated value): 495.2; MS(ESI) m/e (M + 1H)+: 496.2 |
| 12 | 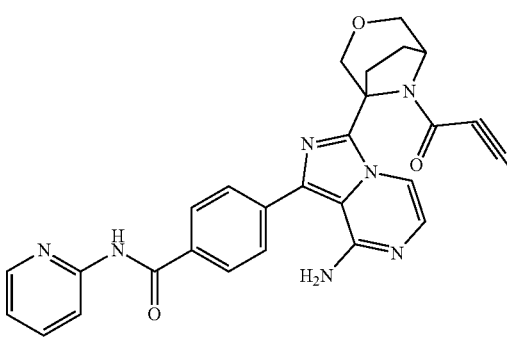 | $^1$H NMR (400 MHz, d6-DMSO) δ 1.51 (1H, s), 1.72-1.76 (1H, m), 1.89-2.00 (5H, m), 3.41-3.63 (4H, m), 3.98-4.03 (1H, m), 6.11-6.20 (2H, m), 7.13-7.17 (2H, m), 7.73-7.88 (4H, m), 8.12 (2H, dd, J = 8.4 Hz, 2.8 Hz), 8.19 (1H, d, J = 8.4 Hz), 8.43 (1H, dd, J = 4.8 Hz, 1.2 Hz), 10.67 (1H, s). EM(calculated value): 507.2; MS(ESI) m/e (M + 1H)+: 508.2 |
| 13 | 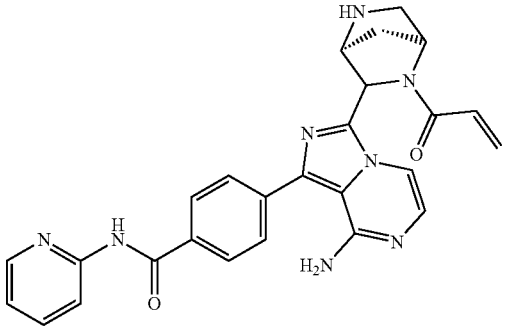 | $^1$H NMR (400 MHz, d6-DMSO) δ 1.74-1.79 (1H, m), 2.02-2.04 (1H, m), 2.88-3.02 (2H, m), 3.71-3.77 (1H, m), 4.74-4.76 (1H, m), 5.25-5.30 (1H, m), 5.46-5.50 (0.4H, m), 5.65-5.70 (1H, m), 6.05-6.29 (3H, m), 6.84 (0.6H, dd, J = 16.8 Hz, 10.4 Hz), 7.18-7.25 (2H, m), 7.68-7.75 (3H, m), 7.84-7.85 (1H, m), 8.14-8.23 (3H, m), 8.41-8.42 (1H, m), 10.85 (1H, s). EM(calculated value): 480.2; MS(ESI) m/e (M + 1H)+: 481.2 |
| 14 | 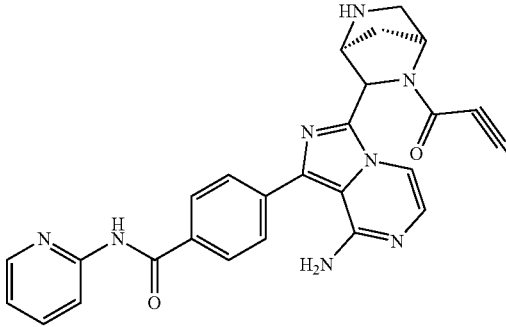 | $^1$H NMR (400 MHz, d6-DMSO) δ 1.52 (1H, s), 1.72-1.79 (1H, m), 2.02-2.04 (3H, m), 2.86-3.02 (2H, m), 3.70-3.73 (1H, m), 4.72-4.75 (1H, m), 5.25-5.29 (1H, m), 6.05-6.22 (2H, m), 7.19-7.25 (2H, m), 7.68-7.75 (3H, m), 7.83-7.85 (1H, m), 8.14-8.20 (3H, m), 8.41-8.42 (1H, m), 10.84-10.85 (1H, m). EM(calculated value): 492.2; MS(ESI) m/e (M + 1H)+: 493.2 |

TABLE 1-continued

Structures and structural analysis data of the compounds prepared in Examples 3-21

| Examples | Structures | Analysis data |
|---|---|---|
| 15 | 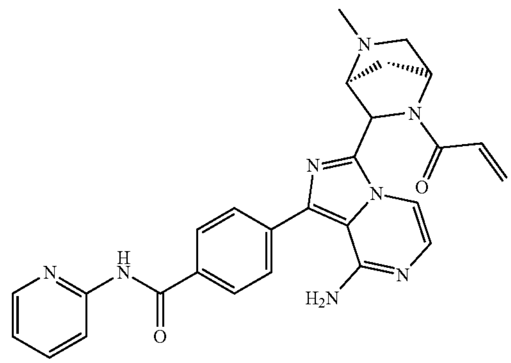 | $^1$H NMR (400 MHz, d$_6$-DMSO) δ 1.52-1.55 (1H, m), 1.77-1.81 (1H, m), 2.33 (3H, s), 3.36-3.39 (1H, m), 3.49-3.54 (2H, m), 3.69-3.71 (1H, m), 4.99-5.02 (1H, m), 5.44-5.46 (0.4H, m), 5.63-5.65 (0.6H, m), 5.83 (0.4H, dd, J = 16.8 Hz, 10.4 Hz), 6.06-6.18 (3H, m), 6.74 (0.6H, dd, J = 16.8 Hz, 10.4 Hz), 7.13 (1H, d, J = 5.2 Hz), 7.16-7.20 (1H, m), 7.70 (2H, dd, J = 8.4 Hz, 4.0 Hz), 7.85-7.88 (1H, m), 7.91 (1H, d, J = 5.2 Hz), 8.15 (2H, d, J = 8.4 Hz), 8.21 (1H, d, J = 8.4 Hz), 8.40-8.42 (1H, m), 10.83 (1H, s). EM(calculated value): 494.2; MS(ESI) m/e (M + 1H)$^+$: 495.2 |
| 16 | 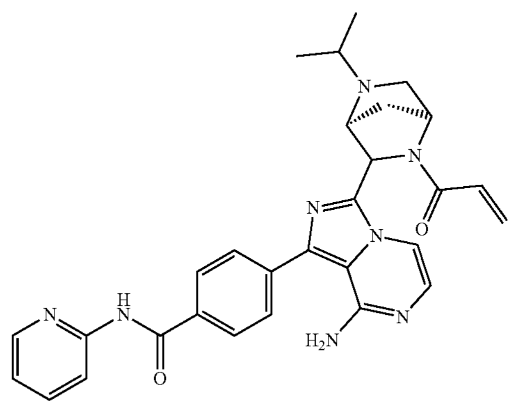 | $^1$H NMR (400 MHz, d$_6$-DMSO) δ 1.19-1.22 (6H, m), 1.53-1.55 (1H, m), 1.77-1.80 (1H, m), 2.84-2.86 (1H, m), 3.36-3.39 (1H, m), 3.49-3.54 (2H, m), 3.69-3.71 (1H, m), 4.99-5.01 (1H, m), 5.44-5.46 (0.5H, m), 5.63-5.65 (0.5H, m), 5.84 (0.5H, dd, J = 16.8 Hz, 10.4 Hz), 6.10-6.18 (3H, m), 6.73 (0.5H, dd, J = 16.8 Hz, 10.4 Hz), 7.13 (1H, d, J = 5.2 Hz), 7.17-7.20 (1H, m), 7.70 (2H, dd, J = 8.4 Hz, 4.0 Hz), 7.85-7.87 (1H, m), 7.91 (1H, d, J = 5.2 Hz), 8.13 (2H, d, J = 8.4 Hz), 8.20 (1H, d, J = 8.4 Hz), 8.40-8.41 (1H, m), 10.84 (1H, s). EM (calculated value): 522.2; MS(ESI) m/e (M + 1H)$^+$: 523.2 |
| 17 | 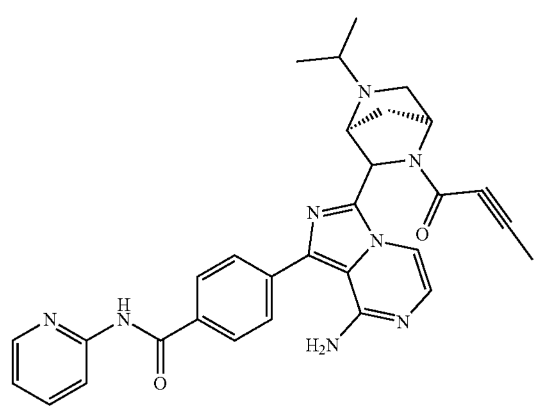 | $^1$H NMR (400 MHz, d$_6$-DMSO) δ 1.19-1.21 (6H, m), 1.50-1.55 (2H, m), 1.77-1.81 (1H, m), 2.05 (2H, s), 2.84-2.86 (1H, m), 3.37-3.39 (1H, m), 3.49-3.54 (2H, m), 3.69-3.72 (1H, m), 4.99-5.02 (1H, m), 6.09-6.18 (2H, m), 7.15-7.20 (2H, m), 7.71-7.75 (2H, m), 7.85-7.88 (2H, m), 8.15-8.17 (2H, m), 8.22 (1H, d, J = 8.4 Hz), 8.40-8.42 (1H, m), 10.85-10.86 (1H, m). EM(calculated value): 534.2; MS(ESI) m/e (M + 1H)$^+$: 535.3 |

TABLE 1-continued

Structures and structural analysis data of the compounds prepared in Examples 3-21

| Examples | Structures | Analysis data |
| --- | --- | --- |
| 18 | 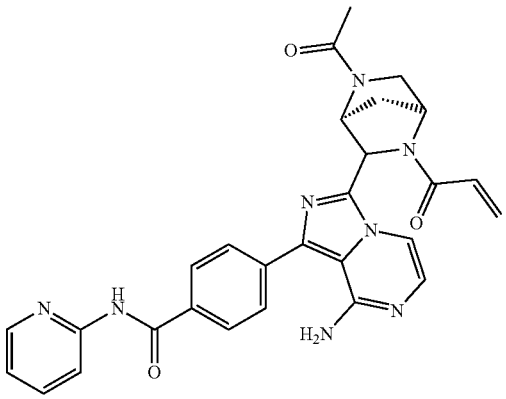 | $^1$H NMR (400 MHz, d$_6$-DMSO) δ 1.67-1.69 (1H, m), 1.83-1.86 (1H, m), 2.47 (3H, s), 3.48-3.49 (1H, m), 3.52-3.56 (2H, m), 3.77-3.79 (1H, m), 5.03-5.04 (1H, m), 5.43-5.44 (0.4H, m), 5.63-5.65 (0.6H, m), 5.82 (0.4H, dd, J = 16.8 Hz, 10.4 Hz), 6.05-6.17 (3H, m), 6.72 (0.6H, dd, J = 16.8 Hz, 10.4 Hz), 7.13 (1H, d, J = 5.2 Hz), 7.18-7.20 (1H, m), 7.70 (2H, dd, J = 8.4 Hz, 4.0 Hz), 7.85-7.87 (1H, m), 7.91 (1H, d, J = 5.2 Hz), 8.13 (2H, d, J = 8.4 Hz), 8.21 (1H, d, J = 8.4 Hz), 8.40-8.42 (1H, m), 10.85 (1H, s). EM(calculated value): 522.2; MS(ESI) m/e (M + 1H)$^+$: 523.2 |
| 19 | 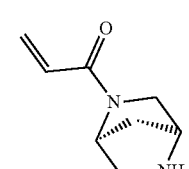 | $^1$H NMR (400 MHz, d$_6$-DMSO) δ 1.50-1.56 (1H, m), 1.74-1.79 (1H, m), 3.35-3.37 (1H, m), 3.47-3.51 (2H, m), 3.67-3.70 (1H, m), 4.11-4.14 (1H, m), 4.59 (0.6H, s), 4.76 (0.4H, s), 5.44-5.46 (0.4H, m), 5.63-5.66 (0.6H, m), 5.82 (0.4H, dd, J = 16.8 Hz, 10.4 Hz), 6.02-6.15 (3H, m), 6.74 (0.6H, dd, J = 16.8 Hz, 10.4 Hz), 7.14 (1H, d, J = 5.2 Hz), 7.17-7.20 (1H, m), 7.69 (2H, dd, J = 8.4 Hz, 4.0 Hz), 7.84-7.88 (1H, m), 7.91 (1H, d, J = 5.2 Hz), 8.13 (2H, d, J = 8.4 Hz), 8.21 (1H, d, J = 8.4 Hz), 8.40-8.41 (1H, m), 10.84-10.85 (1H, m). EM(calculated value): 480.2; MS(ESI) m/e (M + 1H)$^+$: 481.2 |
| 20 | 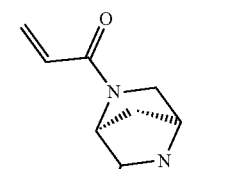 | $^1$H NMR (400 MHz, d$_6$-DMSO) δ 1.72-1.75 (1H, m), 1.89-1.91 (1H, m), 2.44 (3H, s), 3.50-3.51 (1H, m), 3.58-3.60 (2H, m), 3.83-3.85 (1H, m), 5.07-5.08 (1H, m), 5.43-5.45 (0.4H, m), 5.63-5.66 (0.6H, m), 5.83 (0.4H, dd, J = 16.8 Hz, 10.4 Hz), 6.05-6.15 (3H, m), 6.72 (0.6H, dd, J = 16.8 Hz, 10.4 Hz), 7.14 (1H, d, J = 5.2 Hz), 7.19-7.20 (1H, m), 7.70 (2H, dd, J = 8.4 Hz, 4.0 Hz), 7.85-7.87 (1H, m), 7.90 (1H, d, J = 5.2 Hz), 8.14 (2H, d, J = 8.4 Hz), 8.21 (1H, d, J = 8.4 Hz), 8.40-8.42 (1H, m), 10.84 (1H, s). EM(calculated value): 522.2; MS(ESI) m/e (M + 1H)$^+$: 523.2 |

TABLE 1-continued

Structures and structural analysis data of the compounds prepared in Examples 3-21

| Examples | Structures | Analysis data |
|---|---|---|
| 21 | 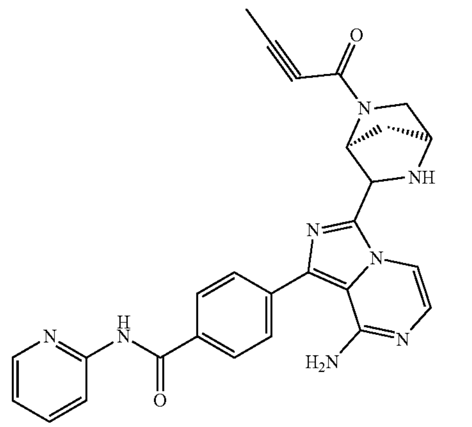 | $^1$H NMR (400 MHz, d$_6$-DMSO) δ 1.44-1.50 (2H, m), 1.68-1.73 (1H, m), 2.04 (2H, s), 3.38-3.42 (1H, m), 3.50-3.54 (2H, m), 3.65-3.69 (1H, m), 4.11-4.14 (1H, m), 4.59 (0.75H, s), 4.76 (0.25H, s), 6.06-6.18 (2H, m), 7.14 (1H, d, J = 5.2 Hz), 7.16-7.20 (1H, m), 7.73 (2H, dd, J = 8.4 Hz, 4.0 Hz), 7.83-7.85 (1H, m), 7.91 (1H, d, J = 5.2 Hz), 8.13 (2H, d, J = 8.4 Hz), 8.18 (1H, d, J = 8.4 Hz), 8.37-8.40 (1H, m), 10.85 (1H, s). EM(calculated value): 492.2; MS(ESI) m/e (M + 1H)$^+$: 493.2 |

Example 22: Preparation of 4-(3-((1R,3S,4S)-2-acryloyl-2-azabicyclo[2.2.1]heptan-3-yl)-8-amin-oimidazo[1,5-a]pyrazin-1-yl)-N-(pyridin-2-yl)benz-amide The synthesis steps are as follows:

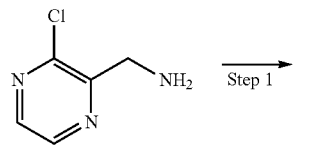

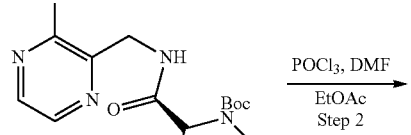

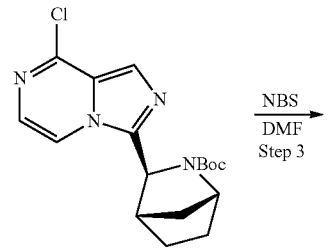

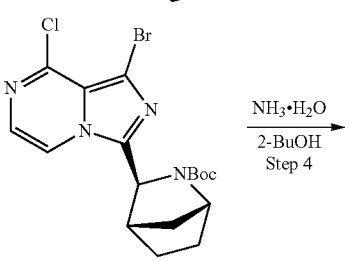

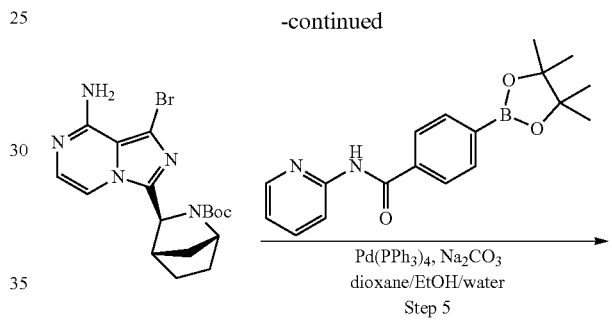

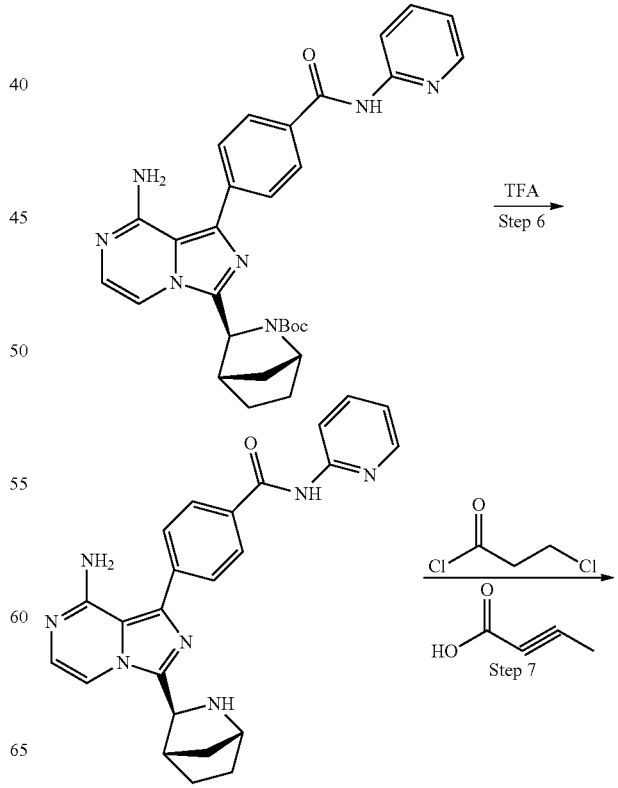

-continued

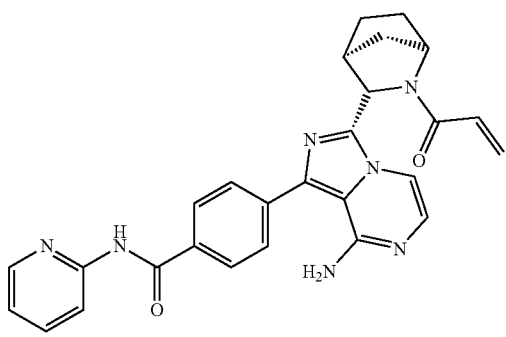

Example 22

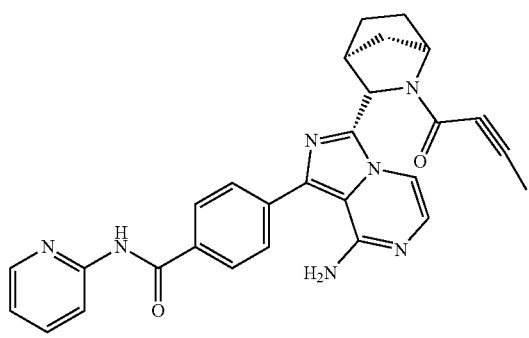

Example 23

Step 1: Preparation of (1R,3R,4S)-tert-butyl 3-(((3-chloropyrazin-2-yl)methyl)carbamoyl)-2-azabicyclo[2.2.1]heptane-2-carboxylate

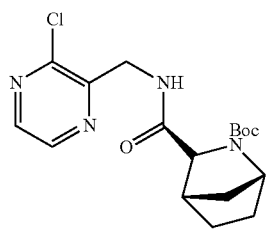

Under the protection of nitrogen, to a solution of (3-chloropyrazin-2-yl)methylamine (3.43 g, 24 mmol), (1R, 3R, 4S)-2-(tert-butoxycarbonyl)-2-azabicyclo[2.2.1]heptane-3-carboxylic acid (5.80 g, 20 mmol), HOBt (4.21 g, 31.2 mmol) and TEA (4.37 g, 43.2 mmol) in 30 mL DMF (0° C.), EDCI (5.97 g, 31.2 mmol) was added in portions. The reaction mixture reacted under stirring at room temperature overnight. After TLC showed the raw materials reacted completely, the reaction mixture was quenched with water and extracted with EA (50 mL×3). The organic phase was backwashed with saturated brine, dried with anhydrous Na₂SO₄, evaporated under vacuum and then purified by column chromatography (PE/EA=5/1-3/1) to obtain 8.0 g of the target compound which was a brown solid.

Step 2: Preparation of (1R,3S,4S)-tert-butyl 3-(8-chloroimidazo[1,5-a]pyrazin-3-yl)-2-azabicyclo[2.2.1]heptane-2-carboxylate

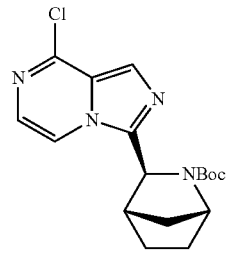 [SMILES: CC(C)(C)OC(=O)N1[C@@H]2CC[C@@H](C2)[C@H]1c1ncc2c(Cl)nccn12]

In an ice salt bath, to a mixed solution of (1R,3R,4S)-tert-butyl 3-(((3-chloropyrazin-2-yl)methyl)carbamoyl)-2-azabicyclo[2.2.1]heptane-2-carboxylate (6.3 g, 17.18 mmol) in DMF/EA (7.5 mL/50 mL), POCl₃ (12.6 mL, 103.08 mmol) was slowly added dropwise. After the addition, the reaction mixture was stirred for 2 hours at room temperature. After TLC showed that raw materials reacted completely, the reaction mixture was slowly added to a solution of Na₂CO₃ (6 mol/L) and pH was maintained to be greater than 8. The organic phase was separated and the aqueous phase was extracted with EA (20 mL×3). The organic phase was pooled, thoroughly dried with anhydrous Na₂SO₄, evaporated under vacuum and then purified by column chromatography (PE/EA=3/1) to obtain 5.6 g of the target compound which was a yellow solid.

Step 3: Preparation of (1R,3S,4S)-tert-butyl 3-(1-bromo-8-chloroimidazo[1,5-a]pyrazine-3-yl)-2-azabicyclo[2.2.1]heptanes-2-carboxylate

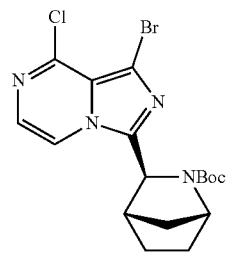 [SMILES: CC(C)(C)OC(=O)N1[C@@H]2CC[C@@H](C2)[C@H]1c1nc(Br)c2c(Cl)nccn12]

In an ice salt bath, to a solution of (1R,3S,4S)-tert-butyl 3-(8-chloroimidazo[1,5-a]pyrazin-3-yl)-2-azabicyclo[2.2.1]heptane-2-carboxylate (4.95 g, 14.19 mmol) in 50 mL DMF, NBS (2.66 g, 14.9 mmol) was added in portions. The reaction mixture was stirred for 1 hour in an ice salt bath. After TLC showed that raw materials reacted completely, the reaction mixture was slowly added to a solution of Na₂HCO₃ (1 mol/L) to quench the reaction, the reaction mixture was extracted with EA (20 mL×3). The organic phase was washed with saturated NaCl, thoroughly dried with anhydrous Na₂SO₄, evaporated under vacuum and then purified by column chromatography (PE/EA=5/1) to obtain 5.2 g of the target compound which was a light yellow solid.

Step 4: Preparation of (1R,3S,4S)-tert-butyl 3-(8-amino-1-bromoimidazo[1,5-a]pyrazin-3-yl)-2-azabicyclo[2.2.1]heptane-2-carboxylate

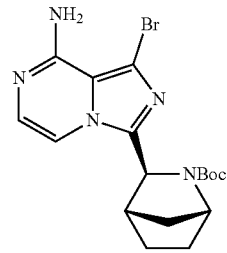 [SMILES: CC(C)(C)OC(=O)N1[C@@H]2CC[C@@H](C2)[C@H]1c1nc(Br)c2c(N)nccn12]

At room temperature, to a high pressure reactor of (1R,3S,4S)-tert-butyl 3-(1-bromo-8-chloroimidazo[1,5-a]pyrazine-3-yl)-2-azabicyclo[2.2.1]heptanes-2-carboxy late (4.4 g, 10.29 mmol), 15 mL of 2-BuOH and 30 mL of aqueous ammonia were added. The reaction mixture was stirred at 90° C. for 15 hours. After TLC showed the raw materials reacted completely, the reaction mixture was concentrated under vacuum to obtain a solid crude product. The crude product was pulped with EA/PE (5/1) to obtain 3.2 g of pure target compound which was a light yellow solid.

Step 5: Preparation of (1R,3S,4S)-tert-butyl 3-(8-amino-1-(4-(pyridin-2-ylcarbamoyl)phenyl)imidazo[1,5-a]pyrazin-3-yl)-2-azabicyclo [2.2.1]heptane-2-carboxylate

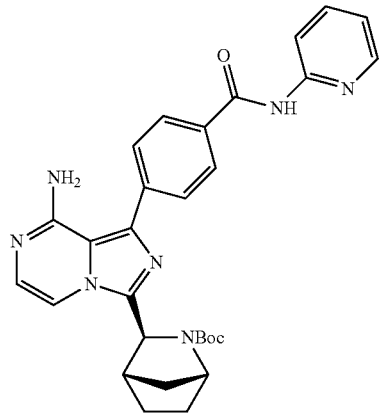 [SMILES: CC(C)(C)OC(=O)N1[C@@H]2CC[C@@H](C2)[C@H]1c1nc(-c2ccc(C(=O)Nc3ccccn3)cc2)c2c(N)nccn12]

Under the protection of nitrogen, to a mixed solution of (1R,3S,4S)-tert-butyl 3-(8-amino-1-bromoimidazo[1,5-a]pyrazin-3-yl)-2-azabicyclo[2.2.1]heptane-2-carboxylate (3.5 g, 8.57 mmol), N-(pyridin-2-yl)-4-(4,4,5,5-tetramethyl-1,3,2-dioxaborolan-2-yl)benzamide (3.33 g, 10.28 mmol), Na$_2$CO$_3$ (1.82 g, 17.14 mmol) in dioxane/EtOH/water (36 mL/12 mL/12 mL), Pd(PPh$_3$)$_4$ (496.89 mg, 0.43 mmol) was added. The reaction mixture reacted under stirring at 90° C. overnight. After TLC showed the raw materials reacted completely, the reaction mixture was quenched with water, and extracted with EA (40 mL×3). The organic phase was backwashed with saturated brine, dried with anhydrous Na$_2$SO$_4$, evaporated under vacuum and then purified by column chromatography (DCM/MeOH=60/1) to obtain 2.8 g of the target compound which was a light yellow solid.

Step 6: Preparation of 4-(8-amino-3-((1R,3S,4S)-2-azabicyclo[2.2.1]heptan-3-yl)imidazo[1,5-a]pyrazin-1-yl)-N-(pyridin-2-yl)benzamide

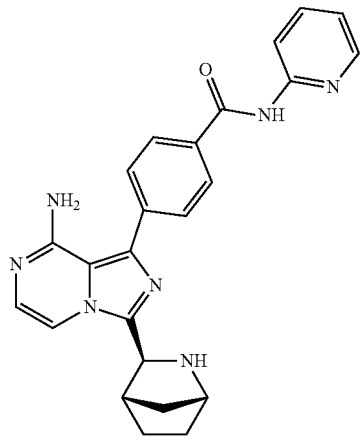 [SMILES: Nc1nccn2c([C@H]3N[C@@H]4CC[C@H]3C4)nc(-c3ccc(C(=O)Nc4ccccn4)cc3)c12]

To a solution of (1R,3S,4S)-tert-butyl 3-(8-amino-1-(4-(pyridin-2-ylcarbamoyl)phenyl)imidazo[1,5-a]pyrazin-3-yl)-2-azabicyclo [2.2.1]heptane-2-carboxylate (2.98 g, 5.68 mmol) in DCM (20 mL), TFA (3.5 mL) was added. The reaction mixture reacted under stirring at room temperature overnight. After TLC showed the raw materials reacted completely, the reaction system was concentrated and pH was adjusted to 8 with Na$_2$CO$_3$ (3 mol/L). The reaction mixture was extracted with DCM/MeOH (10/1). The organic phase was dried with anhydrous Na$_2$SO$_4$, evaporated under vacuum and then purified by column chromatography (DCM/MeOH=60/1-10/1) to obtain 2.0 g of the target compound which was a white solid.

Step 7: Preparation of 4-(3-((1R,3S,4S)-2-acryloyl-2-azabicyclo[2.2.1]heptan-3-yl)-8-aminoimidazo[1,5-a] pyrazin-1-yl)-N-(pyridin-2-yl)benzamide

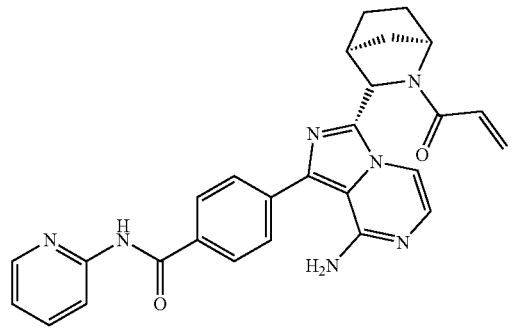

Under the protection of nitrogen, to a solution of 4-(8-amino-3-((1R,3S,4S)-2-azabicyclo[2.2.1]heptan-3-yl)imidazo[1,5-a]pyrazin-1-yl)-N-(pyridin-2-yl)benzamide (180 mg, 0.42 mmol), TEA (170 mg, 1.68 mmol) in DCM (10 mL), 3-chloropropionyl chloride (53.4 mg, 0.42 mmol) was added dropwise at 0° C. The reaction mixture reacted under stirring at room temperature overnight. After TLC showed the raw materials reacted completely, the reaction system was quenched with water and extracted with EA (10 mL×3).

The organic phase was dried with anhydrous Na₂SO₄, evaporated under vacuum and then purified by preparative silica gel plate (DCM/MeOH=15/1) to obtain 48 mg of the target compound which was a yellow solid.

The structure of the product was characterized by nuclear magnetic resonance and mass spectrometry and the results were as follows:

$^1$H NMR (400 MHz, d$_6$-DMSO) δ 1.49-1.55 (2H, m), 1.74-1.80 (3H, m), 2.57-2.58 (1H, m), 2.67-2.73 (1H, m), 4.66 (0.2H, s), 4.74 (0.8H, s), 5.04 (0.2H, s), 5.25 (0.8H, s), 5.44-5.47 (0.2H, m), 5.65-5.68 (0.8H, m), 5.85 (0.2H, dd, J=16.8 Hz, 10.4 Hz), 6.06-6.13 (3H, m), 6.76 (0.8H, dd, J=16.8 Hz, 10.4 Hz), 7.13 (1H, d, J=5.2 Hz), 7.16-7.20 (1H, m), 7.71 (2H, dd, J=8.4 Hz, 4.0 Hz), 7.82-7.88 (1H, m), 7.92 (1H, d, J=5.2 Hz), 8.15 (2H, d, J=8.4 Hz), 8.22 (1H, d, J=8.4 Hz), 8.40-8.41 (1H, m), 10.84-10.85 (1H, m).

EM (calculated value): 479.2; MS (ESI) m/e (M+1H)+: 480.2

It can be seen that the compound prepared by the present application has the same structure as the compound in the above reaction scheme.

Example 23: Preparation of 4-(8-amino-3-((1R,3S,4S)-2-(but-2-ynoyl)-2-azabicyclo[2.2.1]heptan-3-yl)imidazo[1,5-a]pyrazin-1-yl)-N-(pyridin-2-yl)benzamide

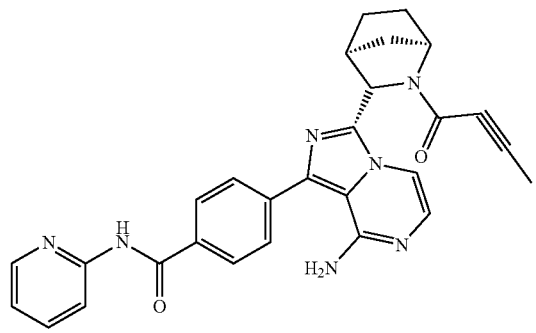

Under the protection of nitrogen, to a solution of 4-(8-amino-3-((1R,3S,4S)-2-azabicyclo[2.2.1]heptan-3-yl)imidazo[1,5-a]pyrazin-1-yl)-N-(pyridin-2-yl)benzamide (180 mg, 0.424 mmol), 2-butynoic acid (39.2 mg, 0.466 mmol), DIPEA (164 mg, 1.27 mmol) in DMF (10 mL), HBTU (192.8 mg, 0.51 mmol) was added. The reaction mixture reacted under stirring at room temperature for 1 hour. After TLC showed that the raw materials reacted completely, the reaction system was quenched with water and extracted with EA (10 mL×3). The organic phase was backwashed with saturated brine, dried with anhydrous Na₂SO₄, evaporated under vacuum and then purified by preparative silica gel plate (DCM/MeOH=20/1) to obtain 95 mg of the target compound which was a yellow solid.

The structure of the product was characterized by nuclear magnetic resonance and mass spectrometry and the results were as follows:

$^1$H NMR (400 MHz, d$_6$-DMSO) δ 1.46-1.50 (2H, m), 1.67-1.86 (4H, m), 2.03 (2H, s), 2.60-2.63 (2H, m), 4.56-4.63 (1H, m), 5.01-5.21 (1H, m), 6.15-6.20 (2H, m), 7.12-7.20 (2H, m), 7.71-7.76 (2H, m), 7.84-7.88 (2H, m), 8.15-8.18 (2H, m), 8.22 (1H, d, J=8.4 Hz), 8.40-8.42 (1H, m), 10.85-10.86 (1H, m).

EM (calculated value): 491.2; MS (ESI) m/e (M+1H)+: 492.2.

It can be seen that the compound prepared by the present application has the same structure as the compound in the above reaction scheme.

Examples 24-39

The following compounds were prepared by the preparation method of Example 22 or Example 23. The structures and nuclear magnetic characterization data of the compounds are shown in Table 2. Table 2 summarizes the structures and structural analysis data of the compounds prepared in Examples 24-39 of the present application.

TABLE 2

Structures and structural analysis data of the compounds prepared in Examples 24-39

| | | |
|---|---|---|
| 24 | 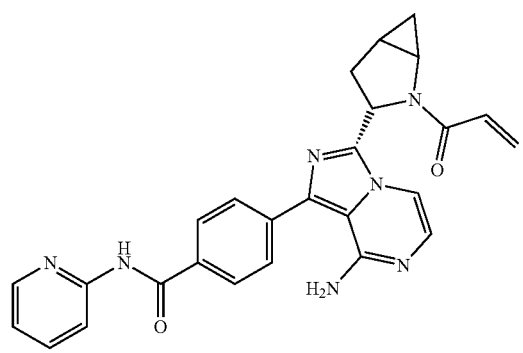 | $^1$H NMR (400 MHz, d$_6$-DMSO) δ 0.37-0.39 (1H, m), 0.81-0.84 (1H, m), 0.92-0.94 (1H, m), 1.86-2.02 (2H, m), 3.16-3.19 (1H, m), 3.83-3.88 (0.3H, s), 4.02-4.07 (0.7H, s), 5.61-5.64 (1H, m), 5.85 (0.3H, dd, J = 16.8 Hz, 10.4 Hz), 6.06-6.19 (3H, m), 6.78 (0.7H, dd, J = 16.8 Hz, 10.4 Hz), 7.14 (1H, d, J = 5.2 Hz), 7.16-7.20 (1H, m), 7.70 (2H, dd, J = 8.4 Hz, 4.0 Hz), 7.86-7.88 (1H, m), 7.91 (1H, d, J = 5.2 Hz), 8.15 (2H, d, J = 8.4 Hz), 8.20 (1H, d, J = 8.4 Hz), 8.38-8.41 (1H, m), 10.76-10.79 (1H, m). EM (calculated value): 465.2; MS (ESI) m/e (M + 1H)⁺: 466.2 |

TABLE 2-continued

Structures and structural analysis data of the compounds prepared in Examples 24-39

| 25 | 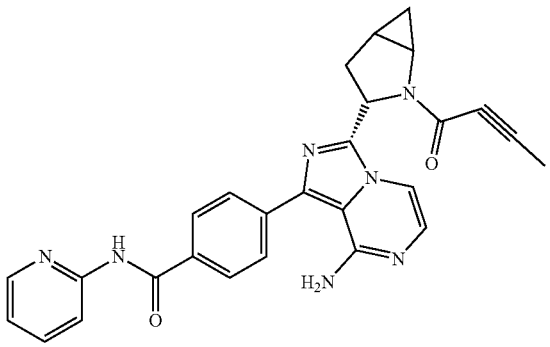 | ¹H NMR (400 MHz, d₆-DMSO) δ 0.36-0.38 (1H, m), 0.81-0.83 (1H, m), 0.90-0.94 (1H, m), 1.52 (1H, s), 1.86-2.03 (4H, m), 3.16-3.19 (1H, m), 3.83-3.86 (0.3H, s), 4.02-4.06 (0.7H, s), 6.06-6.15 (2H, m), 7.14 (1H, d, J = 5.2 Hz), 7.17-7.20 (1H, m), 7.69 (2H, dd, J = 8.4 Hz, 4.0 Hz), 7.84-7.88 (1H, m), 7.90 (1H, d, J = 5.2 Hz), 8.16 (2H, d, J = 8.4 Hz), 8.20 (1H, d, J = 8.4 Hz), 8.39-8.41 (1H, m), 10.76 (1H, s). EM (calculated value): 477.2; MS (ESI) m/e (M + 1H)⁺: 478.2 |
|---|---|---|
| 26 | 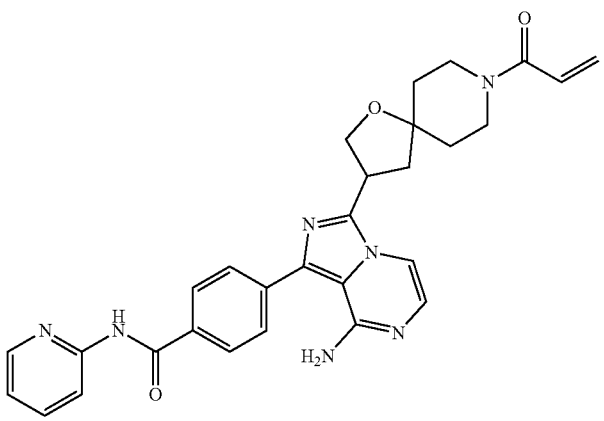 [SMILES: C=CC(=O)N1CCC2(CC1)CC(c1nc(-c3ccc(C(=O)Nc4ccccn4)cc3)c3c(N)nccn13)CO2] | ¹H NMR (400 MHz, d₆-DMSO) δ 1.65-1.92 (4H, m), 2.42 (2H, d, J = 7.6 Hz), 3.34-3.37 (1H, m), 3.53-3.54 (1H, m), 3.68-3.69 (1H, m), 3.85-3.88 (1H, m), 4.11-4.15 (1H, m), 4.25-4.29 (1H, m), 5.59-5.68 (2H, m), 6.10-6.20 (3H, m), 6.80-6.87 (1H, m), 7.14 (1H, d, J = 5.2 Hz), 7.16-7.20 (1H, m), 7.71 (2H, dd, J = 8.4 Hz, 4.0 Hz), 7.82-7.88 (1H, m), 7.91 (1H, d, J = 5.2 Hz), 8.14 (2H, d, J = 8.4 Hz), 8.20 (1H, d, J = 8.4 Hz), 8.39-8.41 (1H, m), 10.84-10.86 (1H, m). EM (calculated value): 523.3; MS (ESI) m/e (M + 1H)⁺: 524.3 |
| 27 | 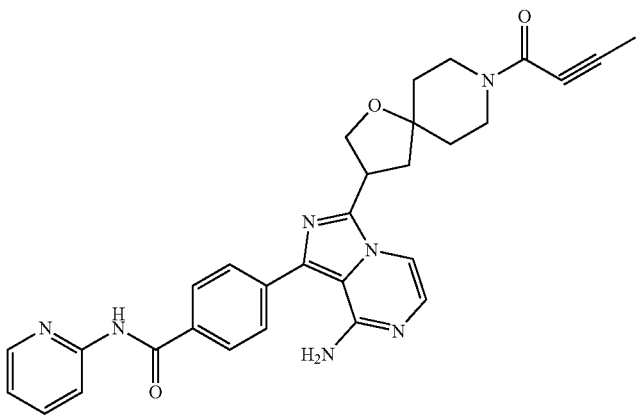 [SMILES: CC#CC(=O)N1CCC2(CC1)CC(c1nc(-c3ccc(C(=O)Nc4ccccn4)cc3)c3c(N)nccn13)CO2] | ¹H NMR (400 MHz, d₆-DMSO) δ 1.49 (1H, s), 1.69-1.92 (4H, m), 2.02 (2H, s), 2.40 (2H, d, J = 7.6 Hz), 3.32-3.37 (1H, m), 3.56-3.67 (2H, m), 3.85-3.89 (1H, m), 4.11-4.15 (1H, m), 4.25-4.27 (1H, m), 5.59-5.63 (1H, m), 6.17-6.16 (2H, m), 7.14 (1H, d, J = 5.2 Hz), 7.16-7.20 (1H, m), 7.71 (2H, dd, J = 8.4 Hz, 4.0 Hz), 7.82-7.88 (1H, m), 7.91 (1H, d, J = 5.2 Hz), 8.14 (2H, d, J = 8.4 Hz), 8.20 (1H, d, J = 8.4 Hz), 8.39-8.41 (1H, m), 10.84-10.86 (1H, m). EM (calculated value): 535.3; MS (ESI) m/e (M + 1H)⁺: 536.3 |
| 28 | 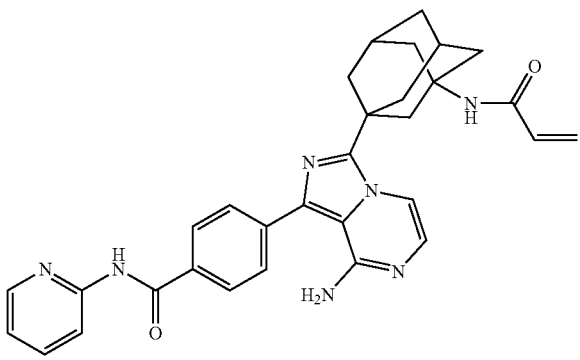 [SMILES: C=CC(=O)NC12CC3CC(C1)CC(c1nc(-c4ccc(C(=O)Nc5ccccn5)cc4)c4c(N)nccn14)(C3)C2] | ¹H NMR (400 MHz, d₆-DMSO) δ 1.24-1.85 (12H, m), 2.03-2.11 (2H, m), 5.49-5.53 (1H, m), 6.03-6.15 (3H, m), 6.42 (1H, s), 6.74 (1H, dd, J = 16.8 Hz, 10.4 Hz), 7.11 (1H, d, J = 5.2 Hz), 7.19-7.25 (1H, m), 7.70 (2H, dd, J = 8.4 Hz, 4.0 Hz), 7.85-7.89 (1H, m), 7.92 (1H, d, J = 5.2 Hz), 8.13 (2H, d, J = 8.4 Hz), 8.20 (1H, d, J = 8.4 Hz), 8.40-8.43 (1H, m), 10.84 (1H, brs). EM (calculated value): 533.3; MS (ESI) m/e (M + 1H)⁺: 534.3 |

TABLE 2-continued

Structures and structural analysis data of the compounds prepared in Examples 24-39

| 29 | 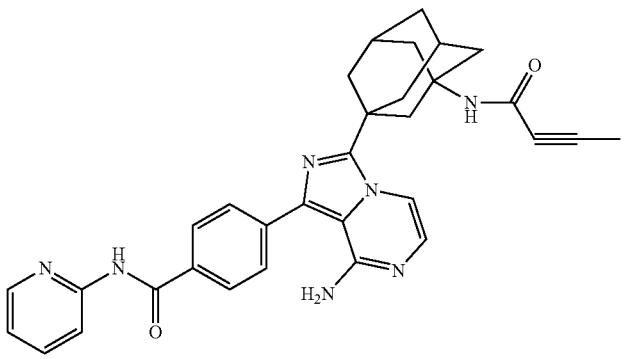 [SMILES: CC#CC(=O)NC12CC3CC(C1)CC(c1nc(-c4ccc(C(=O)Nc5ccccn5)cc4)c4c(N)nccn14)(C3)C2] | $^1$H NMR (400 MHz, d$_6$-DMSO) δ 1.27-1.82 (13H, m), 2.01 (2H, s), 2.08-2.15 (2H, m), 6.03-6.09 (2H, m), 6.40 (1H, s), 7.13 (1H, d, J = 5.2 Hz), 7.19-7.22 (1H, m), 7.71 (2H, dd, J = 8.4 Hz, 4.0 Hz), 7.86-7.89 (1H, m), 7.90 (1H, d, J = 5.2 Hz), 8.15 (2H, d, J = 8.4 Hz), 8.19 (1H, d, J = 8.4 Hz), 8.40-8.43 (1H, m), 10.79 (1H, brs).<br>EM (calculated value): 545.3; MS (ESI) m/e (M + 1H)$^+$: 546.3 |
|---|---|---|
| 30 | 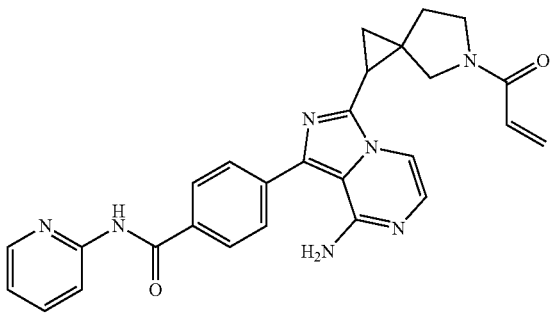 [SMILES: C=CC(=O)N1CCC2(CC2c2nc(-c3ccc(C(=O)Nc4ccccn4)cc3)c3c(N)nccn23)C1] | $^1$H NMR (400 MHz, d$_6$-DMSO) δ 0.79-0.84 (2H, m), 1.76-1.78 (1H, m), 2.31-2.35 (1.5H, m), 3.58-3.66 (2.5H, m), 3.85-3.89 (2H, m), 5.65-5.68 (1H, m), 6.05-6.17 (3H, m), 6.56 (1H, dd, J = 16.8 Hz, 10.4 Hz), 7.11-7.19 (2H, m), 7.70-7.74 (2H, m), 7.83-7.88 (2H, m), 8.14 (2H, , J = 8.4 Hz), 8.22 (1H, d, J = 8.4 Hz), 8.41 (1H, d, J = 3.6 Hz), 10.84 (1H, s).<br>EM (calculated value): 479.2; MS (ESI) m/e (M + 1H)$^+$: 480.2 |
| 31 | 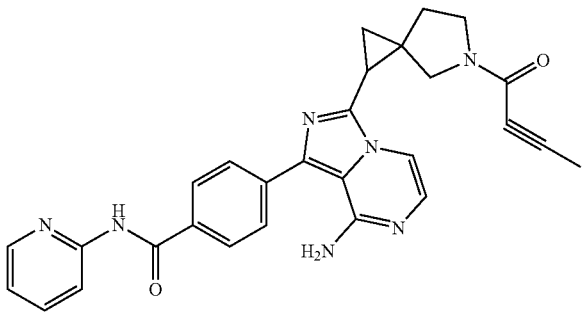 [SMILES: CC#CC(=O)N1CCC2(CC2c2nc(-c3ccc(C(=O)Nc4ccccn4)cc3)c3c(N)nccn23)C1] | $^1$H NMR (400 MHz, d$_6$-DMSO) δ 0.77-0.84 (2H, m), 1.51 (1H, s), 1.76-1.79 (1H, m), 2.02 (2H, s), 2.31-2.35 (1.5H, m), 3.52-3.63 (2.5H, m), 3.81-3.85 (2H, m), 6.08-6.17 (2H, m), 7.13-7.19 (2H, m), 7.71-7.74 (2H, m), 7.83-7.88 (2H, m), 8.15 (2H, , J = 8.4 Hz), 8.22 (1H, d, J = 8.4 Hz), 8.41 (1H, d, J = 3.6 Hz), 10.88 (1H, s).<br>EM (calculated value): 491.2; MS (ESI) m/e (M + 1H)$^+$: 492.2 |
| 32 | 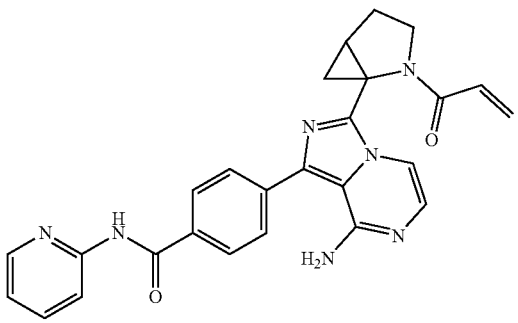 [SMILES: C=CC(=O)N1CCC2CC21c1nc(-c2ccc(C(=O)Nc3ccccn3)cc2)c2c(N)nccn12] | $^1$H NMR (400 MHz, d$_6$-DMSO) δ 0.75-0.78 (1H, m), 0.92-0.94 (1H, m), 1.24-1.80 (3H, m), 3.83-3.88 (1.25H, s), 4.02-4.07 (0.75H, s), 5.61-5.64 (1H, m), 5.85 (0.25H, dd, J = 16.8 Hz, 10.4 Hz), 6.06-6.20 (3H, m), 6.76 (0.75H, dd, J = 16.8 Hz, 10.4 Hz), 7.14 (1H, d, J = 5.2 Hz), 7.16-7.20 (1H, m), 7.70 (2H, dd, J = 8.4 Hz, 4.0 Hz), 7.84-7.88 (1H, m), 7.91 (1H, d, J = 5.2 Hz), 8.16 (2H, d, J = 8.4 Hz), 8.20 (1H, d, J = 8.4 Hz), 8.39-8.41 (1H, m), 10.77-10.79 (1H, m).<br>EM (calculated value): 465.2; MS (ESI) m/e (M + 1H)$^+$: 466.2 |

TABLE 2-continued

Structures and structural analysis data of the compounds prepared in Examples 24-39

| 33 | 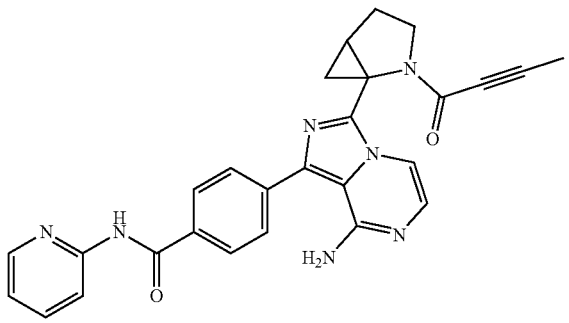 [SMILES: CC#CC(=O)N1CCC2CC21c1nc(-c2ccc(C(=O)Nc3ccccn3)cc2)c2c(N)nccn12] | ¹H NMR (400 MHz, d₆-DMSO) δ 0.75-0.79 (1H, m), 0.92-0.94 (1H, m), 1.24-1.85 (4H, m), 2.03 (2H, s), 3.83-3.88 (1.25H, s), 4.04-4.07 (0.75H, s), 6.06-6.16 (2H, m), 7.15 (1H, d, J = 5.2 Hz), 7.18-7.20 (1H, m), 7.68 (2H, dd, J = 8.4 Hz, 4.0 Hz), 7.85-7.88 (1H, m), 7.91 (1H, d, J = 5.2 Hz), 8.17 (2H, d, J = 8.4 Hz), 8.20 (1H, d, J = 8.4 Hz), 8.37-8.41 (1H, m), 10.78 (1H, s). EM (calculated value): 477.2; MS (ESI) m/e (M + 1H)⁺: 478.2 |
|---|---|---|
| 34 | 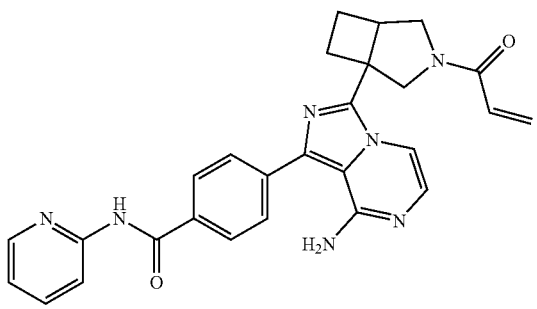 [SMILES: C=CC(=O)N1CC2CCC2(c2nc(-c3ccc(C(=O)Nc4ccccn4)cc3)c3c(N)nccn23)C1] | ¹H NMR (400 MHz, d₆-DMSO) δ 1.62-2.24 (3H, m), 2.67-2.69 (1H, m), 3.55-3.63 (2H, s), 3.88-3.92 (2H, s), 4.09-4.13 (1H, s), 5.61-5.65 (1H, m), 6.06-6.19 (3H, m), 6.72-6.74 (1H, m), 7.12 (1H, d, J = 5.2 Hz), 7.18-7.20 (1H, m), 7.75 (2H, dd, J = 8.4 Hz, 4.0 Hz), 7.86-7.88 (1H, m), 7.81 (1H, d, J = 5.2 Hz), 8.15 (2H, d, J = 8.4 Hz), 8.22 (1H, d, J = 8.4 Hz), 8.37-8.41 (1H, m), 10.83-10.85 (1H, m). EM (calculated value): 479.2; MS (ESI) m/e (M + 1H)⁺: 480.2 |
| 35 | 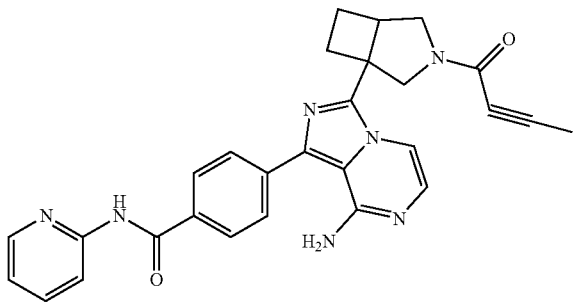 [SMILES: CC#CC(=O)N1CC2CCC2(c2nc(-c3ccc(C(=O)Nc4ccccn4)cc3)c3c(N)nccn23)C1] | ¹H NMR (400 MHz, d₆-DMSO) δ 1.55-2.24 (4H, m), 2.01 (2H, s), 2.64-2.69 (1H, m), 3.52-3.63 (2H, s), 3.88-3.92 (2H, s), 4.07-4.13 (1H, s), 6.06-6.18 (2H, m), 7.15 (1H, d, J = 5.2 Hz), 7.18-7.21 (1H, m), 7.69 (2H, dd, J = 8.4 Hz, 4.0 Hz), 7.86-7.87 (1H, m), 7.81 (1H, d, J = 5.2 Hz), 8.13 (2H, d, J = 8.4 Hz), 8.22 (1H, d, J = 8.4 Hz), 8.37-8.40 (1H, m), 10.87-10.88 (1H, m). EM (calculated value): 491.2; MS (ESI) m/e (M + 1H)⁺: 492.2 |
| 36 | 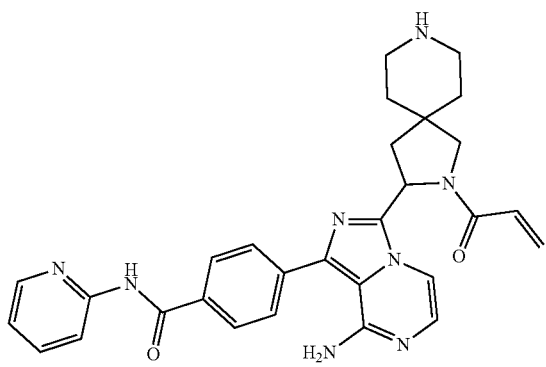 [SMILES: C=CC(=O)N1CC2(CCNCC2)CC1c1nc(-c2ccc(C(=O)Nc3ccccn3)cc2)c2c(N)nccn12] | ¹H NMR (400 MHz, d₆-DMSO) δ 1.19-1.71 (5H, m), 1.97-2.01 (1H, m), 2.86-3.11 (4H, m), 3.52-3.55 (1H, m), 3.90-3.96 (1H, m), 5.05 (1H, d, J = 2.0 Hz), 5.62-5.75 (2H, m), 6.08-6.19 (3H, m), 6.86 (1H, dd, J = 16.8 Hz, 10.4 Hz), 7.14 (1H, d, J = 5.2 Hz), 7.19 (1H, dd, J = 6.8 Hz, 5.2 Hz), 7.71-7.74 (2H, m), 7.84-7.90 (2H, m), 8.14 (2H, d, J = 8.4 Hz), 8.23 (1H, d, J = 8.4 Hz), 8.40 (1H, d, J = 4.0 Hz), 10.82 (1H, s). EM (calculated value): 522.2; MS (ESI) m/e (M + 1H)⁺: 523.3 |

TABLE 2-continued

Structures and structural analysis data of the compounds prepared in Examples 24-39

| 37 | (structure) | $^1$H NMR (400 MHz, d$_6$-DMSO) δ 1.16-1.71 (6H, m), 1.97-2.04 (3H, m), 2.86-3.14 (4H, m), 3.53-3.55 (1H, m), 3.89-3.96 (1H, m), 5.03 (1H, d, J = 2.0 Hz), 5.66-5.75 (1H, m), 6.10-6.19 (2H, m), 7.15 (1H, d, J = 5.2 Hz), 7.21 (1H, dd, J = 6.8 Hz, 5.2 Hz), 7.71-7.74 (2H, m), 7.85-7.90 (2H, m), 8.15 (2H, d, J = 8.4 Hz), 8.26 (1H, d, J = 8.4 Hz), 8.37 (1H, d, J = 4.0 Hz), 10.77 (1H, s). EM (calculated value): 534.2; MS (ESI) m/e (M + 1H)$^+$: 535.3 |
|---|---|---|
| 38 | (structure) | $^1$H NMR (400 MHz, d$_6$-DMSO) δ 3.03-3.06 (1H, m), 3.56-3.63 (4H, m), 4.11-4.20 (2.2H, m), 4.31-4.33 (1.8H, m), 5.65-5.67 (1H, m), 6.09-6.20 (3H, m), 6.72-6.75 (1H, m), 7.13 (1H, d, J = 5.2 Hz), 7.20 (1H, dd, J = 6.8 Hz, 5.2 Hz), 7.71-7.74 (2H, m), 7.85-7.91 (2H, m), 8.14 (2H, d, J = 8.4 Hz), 8.24 (1H, d, J = 8.4 Hz), 8.41 (1H, d, J = 4.0 Hz), 10.79 (1H, s). EM (calculated value): 495.2; MS (ESI) m/e (M + 1H)$^+$: 496.2 |
| 39 | (structure) | $^1$H NMR (400 MHz, d$_6$-DMSO) δ 1.52 (1H, s), 2.02 (2H, s), 3.03-3.07 (1H, m), 3.58-3.63 (4H, m), 4.13-4.20 (2.3H, m), 4.30-4.33 (1.7H, m), 6.09-6.20 (2H, m), 7.13 (1H, d, J = 5.2 Hz), 7.21 (1H, dd, J = 6.8 Hz, 5.2 Hz), 7.67-7.69 (2H, m), 7.85-7.89 (2H, m), 8.14 (2H, d, J = 8.4 Hz), 8.24 (1H, d, J = 8.4 Hz), 8.40 (1H, d, J = 4.0 Hz), 10.83 (1H, s). EM (calculated value): 507.2; MS (ESI) m/e (M + 1H)$^+$: 508.2 |

Example 40

Preparation of (S)-4-(8-amino-3-(5-(but-2-ynoyl)-5-azaspiro[2.4]heptan-6-yl)imidazo[1,5-a]pyrazin-1-yl1)-N-(4-(trifluoromethyl) pyridin-2-yl)benzamide The steps of synthesis are as follows:

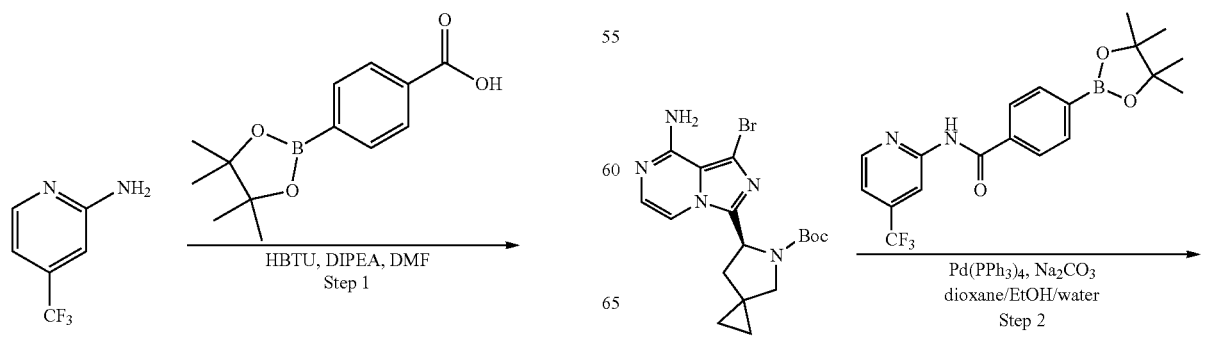

79

-continued

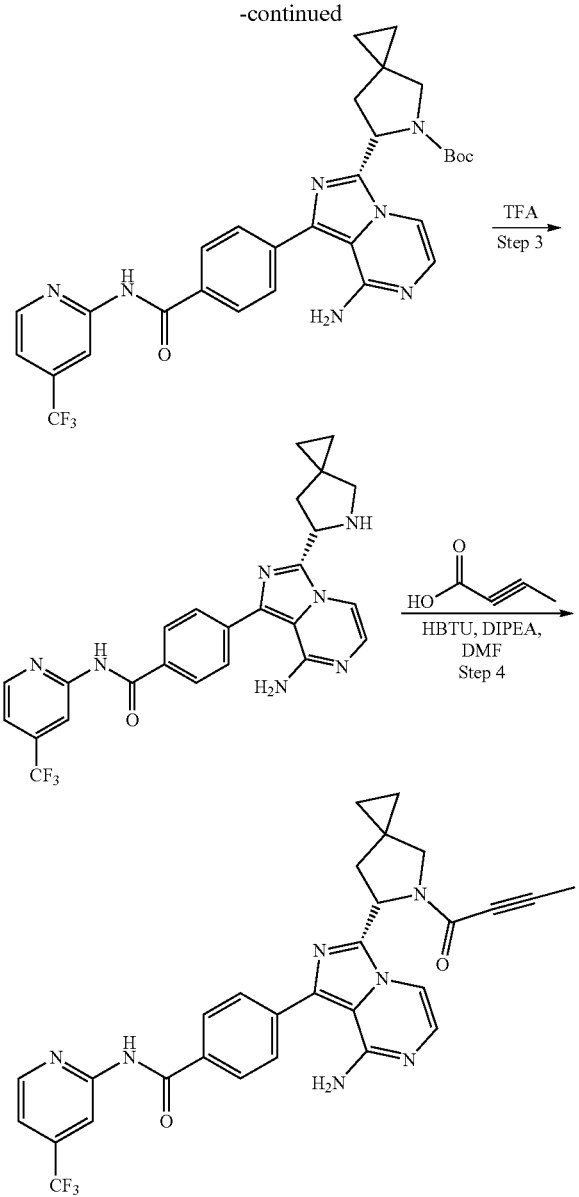

Example 40

Step 1: Preparation of 4-(4,4,5,5-tetramethyl-1,3,2-dioxaborolan-2-yl)-N-(4-(trifluoromethyl)pyridin-2-yl) benzamide

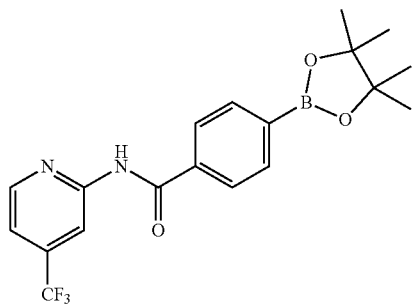 [SMILES: CC1(C)OB(c2ccc(C(=O)Nc3cc(C(F)(F)F)ccn3)cc2)OC1(C)C]

80

Under the protection of nitrogen, to a solution of 4-(trifluoromethyl)pyridin-2-amine (4 g, 24.69 mmol), 4-(4,4,5,5-tetramethyl-1,3,2-dioxaborolan-2-yl)benzoic acid (6.13 g, 24.69 mmol), DIPEA (6.37 g, 49.38 mmol) in 30 mL DMF (0° C.), HBTU (11.23 g, 29.63 mmol) was added in portions. The reaction mixture reacted under stirring at room temperature overnight. After TLC showed the raw materials reacted completely, the reaction mixture was quenched with water and extracted with EA (20 mL×3). The organic phase was backwashed with saturated brine, dried with anhydrous $Na_2SO_4$, evaporated under vacuum and then purified by column chromatography (PE/EA=20/1) to obtain 7.75 g of the target compound which was an off-white solid.

Step 2: Preparation of (S)-tert-butyl 6-(8-amino-1-(4-((4-(trifluoromethyl)pyridin-2-yl)carbamoyl)phenyl)imidazo[1,5-a pyrazin-3-yl)-5-azaspiro[2.4]heptane-5-carboxylate

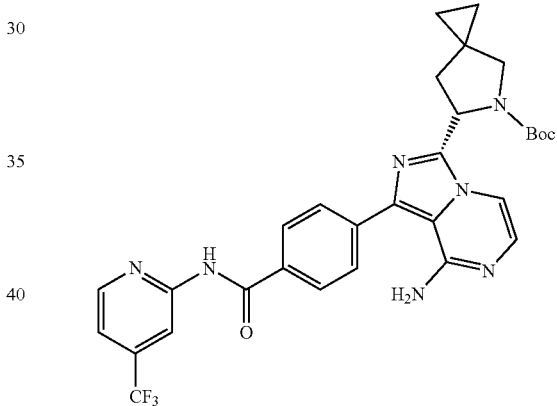

Under the protection of nitrogen, to a mixed solution of (S)-tert-butyl 6-(8-amino-1-bromoimidazo[1,5-a]pyrazin-3-yl)-5-azaspiro[2.4]heptane-5-carboxylate (3.5 g, 8.57 mmol), 4-(4,4,5,5-tetramethyl-1,3,2-dioxaborolan-2-yl)-N-(4-(trifluoromethyl)pyridin-2-yl) benzamide (4.03 g, 10.28 mmol), $Na_2CO_3$ (1.82 g, 17.14 mmol) in dioxane/EtOH/water (36 mL/12 mL/12 mL), $Pd(PPh_3)_4$ (496.89 mg, 0.43 mmol) was added. The reaction mixture reacted under stirring at 90° C. overnight. After TLC showed the raw materials reacted completely, the reaction mixture was quenched with water and extracted with EA (40 mL×3). The organic phase was backwashed with saturated brine, dried with anhydrous $Na_2SO_4$, evaporated under vacuum and then purified by column chromatography (DCM/MeOH=60/1) to obtain 3.2 g of the target compound which was a light yellow solid.

Step 3: Preparation of (S)-4-(8-amino-3-(5-azaspiro[2.4]heptan-6-yl)imidazo[1,5-a]pyrazin-1-yl)-N-(4-(trifluoromethyl)pyridin-2-yl)benzamide

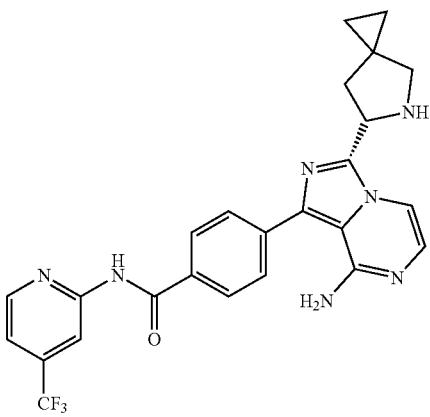

To a solution of (S)-tert-butyl 6-(8-amino-1-(4-((4-(trifluoromethyl)pyridin-2-yl)carbamoyl)phenyl)imidazo[1,5-a pyrazin-3-yl)-5-azaspiro[2.4]heptane-5-carboxylate (3.2 g, 5.39 mmol) in DCM (20 mL), TFA (3 mL) was added. The reaction mixture reacted under stirring at room temperature overnight. After TLC showed the raw materials reacted completely, the reaction system was concentrated and pH was adjusted to 8 with $Na_2CO_3$ (3 mol/L). The reaction mixture was extracted with DCM/MeOH (10/1). The organic phase was dried with anhydrous $Na_2SO_4$, evaporated under vacuum and then purified by column chromatography (DCM/MeOH=60/1-10/1) to obtain 2.53 g of the target compound which was a white solid.

Step 4: Preparation of (S)-4-(8-amino-3-(5-(but-2-ynoyl)-5-azaspiro[2.4]heptan-6-yl)imidazo[1,5-a]pyrazin-1-yl 1)-N-(4-(trifluoromethyl)pyridin-2-yl) benzamide

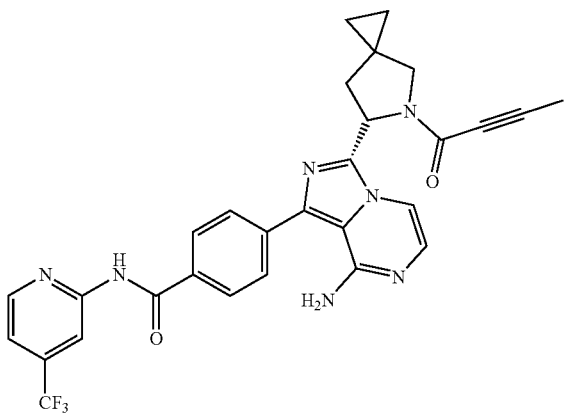

Under the protection of nitrogen, to a solution of (S)-4-(8-amino-3-(5-azaspiro[2.4]heptan-6-yl)imidazo[1,5-a]pyrazin-1-yl)-N-(4-(trifluoromethyl)pyridin-2-yl)benzamide (100 mg, 0.203 mmol), 2-butynoic acid (20.5 mg, 0.244 mmol), DIPEA (78.56 mg, 0.609 mmol) in DMF (5 mL), HBTU (92.5 mg, 0.244 mmol) was added. The reaction mixture reacted under stirring at room temperature for 1 hour. After TLC showed the raw materials reacted completely, the reaction system was quenched with water and extracted with EA (15 mL×3). The organic phase was backwashed with saturated brine, dried with anhydrous $Na_2SO_4$, evaporated under vacuum and then purified by preparative silica gel plate (DCM/MeOH=20/1) to obtain 60 mg of the target compound which was a yellow solid.

The structure of the product was characterized by nuclear magnetic resonance and mass spectrometry and the results were as follows:

$^1$H NMR (400 MHz, $d_6$-DMSO) δ 0.58-0.79 (4H, m), 1.58 (1H, s), 1.97 (2H, s), 2.24-2.33 (2H, m), 3.50-3.85 (2H, m), 5.57-5.59 (0.65H, m), 5.80-5.82 (0.35H, m), 6.14-6.22 (2H, m), 7.14 (0.65H, d, J=4.8 Hz), 7.18 (0.35H, d, J=4.8 Hz), 7.58 (1H, d, J=4.8 Hz), 7.74-7.79 (2H, m), 7.89-8.04 (1H, m), 8.17-8.20 (2H, m), 8.62 (1H, s), 8.70 (1H, d, J=5.2 Hz), 10.82 (1H, s).

EM (calculated value): 559.2; MS (ESI) m/e (M+1H)+: 560.2

It can be seen that the compound prepared by the present application has the same structure as the compound above.

Example 41

Preparation of (S)-4-(3-(5-acryloyl-5-azaspiro[2.4]heptan-6-yl)-8-aminoimidazo[1,5-a]pyrazin-1-yl)-N-(4-(trifluoromethyl)pyridin-2-yl)benzamide

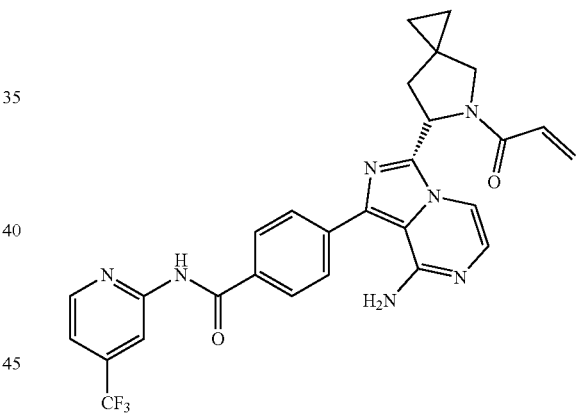

Under the protection of nitrogen, to a solution of (S)-4-(8-amino-3-(5-azaspiro[2.4]heptan-6-yl)imidazo[1,5-a]pyrazin-1-yl)-N-(4-(trifluoromethyl)pyridin-2-yl)benzamide (100 mg, 0.203 mmol), TEA (103.1 mg, 1.02 mmol) in DCM (10 mL), 3-chloropropionyl chloride (25.8 mg, 0.203 mmol) was added dropwise at 0° C. The reaction mixture reacted under stirring at room temperature overnight. After TLC showed the raw materials reacted completely, the reaction system was quenched with water and extracted with EA (10 mL×3). The organic phase was dried with anhydrous $Na_2SO_4$, evaporated under vacuum and then purified by preparative silica gel plate (DCM/MeOH=15/1) to obtain 32 mg of the target compound which was a yellow solid.

The structure of the product was characterized by nuclear magnetic resonance and mass spectrometry and the results were as follows:

$^1$H NMR (400 MHz, $d_6$-DMSO) δ 0.56-0.76 (4H, m), 2.24-2.28 (1.5H, m), 3.61-3.66 (1.5H, m), 3.87 (1H, d,

J=10.4 Hz), 5.60-5.66 (2H, m), 6.05-6.19 (3H, m), 6.57 (1H, dd, J=16.4 Hz, 10.4 Hz), 7.15 (0.7H, d, J=5.2 Hz), 7.19 (0.3H, d, J=5.2 Hz), 7.52-7.56 (1H, m), 7.76 (2H, dd, J=8.0 Hz, 4.0 Hz), 7.83 (0.7H, d, J=5.2 Hz), 7.97 (0.3H, d, J=5.2 Hz), 8.17 (2H, d, J=8.0 Hz), 8.57 (1H, s), 8.71 (1H, d, J=5.2 Hz), 11.12 (1H, s).

EM (calculated value): 547.2; MS (ESI) m/e (M+1H)$^+$: 548.2

It can be seen that the compound prepared by the present application has the same structure as the above compound.

Examples 42-72

The following compounds were prepared by the preparation method of Example 40 or Example 41 using compounds with similar structures as the starting materials. The structures and nuclear magnetic characterization data of the compounds are shown in Table 3. Table 3 summarizes the structures and structural analysis data of the compounds prepared in Examples 42 to 72 of the present application.

TABLE 3

Summary of structures and structural analysis data of the compounds prepared in Examples 42-72

| Examples | Structures | Analysis data |
|---|---|---|
| 42 | 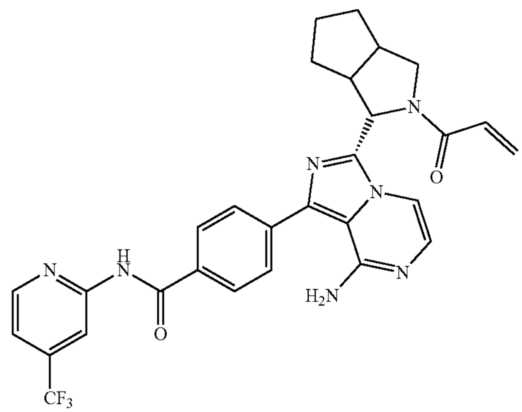 | $^1$H NMR (400 MHz, d$_6$-DMSO) δ 1.45-1.59 (3H, m), 1.76-1.84 (1H, m), 1.85-2.01 (2H, m), 2.67-2.71 (1H, m), 2.90-2.92 (1H, m), 3.63-3.66 (1H, m), 3.86-3.94 (1H, m), 5.45 (1H, d, J = 2.0 Hz), 5.67-5.72 (1H, m), 5.84 (0.25H, dd, J = 16.4 Hz, 10.4 Hz), 6.03-6.22 (3H, m), 6.79 (0.75H, dd, J = 16.4 Hz, 10.4 Hz), 7.14 (0.75H, d, J = 5.2 Hz), 7.19 (0.25H, d, J = 5.2 Hz), 7.55-7.59 (1H, m), 7.73 (2H, dd, J = 8.0 Hz, 4.0 Hz), 7.83 (0.25H, d, J = 5.2 Hz), 7.99 (0.75H, d, J = 5.2 Hz), 8.17 (2H, d, J = 8.0 Hz), 8.55 (1H, s), 8.70 (1H, d, J = 5.2 Hz), 11.37 (1H, s). EM(calculated value): 561.2; MS(ESI) m/e (M + 1H)$^+$: 562.2 |
| 43 | 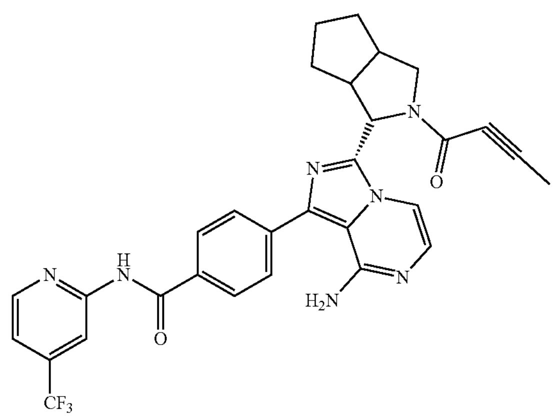 | $^1$H NMR (400 MHz, d$_6$-DMSO) δ 1.50-1.64 (3H, m), 1.74-1.80 (2H, m), 1.85-1.97 (4H, m), 2.73-2.77 (0.35H, m), 2.94-2.99 (0.65H, m), 3.46-3.52 (0.35H, m), 3.70-3.76 (0.65H, m), 3.79-3.85 (0.35H, m), 3.90-3.93 (0.65H, m), 5.41 (0.65H, d, J = 2.8 Hz), 5.56 (0.35H, d, J = 2.8 Hz), 6.05-6.22 (2H, m), 7.14 (0.65H, d, J = 4.8 Hz), 7.18 (0.35H, d, J = 4.8 Hz), 7.54 (1H, d, J = 4.8 Hz), 7.73-7.79 (2H, m), 7.88 (0.65H, d, J = 5.2 Hz), 8.01 (0.35H, d, J = 5.2 Hz), 8.17-8.22 (2H, m), 8.57 (1H, s), 8.71 (1H, d, J = 5.2 Hz), 11.33 (1H, brs). EM(calculated value): 573.2; MS(ESI) m/e (M + 1H)$^+$: 574.2 |
| 44 | 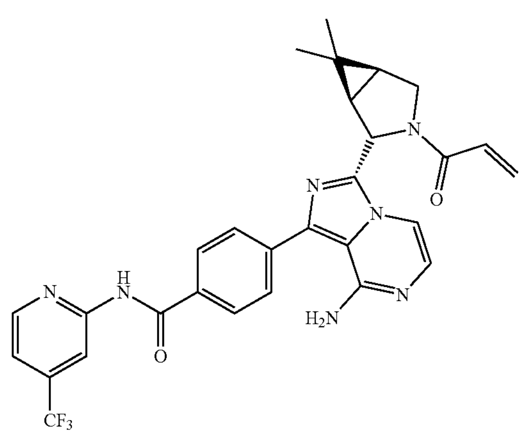 | $^1$H NMR (400 MHz, d$_6$-DMSO) δ 1.02-1.13 (6H, m), 1.49-1.55 (1H, m), 1.63-1.68 (0.4H, m), 1.74-1.79 (0.6H, m), 3.68-3.73 (0.4H, m), 3.73-3.79 (0.6H, m), 3.85-3.89 (0.4H, m), 4.04-4.08 (0.6H, m), 5.40 (0.6H, s), 5.49-5.53 (0.4H, m), 5.60 (0.4H, s), 5.66-5.70 (0.6H, m), 6.03-6.21 (3H, m), 6.38-6.51 (1H, m), 7.14 (0.6H, d, J = 5.2 Hz), 7.20 (0.4H, d, J = 5.2 Hz), 7.55-7.56 (1H, m), 7.73 (2H, dd, J = 8.0 Hz, 4.0 Hz), 7.83 (0.4H, d, J = 5.2 Hz), 7.93 (0.6H, d, J = 5.2 Hz), 8.17 (2H, d, J = 8.0 Hz), 8.57 (1H, s), 8.70 (1H, d, J = 5.2 Hz), 11.34 (1H, s). EM(calculated value): 561.2; MS(ESI) m/e (M + 1H)$^+$: 562.2 |

TABLE 3-continued

Summary of structures and structural analysis data of the compounds prepared in Examples 42-72

| Examples | Structures | Analysis data |
|---|---|---|
| 45 | 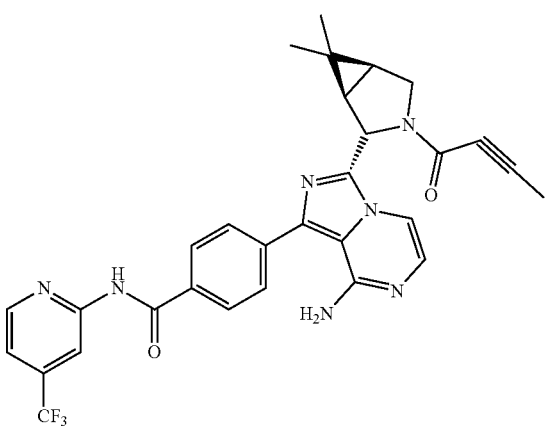 | $^1$H NMR (400 MHz, d$_6$-DMSO) δ 1.05 (6H, s), 1.49-1.56 (1H, m), 1.67-1.70 (1H, m), 1.74 (1.3H, s), 2.05 (1.7H, s), 3.63 (0.45H, d, J = 12.4 Hz), 3.76-3.85 (1H, m), 4.02 (0.55H, dd, J = 11.2 Hz, 5.2 Hz), 5.36 (0.55H, s), 5.57 (0.45H, s), 6.09-6.21 (2H, m), 7.14-7.17 (1H, m), 7.56 (1H, d, J = 4.8 Hz), 7.74-7.79 (2H, m), 7.88 (1H, d, J = 5.2 Hz), 8.17-8.23 (2H, m), 8.55 (1H, s), 8.71 (1H, d, J = 5.2 Hz), 10.99 (1H, brs). EM(calculated value): 573.2; MS(ESI) m/e (M + 1H)$^+$: 574.2 |
| 46 | 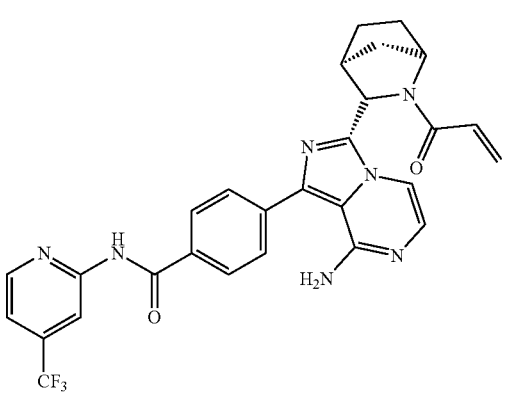 | $^1$H NMR (400 MHz, d$_6$-DMSO) δ 1.50-1.81 (5H, m), 2.53-2.58 (1H, m), 2.71-2.73 (1H, m), 4.62 (0.2H, s), 4.74 (0.8H, s), 5.04 (0.8H, s), 5.25 (0.2H, s), 5.44 (0.2H, d, J = 10.4 Hz), 5.66 (0.8H, dd, J = 10.4 Hz, 2.4 Hz), 5.84 (0.2H, dd, J = 16.4 Hz, 10.4 Hz), 6.03-6.22 (3H, m), 6.75 (0.8H, dd, J = 16.4 Hz, 10.4 Hz), 7.14 (0.8H, d, J = 5.2 Hz), 7.20 (0.2H, d, J = 5.2 Hz), 7.55-7.56 (1H, m), 7.73 (2H, dd, J = 8.0 Hz, 4.0 Hz), 7.83 (0.2H, d, J = 5.2 Hz), 7.93 (0.8H, d, J = 5.2 Hz), 8.17 (2H, d, J = 8.0 Hz), 8.57 (1H, s), 8.70 (1H, d, J = 5.2 Hz), 11.34 (1H, s). EM(calculated value): 547.2; MS(ESI) m/e (M + 1H)$^+$: 548.2 |
| 47 | 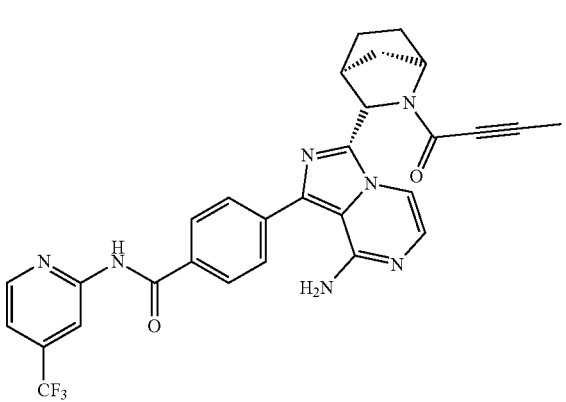 | $^1$H NMR (400 MHz, d$_6$-DMSO) δ 1.46-1.51 (2H, m), 1.60-1.90 (4H, m), 2.03 (2H, s), 2.61-2.63 (2H, m), 4.56 (0.3H, s), 4.64 (0.7H, s), 5.01 (0.7H, s), 5.22 (0.3H, s), 6.16-6.22 (2H, m), 7.14 (0.7H, d, J = 4.8 Hz), 7.18 (0.3H, d, J = 4.8 Hz), 7.56 (1H, d, J = 4.8 Hz), 7.74-7.79 (2H, m), 7.88 (0.7H, d, J = 5.2 Hz), 8.01 (0.3H, d, J = 5.2 Hz), 8.17-8.20 (2H, m), 8.59 (1H, s), 8.70 (1H, d, J = 5.2 Hz), 11.36 (1H, brs). EM(calculated value): 559.2; MS(ESI) m/e (M + 1H)$^+$: 560.2 |

TABLE 3-continued

Summary of structures and structural analysis data of the compounds prepared in Examples 42-72

| Examples | Structures | Analysis data |
|---|---|---|
| 48 | 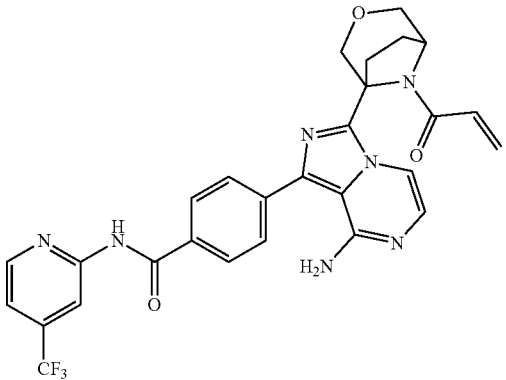 [SMILES: C=CC(=O)N1C2CCC1(c1nc(-c3ccc(C(=O)Nc4cc(C(F)(F)F)ccn4)cc3)c3c(N)nccn13)COC2] | $^1$H NMR (400 MHz, d$_6$-DMSO) δ 1.72-1.77 (1H, m), 1.92-2.05 (3H, m), 3.40-3.63 (4H, m), 3.98-4.03 (1H, m), 5.65-5.67 (1H, m), 6.09-6.20 (3H, m), 6.70-6.74 (1H, m), 7.14 (0.8H, d, J = 5.2 Hz), 7.21 (0.2H, d, J = 5.2 Hz), 7.55-7.57 (1H, m), 7.73 (2H, dd, J = 8.0 Hz, 4.0 Hz), 7.91 (1H, d, J = 5.2 Hz), 8.15 (2H, d, J = 8.0 Hz), 8.57 (1H, s), 8.69 (1H, d, J = 5.2 Hz), 11.36 (1H, s). EM(calculated value): 563.2; MS(ESI) m/e (M + 1H)$^+$: 564.2 |
| 49 | 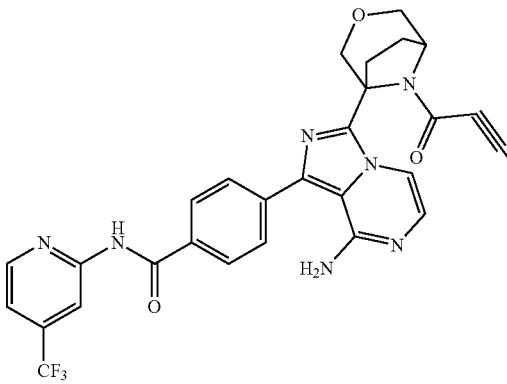 | $^1$H NMR (400 MHz, d$_6$-DMSO) δ 1.52 (1H, s), 1.72-1.77 (1H, m), 1.89-1.98 (5H, m), 3.45-3.63 (4H, m), 3.98-4.04 (1H, m), 6.08-6.20 (2H, m), 7.14 (0.8H, d, J = 4.8 Hz), 7.19 (0.2H, d, J = 4.8 Hz), 7.54 (1H, d, J = 4.8 Hz), 7.74-7.78 (2H, m), 7.88 (0.8H, d, J = 5.2 Hz), 8.03 (0.2H, d, J = 5.2 Hz), 8.16-8.20 (2H, m), 8.59 (1H, s), 8.72 (1H, d, J = 5.2 Hz), 11.36 (1H, s). EM(calculated value): 575.2; MS(ESI) m/e (M + 1H)$^+$: 576.2 |
| 50 | 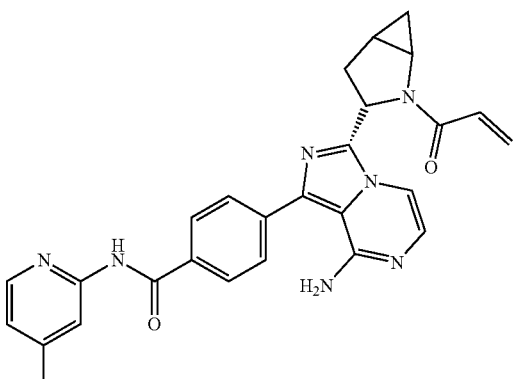 | $^1$H NMR (400 MHz, d$_6$-DMSO) δ 0.37-0.38 (1H, m), 0.81-0.83 (1H, m), 0.92-0.94 (1H, m), 1.89-2.04 (2H, m), 3.16-3.20 (1H, m), 3.83-3.88 (0.3H, s), 4.03-4.07 (0.7H, s), 5.60-5.64 (1H, m), 5.84 (0.3H, dd, J = 16.8 Hz, 10.4 Hz), 6.06-6.22 (3H, m), 6.76 (0.7H, dd, J = 16.8 Hz, 10.4 Hz), 7.13 (0.7H, d, J = 5.2 Hz), 7.21 (0.3H, d, J = 5.2 Hz), 7.54-7.57 (1H, m), 7.71 (2H, dd, J = 8.0 Hz, 4.0 Hz), 7.91 (1H, d, J = 5.2 Hz), 8.13 (2H, d, J = 8.0 Hz), 8.57 (1H, s), 8.68 (1H, d, J = 5.2 Hz), 11.33 (1H, brs). EM(calculated value): 533.2; MS(ESI) m/e (M + 1H)$^+$: 534.2 |

TABLE 3-continued

Summary of structures and structural analysis data of the compounds prepared in Examples 42-72

| Examples | Structures | Analysis data |
|---|---|---|
| 51 | 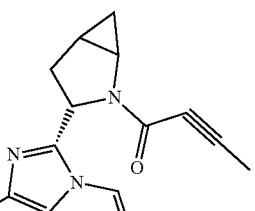 | $^1$H NMR (400 MHz, d$_6$-DMSO) δ 0.36-0.38 (1H, m), 0.81-0.84 (1H, m), 0.90-0.93 (1H, m), 1.52 (1H, s), 1.86-2.03 (4H, m), 3.16-3.19 (1H, m), 3.83-3.86 (0.3H, s), 4.02-4.06 (0.7H, s), 6.06-6.18 (2H, m), 7.14 (0.8H, d, J = 4.8 Hz), 7.21 (0.2H, d, J = 4.8 Hz), 7.53 (1H, d, J = 4.8 Hz), 7.76-7.78 (2H, m), 7.88 (0.8H, d, J = 5.2 Hz), 8.01 (0.2H, d, J = 5.2 Hz), 8.17-8.20 (2H, m), 8.59 (1H, s), 8.71 (1H, d, J = 5.2 Hz), 11.33 (1H, s). EM(calculated value): 545.2; MS(ESI) m/e (M + 1H)$^+$: 546.2 |
| 52 | 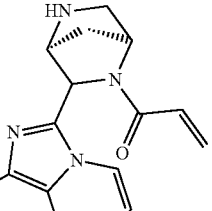 | $^1$H NMR (400 MHz, d$_6$-DMSO) δ 1.73-1.77 (1H, m), 2.01-2.03 (1H, m), 2.89-3.02 (2H, m), 3.73-3.77 (1H, m), 4.74-4.77 (1H, m), 5.26-5.30 (1H, m), 5.48-5.50 (0.4H, m), 5.65-5.69 (1H, m), 6.05-6.20 (3H, m), 6.82 (0.6H, dd, J = 16.8 Hz, 10.4 Hz), 7.15 (0.6H, d, J = 5.2 Hz), 7.21 (0.4H, d, J = 5.2 Hz), 7.54-7.58 (1H, m), 7.71 (2H, dd, J = 8.0 Hz, 4.0 Hz), 7.90 (1H, d, J = 5.2 Hz), 8.13 (2H, d, J = 8.0 Hz), 8.57 (1H, s), 8.70 (1H, d, J = 5.2 Hz), 11.35 (1H, brs). EM(calculated value): 548.2; MS(ESI) m/e (M + 1H)$^+$: 549.2 |
| 53 | 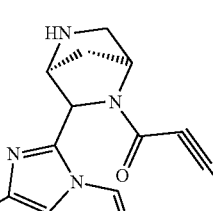 | $^1$H NMR (400 MHz, d$_6$-DMSO) δ 1.54 (1H, s), 1.72-1.77 (1H, m), 2.02-2.06 (3H, m), 2.89-3.02 (2H, m), 3.70-3.72 (1H, m), 4.73-4.75 (1H, m), 5.26-5.29 (1H, m), 6.05-6.25 (2H, m), 7.13 (0.7H, d, J = 4.8 Hz), 7.20 (0.3H, d, J = 4.8 Hz), 7.53 (1H, d, J = 4.8 Hz), 7.76-7.79 (2H, m), 7.86 (0.7H, d, J = 5.2 Hz), 8.01 (0.3H, d, J = 5.2 Hz), 8.17-8.19 (2H, m), 8.61 (1H, s), 8.73 (1H, d, J = 5.2 Hz), 11.30 (1H, s). EM(calculated value): 560.2; MS(ESI) m/e (M + 1H)$^+$: 561.2 |

TABLE 3-continued

Summary of structures and structural analysis data of the compounds prepared in Examples 42-72

| Examples | Structures | Analysis data |
|---|---|---|
| 54 | 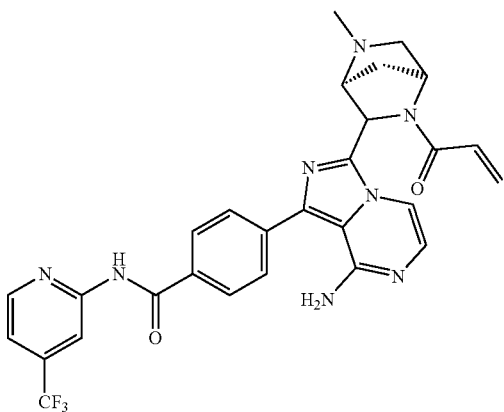 | $^1$H NMR (400 MHz, d$_6$-DMSO) δ 1.53-1.54 (1H, m), 1.77-1.80 (1H, m), 2.34 (3H, s), 3.36-3.38 (1H, m), 3.49-3.53 (2H, m), 3.68-3.71 (1H, m), 5.00-5.02 (1H, m), 5.44-5.45 (0.4H, m), 5.63-5.65 (0.6H, m), 5.82 (0.4H, dd, J = 16.8 Hz, 10.4 Hz), 6.06-6.15 (3H, m), 6.74 (0.6H, dd, J = 16.8 Hz, 10.4 Hz), 7.13 (1H, d, J = 5.2 Hz), 7.55-7.57 (1H, m), 7.73 (2H, dd, J = 8.0 Hz, 4.0 Hz), 7.91 (1H, d, J = 5.2 Hz), 8.17 (2H, d, J = 8.0 Hz), 8.55 (1H, s), 8.71 (1H, d, J = 5.2 Hz), 11.35 (1H, s). EM(calculated value): 562.3; MS(ESI) m/e (M + 1H)$^+$: 563.3 |
| 55 | 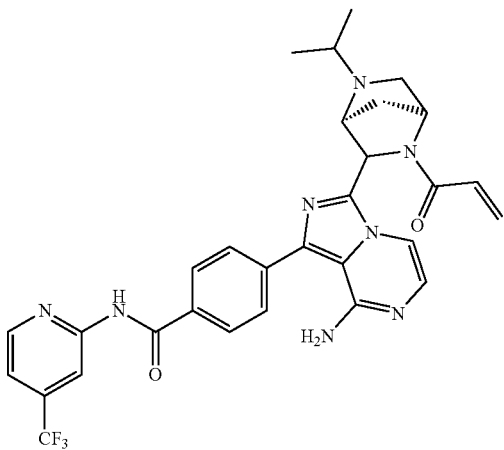 | $^1$H NMR (400 MHz, d$_6$-DMSO) δ 1.20-1.22 (6H, m), 1.54-1.55 (1H, m), 1.77-1.79 (1H, m), 2.85-2.86 (1H, m), 3.37-3.39 (1H, m), 3.49-3.53 (2H, m), 3.68-3.71 (1H, m), 4.99-5.01 (1H, m), 5.45-5.46 (0.3H, m), 5.63-5.65 (0.7H, m), 5.86 (0.3H, dd, J = 16.8 Hz, 10.4 Hz), 6.04-6.18 (3H, m), 6.71 (0.7H, dd, J = 16.8 Hz, 10.4 Hz), 7.14 (0.7H, d, J = 5.2 Hz), 7.21 (0.3H, d, J = 5.2 Hz), 7.55-7.56 (1H, m), 7.73 (2H, dd, J = 8.0 Hz, 4.0 Hz), 7.82 (0.3H, d, J = 5.2 Hz), 7.95 (0.7H, d, J = 5.2 Hz), 8.17 (2H, d, J = 8.0 Hz), 8.56 (1H, s), 8.71 (1H, d, J = 5.2 Hz), 11.34 (1H, s). EM(calculated value): 590.2; MS(ESI) m/e (M + 1H)$^+$: 591.2 |
| 56 | 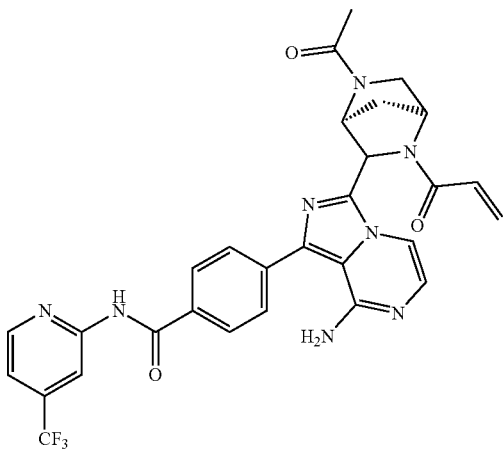 | $^1$H NMR (400 MHz, d$_6$-DMSO) δ 1.68-1.69 (1H, m), 1.85-1.86 (1H, m), 2.44 (3H, s), 3.47-3.49 (1H, m), 3.50-3.56 (2H, m), 3.77-3.80 (1H, m), 5.02-5.04 (1H, m), 5.43-5.45 (0.4H, m), 5.63-5.67 (0.6H, m), 5.81 (0.4H, dd, J = 16.8 Hz, 10.4 Hz), 6.10-6.22 (3H, m), 6.71 (0.6H, dd, J = 16.8 Hz, 10.4 Hz), 7.14 (0.6H, d, J = 4.8 Hz), 7.20 (0.4H, d, J = 4.8 Hz), 7.53 (1H, d, J = 4.8 Hz), 7.75-7.78 (2H, m), 7.88 (0.6H, d, J = 5.2 Hz), 8.03 (0.4H, d, J = 5.2 Hz), 8.17-8.20 (2H, m), 8.58 (1H, s), 8.72 (1H, d, J = 5.2 Hz), 11.33 (1H, brs). EM(calculated value): 590.2; MS(ESI) m/e (M + 1H)$^+$: 591.2 |

TABLE 3-continued

Summary of structures and structural analysis data of the compounds prepared in Examples 42-72

| Examples | Structures | Analysis data |
|---|---|---|
| 57 | 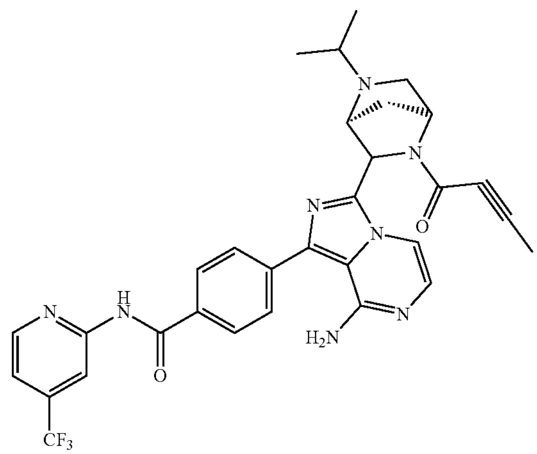 | $^1$H NMR (400 MHz, d$_6$-DMSO) δ 1.19-1.22 (6H, m), 1.52-1.54 (2H, m), 1.77-1.80 (1H, m), 2.03 (2H, s), 2.85-2.86 (1H, m), 3.37-3.39 (1H, m), 3.48-3.54 (2H, m), 3.69-3.71 (1H, m), 4.99-5.01 (1H, m), 6.06-6.18 (2H, m), 7.14-7.16 (1H, m), 7.56 (1H, d, J = 4.8 Hz), 7.75-7.79 (2H, m), 7.87 (1H, d, J = 5.2 Hz), 8.17-8.22 (2H, m), 8.54 (1H, s), 8.71 (1H, d, J = 5.2 Hz), 10.98 (1H, brs). EM(calculated value): 602.2; MS(ESI) m/e (M + 1H)$^+$: 603.3 |
| 58 | 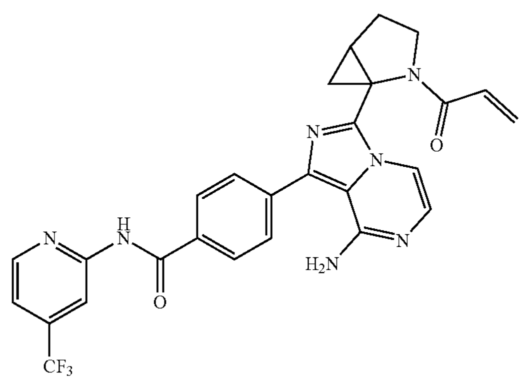 [SMILES: C=CC(=O)N1CCC2CC21c1nc(-c2ccc(C(=O)Nc3cc(C(F)(F)F)ccn3)cc2)c2c(N)nccn12] | $^1$H NMR (400 MHz, d$_6$-DMSO) δ 0.75-0.78 (1H, m), 0.91-0.94 (1H, m), 1.24-1.76 (3H, m), 3.85-3.88 (1.25H, s), 4.03-4.07 (0.75H, s), 5.60-5.63 (1H, m), 5.85 (0.25H, dd, J = 16.8 Hz, 10.4 Hz), 6.06-6.18 (3H, m), 6.76 (0.75H, dd, J = 16.8 Hz, 10.4 Hz), 7.12 (0.75H, d, J = 5.2 Hz), 7.20 (0.25H, d, J = 5.2 Hz), 7.53-7.55 (1H, m), 7.69 (2H, dd, J = 8.0 Hz, 4.0 Hz), 7.88 (0.25H, d, J = 5.2 Hz), 7.94 (0.75H, d, J = 5.2 Hz), 8.15 (2H, d, J = 8.0 Hz), 8.57 (1H, s), 8.70 (1H, d, J = 5.2 Hz), 11.33 (1H, s). EM(calculated value): 533.2; MS(ESI) m/e (M + 1H)$^+$: 534.2 |
| 59 | 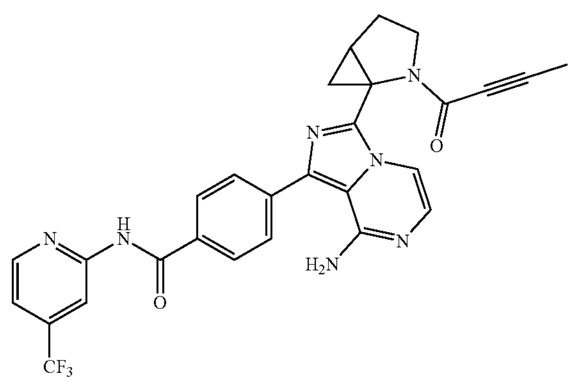 [SMILES: CC#CC(=O)N1CCC2CC21c1nc(-c2ccc(C(=O)Nc3cc(C(F)(F)F)ccn3)cc2)c2c(N)nccn12] | $^1$H NMR (400 MHz, d$_6$-DMSO) δ 0.78-0.81 (1H, m), 0.92-0.94 (1H, m), 1.29-1.85 (4H, m), 2.03 (2H, s), 3.84-3.88 (1.25H, s), 4.01-4.07 (0.75H, s), 6.06-6.16 (2H, m), 7.14 (0.75H, d, J = 4.8 Hz), 7.18 (0.25H, d, J = 4.8 Hz), 7.56 (1H, d, J = 4.8 Hz), 7.74-7.79 (2H, m), 7.85 (0.75H, d, J = 5.2 Hz), 8.01 (0.25H, d, J = 5.2 Hz), 8.17-8.22 (2H, m), 8.59 (1H, s), 8.71 (1H, d, J = 5.2 Hz), 11.36 (1H, brs). EM(calculated value): 545.2; MS(ESI) m/e (M + 1H)$^+$: 546.2 |

US 10,793,576 B2

TABLE 3-continued

Summary of structures and structural analysis data of the compounds prepared in Examples 42-72

| Examples | Structures | Analysis data |
|---|---|---|
| 60 | 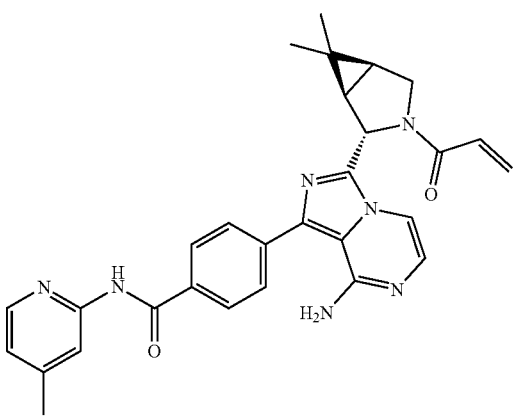 [SMILES: C=CC(=O)N1C[C@H]2[C@@H]([C@H]1c1nc(-c3ccc(C(=O)Nc4cc(C)ccn4)cc3)c3c(N)nccn13)C2(C)C] | $^1$H NMR (400 MHz, $d_6$-DMSO) δ 1.00-1.04 (6H, m), 1.49-1.53 (1H, m), 1.64-1.65 (0.3H, m), 1.74-1.77 (0.7H, m), 2.37 (3H, s), 3.69-3.73 (0.3H, m), 3.77-3.79 (0.7H, m), 3.85-3.90 (0.3H, m), 4.04-4.06 (0.7H, m), 5.41 (0.7H, s), 5.51-5.53 (0.3H, m), 5.60 (0.3H, s), 5.66-5.69 (0.7H, m), 6.03-6.19 (3H, m), 6.37 (0.3H, dd, J = 16.8 Hz, 10.4 Hz), 6.55 (0.7H, dd, J = 16.8 Hz, 10.4 Hz), 7.16-7.21 (1H, m), 7.54-7.58 (1H, m), 7.72 (2H, dd, J = 8.0 Hz, 4.0 Hz), 7.84 (0.3H, d, J = 5.2 Hz), 7.95 (0.7H, d, J = 5.2 Hz), 8.13 (2H, d, J = 8.0 Hz), 8.21 (1H, s), 8.70 (1H, d, J = 5.2 Hz), 11.32-11.35 (1H, m). EM(calculated value): 507.2; MS(ESI) m/e (M + 1H)$^+$: 508.2 |
| 61 | 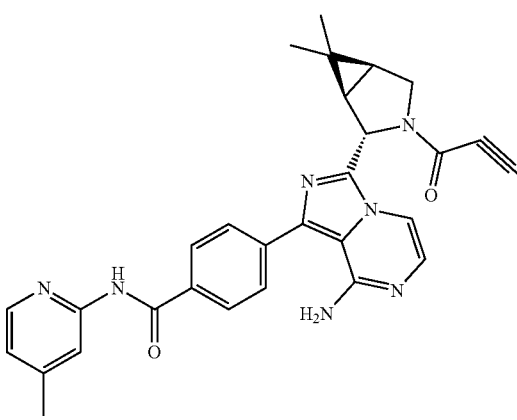 | $^1$H NMR (400 MHz, $d_6$-DMSO) δ 1.2-1.05 (6H, m), 1.49-1.52 (2H, m), 1.62-1.65 (0.3H, m), 1.73-1.77 (0.7H, m), 2.02 (2H, s), 2.36 (3H, s), 3.68-3.71 (0.3H, m), 3.77-3.78 (0.7H, m), 3.88-3.90 (0.3H, m), 4.04-4.08 (0.7H, m), 5.42 (0.7H, s), 5.51-5.54 (0.3H, m), 6.03-6.15 (2H, m), 7.16-7.20 (1H, m), 7.55-7.58 (1H, m), 7.75 (2H, dd, J = 8.0 Hz, 4.0 Hz), 7.83 (0.3H, d, J = 5.2 Hz), 7.94 (0.7H, d, J = 5.2 Hz), 8.13 (2H, d, J = 8.0 Hz), 8.22 (1H, s), 8.71 (1H, d, J = 5.2 Hz), 11.32-11.33 (1H, m). EM(calculated value): 519.2; MS(ESI) m/e (M + 1H)$^+$: 520.2 |
| 62 | 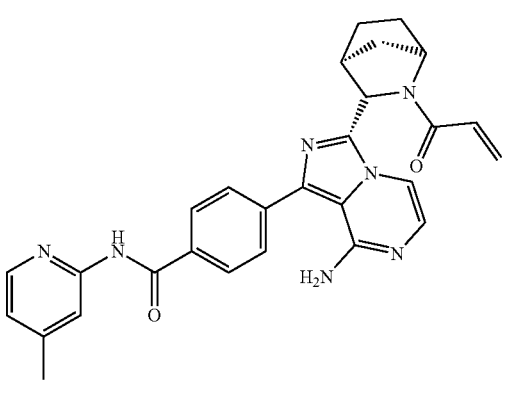 | $^1$H NMR (400 MHz, $d_6$-DMSO) δ 1.45-1.53 (2H, m), 1.80-1.86 (3H, m), 2.39 (3H, s), 2.57-2.58 (1H, m), 2.67-2.73 (1H, m), 4.66-4.74 (1H, m), 5.10-5.25 (1H, m), 5.65-5.68 (1H, m), 6.06-6.20 (3H, m), 6.73-6.77 (1H, m), 7.14 (0.65H, d, J = 5.2 Hz), 7.25 (0.35H, d, J = 5.2 Hz), 7.55-7.58 (1H, m), 7.73 (2H, dd, J = 8.0 Hz, 4.0 Hz), 7.86 (0.35H, d, J = 5.2 Hz), 7.93 (0.65H, d, J = 5.2 Hz), 8.16 (2H, d, J = 8.0 Hz), 8.22 (1H, s), 8.70 (1H, d, J = 5.2 Hz), 11.32-11.34 (1H, m). EM(calculated value): 493.2; MS(ESI) m/e (M + 1H)$^+$: 494.2 |

TABLE 3-continued

Summary of structures and structural analysis data of the compounds prepared in Examples 42-72

| Examples | Structures | Analysis data |
|---|---|---|
| 63 | 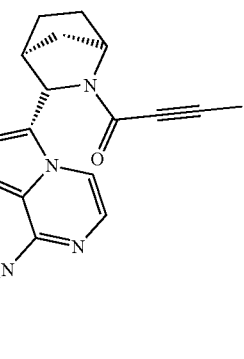 | $^1$H NMR (400 MHz, d$_6$-DMSO) δ 1.39-1.53 (3H, m), 1.83-1.86 (3H, m), 2.05 (2H, s), 2.37 (3H, s), 2.57-2.59 (1H, m), 2.67-2.73 (1H, m), 4.69-4.74 (1H, m), 5.10-5.25 (1H, m), 6.06-6.20 (2H, m), 7.14 (0.7H, d, J = 5.2 Hz), 7.27 (0.3H, d, J = 5.2 Hz), 7.55-7.59 (1H, m), 7.71 (2H, dd, J = 8.0 Hz, 4.0 Hz), 7.83 (0.3H, d, J = 5.2 Hz), 7.93 (0.7H, d, J = 5.2 Hz), 8.19 (2H, d, J = 8.0 Hz), 8.22 (1H, s), 8.70 (1H, d, J = 5.2 Hz), 11.32-11.35 (1H, m). EM(calculated value): 505.2; MS(ESI) m/e (M + 1H)$^+$: 506.2 |
| 64 | 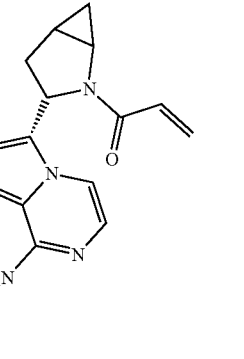 | $^1$H NMR (400 MHz, d$_6$-DMSO) δ 0.36-0.38 (1H, m), 0.81-0.82 (1H, m), 0.92-0.95 (1H, m), 1.92-2.04 (2H, m), 2.36 (3H, s), 3.15-3.20 (1H, m), 3.85-3.88 (0.35H, s), 4.03-4.06 (0.65H, s), 5.61-5.64 (1H, m), 5.84 (0.35H, dd, J = 16.8 Hz, 10.4 Hz), 6.06-6.19 (3H, m), 6.75 (0.65H, dd, J = 16.8 Hz, 10.4 Hz), 7.14 (0.65H, d, J = 5.2 Hz), 7.24 (0.35H, d, J = 5.2 Hz), 7.55-7.57 (1H, m), 7.74 (2H, dd, J = 8.0 Hz, 4.0 Hz), 7.86 (0.35H, d, J = 5.2 Hz), 7.93 (0.65H, d, J = 5.2 Hz), 8.14 (2H, d, J = 8.0 Hz), 8.20 (1H, s), 8.69 (1H, d, J = 5.2 Hz), 11.32-11.35 (1H, m). EM(calculated value): 479.2; MS(ESI) m/e (M + 1H)$^+$: 480.2 |
| 65 | 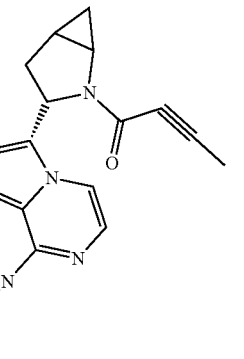 | $^1$H NMR (400 MHz, d$_6$-DMSO) δ 0.35-0.37 (1H, m), 0.81-0.83 (1H, m), 0.93-0.95 (1H, m), 1.52 (1H, s), 1.92-2.02 (4H, m), 2.37 (3H, s), 3.16-3.20 (1H, m), 3.85-3.87 (0.35H, s), 4.05-4.06 (0.65H, s), 6.06-6.15 (2H, m), 7.13 (0.65H, d, J = 5.2 Hz), 7.21 (0.35H, d, J = 5.2 Hz), 7.53-7.57 (1H, m), 7.71 (2H, dd, J = 8.0 Hz, 4.0 Hz), 7.83 (0.35H, d, J = 5.2 Hz), 7.88 (0.65H, d, J = 5.2 Hz), 8.13 (2H, d, J = 8.0 Hz), 8.20 (1H, s), 8.70 (1H, d, J = 5.2 Hz), 11.32-11.35 (1H, m). EM(calculated value): 491.2; MS(ESI) m/e (M + 1H)$^+$: 492.2 |
| 66 | 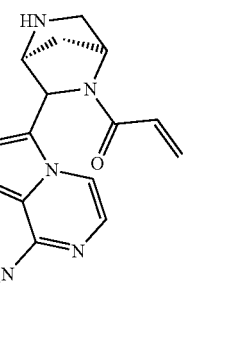 | $^1$H NMR (400 MHz, d$_6$-DMSO) δ 1.72-1.76 (1H, m), 2.01-2.04 (1H, m), 2.37 (3H, s), 2.86-3.02 (2H, m), 3.73-3.75 (1H, m), 4.75-4.77 (1H, m), 5.27-5.30 (1H, m), 5.48-5.49 (0.4H, m), 5.65-5.70 (1H, m), 6.05-6.25 (3H, m), 6.82 (0.6H, dd, J = 16.8 Hz, 10.4 Hz), 7.14 (0.6H, d, J = 5.2 Hz), 7.26 (0.4H, d, J = 5.2 Hz), 7.57-7.58 (1H, m), 7.73 (2H, dd, J = 8.0 Hz, 4.0 Hz), 7.85 (0.4H, d, J = 5.2 Hz), 7.93 (0.6H, d, J = 5.2 Hz), 8.14 (2H, d, J = 8.0 Hz), 8.22 (1H, s), 8.70 (1H, d, J = 5.2 Hz), 11.32 (1H, brs). EM(calculated value): 494.2; MS(ESI) m/e (M + 1H)$^+$: 495.2 |

TABLE 3-continued

Summary of structures and structural analysis data of the compounds prepared in Examples 42-72

| Examples | Structures | Analysis data |
|---|---|---|
| 67 | 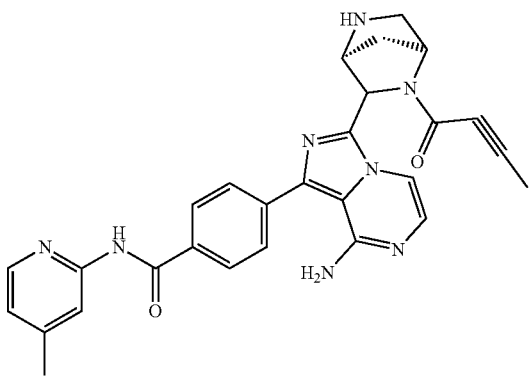 | $^1$H NMR (400 MHz, d$_6$-DMSO) δ1.52 (1H, s), 1.72-1.75 (1H, m), 2.01-2.06 (3H, m), 2.35 (3H, s), 2.88-3.01 (2H, m), 3.69-3.72 (1H, m), 4.72-4.75 (1H, m), 5.26-5.28 (1H, m), 6.09-6.26 (2H, m), 7.14 (0.6H, d, J = 5.2 Hz), 7.26 (0.4H, d, J = 5.2 Hz), 7.57-7.59 (1H, m), 7.72 (2H, dd, J = 8.0 Hz, 4.0 Hz), 7.85 (0.4H, d, J = 5.2 Hz), 7.92 (0.6H, d, J = 5.2 Hz), 8.14 (2H, d, J = 8.0 Hz), 8.22 (1H, s), 8.71 (1H, d, J = 5.2 Hz), 11.32 (1H, brs). EM(calculated value): 506.2; MS(ESI) m/e (M + 1H)$^+$: 507.2 |
| 68 | 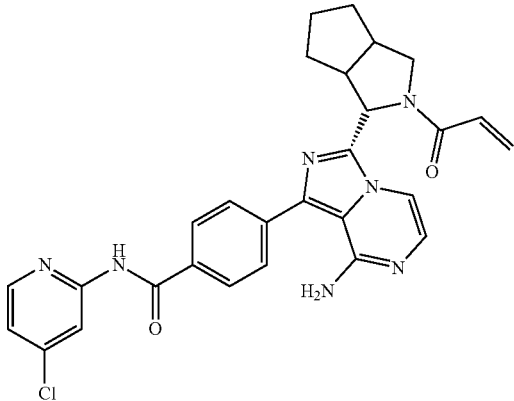 | $^1$H NMR (400 MHz, d$_6$-DMSO) δ 1.47-1.61 (3H, m), 1.75-1.80 (1H, m), 1.85-1.95 (2H, m), 2.67-2.68 (1H, m), 2.89-2.92 (1H, m), 3.64-3.66 (1H, m), 3.90-3.94 (1H, m), 5.45 (1H, d, J = 2.0 Hz), 5.67-5.71 (1H, m), 6.02-6.13 (3H, m), 6.77 (1H, dd, J = 16.8 Hz, 10.4 Hz), 7.13 (1H, d, J = 5.2 Hz), 7.34 (1H, s), 7.73 (2H, dd, J = 8.0 Hz, 4.0 Hz), 7.94 (1H, d, J = 5.2 Hz), 8.10 (2H, d, J = 8.0 Hz), 8.25 (1H, s), 8.36 (1H, d, J = 5.2 Hz), 11.37 (1H, s). EM(calculated value): 527.2; MS(ESI) m/e (M + 1H)$^+$: 528.2 |
| 69 | 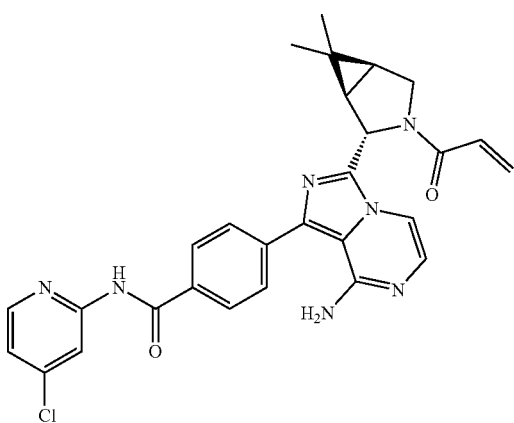 [SMILES: C=CC(=O)N1C[C@H]2[C@@H]([C@H]1c1nc(-c3ccc(C(=O)Nc4cc(Cl)ccn4)cc3)c3c(N)nccn13)C2(C)C] | $^1$H NMR (400 MHz, d$_6$-DMSO) δ 1.01-1.04 (6H, m), 1.51-1.55 (1H, m), 1.63-1.64 (0.3H, m), 1.74-1.76 (0.7H, m), 3.72-3.73 (0.3H, m), 3.77-3.81 (0.7H, m), 3.85-3.87 (0.3H, m), 4.04-4.08 (0.7H, m), 5.41 (0.7H, s), 5.51-5.53 (0.3H, m), 5.62 (0.3H, s), 5.68-5.71 (0.7H, m), 6.06-6.18 (3H, m), 6.38 (0.3H, dd, J = 16.8 Hz, 10.4 Hz), 6.57 (0.7H, dd, J = 16.8 Hz, 10.4 Hz), 7.14 (1H, d, J = 5.2 Hz), 7.33 (1H, s), 7.70 (2H, dd, J = 8.0 Hz, 4.0 Hz), 7.92 (1H, d, J = 5.2 Hz), 8.11 (2H, d, J = 8.0 Hz), 8.25 (1H, s), 8.36 (1H, d, J = 5.2 Hz), 11.35 (1H, s). EM(calculated value): 527.2; MS(ESI) m/e (M + 1H)$^+$: 528.2 |

TABLE 3-continued

Summary of structures and structural analysis data of the compounds prepared in Examples 42-72

| Examples | Structures | Analysis data |
|---|---|---|
| 70 | 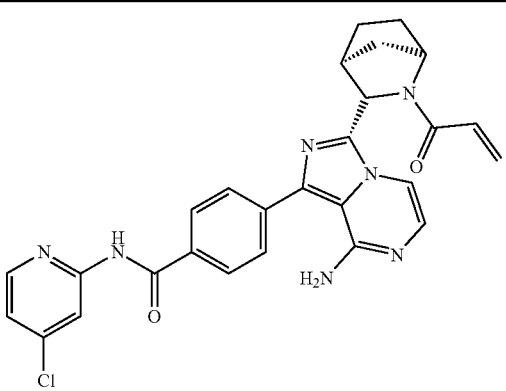 | ¹H NMR (400 MHz, d₆-DMSO) δ 1.54-1.79 (5H, m), 2.55-2.58 (1H, m), 2.71-2.73 (1H, m), 4.62 (0.25H, s), 4.73 (0.75H, s), 5.04 (0.75H, s), 5.26 (0.25H, s), 5.43 (0.25H, d, J = 10.4 Hz), 5.65 (0.75H, dd, J = 10.4 Hz, 2.4 Hz), 5.84 (0.25H, dd, J = 16.4 Hz, 10.4 Hz), 6.03-6.19 (3H, m), 6.74 (0.75H, dd, J = 16.4 Hz, 10.4 Hz), 7.14 (1H, d, J = 5.2 Hz), 7.31 (1H, s), 7.71 (2H, dd, J = 8.0 Hz, 4.0 Hz), 7.90 (1H, d, J = 5.2 Hz), 8.13 (2H, d, J = 8.0 Hz), 8.25 (1H, s), 8.36 (1H, d, J = 5.2 Hz), 11.33 (1H, s). EM(calculated value): 513.2; MS(ESI) m/e (M + 1H)⁺: 514.2 |
| 71 | 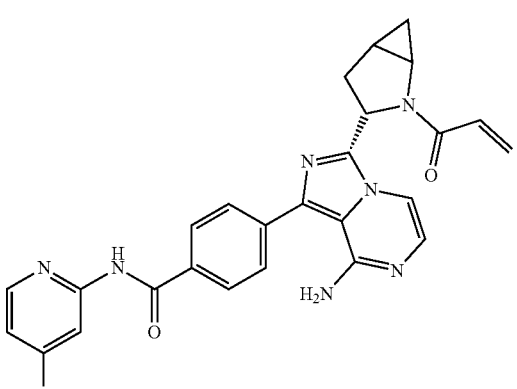 | ¹H NMR (400 MHz, d₆-DMSO) δ 0.37-0.39 (1H, m), 0.82-0.84 (1H, m), 0.92-0.94 (1H, m), 1.89-2.02 (2H, m), 3.17-3.19 (1H, m), 3.83-3.84 (0.3H, s), 4.02-4.05 (0.7H, s), 5.61-5.63 (1H, m), 5.85 (0.3H, dd, J = 16.8 Hz, 10.4 Hz), 6.06-6.17 (3H, m), 6.77 (0.7H, dd, J = 16.8 Hz, 10.4 Hz), 7.13 (1H, d, J = 5.2 Hz), 7.31 (1H, s), 7.75 (2H, dd, J = 8.0 Hz, 4.0 Hz), 7.88 (1H, d, J = 5.2 Hz), 8.14 (2H, d, J = 8.0 Hz), 8.25 (1H, s), 8.35 (1H, d, J = 5.2 Hz), 11.33 (1H, brs). EM(calculated value): 499.2; MS(ESI) m/e (M + 1H)⁺: 500.2 |
| 72 | 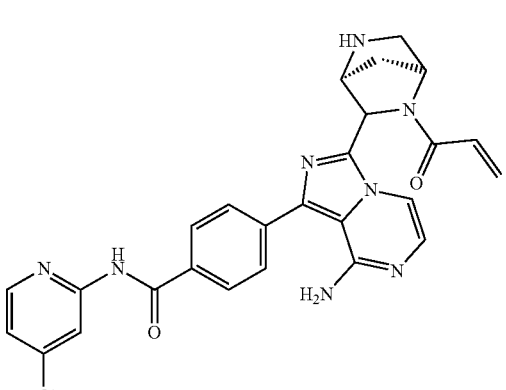 | ¹H NMR (400 MHz, d₆-DMSO) δ1.74-1.76 (1H, m), 2.01-2.03 (1H, m), 2.89-3.01 (2H, m), 3.72-3.75 (1H, m), 4.74-4.77 (1H, m), 5.25-5.28 (1H, m), 5.47-5.49 (0.4H, m), 5.65-5.70 (1H, m), 6.05-6.21 (3H, m), 6.80 (0.6H, dd, J = 16.8 Hz, 10.4 Hz), 7.13 (1H, d, J = 5.2 Hz), 7.34 (1H, s), 7.73 (2H, dd, J = 8.0 Hz, 4.0 Hz), 7.94 (1H, d, J = 5.2 Hz), 8.10 (2H, d, J = 8.0 Hz), 8.25 (1H, s), 8.36 (1H, d, J = 5.2 Hz), 11.37 (1H, s). EM(calculated value): 514.2; MS(ESI) m/e (M + 1H)⁺: 515.2 |

Example 73

Preparation of 1-((6S)-6-(8-amino-1-(4-(1-hydroxy-1-phenylethyl)phenyl)imidazo[1,5-a]pyrazin-3-yl)-5-azaspiro[2.4]heptan-5-yl)but-2-yn-1-one The synthesis steps are as follows:

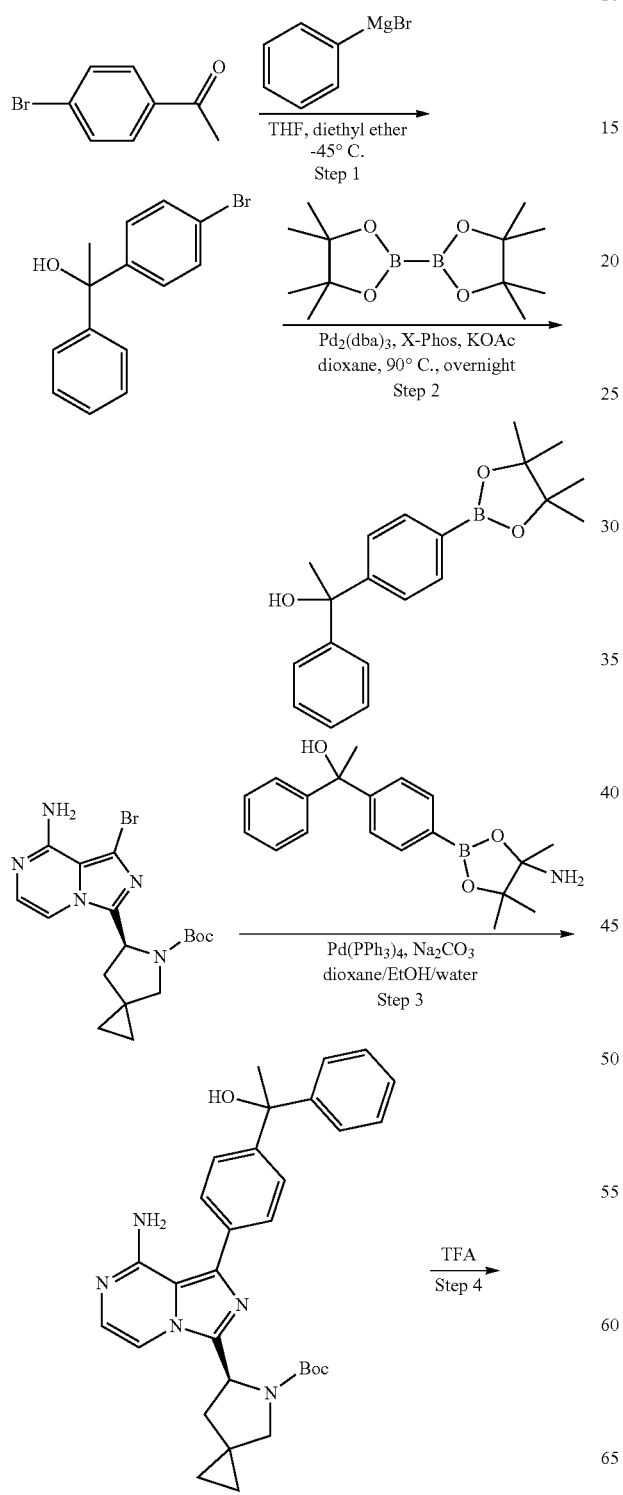

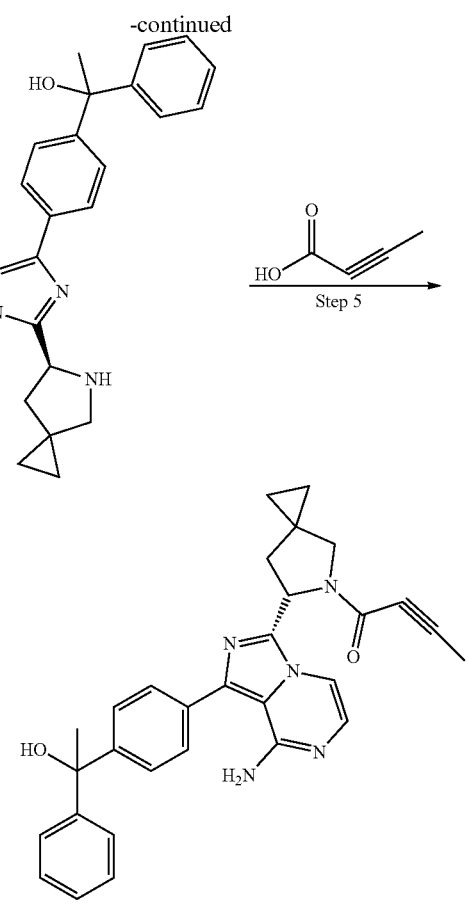

Example 73

Step 1: Preparation of 1-(4-bromophenyl)-1-phenylethanol

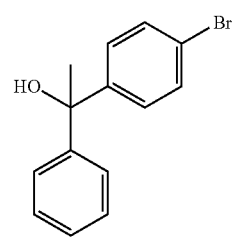 [SMILES: CC(O)(c1ccccc1)c1ccc(Br)cc1]

Under the protection of nitrogen, at −45° C., to a solution of 1-(4-bromophenyl)ethan-1-one (5 g, 25.13 mmol) in 30 mL of THF, phenylmagnesium bromide (10.05 mL, 30.15 mmol, 3M in Et20) was added dropwise. The reaction mixture reacted under stirring at −45° C. for 1 hour. After TLC showed the raw materials reacted completely, the reaction was quenched by adding saturated NH$_4$Cl slowly and stirred to react for 0.5 hours. The aqueous phase was extracted with EA (30 mL×3), and the organic phase was pooled then backwashed with saturated brine, thoroughly dried with anhydrous Na$_2$SO$_4$, evaporated under vacuum and purified by column chromatography (PE/EA=60/1-10/1) to obtain 5.8 g of the target compound.

Step 2: Preparation of 1-phenyl-1-(4-(4,4,5,5-tetramethyl-1,3,2-dioxaborolan-2-yl)phenyl)ethanol

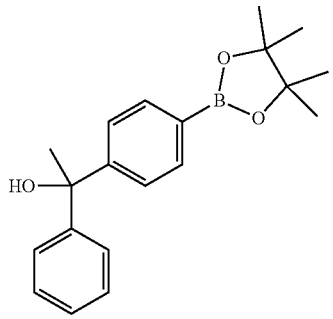 [SMILES: CC(O)(c1ccccc1)c1ccc(B2OC(C)(C)C(C)(C)O2)cc1]

Under the protection of nitrogen, to a solution of 1-(4-bromophenyl)-1-phenylethanol (5.2 g, 18.76 mmol), bis(pinacolato)diboron (6.19 g, 24.39 mmol), KOAc (3.68 g, 37.52 mmol) and X-Phos (894.2 mg, 1.876 mmol) in 30 mL of dioxane solution, $Pd_2(dba)_3$ (858.9 mg, 0.938 mmol) was added. The reaction mixture reacted under stirring at 90° C. overnight. After TLC showed the raw materials reacted completely, the reaction mixture was quenched with water and extracted with EA (20 mL×3). The organic phase was backwashed with saturated brine, dried with anhydrous $Na_2SO_4$, evaporated under vacuum and then purified by column chromatography (PE/EA=60/1-10/1) to obtain 4.8 g of the target compound which was an off-white solid.

Step 3: Preparation of (6S)-6-(8-amino-1-(4-(1-hydroxy-1-phenylethyl)phenyl)imidazo[1,5-a]pyrazin-3-yl)-5-azaspiro[2.4]heptane-5-carboxylate

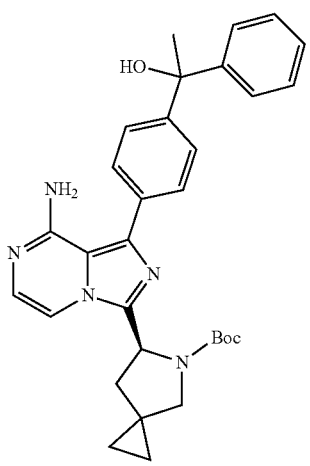 [SMILES: CC(C)(C)OC(=O)N1CC2(CC2)C[C@H]1c1nc(-c2ccc(C(C)(O)c3ccccc3)cc2)c2c(N)nccn12]

Under the protection of nitrogen, to a mixed solution of (S)-tert-butyl 6-(8-amino-1-bromoimidazo[1,5-a]pyrazin-3-yl)-5-azaspiro[2.4]heptane-5-carboxylate (1 g, 2.45 mmol), 1-phenyl-1-(4-(4,4,5,5-tetramethyl-1,3,2-dioxaborolan-2-yl)phenyl)ethanol (872.2 mg, 2.69 mmol), $Na_2CO_3$ (519.4 mg, 4.9 mmol) in dioxane/EtOH/water (12 mL/4 mL/4 mL), $Pd(PPh_3)_4$ (141.56 mg, 0.1225) was added. The reaction mixture reacted under stirring at 90° C. overnight. After TLC showed the raw materials reacted completely, the reaction solution was quenched with water and extracted with EA (10 mL×3). The organic phase was backwashed with saturated brine, dried with anhydrous $Na_2SO_4$, evaporated under vacuum and then purified by column chromatography (DCM/MeOH=60/1-30/1) to obtain 837.1 mg of the target compound which was a light yellow solid.

Step 4: Preparation of 1-(4-(8-amino-3-((S)-5-azaspiro[2.4]heptan-6-yl)imidazo[1,5-a]pyrazin-1-yl) phenyl)-1-phenylethanol

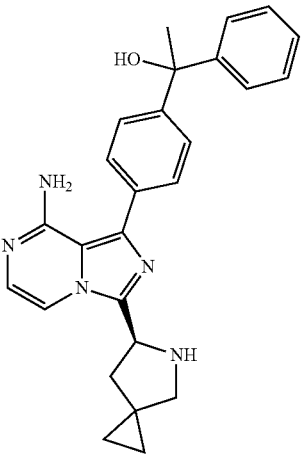 [SMILES: CC(O)(c1ccccc1)c1ccc(-c2nc([C@@H]3CC4(CC4)CN3)n3ccnc(N)c23)cc1]

At room temperature, to a solution of (6S)-6-(8-amino-1-(4-(1-hydroxy-1-phenylethyl)phenyl)imidazo[1,5-a]pyrazin-3-yl)-5-azaspiro[2.4]heptane-5-carboxylate (837 mg, 1.59 mmol) in 15 mL DCM, TFA (1 mL) was slowly added dropwise. The reaction mixture was stirred at room temperature for 3 hours. After TLC showed the raw materials reacted completely, the reaction system was concentrated, and the pH of the concentrated system was adjusted to 8 with $Na_2CO_3$ (3 mol/L) and the obtained system was extracted with DCM/MeOH (10/1). The organic phase was dried with anhydrous $Na_2SO_4$, evaporated under vacuum to obtain 642.8 mg of the target compound which was a white solid.

107

Step 5: Preparation of 1-((6S)-6-(8-amino-1-(4-(1-hydroxy-1-phenylethyl)phenyl)imidazo[1,5-a]pyrazin-3-yl)-5-azaspiro[2.4]heptan-5-yl)but-2-yn-1-one

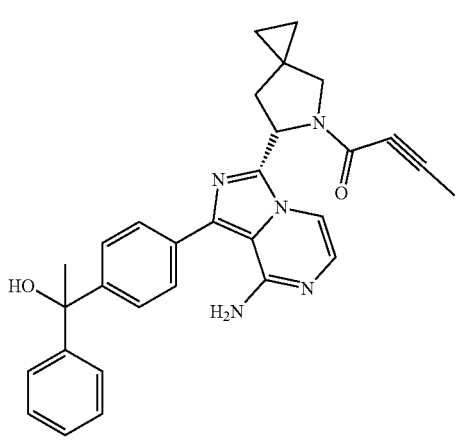

Under the protection of nitrogen, to a solution of 1-(4-(8-amino-3-((S)-5-azaspiro[2.4]heptan-6-yl)imidazo[1,5-a]pyrazin-1-yl) phenyl)-1-phenylethanol (80 mg, 0.188 mmol), 2-butynoic acid (19 mg, 0.226 mmol), DIPEA (72.8 mg, 0.564 mmol) in DMF (3 mL), HBTU (85.7 mg, 0.226 mmol) was added. The reaction mixture reacted under stirring at room temperature for 2 hours. After TLC showed the raw materials reacted completely, the reaction system was quenched with water and extracted with EA (15 mL×3). The organic phase was backwashed with saturated brine, dried with anhydrous $Na_2SO_4$, evaporated under vacuum and then purified by preparative silica gel plate (DCM/MeOH=15/1) to obtain 20 mg of the target compound which was a yellow solid.

The structure of the product was characterized by nuclear magnetic resonance and mass spectrometry and the results were as follows:

$^1$H NMR (400 MHz, $d_6$-DMSO) δ 0.55-0.73 (4H, m), 1.58 (1H, s), 1.90 (3H, s), 2.01 (2H, s), 2.25-2.32 (2H, m), 3.52 (0.3H, d, J=16.4 Hz), 3.62-3.65 (0.3H, m), 3.73 (0.7H, d, J=10.8 Hz), 3.82 (0.7H, d, J=10.8 Hz), 5.57-5.59 (1H, m), 5.71 (1H, s), 6.10-6.20 (2H, m), 7.08 (1H, d, J=4.8 Hz), 7.12-7.18 (1H, m), 7.27-7.33 (2H, m), 7.44-7.55 (6H, m), 7.78 (0.3H, d, J=4.8 Hz), 7.86 (0.7H, d, J=4.8 Hz).

EM (calculated value): 491.2; MS (ESI) m/e (M+1H)+: 492.2

It can be seen that the compound prepared by the present application has the same structure as the compound above.

108

Example 74

Preparation of 1-((6S)-6-(8-amino-1-(4-(1-hydroxy-1-phenylethyl)phenyl)imidazo[1,5-a]pyrazin-3-yl)-5-azaspiro[2.4]heptan-5-yl)prop-2-en-1-one

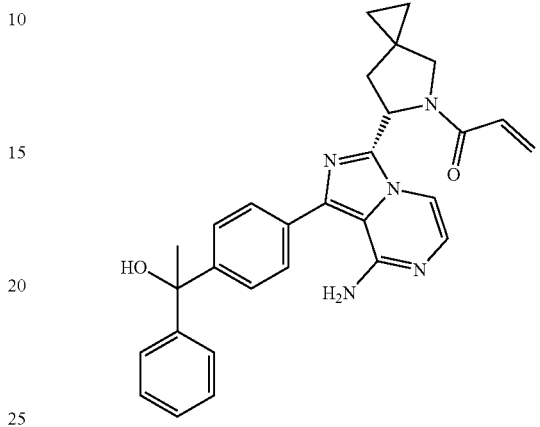

Under the protection of nitrogen, to a solution of 1-(4-(8-amino-3-((S)-5-azaspiro[2.4]heptan-6-yl)imidazo[1,5-a]pyrazin-1-yl) phenyl)-1-phenylethanol (80 mg, 0.188 mmol), TEA (94.9 mg, 0.94 mmol) in DCM (10 mL), 3-chloropropionyl chloride (23.9 mg, 0.188 mmol) was added dropwise at 0° C. The reaction mixture reacted under stirring at room temperature overnight. After TLC showed the raw materials reacted completely, the reaction system was quenched with water and extracted with EA (10 mL×3). The organic phase was dried with anhydrous $Na_2SO_4$, evaporated under vacuum and then purified by preparative silica gel plate (DCM/MeOH=15/1) to obtain 15 mg of the target compound which was a yellow solid.

The structure of the product was characterized by nuclear magnetic resonance and mass spectrometry and the results were as follows:

$^1$H NMR (400 MHz, $d_6$-DMSO) δ 0.58-0.73 (4H, m), 1.91 (3H, s), 2.22-2.32 (2H, m), 3.50-3.67 (0.6H, m), 3.75-3.80 (1.4H, d, J=10.8 Hz), 5.57-5.60 (1H, m), 5.65-5.67 (1H, m), 5.71 (1H, s), 6.08-6.20 (3H, m), 6.76 (1H, dd, J=16.8 Hz, 10.4 Hz), 7.06 (1H, d, J=4.8 Hz), 7.10-7.18 (1H, m), 7.28-7.33 (2H, m), 7.46-7.55 (6H, m), 7.77 (0.4H, d, J=4.8 Hz), 7.86 (0.6H, d, J=4.8 Hz).

EM (calculated value): 479.2; MS (ESI) m/e (M+1H)+: 480.2

It can be seen that the compound prepared by the present application has the same structure as the compound above.

Examples 75-91

The following compounds were prepared by the preparation method of Example 73 or Example 74 using compounds with similar structures as the starting materials. The structures and nuclear magnetic characterization data of the compounds are shown in Table 4. Table 4 summarizes the structures and structural analysis data of the compounds prepared in Examples 75 to 91 of the present application.

TABLE 4

Summary of structures and structural analysis data of the compounds prepared in Examples 75-91

| Examples | Structures | Analysis data |
|---|---|---|
| 75 | 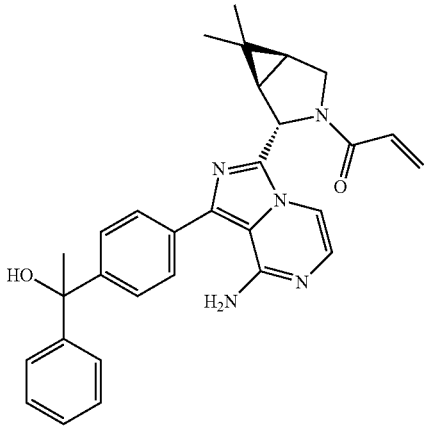 [SMILES: C=CC(=O)N1C[C@H]2[C@@H]([C@H]1c1nc(-c3ccc(C(C)(O)c4ccccc4)cc3)c3c(N)nccn13)C2(C)C] | ¹H NMR (400 MHz, d₆-DMSO) δ 1.00-1.07 (6H, m), 1.49-1.54 (1H, m), 1.64-1.65 (0.3H, m), 1.73-1.77 (0.7H, m), 1.92 (3H, s), 3.71-3.73 (0.3H, m), 3.77-3.81 (0.7H, m), 3.87-3.90 (0.3H, m), 4.04-4.08 (0.7H, m), 5.40 (0.7H, s), 5.51-5.52 (0.3H, m), 5.60 (0.3H, s), 5.66-5.70 (0.7H, m), 5.71 (1H, s), 6.03-6.20 (3H, m), 6.36 (0.3H, dd, J = 16.8 Hz, 10.4 Hz), 6.58 (0.7H, dd, J = 16.8 Hz, 10.4 Hz), 7.08 (1H, d, J = 4.8 Hz), 7.10-7.22 (1H, m), 7.29-7.33 (2H, m), 7.47-7.54 (6H, m), 7.76 (0.3H, d, J = 4.8 Hz), 7.87 (0.7H, d, J = 4.8 Hz). EM(calculated value): 493.2; MS(ESI) m/e (M + 1H)⁺: 494.3 |
| 76 | 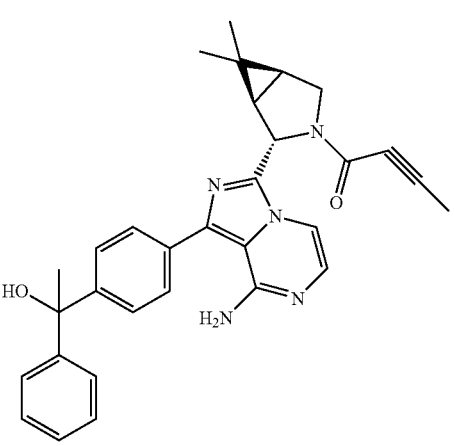 [SMILES: CC#CC(=O)N1C[C@H]2[C@@H]([C@H]1c1nc(-c3ccc(C(C)(O)c4ccccc4)cc3)c3c(N)nccn13)C2(C)C] | ¹H NMR (400 MHz, d₆-DMSO) δ 1.02-1.07 (6H, m), 1.49-1.53 (2H, m), 1.63-1.65 (0.3H, m), 1.73-1.77 (0.7H, m), 1.90 (3H, s), 2.06 (2H, s), 3.71-3.72 (0.3H, m), 3.77-3.83 (0.7H, m), 3.87-3.90 (0.3H, m), 4.04-4.07 (0.7H, m), 5.41 (0.7H, s), 5.51-5.52 (0.3H, m), 5.71 (1H, s), 6.03-6.19 (2H, m), 7.07 (1H, d, J = 4.8 Hz), 7.12-7.20 (1H, m), 7.29-7.32 (2H, m), 7.46-7.53 (6H, m), 7.76-7.86 (1H, m). EM(calculated value): 505.2; MS(ESI) m/e (M + 1H)⁺: 506.3 |
| 77 | 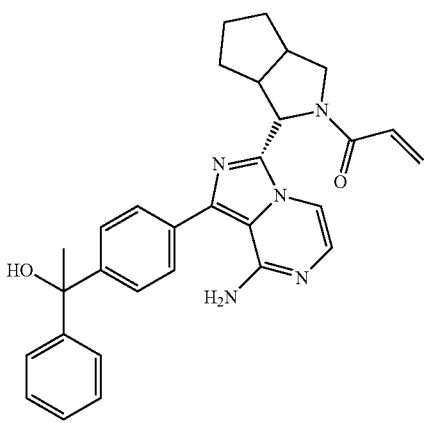 | ¹H NMR (400 MHz, d₆-DMSO) δ 1.45-1.62 (3H, m), 1.74-1.80 (1H, m), 1.80-2.01 (5H, m), 2.66-2.69 (1H, m), 2.90-2.93 (1H, m), 3.64-3.66 (1H, m), 3.90-3.93 (1H, m), 5.45 (1H, d, J = 2.0 Hz), 5.67-5.72 (2H, m), 6.08-6.18 (3H, m), 6.74 (1H, dd, J = 16.8 Hz, 10.4 Hz), 7.08 (1H, d, J = 4.8 Hz), 7.10-7.19 (1H, m), 7.29-7.33 (2H, m), 7.46-7.55 (6H, m), 7.85 (1H, d, J = 4.8 Hz). EM(calculated value): 493.2; MS(ESI) m/e (M + 1H)⁺: 494.2 |

TABLE 4-continued

Summary of structures and structural analysis data of the compounds prepared in Examples 75-91

| Examples | Structures | Analysis data |
|---|---|---|
| 78 | 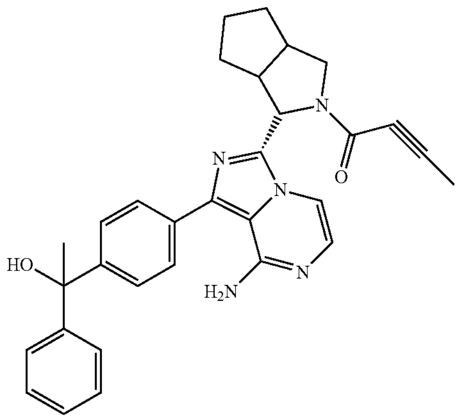 | $^1$H NMR (400 MHz, d$_6$-DMSO) δ 1.42-1.63 (4H, m), 1.74-1.79 (1H, m), 1.80-2.05 (7H, m), 2.66-2.68 (1H, m), 2.90-2.94 (1H, m), 3.63-3.67 (1H, m), 3.91-3.93 (1H, m), 5.44 (1H, d, J = 2.0 Hz), 5.69 (1H, s), 6.08-6.20 (2H, m), 7.06 (1H, d, J = 4.8 Hz), 7.08-7.18 (1H, m), 7.29-7.32 (2H, m), 7.47-7.53 (6H, m), 7.86 (1H, d, J = 4.8 Hz). EM(calculated value): 505.2; MS(ESI) m/e (M + 1H)$^+$: 506.2 |
| 79 | 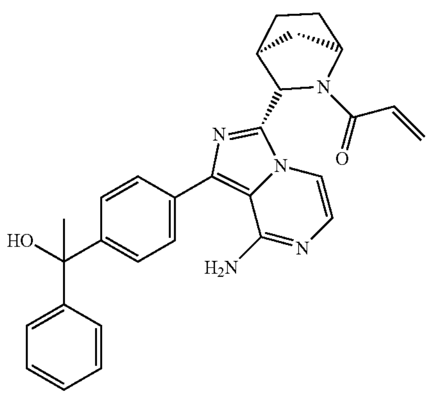 | $^1$H NMR (400 MHz, d$_6$-DMSO) δ 1.45-1.55 (2H, m), 1.74-1.82 (3H, m), 1.91 (3H, s), 2.57-2.59 (1H, m), 2.67-2.70 (1H, m), 4.65 (0.2H, s), 4.73 (0.8H, s), 5.04 (0.2H, s), 5.23 (0.8H, s), 5.44-5.46 (0.2H, m), 5.65-5.72 (1.8H, m), 5.85 (0.2H, dd, J = 16.8 Hz, 10.4 Hz), 6.06-6.18 (3H, m), 6.75 (0.8H, dd, J = 16.8 Hz, 10.4 Hz), 7.07 (1H, d, J = 4.8 Hz), 7.12-7.20 (1H, m), 7.28-7.32 (2H, m), 7.46-7.55 (6H, m), 7.78 (0.2H, d, J = 4.8 Hz), 7.87 (0.8H, d, J = 4.8 Hz). EM(calculated value): 479.2; MS(ESI) m/e (M + 1H)$^+$: 480.2 |
| 80 | 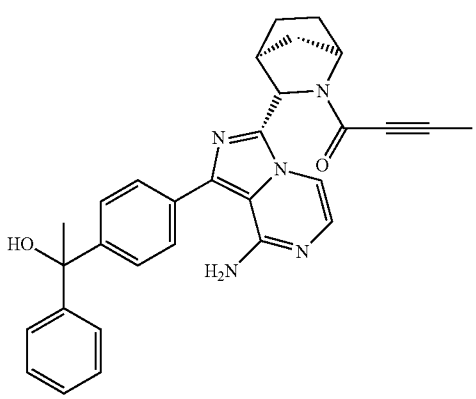 | $^1$H NMR (400 MHz, d$_6$-DMSO) δ 1.49-1.58 (3H, m), 1.74-1.80 (3H, m), 1.92 (3H, s), 2.05 (2H, s), 2.57-2.60 (1H, m), 2.67-2.71 (1H, m), 4.65 (0.2H, s), 4.72 (0.8H, s), 5.04 (0.2H, s), 5.24 (0.8H, s), 5.44-5.45 (0.2H, m), 5.72 (1H, s), 6.06-6.15 (2H, m), 7.06 (1H, d, J = 4.8 Hz), 7.13-7.22 (1H, m), 7.27-7.32 (2H, m), 7.48-7.56 (6H, m), 7.77 (0.2H, d, J = 4.8 Hz), 7.86 (0.8H, d, J = 4.8 Hz). EM(calculated value): 491.2; MS(ESI) m/e (M + 1H)$^+$: 492.2 |

TABLE 4-continued

Summary of structures and structural analysis data of the compounds prepared in Examples 75-91

| Examples | Structures | Analysis data |
|---|---|---|
| 81 | 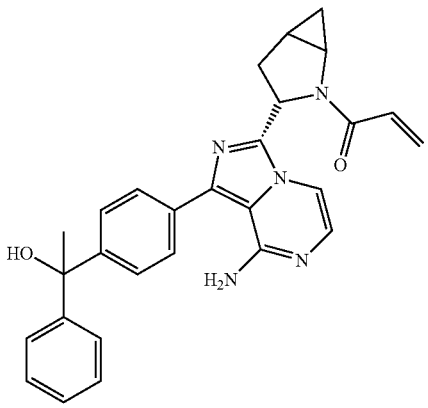 | $^1$H NMR (400 MHz, d$_6$-DMSO) δ 0.37-0.39 (1H, m), 0.81-0.83 (1H, m), 0.92-0.94 (1H, m), 1.89-2.05 (5H, m), 3.16-3.19 (1H, m), 3.83-3.85 (0.3H, s), 4.03-4.07 (0.7H, s), 5.60-5.64 (1H, m), 5.71 (1H, s), 5.84 (0.3H, dd, J = 16.8 Hz, 10.4 Hz), 6.06-6.19 (3H, m), 6.76 (0.7H, dd, J = 16.8 Hz, 10.4 Hz), 7.05 (1H, d, J = 4.8 Hz), 7.15-7.18 (1H, m), 7.29-7.35 (2H, m), 7.47-7.55 (6H, m), 7.78 (0.3H, d, J = 4.8 Hz), 7.85 (0.7H, d, J = 4.8 Hz). EM(calculated value): 465.2; MS(ESI) m/e (M + 1H)$^+$: 66.2 |
| 82 | 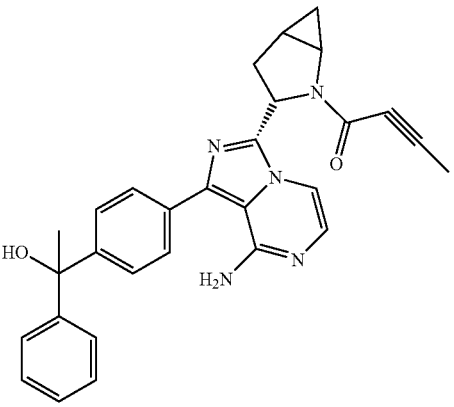 | $^1$H NMR (400 MHz, d$_6$-DMSO) δ 0.39-0.40 (1H, m), 0.81-0.82 (1H, m), 0.94-0.96 (1H, m), 1.52 (1H, s), 1.89-2.07 (7H, m), 3.17-3.19 (1H, m), 3.82-3.85 (0.3H, s), 4.03-4.06 (0.7H, s), 5.70 (1H, s), 6.06-6.15 (2H, m), 7.07 (1H, d, J = 4.8 Hz), 7.15-7.22 (1H, m), 7.26-7.32 (2H, m), 7.47-7.55 (6H, m), 7.77 (0.3H, d, J = 4.8 Hz), 7.85 (0.7H, d, J = 4.8 Hz). EM(calculated value): 477.2; MS(ESI) m/e (M + 1H)$^+$: 478.2 |
| 83 | 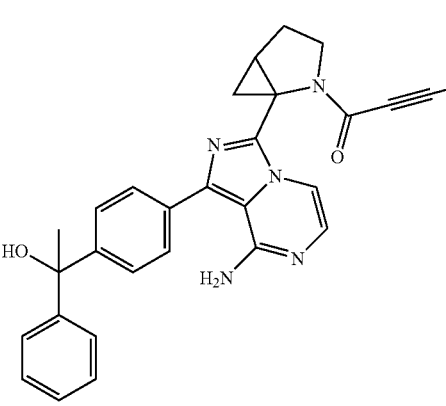 | $^1$H NMR (400 MHz, d$_6$-DMSO) δ 0.78-0.80 (1H, m), 0.92-0.93 (1H, m), 1.29-1.72 (4H, m), 1.92 (3H, s), 2.02 (2H, s), 3.84-3.88 (1.25H, s), 4.03-4.07 (0.75H, s), 5.70 (1H, s), 6.03-6.16 (2H, m), 7.07 (1H, d, J = 4.8 Hz), 7.12-7.19 (1H, m), 7.28-7.31 (2H, m), 7.46-7.54 (6H, m), 7.78 (0.25H, d, J = 4.8 Hz), 7.86 (0.75H, d, J = 4.8 Hz). EM(calculated value): 477.2; MS(ESI) m/e (M + 1H)$^+$: 478.2 |

TABLE 4-continued

Summary of structures and structural analysis data of the compounds prepared in Examples 75-91

| Examples | Structures | Analysis data |
|---|---|---|
| 84 | 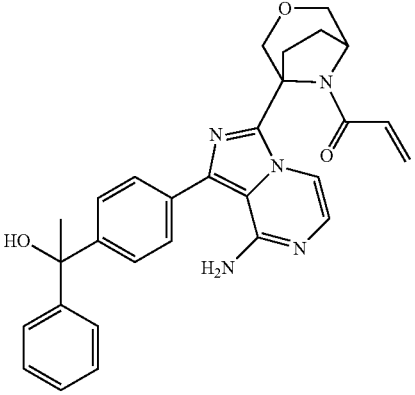 [SMILES: C=CC(=O)N1C2CCC1(c1nc(-c3ccc(C(C)(O)c4ccccc4)cc3)c3c(N)nccn13)COC2] | $^1$H NMR (400 MHz, d$_6$-DMSO) δ 1.75-1.79 (1H, m), 1.92-2.07 (6H, m), 3.40-3.60 (4H, m), 3.98-4.01 (1H, m), 5.66-5.70 (2H, m), 6.09-6.20 (3H, m), 6.70-6.74 (1H, m), 7.06 (1H, d, J = 4.8 Hz), 7.14-7.21 (1H, m), 7.26-7.31 (2H, m), 7.46-7.53 (6H, m), 7.85-7.87 (1H, m). EM(calculated value): 495.2; MS(ESI) m/e (M + 1H)$^+$: 496.2 |
| 85 | 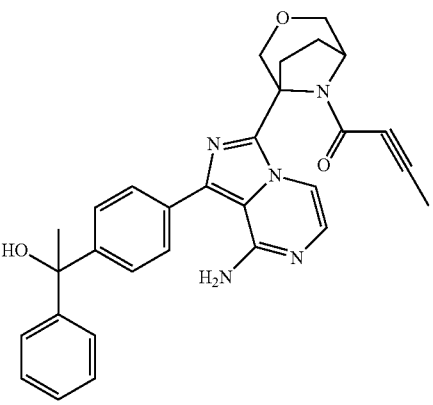 [SMILES: CC#CC(=O)N1C2CCC1(c1nc(-c3ccc(C(C)(O)c4ccccc4)cc3)c3c(N)nccn13)COC2] | $^1$H NMR (400 MHz, d$_6$-DMSO) δ 1.53 (1H, s), 1.75-1.78 (1H, m), 1.93-2.08 (8H, m), 3.44-3.60 (4H, m), 3.98-4.01 (1H, m), 5.66-5.69 (1H, m), 6.09-6.17 (2H, m), 7.07 (1H, d, J = 4.8 Hz), 7.14-7.21 (1H, m), 7.27-7.31 (2H, m), 7.48-7.53 (6H, m), 7.86-7.87 (1H, m). EM(calculated value): 507.2; MS(ESI) m/e (M + 1H)$^+$: 508.2 |
| 86 | 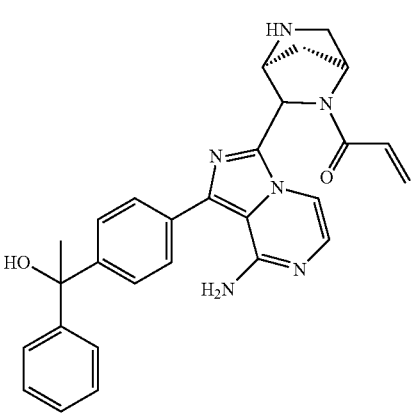 | $^1$H NMR (400 MHz, d$_6$-DMSO) δ 1.73-1.76 (1H, m), 1.95 (3H, s), 2.00-2.03 (1H, m), 2.90-3.01 (2H, m), 3.72-3.73 (1H, m), 4.75-4.77 (1H, m), 5.24-5.28 (1H, m), 5.45-5.47 (0.4H, m), 5.66-5.72 (2H, m), 6.05-6.21 (3H, m), 6.82 (0.6H, dd, J = 16.8 Hz, 10.4 Hz), 7.06 (1H, d, J = 4.8 Hz), 7.12-7.20 (1H, m), 7.28-7.32 (2H, m), 7.47-7.53 (6H, m), 7.86 (1H, d, J = 4.8 Hz). |

TABLE 4-continued

Summary of structures and structural analysis data of the compounds prepared in Examples 75-91

| Examples | Structures | Analysis data |
|---|---|---|
| 87 | 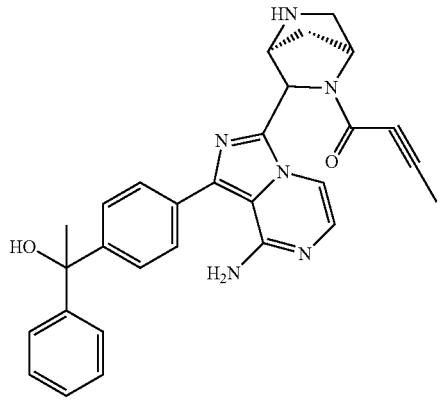 | $^1$H NMR (400 MHz, d$_6$-DMSO) δ 1.55 (1H, s), 1.72-1.74 (1H, m), 1.93 (3H, s), 2.01-2.06 (3H, m), 2.88-3.02 (2H, m), 3.68-3.71 (1H, m), 4.72-4.75 (1H, m), 5.26-5.30 (1H, m), 5.69 (1H, s), 6.08-6.22 (2H, m), 7.07 (1H, d, J = 4.8 Hz), 7.12-7.21 (1H, m), 7.28-7.33 (2H, m), 7.45-7.53 (6H, m), 7.87 (1H, d, J = 4.8 Hz). EM(calculated value): 492.2; MS(ESI) m/e (M + 1H)$^+$: 493.2 |
| 88 | 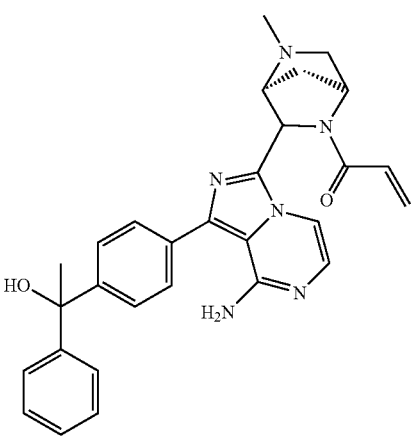 | $^1$H NMR (400 MHz, d$_6$-DMSO) δ 1.50-1.52 (1H, m), 1.78-1.81 (1H, m), 1.92 (3H, s), 2.33-2.35 (3H, m), 3.34-3.36 (1H, m), 3.47-3.51 (2H, m), 3.66-3.67 (1H, m), 4.94 (0.6H, s), 5.00 (0.4H, s), 5.44-5.46 (0.4H, m), 5.65-5.69 (1.6H, m), 5.84 (0.4H, dd, J = 16.8 Hz, 10.4 Hz), 6.04-6.13 (3H, m), 6.71 (0.6H, dd, J = 16.8 Hz, 10.4 Hz), 7.06 (1H, d, J = 4.8 Hz), 7.10-7.21 (1H, m), 7.27-7.32 (2H, m), 7.47-7.54 (6H, m), 7.78 (0.4H, d, J = 4.8 Hz), 7.87 (0.6H, d, J = 4.8 Hz). EM(calculated value): 494.2; MS(ESI) m/e (M + 1H)$^+$: 495.2 |
| 89 | 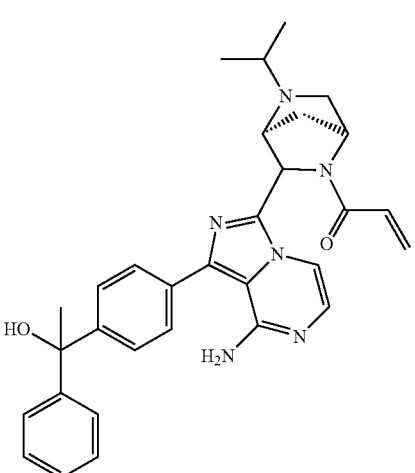 | $^1$H NMR (400 MHz, d$_6$-DMSO) δ 1.18-1.21 (6H, m), 1.50-1.53 (1H, m), 1.78-1.83 (1H, m), 1.91 (3H, s), 2.84-2.86 (1H, m), 3.33-3.36 (1H, m), 3.46-3.51 (2H, m), 3.66-3.67 (1H, m), 4.92 (0.6H, s), 4.98 (0.4H, s), 5.45-5.46 (0.4H, m), 5.66-5.69 (1.6H, m), 5.84 (0.4H, dd, J = 16.8 Hz, 10.4 Hz), 6.08-6.16 (3H, m), 6.71 (0.6H, dd, J = 16.8 Hz, 10.4 Hz), 7.08 (1H, d, J = 4.8 Hz), 7.12-7.21 (1H, m), 7.28-7.34 (2H, m), 7.47-7.53 (6H, m), 7.77 (0.4H, d, J = 4.8 Hz), 7.87 (0.6H, d, J = 4.8 Hz). EM(calculated value): 522.3; MS(ESI) m/e (M + 1H)$^+$: 523.3 |

TABLE 4-continued

Summary of structures and structural analysis data of the compounds prepared in Examples 75-91

| Examples | Structures | Analysis data |
|---|---|---|
| 90 | 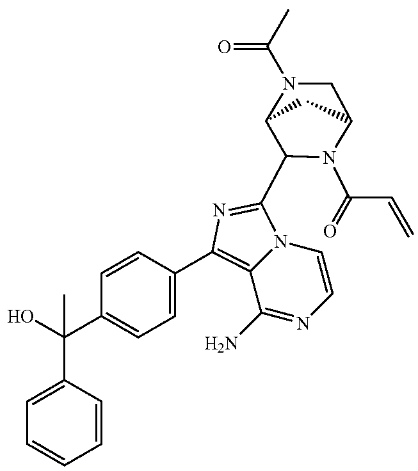 | $^1$H NMR (400 MHz, d$_6$-DMSO) δ 1.50-1.53 (1H, m), 1.79-1.81 (1H, m), 1.93 (3H, s), 2.45 (3H, s), 3.34-3.36 (1H, m), 3.48-3.51 (2H, m), 3.65-3.67 (1H, m), 4.95 (0.6H, s), 5.00 (0.4H, s), 5.45-5.46 (0.4H, m), 5.65-5.68 (1.6H, m), 5.84 (0.4H, dd, J = 16.8 Hz, 10.4 Hz), 6.04-6.18 (3H, m), 6.71 (0.6H, dd, J = 16.8 Hz, 10.4 Hz), 7.06 (1H, d, J = 4.8 Hz), 7.10-7.20 (1H, m), 7.28-7.31 (2H, m), 7.49-7.56 (6H, m), 7.78 (0.4H, d, J = 4.8 Hz), 7.88 (0.6H, d, J = 4.8 Hz). EM(calculated value): 522.2; MS(ESI) m/e (M + 1H)$^+$: 523.2 |
| 91 | 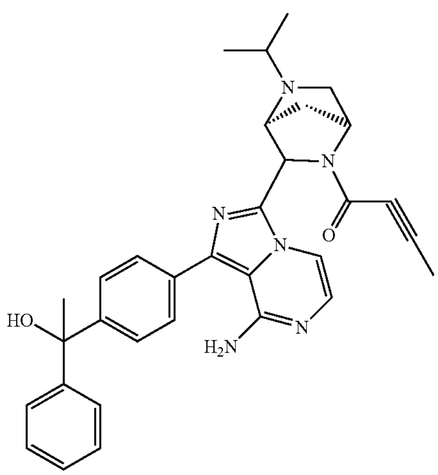 | $^1$H NMR (400 MHz, d$_6$-DMSO) δ 1.18-1.22 (6H, m), 1.50-1.55 (2H, m), 1.79-1.83 (1H, m), 1.92 (3H, s), 2.03 (2H, s), 2.84-2.86 (1H, m), 3.33-3.35 (1H, m), 3.46-3.53 (2H, m), 3.66-3.67 (1H, m), 4.93 (0.6H, s), 4.98 (0.4H, s), 5.45-5.46 (0.4H, m), 5.66-5.69 (0.6H, m), 6.08-6.19 (2H, m), 7.07 (1H, d, J = 4.8 Hz), 7.12-7.21 (1H, m), 7.26-7.32 (2H, m), 7.47-7.54 (6H, m), 7.76 (0.4H, d, J = 4.8 Hz), 7.87 (0.6H, d, J = 4.8 Hz). EM(calculated value): 534.3; MS(ESI) m/e (M + 1H)$^+$: 535.3 |

Example 92

Preparation of (S)-1-(6-(8-amino-1-(4-phenoxyphenyl)imidazo[1,5-a]pyrazin-3-yl)-5-azaspiro[2.4]heptan-5-yl) but-2-yn-1-one The synthesis steps are as follows:

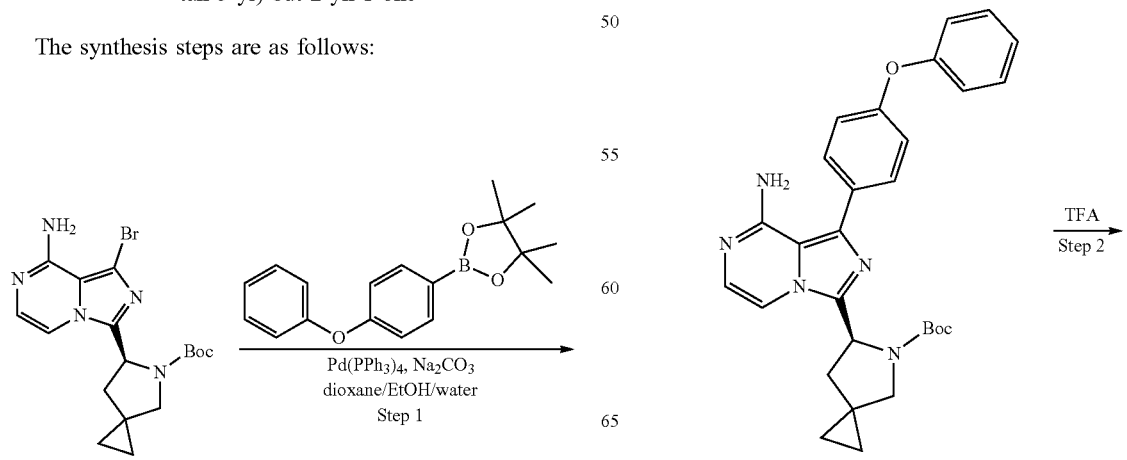

-continued

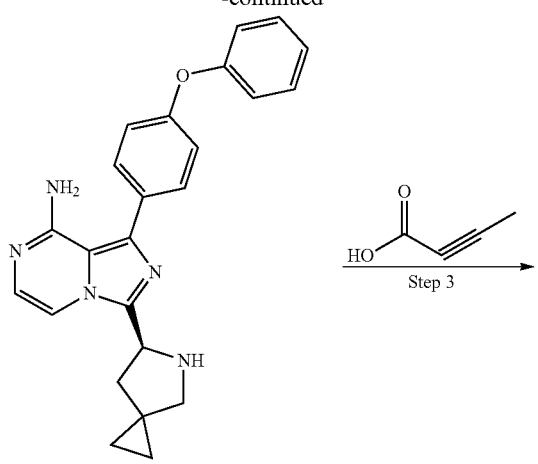

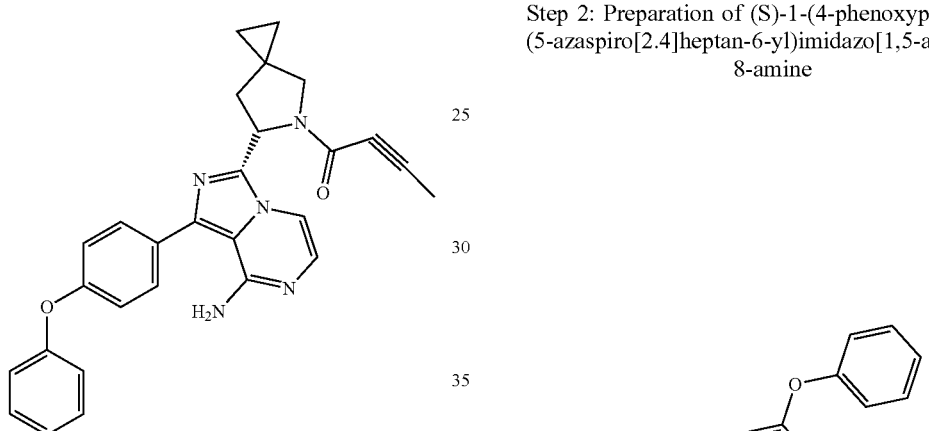

Example 92

Step 1: Preparation of (S)-tert-butyl 6-(8-amino-1-(4-phenoxyphenyl)imidazo[1,5-a]pyrazin-3-yl)-5-azaspiro[2.4]heptane-5-carboxylate

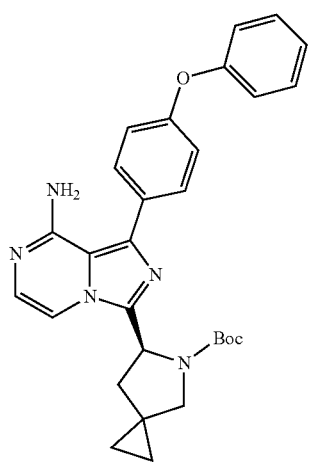 [SMILES: CC(C)(C)OC(=O)N1CC2(CC2)C[C@H]1c1nc(-c2ccc(Oc3ccccc3)cc2)c2c(N)nccn12]

Under the protection of nitrogen, to a mixed solution of (S)-tert-butyl 6-(8-amino-1-bromoimidazo[1,5-a]pyrazin-3-yl)-5-azaspiro[2.4]heptane-5-carboxylate (1 g, 2.45 mmol), 4,4,5,5-tetramethyl-2-(4-phenoxyphenyl)-1,3,2-dioxaborolan (796.7 mg, 2.69 mmol), $Na_2CO_3$ (519.4 mg, 4.9 mmol) in dioxane/EtOH/water (12 mL/4 mL/4 mL), $Pd(PPh_3)_4$ (141.56 mg, 0.1225 mmol) was added. The reaction mixture reacted under stirring at 90° C. for 3 hours. After TLC showed the raw materials reacted completely, the reaction solution was quenched with water and extracted with EA (10 mL×3). The organic phase was backwashed with saturated brine, dried with anhydrous $Na_2SO_4$, evaporated under vacuum and purified by column chromatography (DCM/MeOH=60/1-30/1) to obtain 865.6 mg of the target compound which was a light yellow solid.

Step 2: Preparation of (S)-1-(4-phenoxyphenyl)-3-(5-azaspiro[2.4]heptan-6-yl)imidazo[1,5-a]pyrazin-8-amine At room temperature, to a solution of (S)-tert-butyl 6-(8-amino-1-(4-phenoxyphenyl)imidazo[1,5-a]pyrazin-3-yl)-5-azaspiro[2.4]heptane-5-carboxylate (865 mg, 1.74 mmol) in 15 mL of DCM, TFA (1 mL) was slowly added. The reaction mixture was stirred at room temperature for 3 hours. After TLC showed the raw materials reacted completely, the reaction system was concentrated, and the pH of the concentrated system was adjusted to 8 with $Na_2CO_3$ (3 mol/L), the obtained system was extracted with DCM/MeOH (10/1). The organic phase was dried with anhydrous $Na_2SO_4$, evaporated under vacuum to obtain 690 mg of the target compound which was a white solid.

Step 3: Preparation of (S)-1-(6-(8-amino-1-(4-phenoxyphenyl)imidazo[1,5-a]pyrazin-3-yl)-5-azaspiro[2.4]heptan-5-yl)but-2-yn-1-one

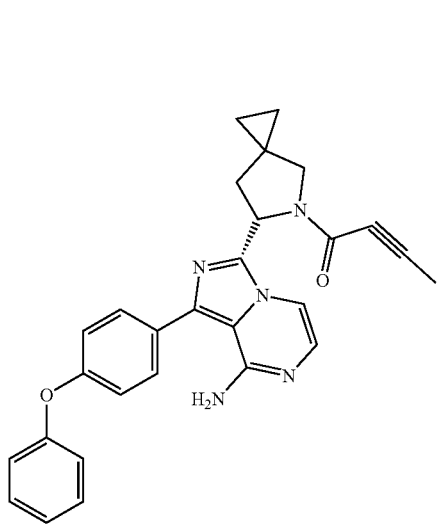

Under the protection of nitrogen, to a solution of (S)-1-(4-phenoxyphenyl)-3-(5-azaspiro[2.4]heptan-6-yl)imidazo[1,5-a]pyrazin-8-amine (80 mg, 0.20 mmol), 2-butynoic acid (20.2 mg, 0.24 mmol), DIPEA (77.4 mg, 0.60 mmol) in DMF (3 mL), HBTU (91 mg, 0.24 mmol) was added. The reaction mixture reacted under stirring at room temperature for 2 hours. After TLC showed the raw materials reacted completely, the reaction system was quenched with water and extracted with EA (15 mL×3). The organic phase was backwashed with saturated brine, dried with anhydrous Na$_2$SO$_4$, evaporated under vacuum and purified by preparative silica gel plate (DCM/MeOH=25/1) to obtain 30 mg of the target compound which was a white solid.

The structure of the product was characterized by nuclear magnetic resonance and mass spectrometry and the results were as follows:

$^1$H NMR (400 MHz, d$_6$-DMSO) δ 0.55-0.76 (4H, m), 1.58 (1H, s), 2.00 (2H, s), 2.26-2.33 (2H, m), 3.51 (0.4H, d, J=16.4 Hz), 3.63 (0.4H, d, J=11.6 Hz), 3.70 (0.6H, d, J=10.8 Hz), 3.84 (0.6H, d, J=10.8 Hz), 5.57-5.59 (0.6H, m), 5.77-5.82 (0.4H, m), 6.14-6.21 (2H, m), 7.03-7.19 (6H, m), 7.41-7.44 (2H, m), 7.57-7.61 (2H, m), 7.82 (0.6H, d, J=5.2 Hz), 7.97 (0.4H, d, J=5.2 Hz).

EM (calculated value): 463.2; MS (ESI) m/e (M+1H)+: 464.2

It can be seen that the compound prepared by the present application has the same structure as the compound above.

Example 93

Preparation of (S)-1-(6-(8-amino-1-(4-phenoxyphenyl)imidazo[1,5-a]pyrazin-3-yl)-5-azaspiro[2.4]heptan-5-yl)prop-2-en-1-one

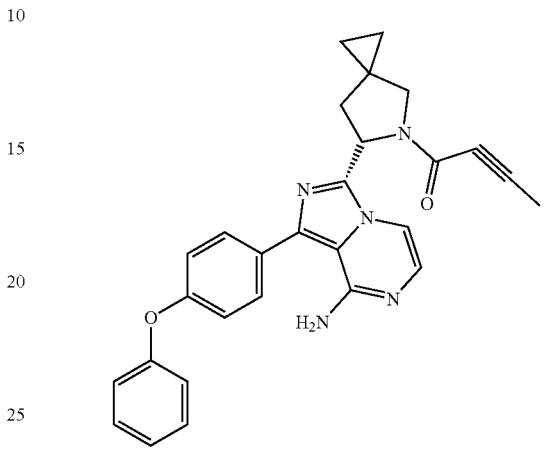

Under the protection of nitrogen, to a solution of (S)-1-(4-phenoxyphenyl)-3-(5-azaspiro[2.4]heptan-6-yl)imidazo[1,5-a]pyrazin-8-amine (80 mg, 0.20 mmol), TEA (101 mg, 1.0 mmol) in DCM (10 mL), 3-chloropropionyl chloride (25.4 mg, 0.20 mmol) was added dropwise at 0° C. The reaction mixture reacted under stirring at room temperature overnight. After TLC showed the raw materials reacted completely, the reaction system was quenched with water and extracted with EA (10 mL×3). The organic phase was dried with anhydrous Na$_2$SO$_4$, evaporated under vacuum and then purified by preparative silica gel plate (DCM/MeOH=25/1) to obtain 20 mg of the target compound which was a white solid.

The structure of the product was characterized by nuclear magnetic resonance and mass spectrometry and the results were as follows:

$^1$H NMR (400 MHz, d$_6$-DMSO) δ 1.25-1.54 (5H, m), 2.47-2.55 (1H, m), 2.68-2.70 (1H, m), 4.61 (0.25H, s), 4.73 (0.75H, s), 5.01 (0.75H, s), 5.19 (0.25H, s), 5.44 (0.25H, d, J=10.4 Hz), 5.65 (0.75H, dd, J=10.4 Hz, 2.4 Hz), 5.70 (0.25H, dd, J=16.8 Hz, 10.4 Hz), 6.04-6.15 (3H, m), 6.74 (0.75H, dd, J=16.8 Hz, 10.4 Hz), 7.03-7.19 (6H, m), 7.42-7.44 (2H, m), 7.55-7.61 (2H, m), 7.81 (0.75H, d, J=5.2 Hz), 7.97 (0.25H, d, J=5.2 Hz).

EM (calculated value): 451.2; MS (ESI) m/e (M+1H)+: 452.2

It can be seen that the compound prepared by the present application has the same structure as the compound above.

Examples 94-111

The following compounds were prepared by the preparation method of Example 92 or Example 93 using compounds with similar structures as the starting materials. The structures and nuclear magnetic characterization data of the compounds are shown in Table 5. Table 5 summarizes the structures and structural analysis data of the compounds prepared in Examples 94 to 111 of the present application.

TABLE 5

Summary of structures and structural analysis data of the compounds prepared in Examples 94-111

| Examples | Structures | Analysis data |
|---|---|---|
| 94 | 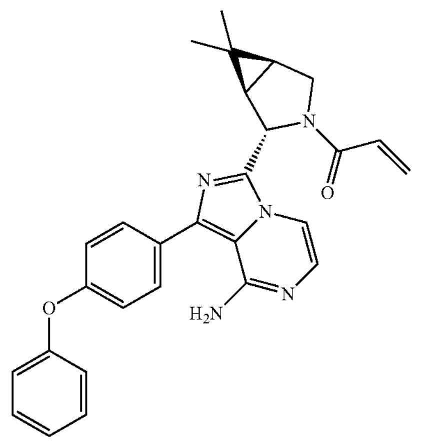 | $^1$H NMR (400 MHz, d$_6$-DMSO) δ 1.00-1.07 (6H, m), 1.49-1.53 (1H, m), 1.61-1.64 (0.3H, m), 1.73-1.77 (0.7H, m), 3.70-3.74 (0.3H, m), 3.77-3.82 (0.7H, m), 3.87-3.90 (0.3H, m), 4.04-4.09 (0.7H, m), 5.40 (0.7H, s), 5.52-5.53 (0.3H, m), 5.61 (0.3H, s), 5.65-5.69 (0.7H, m), 6.03-6.20 (3H, m), 6.36 (0.3H, dd, J = 16.8 Hz, 10.4 Hz), 6.56 (0.7H, dd, J = 16.8 Hz, 10.4 Hz), 7.02-7.19 (6H, m), 7.41-7.44 (2H, m), 7.55-7.61 (2H, m), 7.78 (0.3H, d, J = 5.2 Hz), 7.84 (0.7H, d, J = 5.2 Hz). EM(calculated value): 465.2; MS(ESI) m/e (M + 1H)$^+$: 466.2 |
| 95 | 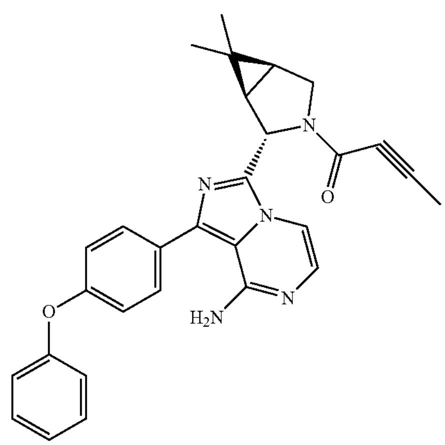 | $^1$H NMR (400 MHz, d$_6$-DMSO) δ 1.06 (6H, s), 1.48-1.53 (1H, m), 1.67-1.71 (1H, m), 1.74 (1.3H, s), 2.04 (1.7H, s), 3.61 (0.45H, d, J = 12.4 Hz), 3.77 (0.45H, dd, J = 12.4 Hz, 5.2 Hz), 3.81 (0.55H, d, J = 11.2 Hz), 4.03 (0.55H, dd, J = 11.2 Hz, 5.2 Hz), 5.34 (0.55H, s), 5.61 (0.45H, s), 6.09-6.21 (2H, m), 7.03-7.22 (6H, m), 7.42-7.45 (2H, m), 7.55-7.61 (2H, m), 7.80 (0.55H, d, J = 5.2 Hz), 7.97 (0.45H, d, J = 5.2 Hz). EM(calculated value): 477.2; MS(ESI) m/e (M + 1H)$^+$: 478.2 |
| 96 | 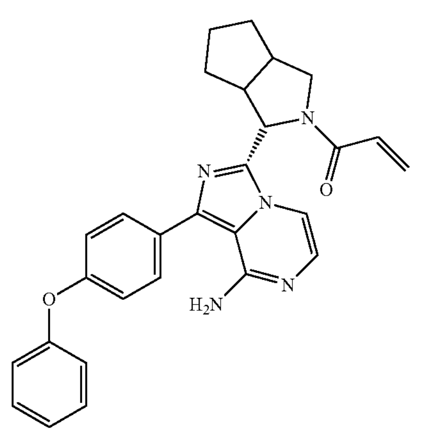 | $^1$H NMR (400 MHz, d$_6$-DMSO) δ 1.43-1.61 (3H, m), 1.76-1.81 (1H, m), 1.85-1.99 (2H, m), 2.66-2.68 (1H, m), 2.90-2.93 (1H, m), 3.63-3.66 (1H, m), 3.90-4.02 (1H, m), 5.45 (1H, d, J = 2.0 Hz), 5.67-5.71 (1H, m), 6.08-6.18 (3H, m), 6.76 (1H, dd, J = 16.8 Hz, 10.4 Hz): 7.02-7.20 (6H, m), 7.41-7.43 (2H, m), 7.55-7.59 (2H, m), 7.79 (0.35H, d, J = 5.2 Hz), 7.83 (0.65H, d, J = 5.2 Hz). EM(calculated value): 465.2; MS(ESI) m/e (M + 1H)$^+$: 466.2 |

TABLE 5-continued

Summary of structures and structural analysis data of the compounds prepared in Examples 94-111

| Examples | Structures | Analysis data |
|---|---|---|
| 97 | 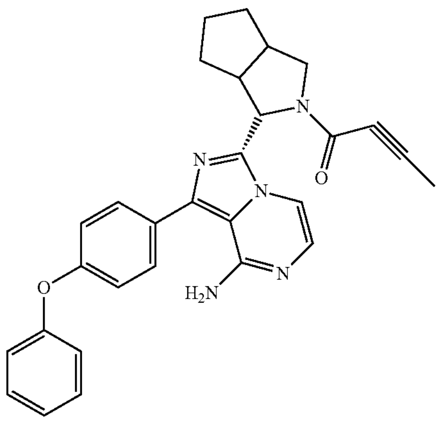 | $^1$H NMR (400 MHz, d$_6$-DMSO) δ 1.50-1.62 (3H, m), 1.76-1.81 (2H, m), 1.88-2.09 (4H, m), 2.71 (0.35H, brs), 2.97 (0.65H, brs), 3.47-3.51 (0.35H, m), 3.69-3.74 (0.65H, m), 3.79-3.81 (0.35H, m), 3.90-3.95 (0.65H, m), 5.41 (0.65H, d, J = 2.8 Hz), 5.50 (0.35H, d, J = 2.8 Hz), 6.15-6.22 (2H, m), 7.05-7.19 (6H, m), 7.37-7.44 (2H, m), 7.56-7.61 (2H, m), 7.80 (0.65H, d, J = 5.2 Hz), 7.94 (0.35H, d, J = 5.2 Hz). EM(calculated value): 477.2; MS(ESI) m/e (M + 1H)$^+$: 478.2 |
| 98 | 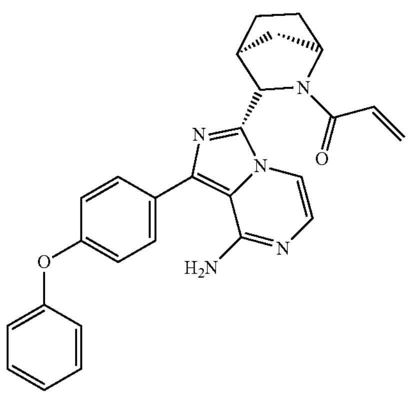 | $^1$H NMR (400 MHz, d$_6$-DMSO) δ 1.23-1.50 (5H, m), 2.50-2.55 (1H, m), 2.70-2.71 (1H, m), 4.62 (0.25H, s), 4.71 (0.75H, s), 5.01 (0.75H, s), 5.21 (0.25H, s), 5.44 (0.25H, d, J = 10.4 Hz), 5.66 (0.75H, dd, J = 10.4 Hz, 2.4 Hz), 5.70 (0.25H, dd, J = 16.8 Hz, 10.4 Hz), 6.04-6.10 (3H, m), 6.75 (0.75H, dd, J = 16.8 Hz, 10.4 Hz), 7.06-7.19 (6H, m), 7.40-7.44 (2H, m), 7.55-7.58 (2H, m), 7.78 (0.25H, d, J = 5.2 Hz), 7.86 (0.75H d, J = 5.2 Hz). EM(calculated value): 451.2; MS(ESI) m/e (M + 1H)$^+$: 452.2 |
| 99 | 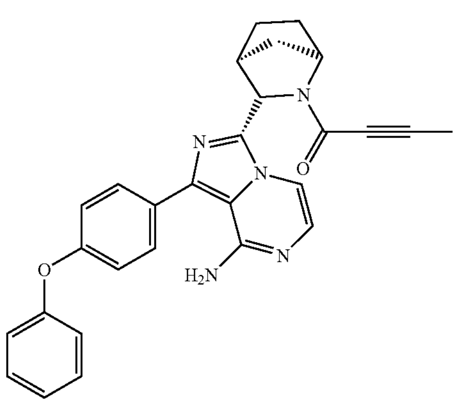 | $^1$H NMR (400 MHz, d$_6$-DMSO) δ 1.36-1.46 (1H, m), 1.50 (1H, s), 1.55-1.82 (4H, m), 2.02 (2H, s), 2.58-2.60 (2H, m), 4.53 (0.35H, s), 4.61 (0.65H, s), 4.98 (0.65H, s), 5.17 (0.35H, s), 6.07-6.12 (2H, m), 7.06-7.19 (6H, m), 7.40-7.44 (2H, m), 7.56-7.61 (2H, m), 7.82 (0.65H, d, J = 5.2 Hz), 7.95 (0.35H, d, J = 5.2 Hz). EM(calculated value): 463.2; MS(ESI) m/e (M + 1H)$^+$: 464.2 |

TABLE 5-continued

Summary of structures and structural analysis data of the compounds prepared in Examples 94-111

| Examples | Structures | Analysis data |
|---|---|---|
| 100 | 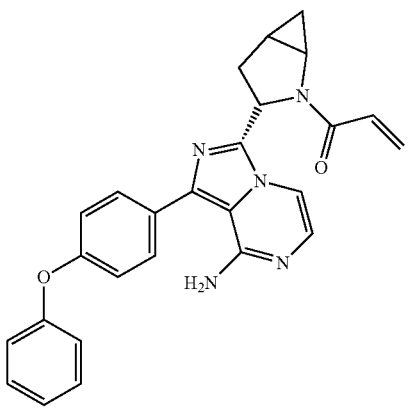 | ¹H NMR (400 MHz, d₆-DMSO) δ 0.37-0.38 (1H, m), 0.81-0.84 (1H, m), 0.93-0.94 (1H, m), 1.87-2.05 (2H, m), 3.16-3.19 (1H, m), 3.83-3.84 (0.3H, s), 4.03-4.07 (0.7H, s), 5.60-5.65 (1H, m), 5.83 (0.3H, dd, J = 16.8 Hz, 10.4 Hz), 6.06-6.18 (3H, m), 6.75 (0.7H, dd, J = 16.8 Hz, 10.4 Hz), 7.06-7.21 (6H, m), 7.41-7.44 (2H, m), 7.57-7.61 (2H, m), 7.82 (0.7H, d, J = 5.2 Hz), 7.93 (0.3H, d, J = 5.2 Hz). EM(calculated value): 437.2; MS(ESI) m/e (M + 1H)⁺: 438.2 |
| 101 | 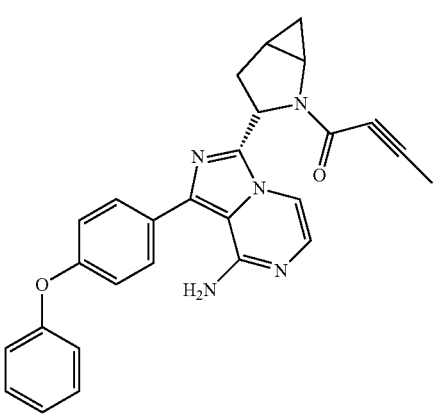 | ¹H NMR (400 MHz, d₆-DMSO) δ 0.36-0.38 (1H, m), 0.81-0.83 (1H, m), 0.90-0.93 (1H, m), 1.51 (1H, s), 1.86-1.99 (4H, m), 3.16-3.18 (1H, m), 3.85-3.86 (0.3H, s), 4.02-4.06 (0.7H, s), 6.06-6.15 (2H, m), 7.04-7.19 (6H, m), 7.40-7.45 (2H, m), 7.54-7.61 (2H, m), 7.81 (0.7H, d, J = 5.2 Hz), 7.93 (0.3H, d, J = 5.2 Hz). EM(calculated value): 449.2; MS(ESI) m/e (M + 1H)⁺: 450.2 |
| 102 | 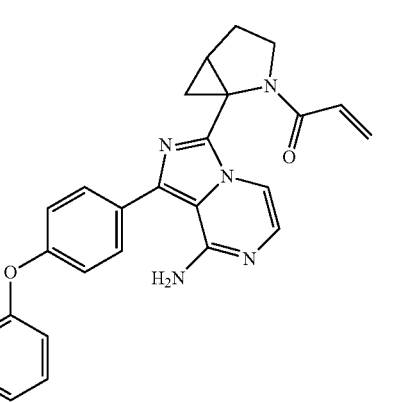 | ¹H NMR (400 MHz, d₆-DMSO) δ 0.76-0.78 (1H, m), 0.92-0.95 (1H, m), 1.35-1.72 (3H, m), 3.83-3.88 (1.25H, s), 4.02-4.05 (0.75H, s), 5.60-5.64 (1H, m), 5.85 (0.25H, dd. J = 16.8 Hz, 10.4 Hz), 6.06-6.19 (3H, m), 6.74 (0.75H, dd, J = 16.8 Hz, 10.4 Hz), 7.02-7.19 (6H, m), 7.40-7.44 (2H, m), 7.56-7.60 (2H, m), 7.82 (0.65H, d. J = 5.2 Hz), 7.92 (0.35H, d, J = 5.2 Hz). EM(calculated value): 437.2; MS(ESI) m/e (M + 1H)⁺: 438.2 |

TABLE 5-continued

Summary of structures and structural analysis data of the compounds prepared in Examples 94-111

| Examples | Structures | Analysis data |
|---|---|---|
| 103 | 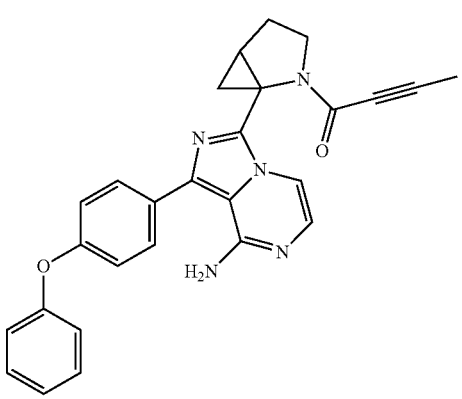 [SMILES: CC#CC(=O)N1CCC2CC21c1nc(-c2ccc(Oc3ccccc3)cc2)c2c(N)nccn12] | $^1$H NMR (400 MHz, d$_6$-DMSO) δ 0.75-0.79 (1H, m), 0.92-0.95 (1H, m), 1.24-1.77 (4H, m), 2.01 (2H, s), 3.83-3.86 (1.25H, s), 4.04-4.08 (0.75H, s), 6.06-6.21 (2H, m), 7.06-7.22 (6H, m), 7.39-7.43 (2H, m), 7.57-7.60 (2H, m), 7.80 (0.75H, d, J = 5.2 Hz), 7.94 (0.25H, d, J = 5.2 Hz). EM(calculated value): 449.2; MS(ESI) m/e (M + 1H)$^+$: 450.2 |
| 104 | 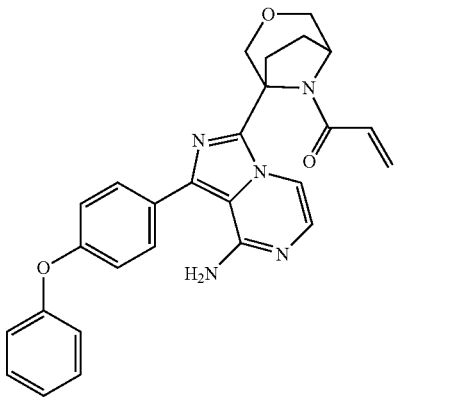 [SMILES: C=CC(=O)N1C2CCC1(c1nc(-c3ccc(Oc4ccccc4)cc3)c3c(N)nccn13)COC2] | $^1$H NMR (400 MHz, d$_6$-DMSO) δ 1.73-1.77 (1H, m), 1.92-2.07 (3H, m), 3.42-3.63 (4H, m), 3.97-4.03 (1H, m), 5.65-5.68 (1H, m), 6.09-6.17 (3H, m), 6.71-6.74 (1H, m), 7.02-7.22 (6H, m), 7.41-7.46 (2H, m), 7.55-7.59 (2H, m), 7.79-7.82 (1H, m). EM(calculated value): 467.2; MS(ESI) m/e (M + 1H)$^+$: 468.2 |
| 105 | 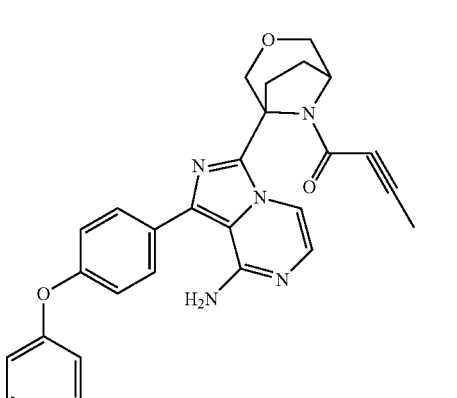 | $^1$H NMR (400 MHz, d$_6$-DMSO) δ 1.56 (1H, s), 1.75-1.77 (1H, m), 1.89-2.00 (5H, m), 3.45-3.66 (4H, m), 3.98-4.01 (1H, m), 6.08-6.15 (2H, m), 7.02-7.17 (6H, m), 7.40-7.44 (2H, m), 7.56-7.59 (2H, m), 7.81 (0.7H, d, J = 5.2 Hz), 7.92 (0.3H, d, J = 5.2 Hz). EM(calculated value): 479.2; MS(ESI) m/e (M + 1H)$^+$: 480.2 |

TABLE 5-continued

Summary of structures and structural analysis data of the compounds prepared in Examples 94-111

| Examples | Structures | Analysis data |
|---|---|---|
| 106 | 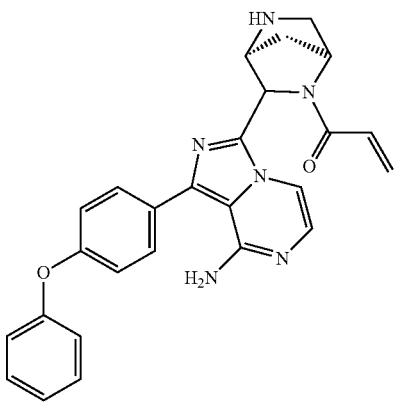 | $^1$H NMR (400 MHz, d$_6$-DMSO) δ 1.75-1.77 (1H, m), 2.00-2.03 (1H, m), 2.91-3.02 (2H, m), 3.74-3.77 (1H, m), 4.74-4.78 (1H, m), 5.27-5.30 (1H, m), 5.49-5.50 (0.4H, m), 5.65-5.67 (1H, m), 6.05-6.17 (3H, m), 6.81 (0.6H, dd, J = 16.8 Hz, 10.4 Hz), 7.05-7.19 (6H, m), 7.40-7.45 (2H, m), 7.57-7.60 (2H, m), 7.81 (0.6H, d, J = 5.2 Hz), 7.93 (0.4H, d, J = 5.2 Hz). EM(calculated value): 452.2; MS(ESI) m/e (M + 1H)$^+$: 453.2 |
| 107 | 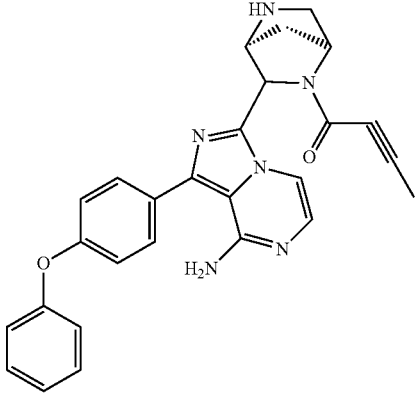 | $^1$H NMR (400 MHz, d$_6$-DMSO) δ 1.54 (1H, s), 1.72-1.74 (1H, m), 2.02-2.06 (3H, m), 2.89-3.00 (2H, m), 3.68-3.73 (1H, m), 4.72-4.75 (1H, m), 5.25-5.28 (1H, m), 6.09-6.21 (2H, m), 7.02-7.18 (6H, m), 7.41-7.45 (2H, m), 7.55-7.58 (2H, m), 7.77-7.82 (1H, m). EM(calculated value): 464.2; MS(ESI) m/e (M + 1H)$^+$: 465.2 |
| 108 | 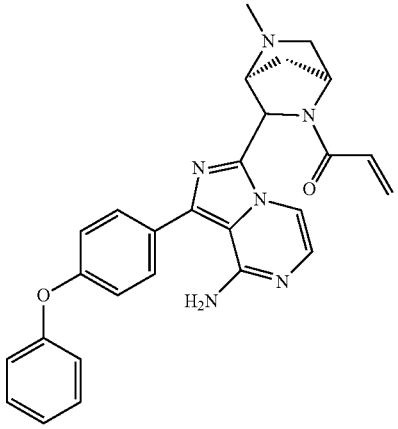 | $^1$H NMR (400 MHz, d$_6$-DMSO) δ 1.52-1.54 (1H, m), 1.79-1.81 (1H, m), 2.33 (3H, s), 3.36-3.39 (1H, m), 3.47-3.53 (2H, m), 3.69-3.71 (1H, m), 4.99-5.01 (1H, m), 5.44-5.45 (0.4H, m), 5.63-5.65 (0.6H, m), 5.83 (0.4H, dd, J = 16.8 Hz, 10.4 Hz), 6.06-6.16 (3H, m), 6.73 (0.6H, dd, J = 16.8 Hz, 10.4 Hz), 7.05-7.21 (6H, m), 7.40-7.44 (2H, m), 7.57-7.60 (2H, m), 7.81 (0.6H, d, J = 5.2 Hz), 7.94 (0.4H, d, J = 5.2 Hz). EM(calculated value): 466.2; MS(ESI) m/e (M + 1H)$^+$: 467.2 |

TABLE 5-continued

Summary of structures and structural analysis data of the compounds prepared in Examples 94-111

| Examples | Structures | Analysis data |
| --- | --- | --- |
| 109 | 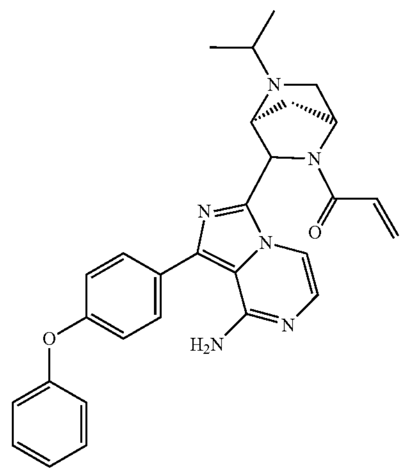 | $^1$H NMR (400 MHz, d$_6$-DMSO) δ 1.18-1.22 (6H, m), 1.52-1.55 (1H, m), 1.77-1.79 (1H, m), 2.84-2.86 (1H, m), 3.36-3.39 (1H, m), 3.50-3.54 (2H, m), 3.69-3.72 (1H, m), 4.99-5.01 (1H, m), 5.45-5.46 (0.5H, m), 5.63-5.65 (0.5H, m), 5.84 (0.5H, dd, J = 16.8 Hz, 10.4 Hz), 6.08-6.18 (3H, m), 6.72 (0.5H, dd, J = 16.8 Hz, 10.4 Hz), 7.05-7.21 (6H, m), 7.41-7.44 (2H, m), 7.57-7.61 (2H, m), 7.83 (0.5H, d, J = 5.2 Hz), 7.92 (0.5H, d, J = 5.2 Hz). EM(calculated value): 494.2; MS(ESI) m/e (M + 1H)$^+$: 495.3 |
| 110 | 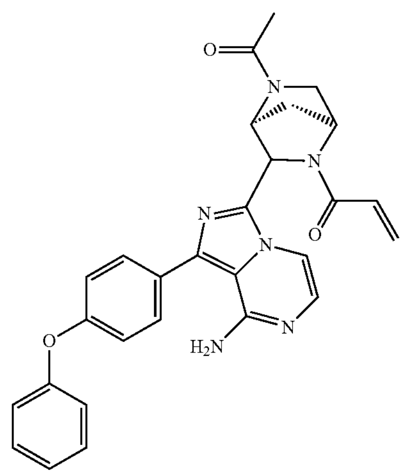 | $^1$H NMR (400 MHz, d$_6$-DMSO) δ 1.66-1.69 (1H, m), 1.84-1.86 (1H, m), 2.47 (3H, s), 3.48-3.50 (1H, m), 3.52-3.55 (2H, m), 3.76-3.79 (1H, m), 5.03-5.05 (1H, m), 5.43-5.44 (0.4H, m), 5.63-5.66 (0.6H, m), 5.81 (0.4H, dd, J = 16.8 Hz, 10.4 Hz), 6.05-6.20 (3H, m), 6.71 (0.6H, dd, J = 16.8 Hz, 10.4 Hz), 7.07-7.21 (6H, m), 7.41-7.45 (2H, m), 7.57-7.61 (2H, m), 7.82 (0.6H, d, J = 5.2 Hz), 7.91 (0.4H, d, J = 5.2 Hz). EM(calculated value): 494.2; MS(ESI) m/e (M + 1H)$^+$: 495.2 |
| 111 | 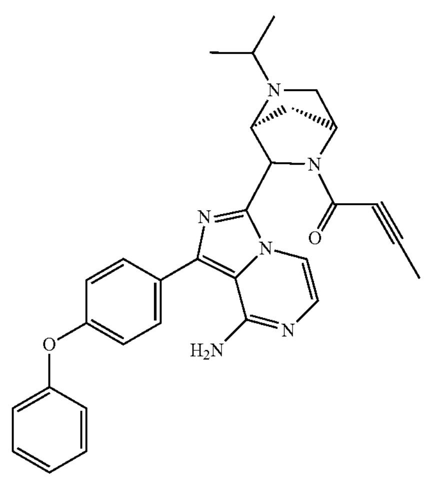 | $^1$H NMR (400 MHz, d$_6$-DMSO) δ 1.19-1.21 (6H, m), 1.51-1.55 (2H, m), 1.77-1.80 (1H, m), 2.05 (2H, s), 2.83-2.86 (1H, m), 3.37-3.39 (1H, m), 3.48-3.54 (2H, m), 3.69-3.71 (1H, m), 4.99-5.02 (1H, m), 6.09-6.15 (2H, m), 7.07-7.20 (6H, m), 7.41-7.45 (2H, m), 7.57-7.62 (2H, m), 7.83 (0.6H, d, J = 5.2 Hz), 7.92 (0.4H, d, J = 5.2 Hz). EM(calculated value): 506.2; MS(ESI) m/e (M + 1H)$^+$: 507.3 |

Example 112

Preparation of (S,E)-4-(8-amino-3-(5-(4-(dimethylamino)but-2-enoyl)-5-azaspiro[2.4]heptan-6-yl)imidazo[1,5-a]pyrazin-1-yl)-N-(pyridin-2-yl)benzamide

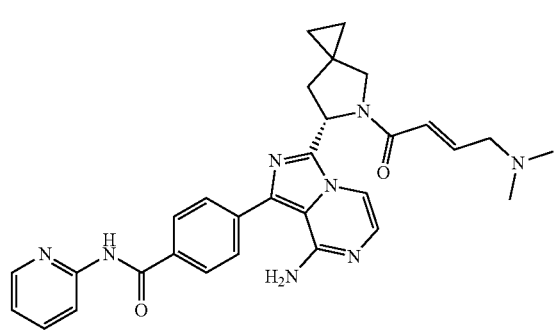 [SMILES: CN(C)C/C=C/C(=O)N1CC2(CC2)C[C@H]1c1nc(-c2ccc(C(=O)Nc3ccccn3)cc2)c2c(N)nccn12]

Under the protection of nitrogen, to a solution of (S)-4-(8-amino-3-(5-azaspiro[2.4]heptan-6-yl)imidazo[1,5-a]pyrazin-1-yl)-N-(pyridin-2-yl)benzamide (100 mg, 0.235 mmol), (E)-4-(dimethylamino)-2-butenoic acid hydrochloride (46.7 mg, 0.282 mmol) and DIPEA (121.26 mg, 0.94 mmol) in DMF (3 mL), HBTU (106.9 mg, 0.282 mmol) was added. The reaction mixture reacted under stirring at room temperature for 3 hours. After TLC showed the raw materials reacted completely, the reaction system was quenched with water, and extracted with EA (15 mL×3). The organic phase was backwashed with saturated brine, dried with anhydrous $Na_2SO_4$, evaporated under vacuum and then purified by preparative silica gel plate (DCM/MeOH=20/1) to obtain 20 mg of the target compound which was a light yellow solid.

Structural Analysis Data:

$^1$H NMR (400 MHz, $d_6$-DMSO) δ 0.56-0.73 (4H, m), 1.82 (2H, s), 2.13 (4H, s), 2.22-2.26 (1.5H, m), 3.05 (2H, d, J=4.4 Hz), 3.62-3.66 (1.5H, m), 3.87 (1H, d, J=10.4 Hz), 5.59-5.66 (1H, m), 6.03-6.15 (2H, m), 6.37-6.54 (2H, m), 7.14-7.21 (2H, m), 7.71 (2H, d, J=8.4 Hz), 7.86-7.92 (2H, m), 8.15 (2H, d, J=8.4 Hz), 8.24 (1H, d, J=8.4 Hz), 8.40 (1H, dd, J=4.8 Hz, 1.8 Hz), 10.85 (1H, s).

EM (calculated value): 536.3; MS (ESI) m/e (M+1H)+: 537.3.

Example 113

Preparation of 4-(8-amino-3-((1S)-2-((E)-4-(dimethylamino)-2-butenoyl)octahydrocyclopenta[c]pyrrol-1-yl)imidazo[1,5-a]pyrazin-1-yl)-N-(pyridin-2-yl)benzamide

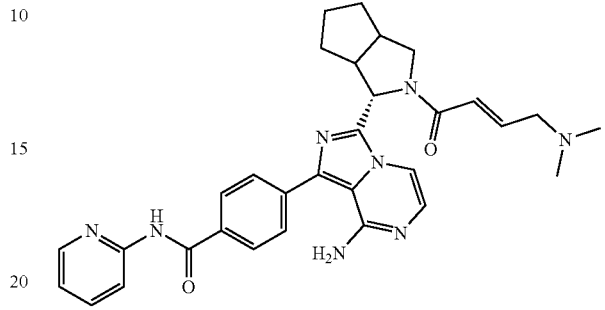

Under the protection of nitrogen, to a solution of 4-(8-amino-3-((1 S)-octahydrocyclopenta[c]pyrrol-1-yl)imidazo[1,5-a]pyrazin-1-yl)-N-(pyridin-2-yl)benzamide (100 mg, 0.228 mmol), (E)-4-(dimethylamino)-2-butenoic acid hydrochloride (45.4 mg, 0.274 mmol) and DIPEA (117.6 mg, 0.912 mmol) in DMF (3 mL), HBTU (86.4 mg, 0.228 mmol) was added. The reaction mixture reacted under stirring at room temperature for 3 hours. After TLC showed the raw materials reacted completely, the reaction system was quenched with water, and extracted with EA (15 mL×3). The organic phase was backwashed with saturated brine, dried with anhydrous $Na_2SO_4$, evaporated under vacuum and then purified by preparative silica gel plate (DCM/MeOH=20/1) to obtain 28 mg of the target compound which was a light yellow solid.

Structural Analysis Data:

$^1$H NMR (400 MHz, $d_6$-DMSO) δ 1.45-1.60 (3H, m), 1.77-1.84 (3H, m), 1.85-2.03 (2H, m), 2.13 (4H, s), 2.68-2.71 (1H, m), 2.89-2.92 (1H, m), 3.05 (2H, d, J=4.4 Hz), 3.63-3.67 (1H, m), 3.88-3.94 (1H, m), 5.43 (1H, d, J=2.0 Hz), 6.03-6.18 (2H, m), 6.41-6.54 (2H, m), 7.15 (1H, d, J=5.2 Hz), 7.18-7.20 (1H, m), 7.71 (2H, d, J=8.4 Hz), 7.86-7.92 (2H, m), 8.13 (2H, d, J=8.4 Hz), 8.23 (1H, d, J=8.4 Hz), 8.42 (1H, dd, J=4.8 Hz, 1.8 Hz), 10.84 (1H, s).

EM (calculated value): 550.3; MS (ESI) m/e (M+1H)+: 551.3

Example 114

The synthetic steps of (S,E)-4-(8-amino-3-(5-(4-(cyclopropyl(methyl)amino)-2-butenoyl)-5-azaspiro[2.4]heptan-6-yl)imidazo[1,5-a]pyrazin-1-yl)-N-(pyridin-2-yl)benzamide are as follows:

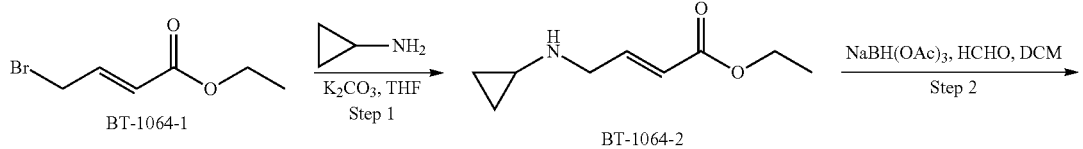

-continued

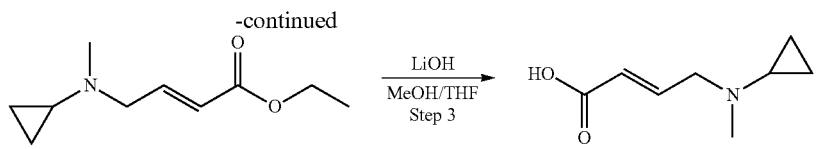

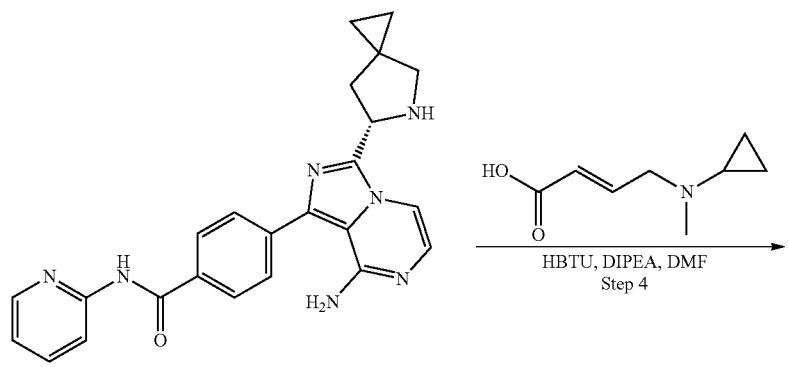

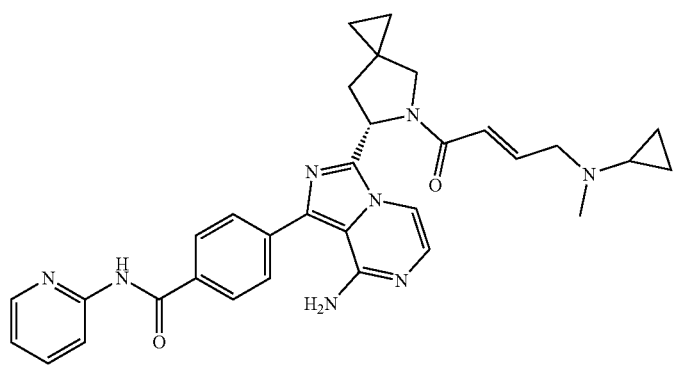

Example 114

Step 1: Preparation of
(E)-ethyl-4-(cyclopropylamino)but-2-enoate

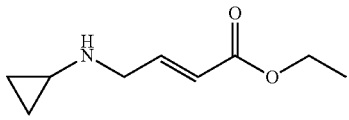

At room temperature, to a solution of cyclopropylamine (2.2 g, 38.85 mol), K₂CO₃ (3.6 g, 25.9 mmol) in 20 mL THF, ethyl bromocrotonate (90% purity, 2.8 g, 12.95 mmol) was added, stirred at room temperature overnight. After TLC detected that reaction was completed, the above reaction mixture was quenched with water, and extracted with EA (15 mL×3). The organic phase was pooled, washed with saturated NaCl, thoroughly dried with anhydrous Na₂SO₄ and evaporated under vacuum to obtain 1.1 g of the target compound which can be used for the reaction of the next step without further purification.

Step 2: Preparation of (E)-ethyl
4-(cyclopropyl(methyl)amino)but-2-enoate

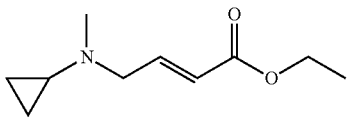

Under the protection of nitrogen, to a solution of (E)-ethyl-4-(cyclopropylamino)but-2-enoate (1.1 g, 6.5 mmol) in DCM, aqueous formaldehyde (38 wt %, 2.6 g, 32.5) was added. In an ice salt bath, STAB (4.1 g, 19.5 mmol) was added in portions. The reaction mixture was naturally warmed to room temperature and stirred for 3 hours. After TLC detected that reaction was completed, the reaction was quenched by slowly adding water dropwise, and extracted with DCM (10 mL×4). The organic phase was pooled, washed with saturated NaCl, thoroughly dried with anhydrous Na₂SO₄, evaporated under vacuum and then purified by column chromatography (PE/EA=20/1) to obtain 860 mg of the target compound which was a yellow oily substance.

Step 3: Preparation of (E)-4-(cyclopropyl(methyl)amino)-2-butenoic acid

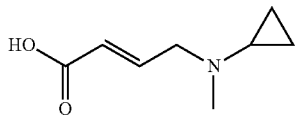

At room temperature, to a mixed solution of (E)-ethyl 4-(cyclopropyl(methyl)amino)but-2-enoate (860 mg, 4.7 mmol) in THF/water (5 mL/3 mL), LiOH (451.2 mg, 18.8 mmol) was added. The reaction mixture was stirred at room temperature for 5 hours. After TLC detected that reaction was completed, the reaction mixture was extracted with DCM/MeOH (10/1, 10 mL×3). The organic phase was thoroughly dried with anhydrous $Na_2SO_4$ and evaporated under vacuum to obtain 750 mg of the target compound which was a white solid.

Step 4: Preparation of (S,E)-4-(8-amino-3-(5-(4-(cyclopropyl(methyl)amino)-2-butenoyl)-5-azaspiro[2.4]heptan-6-yl)imidazo[1,5-a]pyrazin-1-yl)-N-(pyridin-2-yl)benzamide

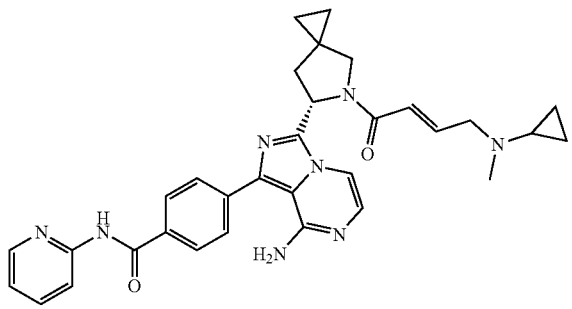 [SMILES: CN(C/C=C/C(=O)N1CC2(CC2)C[C@H]1c1nc(-c2ccc(C(=O)Nc3ccccn3)cc2)c2c(N)nccn12)C1CC1]

Under the protection of nitrogen, to a solution of (S)-4-(8-amino-3-(5-azaspiro[2.4]heptan-6-yl)imidazo[1,5-a]pyrazin-1-yl)-N-(pyridin-2-yl)benzamide (100 mg, 0.235 mmol), (E)-4-(cyclopropyl(methyl)amino)-2-butenoic acid (48.2 mg, 0.282 mmol) and DIPEA (121.26 mg, 0.94 mmol) in DMF (3 mL), HBTU (106.9 mg, 0.282 mmol) was added. The reaction mixture reacted under stirring at room temperature for 3 hours. After TLC showed the raw materials reacted completely, the reaction system was quenched with water, and extracted with EA (15 mL×3). The organic phase was backwashed with saturated brine, dried with anhydrous $Na_2SO_4$, evaporated under vacuum and then purified by preparative silica gel plate (DCM/MeOH=20/1) to obtain 45 mg of the target compound which was a light yellow solid.

Structural Analysis Data:

$^1$H NMR (400 MHz, $d_6$-DMSO) δ 0.24-0.39 (4H, m), 0.56-0.69 (4H, m), 1.44-1.46 (1H, m), 2.24-2.27 (1.5H, m), 3.23 (3H, s), 3.62-3.75 (3.5H, m), 3.85 (1H, d, J=10.4 Hz), 5.65-5.68 (1H, m), 6.05-6.17 (2H, m), 6.37-6.50 (2H, m), 7.11-7.22 (2H, m), 7.66-7.71 (2H, m), 7.83-7.87 (2H, m), 8.13 (2H, J=8.4 Hz), 8.20 (1H, d, J=8.4 Hz), 8.41 (1H, d, J=3.6 Hz), 10.86 (1H, s).

EM (calculated value): 562.3; MS (ESI) m/e (M+1H)+: 563.3

Example 115

Preparation of 4-(8-amino-3-((1S)-2-((E)-4-(cyclopropyl(methyl)amino)-2-butenoyl) octahydrocyclopenta[c]pyrrol-1-yl)imidazo[1,5-a]pyrazin-1-yl)-N-(pyridin-2-yl) benzamide

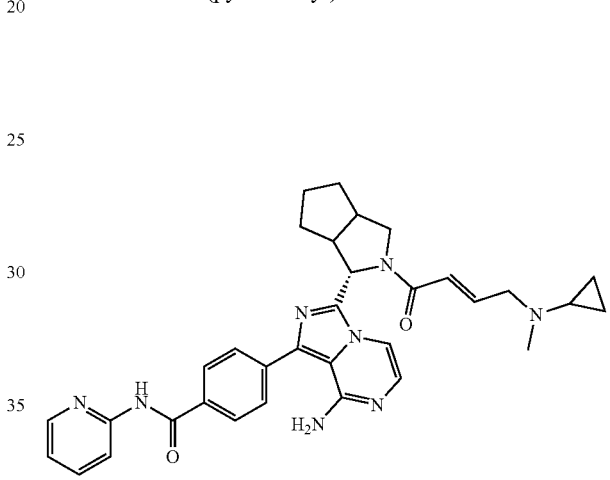

Under the protection of nitrogen, to a solution of 4-(8-amino-3-((1 S)-octahydrocyclopenta[c]pyrrol-1-yl)imidazo[1,5-a]pyrazin-1-yl)-N-(pyridin-2-yl)benzamide (100 mg, 0.228 mmol), (E)-4-(cyclopropyl(methyl)amino)-2-butenoic acid (46.9 mg, 0.274 mmol) and DIPEA (117.6 mg, 0.912 mmol) in DMF (3 mL), HBTU (86.4 mg, 0.228 mmol) was added. The reaction mixture reacted under stirring at room temperature for 3 hours. After TLC showed the raw materials reacted completely, the reaction system was quenched with water, and extracted with EA (15 mL×3). The organic phase was backwashed with saturated brine, dried with anhydrous $Na_2SO_4$, evaporated under vacuum and then purified by preparative silica gel plate (DCM/MeOH=20/1) to obtain 55 mg of the target compound which was a light yellow solid.

Structural Analysis Data:

$^1$H NMR (400 MHz, $d_6$-DMSO) δ 0.24-0.39 (4H, m), 1.48-1.59 (3H, m), 1.79-1.85 (3H, m), 1.91-2.03 (2H, m), 2.13 (2H, s), 2.67-2.71 (1H, m), 2.88-2.92 (1H, m), 3.04 (2H, d, J=4.4 Hz), 3.63-3.66 (1H, m), 3.88-3.92 (1H, m), 5.45 (1H, d, J=2.0 Hz), 6.03-6.15 (2H, m), 6.41-6.54 (2H, m), 7.14 (1H, d, J=5.2 Hz), 7.17-7.20 (1H, m), 7.71 (2H, d, J=8.4 Hz), 7.86-7.91 (2H, m), 8.13 (2H, d, J=8.4 Hz), 8.25 (1H, d, J=8.4 Hz), 8.42 (1H, dd, J=4.8 Hz, 1.8 Hz), 10.86 (1H, s).

EM (calculated value): 576.3; MS (ESI) m/e (M+1H)+: 577.3

Example 116
The synthetic steps of (S,Z)-4-(8-amino-3-(5-(2-cyano-4-methyl-2-pentenoyl)-5-azaspiro [2.4]heptan-6-yl)imidazo [1,5-a]pyrazin-1-yl)-N-(pyridin-2-yl)benzamide are as follows:
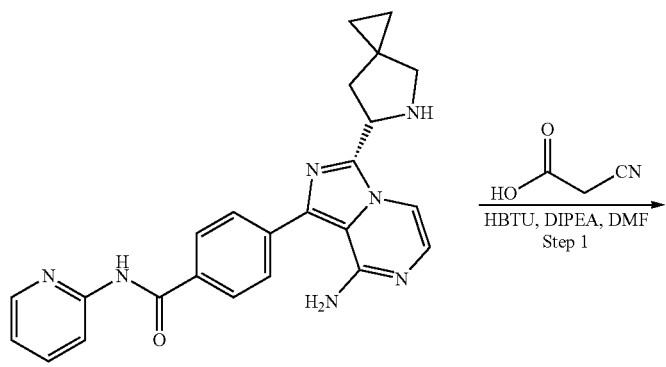
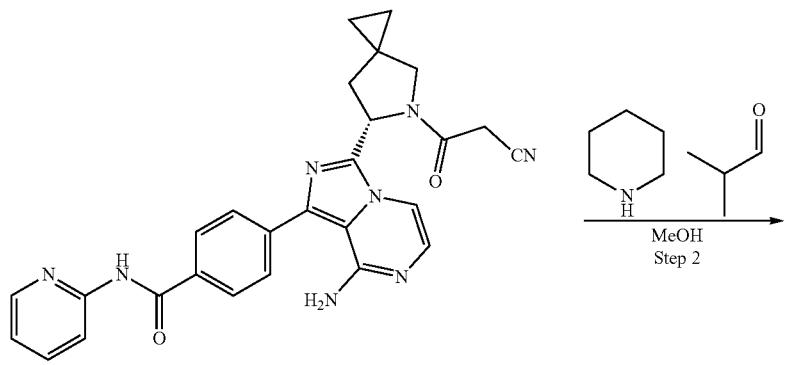
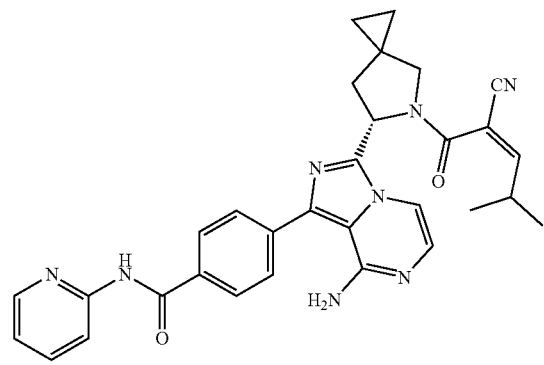
Example 116

Step 1: Preparation of (S)-4-(8-amino-3-(5-(2-cyanoacetyl)-5-azaspiro[2.4]heptan-6-yl)imidazo[1,5-a]pyrazin-1-yl)-N-(pyridin-2-yl)benzamide

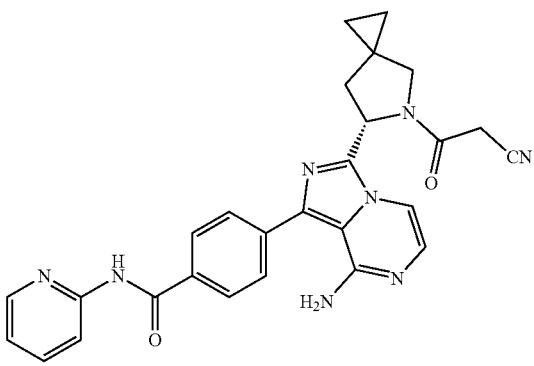 [SMILES: N#CCC(=O)N1CC2(CC2)C[C@H]1c1nc(-c2ccc(C(=O)Nc3ccccn3)cc2)c2c(N)nccn12]

Under the protection of nitrogen, to a solution of (S)-4-(8-amino-3-(5-azaspiro[2.4]heptan-6-yl)imidazo[1,5-a]pyrazin-1-yl)-N-(pyridin-2-yl)benzamide (300 mg, 0.705 mmol), 2-cyanoacetic acid (71.9 mg, 0.846 mmol) and DIPEA (272.8 mg, 2.115 mmol) in DMF (10 mL), HBTU (320.6 mg, 0.846 mmol) was added. The reaction mixture reacted under stirring at room temperature for 3 hours. After TLC showed the raw materials reacted completely, the reaction system was quenched with water, and extracted with EA (15 mL×3). The organic phase was backwashed with saturated brine, dried with anhydrous Na$_2$SO$_4$, evaporated under vacuum and then purified by column chromatography (DCM/MeOH=60/1 20/1) to obtain 150 mg of the target compound which was a yellow solid.

Step 2: Preparation of (S,Z)-4-(8-amino-3-(5-(2-cyano-4-methyl-2-pentenoyl)-5-azaspiro[2.4]heptan-6-yl) imidazo[1,5-a]pyrazin-1-yl)-N-(pyridin-2-yl)benzamide

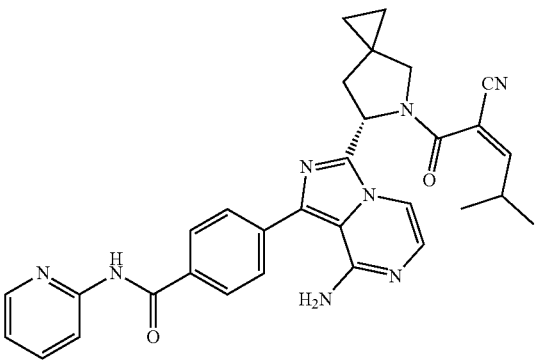 [SMILES: CC(C)/C=C(/C#N)C(=O)N1CC2(CC2)C[C@H]1c1nc(-c2ccc(C(=O)Nc3ccccn3)cc2)c2c(N)nccn12]

Under the protection of nitrogen, to a solution of (S)-4-(8-amino-3-(5-(2-cyanoacetyl)-5-azaspiro[2.4]heptan-6-yl) imidazo[1,5-a]pyrazin-1-yl)-N-(pyridin-2-yl)benzamide (120 mg, 0.244 mmol) and piperidine (24.3 mg, 0.293 mmol) in MeOH (5 mL), isobutyraldehyde (26.4 mg, 0.366 mmol) was added. The reaction mixture reacted under stirring at room temperature for 26 hours. After TLC showed the raw materials reacted completely, the reaction system was quenched with water, and extracted with DCM (15 mL×3), dried with anhydrous Na$_2$SO$_4$, evaporated under vacuum and then purified by silica gel plate (DCM/MeOH=20/1) to obtain 30 mg of the target compound which was a yellow solid.

Structural Analysis Data:

$^1$H NMR (400 MHz, d$_6$-DMSO) δ 0.56-0.76 (4H, m), 1.04-1.09 (6H, m), 2.24-2.26 (1.5H, m), 2.78-2.81 (1H, m), 3.61-3.66 (1.5H, m), 3.87 (1H, d, J=10.4 Hz), 5.60-5.68 (1H, m), 6.05-6.20 (2H, m), 6.74-6.77 (1H, m), 7.11-7.20 (2H, m), 7.66-7.74 (2H, m), 7.83-7.88 (2H, m), 8.15 (2H, J=8.4 Hz), 8.22 (1H, d, J=8.4 Hz), 8.41 (1H, d, J=3.6 Hz), 10.84 (1H, s).

EM (calculated value): 546.2; MS (ESI) m/e (M+1H)+: 547.3

Example 117

Preparation of 4-(8-amino-3-((1S)-2-((Z)-2-cyano-4-methyl-2-pentenoyl) octahydrocyclopenta [c]pyrrol-1-yl)imidazo[1,5-a]pyrazin-1-yl)-N-(pyridin-2-yl)benzamide

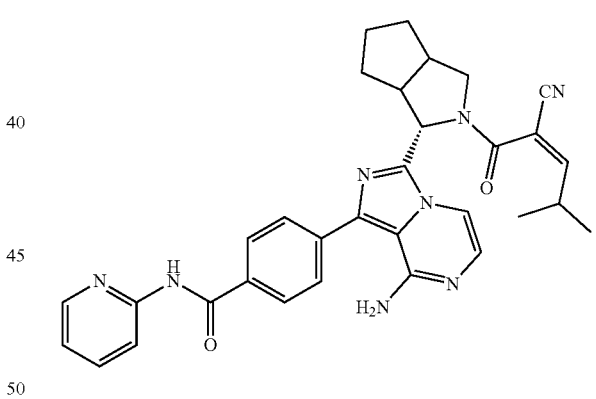

The synthesis method was the same as that in Example 116. 20 mg of the target compound, which was a yellow solid, was obtained by purification with preparative silica gel plate (DCM/MeOH=20/1).

Structural Analysis Data:

$^1$H NMR (400 MHz, d$_6$-DMSO) δ 1.04-1.10 (6H, m), 1.48-1.61 (3H, m), 1.76-1.79 (1H, m), 1.85-2.02 (2H, m), 2.65-2.69 (1H, m), 2.77-2.82 (1H, m), 2.90-2.93 (1H, m), 3.63-3.66 (1H, m), 3.91-4.00 (1H, m), 5.44-5.46 (1H, m), 6.08-6.17 (2H, m), 6.74-6.76 (1H, m), 7.13 (1H, d, J=5.2 Hz), 7.20 (1H, dd, J=6.8 Hz, 5.2 Hz), 7.70-7.73 (2H, m), 7.84-7.90 (2H, m), 8.13 (2H, d, J=8.4 Hz), 8.22 (1H, d, J=8.4 Hz), 8.40 (1H, d, J=4.0 Hz), 10.85 (1H, brs).

EM (calculated value): 560.3; MS (ESI) m/e (M+1H)+: 561.3

Example 118

Preparation of 4-(3-((1R,2S,4S)-7-acryloyl-7-azabicyclo[2.2.1]heptan-2-yl)-8-aminoimidazo[1,5-a]pyrazin-1-yl)-N-(pyridin-2-yl)benzamide

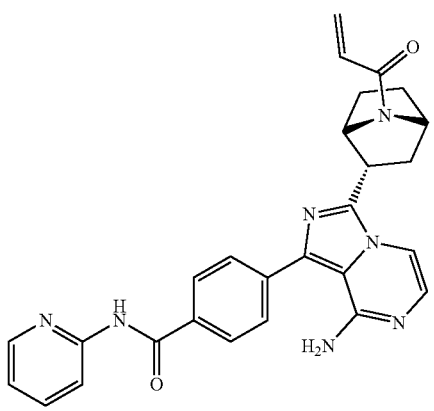

The synthesis method was the same as that in Example 2. 15 mg of the target compound, which was an off-white solid, was obtained by purification with preparative silica gel plate (DCM/MeOH=20/1).

Structural Analysis Data:

$^1$H NMR (400 MHz, $d_6$-DMSO) δ 1.49-1.57 (2H, m), 1.74-1.85 (3H, m), 2.33-2.39 (1H, m), 4.56-4.74 (2H, m), 5.15-5.17 (0.3H, m), 5.28-5.32 (0.7H, m), 5.55-5.69 (1H, m), 6.06-6.18 (3H, m), 6.72 (1H, dd, J=16.8 Hz, 10.4 Hz), 7.13 (1H, d, J=5.2 Hz), 7.16-7.21 (1H, m), 7.71 (2H, dd, J=8.4 Hz, 4.0 Hz), 7.83-7.87 (1H, m), 7.91 (1H, d, J=5.2 Hz), 8.15 (2H, d, J=8.4 Hz), 8.20 (1H, d, J=8.4 Hz), 8.40-8.42 (1H, m), 10.84 (1H, s).

EM (calculated value): 479.2; MS (ESI) m/e (M+1H)+: 479.2

Example 119

Preparation of 4-(8-amino-3-((1R,2S,4S)-7-(but-2-ynoyl)-7-azabicyclo[2.2.1]heptan-2-yl)imidazo[1,5-a]pyrazin-1-yl)-N-(pyridin-2-yl)benzamide

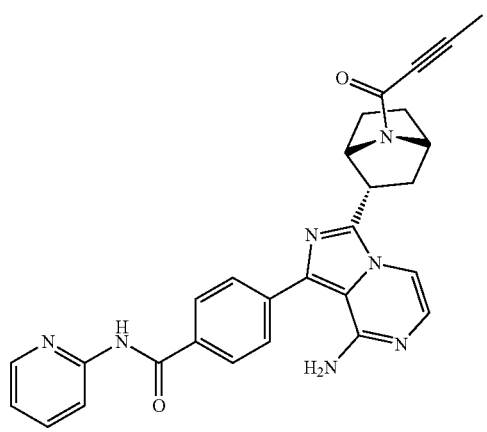

The synthesis method was the same as that in Example 1. 12 mg of the target compound, which was an off-white solid, was obtained by purification with preparative silica gel plate (DCM/MeOH=20/1).

Structural Analysis Data:

$^1$H NMR (400 MHz, $d_6$-DMSO) δ 1.40-1.55 (3H, m), 1.73-1.82 (3H, m), 2.02 (2H, s), 2.33-2.40 (1H, m), 4.53-4.64 (2H, m), 5.13-5.17 (0.4H, m), 5.28-5.32 (0.6H, m), 6.11-6.23 (2H, m), 7.15 (1H, d, J=5.2 Hz), 7.19-7.22 (1H, m), 7.71 (2H, dd, J=8.4 Hz, 4.0 Hz), 7.85-7.87 (1H, m), 7.93 (1H, d, J=5.2 Hz), 8.15 (2H, d, J=8.4 Hz), 8.24 (1H, d, J=8.4 Hz), 8.39-8.42 (1H, m), 10.83 (1H, s).

EM (calculated value): 491.2; MS (ESI) m/e (M+1H)+: 492.2

Example 120

Preparation of 4-(3-(2-acryloyl-2-azabicyclo[2.2.2]octan-1-yl)-8-aminoimidazo[1,5-a]pyrazin-1-yl)-N-(pyridin-2-yl)benzamide

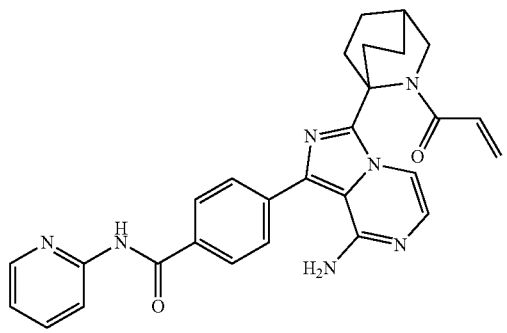 [SMILES: C=CC(=O)N1CC2CCC1(c1nc(-c3ccc(C(=O)Nc4ccccn4)cc3)c3c(N)nccn13)CC2]

The synthesis method was the same as that in Example 2. 10 mg of the target compound, which was a light yellow solid, was obtained by purification with preparative silica gel plate (DCM/MeOH=20/1).

Structural Analysis Data:

$^1$H NMR (400 MHz, $d_6$-DMSO) δ 1.22-1.55 (3H, m), 1.74-1.80 (2H, m), 2.07-2.23 (3H, m), 2.37-2.41 (1H, m), 3.25-3.28 (1H, m), 3.81-3.84 (1H, m), 5.65-5.69 (1H, m), 6.06-6.20 (3H, m), 6.75 (1H, dd, J=16.8 Hz, 10.4 Hz), 7.13 (1H, d, J=5.2 Hz), 7.16-7.21 (1H, m), 7.70 (2H, dd, J=8.4 Hz, 4.0 Hz), 7.83-7.88 (1H, m), 7.90 (1H, d, J=5.2 Hz), 8.15 (2H, d, J=8.4 Hz), 8.21 (1H, d, J=8.4 Hz), 8.39-8.41 (1H, m), 10.84-10.85 (1H, m).

EM (calculated value): 493.2; MS (ESI) m/e (M+1H)+: 494.2

Example 121

Preparation of 4-(8-amino-3-(2-(but-2-ynoyl)-2-azabicyclo[2.2.2]octan-1-yl)imidazo[1,5-a]pyrazin-1-yl)-N-(pyridin-2-yl)benzamide

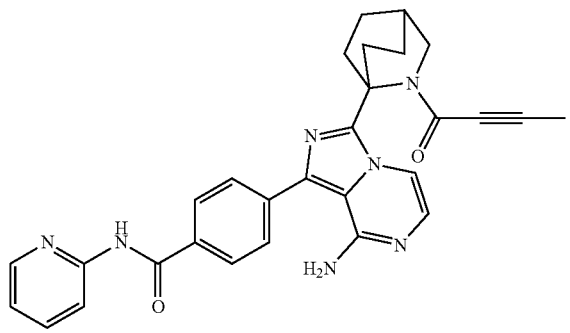 [SMILES: CC#CC(=O)N1CC2CCC1(c1nc(-c3ccc(C(=O)Nc4ccccn4)cc3)c3c(N)nccn13)CC2]

The synthesis method was the same as that in Example 1. 13 mg of the target compound, which was a light yellow solid, was obtained by purification with preparative silica gel plate (DCM/MeOH=20/1).

Structural Analysis Data:

$^1$H NMR (400 MHz, d$_6$-DMSO) δ 1.25-1.53 (4H, m), 1.70-1.76 (2H, m), 2.01 (2H, s), 2.07-2.24 (3H, m), 2.35-2.41 (1H, m), 3.25-3.26 (1H, m), 3.81-3.84 (1H, m), 6.06-6.20 (2H, m), 7.14 (1H, d, J=5.2 Hz), 7.15-7.23 (1H, m), 7.68 (2H, dd, J=8.4 Hz, 4.0 Hz), 7.81-7.85 (1H, m), 7.90 (1H, d, J=5.2 Hz), 8.16 (2H, d, J=8.4 Hz), 8.20 (1H, d, J=8.4 Hz), 8.39-8.41 (1H, m), 10.86-10.88 (1H, m).

EM (calculated value): 505.2; MS (ESI) m/e (M+1H)+: 506.2

Example 122

Preparation of 4-(3-(2-acryloyl-2-azabicyclo[2.2.1]heptan-1-yl)-8-aminoimidazo[1,5-a]pyrazin-1-yl)-N-(pyridin-2-yl)benzamide

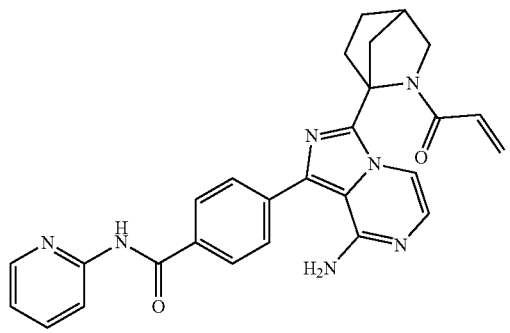 [SMILES: C=CC(=O)N1CC2CCC1(c1nc(-c3ccc(C(=O)Nc4ccccn4)cc3)c3c(N)nccn13)C2]

The synthesis method was the same as that in Example 2. 20 mg of the target compound, which was a light yellow solid, was obtained by purification with preparative silica gel plate (DCM/MeOH=20/1).

Structural Analysis Data:

$^1$H NMR (400 MHz, d$_6$-DMSO) δ 1.25-1.51 (3H, m), 1.69-1.72 (1H, m), 1.90-1.93 (1H, m), 2.61-2.70 (2H, m), 3.03-3.07 (1H, m), 3.43-3.47 (1H, m), 5.61-5.68 (1H, m), 6.10-6.19 (3H, m), 6.73-6.75 (1H, m), 7.11-7.19 (2H, m), 7.73-7.86 (4H, m), 8.15 (2H, dd, J=8.4 Hz, 2.8 Hz), 8.20 (1H, d, J=8.4 Hz), 8.41 (1H, dd, J=4.8 Hz, 1.2 Hz), 10.81 (1H, s).

EM (calculated value): 479.2; MS (ESI) m/e (M+1H)+: 480.2

Example 123

Preparation of 4-(8-amino-3-(2-(but-2-ynoyl)-2-azabicyclo[2.2.1]heptan-1-yl)imidazo[1,5-a]pyrazin-1-yl)-N-(pyridin-2-yl)benzamide

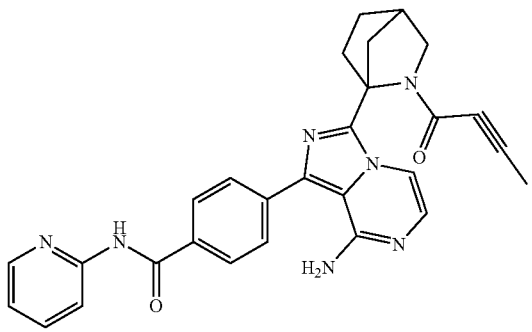 [SMILES: CC#CC(=O)N1CC2CCC1(c1nc(-c3ccc(C(=O)Nc4ccccn4)cc3)c3c(N)nccn13)C2]

The synthesis method was the same as that in Example 1. 15 mg of the target compound, which was a light yellow solid, was obtained by purification with preparative silica gel plate (DCM/MeOH=20/1).

Structural Analysis Data:

$^1$H NMR (400 MHz, d$_6$-DMSO) δ 1.31-1.56 (4H, m), 1.66-1.72 (1H, m), 1.95-1.98 (1H, m), 2.02 (2H, s), 2.59-2.72 (2H, m), 3.07-3.09 (1H, m), 3.44-3.47 (1H, m), 6.10-6.19 (2H, m), 7.12-7.19 (2H, m), 7.71-7.76 (2H, m), 7.84-7.89 (2H, m), 8.15-8.17 (2H, m), 8.21 (1H, d, J=8.4 Hz), 8.40-8.42 (1H, m), 10.85-10.87 (1H, m).

EM (calculated value): 491.2; MS (ESI) m/e (M+1H)+: 492.2

Example 124

Preparation of (S)-3-(3-(5-acryloyl-5-azaspiro[2.4]heptan-6-yl)-8-aminoimidazo[1,5-a]pyrazin-1-yl)-N-(pyridin-2-yl)benzamide

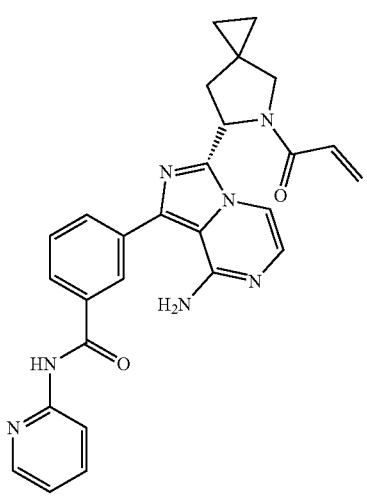

The synthesis method was the same as that in Example 2. 20 mg of the target compound, which was a light yellow solid, was obtained by purification with preparative silica gel plate (DCM/MeOH=20/1).

Structural Analysis Data:

$^1$H NMR (400 MHz, $d_6$-DMSO) δ 0.58-0.72 (4H, m), 2.23-2.25 (1.6H, m), 3.63-3.66 (1.4H, m), 3.85 (1H, d, J=10.4 Hz), 5.62-5.68 (2H, m), 6.05-6.17 (3H, m), 6.54 (1H, dd, J=16.8 Hz, 10.4 Hz), 7.12-7.20 (2H, m), 7.78-7.83 (3H, m), 7.83-7.86 (2H, m), 8.21 (1H, d, J=8.4 Hz), 8.41 (1H, d, J=3.6 Hz), 8.68 (1H, s), 10.82 (1H, s).

EM (calculated value): 479.2; MS(ESI) m/e (M+1H)+: 480.2

Example 125

Preparation of (S)-2-(3-(5-acryloyl-5-azaspiro[2.4]heptan-6-yl)-8-aminoimidazo[1,5-a]pyrazin-1-yl)-N-(pyridin-2-yl)benzamide

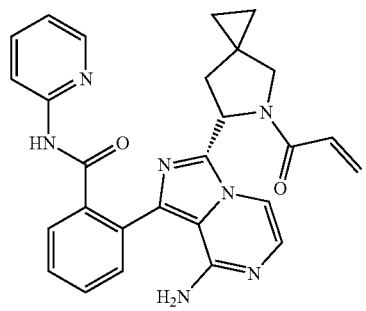

The synthesis method was the same as that in Example 2. 18 mg of the target compound, which was a light yellow solid, was obtained by purification with preparative silica gel plate (DCM/MeOH=20/1).

Structural Analysis Data:

$^1$H NMR (400 MHz, $d_6$-DMSO) δ 0.55-0.76 (4H, m), 2.23-2.26 (1.5H, m), 3.61-3.65 (1.5H, m), 3.86 (1H, d, J=10.4 Hz), 5.62-5.68 (2H, m), 6.07-6.19 (3H, m), 6.55 (1H, dd, J=16.8 Hz, 10.4 Hz), 7.13-7.20 (2H, m), 7.58-7.62 (2H, m), 7.70-7.72 (1H, m), 7.83-7.88 (2H, m), 8.12-8.14 (1H, m), 8.21 (1H, d, J=8.4 Hz), 8.40 (1H, d, J=3.6 Hz), 10.84 (1H, s).

EM (calculated value): 479.2; MS (ESI) m/e (M+1H)+: 480.2

Example 126

Preparation of (1 S,4S)-tert-butyl-5-acryloyl-6-(8-amino-1-(4-(pyridin-2-carbamoyl)phenyl)imidazo[1,5-a]pyrazin-3-yl)-2,5-diazabicyclo[2.2.1]heptane-2-carboxylate

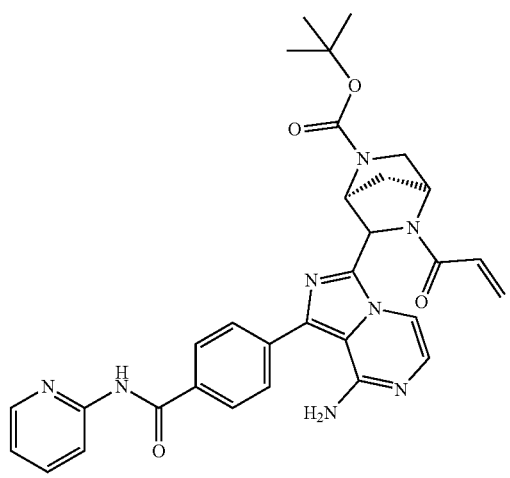

The synthesis method was the same as that in Example 2. 25 mg of the target compound, which was a light yellow solid, was obtained by purification with preparative silica gel plate (DCM/MeOH=20/1).

Structural Analysis Data:

$^1$H NMR (400 MHz, $d_6$-DMSO) δ 1.47-1.52 (9H, m), 1.99-2.01 (1H, m), 2.82-2.84 (1H, m), 3.24-3.48 (2H, m), 4.38-4.52 (1H, m), 4.96-5.24 (2H, m), 5.46-5.52 (0.4H, m), 5.65-5.76 (1H, m), 6.00-6.30 (3H, m), 6.86 (0.6H, dd, J=16.8 Hz, 10.4 Hz), 7.17-7.25 (2H, m), 7.65-7.75 (3H, m), 7.84-7.88 (1H, m), 8.14-8.23 (3H, m), 8.40-8.42 (1H, m), 10.85 (1H, s).

EM (calculated value): 580.3; MS(ESI) m/e (M+1H)+: 581.3

Pharmacodynamic Tests

Test Example 1: In Vitro Assay for the Inhibition of BTK Kinase Activity

1: Test Principle:

Mobility-Shift Assay, which is microfluidic chip technology, applies the basic concept of capillary electrophoresis to microfluidic environments. The substrate used for the experiment is a polypeptide with a fluorescent label. Under the action of enzyme in the reaction system, the substrate is transformed into a product, and the charge the substrate carries also changes accordingly. The use of the charge difference between the substrate and the product involved in Mobility-Shift Assay achieves the separating of the two, and they are tested respectively. The test results are expressed by conversion rates.

2: Test Method:

(1) preparation of samples to be tested: diluted with 100% DMSO to 50 times the final concentration of the reaction, i.e. 25 μmol/L;

(2) dilution: 25 μmol/L is the initial concentration, then diluted with 4 times the concentration and diluted with 10 concentration gradients;

(3) 100% DMSO was added to the positive control well and the negative control well, respectively;
(4) the prepared compounds with 10 concentrations were diluted 10-fold with 1 ×kinase buffer, respectively; wherein, the kinase buffer contained hydroxyethyl piperazine ethanesulfonic acid at a concentration of 50 mmol/L and a pH of 7.5, 0.01% dodecyl polyethylene glycol ether, 10 mmol/L magnesium chloride, 2 mmol/L dithiothreitol;
(5) preparation of 2.5×enzyme solution: the kinase was added to 1×kinase buffer to form 2.5×enzyme solution;
(6) preparation of 2.5×substrate solution: FAM-labeled polypeptide and ATP were added to the 1 ×kinase buffer to form 2.5×substrate solution; (7) addition of the enzyme solution to the 384-well plate: 5 µl of 5×compound dissolved in 10% DMSO contained in the 384-well reaction plate, then 10 µl of 2.5×enzyme solution was added, the obtained system was incubated for 10 minutes at room temperature;
(8) addition of the substrate solution to the 384-well plate: 10 µl of 2.5×substrate solution was added to the 384-well reaction plate;
(9) kinase reaction and termination: after incubation at 28° C. for 1 hour, 25 µl stop solution was added to terminate the reaction; wherein, the stop solution contained hydroxyethyl piperazine ethanesulfonic acid at a concentration of 100 mmol/L and a pH of 7.5, 0.015% dodecyl polyethylene glycol ether, 0.2% surface reagent No. 3, 20 mmol/L ethylenediaminetetraacetic acid; (10) Caliper data reading: conversion rate data was read from Caliper;

Test Example 2: Determination of the Inhibition of Cell Proliferation Inhibitory Activity in vitro of compounds using different cell lines
1: The preparation of the medium is shown in Table 6:

TABLE 6

| Preparation of the medium | |
|---|---|
| Cell lines | Media |
| TMD8 | MEM + 10% FBS |
| OCI-Ly10 | IMDM + 10% FBS + 1% PS + L-Glu |
| DOHH2 | RPMI1640 + 10% FBS |

2: Preparation of the Compounds:
The compounds to be tested were diluted with DMSO to prepare a mother liquor at a final concentration of 10 mM for later use.
3: $IC_{50}$ Determination
3.1. Test of TMD8 and OCI-ly10 Cells by CCK-8 Method
Logarithmic growth phase cells were collected, counted and resuspended in complete medium. The cell concentration was adjusted to a suitable concentration (determined according to the cell density optimization test results), and seeded to 96-well plate and 100 µl of the cell suspension was added to each well. The cells were incubated in an incubator at 37° C., 100% relative humidity and 5% C02 for 24 hours.
The compounds to be tested were diluted with the medium to the set corresponding action concentration, and the cells were added at 25 l/well. The cells were incubated in an incubator at 37° C., 100% relative humidity and 5% C02 for 72 hours.
The medium was aspirated and discarded, and a complete medium containing 10% of the test reagent was added and the obtained system was incubated in a 37° C. incubator for 1 hour-4 hours. The absorbance at a wavelength of 450 nm was measured on SpectraMax M5 Microplate Reader after gentle shaking, and the absorbance at 650 nm was used as a reference to calculate the inhibition rate.
3.2 Test of DOHH2 Cells by CTG Assay
Logarithmic growth phase cells were collected, counted and resuspended in complete medium. The cell concentration was adjusted to a suitable concentration (determined according to the cell density optimization test results), and seeded to 96-well plate and 100 µl of the cell suspension was added to each well. The cells were incubated in an incubator at 37° C., 100% relative humidity and 5% C02 for 24 hours.
The compounds to be tested were diluted with the medium to the set corresponding action concentration, and the cells were added at 10 l/well. The cells were incubated in an incubator set at 37° C., 100% relative humidity and 5% C02 for 72 hours.
The medium was aspirated and discarded, and 30 µl of test reagent was added. The plate was gentle shaken away from the light to lyse the cells. After incubation for 2 minutes at room temperature, determination was carried out on Envision and the inhibition rate was calculated.
4: Data Processing
The inhibition rate of the drug on tumor cell growth was calculated as follows: tumor cell growth inhibition rate %=[(Ac−As)/(Ac−Ab)]×100%
As: OA of the sample (cell+test reagent+test compound)
Ac: OA of the negative control (cell+test reagent+DMSO)
Ab: OA of the positive control (medium+test reagent+DMSO)
$IC_{50}$ curve fitting was performed using the software Graphpad Prism 5 or XLfit and $IC_{50}$ values were calculated.
The results of the inhibition against BTK kinase activity and cell proliferation activity in vitro of the compounds are shown in Table 7:

TABLE 7

Results of the inhibition against BTK kinase activity and cell proliferation activity in vitro of the compounds

| | BTK | Inhibitions of cell activities $IC_{50}$ (nM) | | |
|---|---|---|---|---|
| Examples | $IC_{50}$ (nM) | DOHH2 | TMD8 | OCI-LY10 |
| 1 | 83 | >1000 | | |
| 2 | 24 | 917 | | |
| 3 | 4.7 | 191 | 0.26 | 0.24 |
| 4 | 4.5 | 673 | 2.1 | 3.5 |
| 5 | 21 | 175 | 3.6 | 0.21 |
| 6 | 9.1 | >1000 | 5.4 | 0.21 |
| 7 | 155 | n.d. | n.d. | n.d. |
| 8 | 197 | n.d. | n.d. | n.d. |
| 9 | 2.8 | 74.3 | 0.20 | 0.13 |
| 10 | 72 | >1000 | 6.3 | 2.1 |
| 11 | 2.6 | 133 | 1.5 | 1.8 |
| 12 | 14 | 129 | 4.3 | 7.4 |
| 13 | 3.3 | 138 | 0.38 | 0.67 |
| 14 | 12.5 | >1000 | 7.5 | 1.8 |
| 15 | 17.4 | 716 | 64.5 | 17.6 |
| 16 | 9.5 | >1000 | 1.6 | 3.1 |
| 17 | 48 | >1000 | n.d. | n.d. |
| 18 | 1.4 | 177 | 1.6 | 0.25 |
| 19 | 400 | n.d. | n.d. | n.d. |
| 20 | 372 | n.d. | n.d. | n.d. |
| 21 | 672 | n.d. | n.d. | n.d. |
| 22 | 3.3 | 182 | 4.2 | 0.38 |
| 23 | 49 | >1000 | 1.1 | 2.4 |
| 24 | 176 | n.d. | n.d. | n.d. |
| 25 | 342 | n.d. | n.d. | n.d. |
| 26 | 477 | n.d. | n.d. | n.d. |
| 27 | 673 | n.d. | n.d. | n.d. |
| 28 | 124 | n.d. | n.d. | n.d. |
| 29 | 216 | n.d. | n.d. | n.d. |
| 30 | 724 | n.d. | n.d. | n.d. |

TABLE 7-continued

Results of the inhibition against BTK kinase activity and cell proliferation activity in vitro of the compounds

| Examples | BTK IC$_{50}$ (nM) | Inhibitions of cell activities IC$_{50}$ (nM) | | |
|---|---|---|---|---|
| | | DOHH2 | TMD8 | OCI-LY10 |
| 31 | 736 | n.d. | n.d. | n.d. |
| 32 | 57 | >1000 | n.d. | n.d. |
| 33 | 94 | n.d. | n.d. | n.d. |
| 34 | 66 | n.d. | n.d. | n.d. |
| 35 | 67 | n.d. | n.d. | n.d. |
| 36 | 93 | n.d. | n.d. | n.d. |
| 37 | 46 | n.d. | n.d. | n.d. |
| 38 | 66 | n.d. | n.d. | n.d. |
| 39 | 68 | n.d. | n.d. | n.d. |
| 40 | 97 | n.d. | n.d. | n.d. |
| 41 | 52 | n.d. | n.d | n.d. |
| 42 | 5.3 | 104 | 0.26 | 0.33 |
| 43 | 4.4 | 217 | 2.3 | 0.42 |
| 44 | 34 | 717 | 7.8 | 1.3 |
| 45 | 17 | 285 | 6.4 | 1.1 |
| 46 | 4.2 | 94.3 | 3.4 | 0.37 |
| 47 | 5.2 | 172 | 4.6 | 0.41 |
| 48 | 2.1 | 103 | 0.31 | 0.46 |
| 49 | 4.8 | 436 | 6.4 | 3.4 |
| 50 | 69 | n.d. | n.d. | n.d. |
| 51 | 54 | n.d. | n.d. | n.d. |
| 52 | 2.4 | 174 | 6.4 | 0.35 |
| 53 | 1.8 | 166 | 0.75 | 1.3 |
| 54 | 1.5 | 143 | 0.15 | 0.64 |
| 55 | 2.3 | 97 | 0.48 | 1.87 |
| 56 | 4.3 | 74 | 5.9 | 3.4 |
| 57 | 59 | n.d. | n.d. | n.d. |
| 58 | 78 | n.d. | n.d. | n.d. |
| 59 | 97 | n.d. | n.d. | n.d. |
| 60 | 51 | n.d. | n.d | n.d. |
| 61 | 31 | n.d. | n.d. | n.d. |
| 62 | 13 | 179 | 2.8 | 3.9 |
| 63 | 57 | n.d. | n.d. | n.d. |
| 64 | 87 | n.d. | n.d. | n.d. |
| 65 | 58 | n.d. | n.d | n.d |
| 66 | 34 | >1000 | n.d. | n.d |
| 67 | 69 | >1000 | n.d. | n.d. |
| 68 | 5.3 | 172 | 3.2 | 4.4 |
| 69 | 1.4 | 124 | 0.62 | 0.74 |
| 70 | 2.4 | 677 | 6.8 | 3.2 |
| 71 | 12 | 84 | 8.4 | 1.4 |
| 72 | 97 | n.d. | n.d. | n.d. |
| 73 | 18 | 124 | 42.3 | 1.4 |
| 74 | 24 | 72 | 9.7 | 3.5 |
| 75 | 57 | n.d. | n.d. | n.d. |
| 76 | 46 | n.d. | n.d. | n.d. |
| 77 | 8.5 | 212 | 2.5 | 0.26 |
| 78 | 18.4 | n.d. | n.d. | n.d |
| 79 | 4.9 | 164 | 1.2 | 0.13 |
| 80 | 24 | 618 | 4.3 | 0.67 |
| 81 | 178 | n.d. | n.d. | n.d. |
| 82 | 382 | n.d. | n.d. | n.d. |
| 83 | 46 | n.d. | n.d. | n.d. |
| 84 | 16.3 | 48 | 6.8 | 4.2 |
| 85 | 9.4 | 96 | 18.2 | 0.97 |
| 86 | 29 | 917 | n.d. | n.d. |
| 87 | 42 | 786 | n.d. | n.d. |
| 88 | 51 | n.d. | n.d. | n.d. |
| 89 | 14 | 96 | 2.4 | 0.23 |
| 90 | 79 | n.d. | n.d. | n.d. |
| 91 | 21 | >1000 | 1.4 | 0.41 |
| 92 | 4.3 | 712 | 7.6 | 0.31 |
| 93 | 3.6 | 318 | 0.65 | 0.53 |
| 94 | 14.3 | 314 | 7.4 | 0.67 |
| 95 | 7.2 | 218 | 6.9 | 0.37 |
| 96 | 3.1 | 200 | 3.2 | 0.34 |
| 97 | 2.8 | >1000 | 6.2 | 0.4 |
| 98 | 24 | >1000 | 6.8 | 0.33 |
| 99 | 39 | >1000 | 5.4 | 2.7 |
| 100 | 67 | n.d. | n.d. | n.d. |
| 101 | 77 | n.d. | n.d. | n.d. |
| 102 | 175 | n.d. | n.d. | n.d. |
| 103 | 271 | n.d. | n.d. | n.d. |
| 104 | 4.6 | 718 | 3.6 | 0.42 |
| 105 | 18 | 916 | 8.4 | 0.41 |
| 106 | 47 | >1000 | 21.4 | 0.78 |
| 107 | 41 | 986 | 12.3 | 0.81 |
| 108 | 72 | >1000 | 14.3 | 2.7 |
| 109 | 19 | 184 | 7.2 | 0.31 |
| 110 | 36 | 198 | 1.2 | 0.21 |
| 111 | 30 | 672 | 4.3 | 2.1 |
| 112 | 21 | 902 | 0.31 | 0.41 |
| 113 | 4.6 | >1000 | 12.5 | 7.4 |
| 114 | 81 | n.d. | n.d. | n.d. |
| 115 | 26 | >1000 | 17.6 | 12.1 |
| 116 | 276 | n.d. | n.d. | n.d. |
| 117 | 104 | n.d. | n.d. | n.d. |
| 118 | 5.6 | 712 | 3.9 | 4.1 |
| 119 | 43 | >1000 | 2.4 | 0.42 |
| 120 | 24 | 921 | 6.4 | 4.1 |
| 121 | 43 | n.d. | n.d. | n.d. |
| 122 | 49 | n.d. | n.d. | n.d. |
| 123 | 72 | n.d. | n.d. | n.d. |
| 124 | 18 | 629 | 11.8 | 1.5 |
| 125 | 58 | >1000 | 24.9 | 8.7 |
| 126 | 4.4 | 206 | 1.6 | 0.8 |
| Ibrutinib | 1.3 | 705 | 0.28 | 0.41 |
| ACP-196 | 47 | >1000 | 1.3 | 1.4 |

Test Example 3: hERG Experiment to Investigate Potential Cardiotoxicity

1: Cell Culture

CHO hERG cells were grown in a culture dish containing the above medium, and cultured in an incubator at 37° C. and 5% CO$_2$. CHO hERG cells were transferred to circular glass slides placed in the culture dish 24-48 hours prior to electrophysiological experiments and grown under the same medium and culture conditions as above. The density of CHO hERG cells on each circular slide shall meet the requirement that most of the cells are independent and individual.

2: Preparation of Experimental Solutions

| Components of intracellular fluid and extracellular fluid | | |
|---|---|---|
| Reagents | Extracellular fluids (mM) | Intracellular fluids (mM) |
| CaCl$_2$ | 2 | 5.37 |
| MgCl$_2$ | 1 | 1.75 |
| KCl | 4 | 120 |
| NaCl | 145 | — |
| Glucose | 10 | — |
| HEPES | 10 | 10 |
| EGTA | — | 5 |
| Na-ATP | — | 4 |
| pH | 7.4 (adjusted with NaOH) | 7.25 (adjusted with KOH) |
| Osmotic pressure | Osmotic pressure about 305 mOsm | Osmotic pressure about 295 mOsm |

3: Electrophysiological Recording System

A manual patch clamp system (HEKA EPC-10 signal amplifier and digital conversion system, purchased from HEKA Electronics, Germany) is used in this experiment for whole cell currents recording. A circular slide with CHO hERG cells grown on its surface was placed in an electrophysiology recording tank under an inverted microscope. The extracellular fluid was continuously perfused in the recording tank (about 1 ml per minute). A conventional whole cell patch clamp current recording technique was used in the experimental procedure. Unless otherwise specified, the experiments were carried out at conventional room temperature (about 25° C.). The cells were clamped at a voltage of −80 mV. The clamp voltage for cells was depolarized to +20 mV to activate the hERG potassium channel, and after 5 seconds, the cells were clamped to −50 mV to eliminate inactivation and generate a tail current. The tail current peak was used as the value of the hERG current magnitude. After the hERG potassium current recorded in the above step was stable under the continuous extracellular fluid perfusion in the recording tank, the drug to be tested can be perfused simultaneously and filled until the inhibitory effect of the drug on the hERG current reached a steady state. Generally, the superposition of the last three consecutive current recording lines was used as a criterion for judging whether or not the state was stable. After reaching a steady state, a wash with extracellular fluid perfusion was conducted until the hERG returned to that before the drug was added. One cell can be used to test one or more drugs, or multiple concentrations of the same drug, but need to be washed with an extracellular fluid between different drugs. Cisapride (purchased from Sigma) was used as a positive control in the experiment to ensure that the cells used were of normal quality.

4: Treatment and Dilution of Compounds

In order to obtain the $IC_{50}$ of the compounds, we selected the following concentrations (30, 10, 3, 1, 0.3 and 0.1 μM) for testing. Prior to testing, the compounds were first diluted to 10, 3, 1, 0.3, and 0.1 mM stock solutions by a method of gradual dilution with DMSO, and were then diluted to the final M test concentration with extracellular fluids. The final concentration of DMSO in each of the other compound solutions was 0.1%, except that the DMSO concentration in the 30 μM compound test solution was 0.3%. The test concentration of the positive control (Cisapride) was 0.1 μM. All compound solutions were sonicated and shaken for a routine of 5 to 10 minutes to ensure complete dissolution of the compounds.

5: Data Processing

The test data were analyzed by HEKA Patchmaster, Microsoft Excel and data analysis software provided by Graphpad Prism.

The test results of cardiac hERG potassium current of some of the compounds are shown in Table 8:

TABLE 8

Test results of cardiac hERG potassium current of some of the compounds

| Examples | hERG $IC_{50}$ values (μm) |
|---|---|
| 3 | >30 |
| 5 | >30 |
| 11 | >30 |
| 18 | >30 |
| 22 | >30 |
| 47 | >30 |
| 79 | >30 |
| 96 | >30 |
| Ibrutinib | 1.5 |

Test Example 4: Pharmacokinetic Test of the Compounds of the Present Invention

SD rat, male (purchased from Shanghai Sippr-Bk Laboratory Animal Co., Ltd.), each tested compound was administered at a single dose to SD rats by oral administration (10 mg/kg, 3 rats in each group) and intravenous administration (1 mg/kg, 3 rats in each group) for the pharmacokinetic study. The tested compounds were dissolved using DMSO/9% sodium chloride injection=5/95 (V/V), and vortexed for 1 minute, and after 1 minute of sonication, the compounds were formulated into solutions for administrations. Animals were fasted for 16-17 hours prior to oral administration and feeding was restored 4 hours after administration. After oral and intravenous administration, pharmacokinetic samples were collected from SD rats by jugular vein or cardiac puncture at the following time points: before administration, 5 minute, 15 minute, 30 minute, 1 hour, 2 hours, 4 hours, 6 hours, 8 hours and 24 hours after administration. 3 whole blood samples were collected at each time point, and the collected amount was about 0.2 mL, and the collected samples were anticoagulated by heparin sodium. After collection, the blood samples were immediately placed on ice and centrifuged to separate plasma within 30 minutes (centrifugation conditions: 8000 rpm, 6 minute, 2-8° C.). The collected plasma was stored at −70° C. prior to analysis. 50 μL of plasma sample was brought into a 1.5 mL centrifuge tube, 250 μL of internal standard solution (blank with no internal standard but the same volume of methanol added) was added, blended with vortex, centrifuged at 15000 rpm for 5 minutes. 200 μL of supernatant was taken and added to a 96-well sample plate and the samples were analyzed by LC-MS/MS.

The pharmacokinetic test results of some of the compounds of the present invention are shown in Table 9 below:

TABLE 9

Pharmacokinetic test results of some of the compounds of the present invention

| Examples | T½ (iv) h | Tmax (po) h | Cmax (po) ng/ml | AUC (po) ng/ml * h | Cl (iv) ml/hr/kg | F (po) % |
|---|---|---|---|---|---|---|
| Example 3 | 0.62 | 0.27 | 1619.79 | 1492.19 | 3420.38 | 52.55 |
| Example 5 | 0.13 | 0.10 | 303.06 | 278.20 | 7278.25 | 20.64 |
| Example 11 | 0.47 | 0.33 | 1612.51 | 1583.67 | 2187.37 | 34.59 |
| Example 22 | 0.60 | 0.25 | 1156.00 | 1038.16 | 3510.37 | 36.56 |
| Example 47 | 0.30 | 0.25 | 1121.14 | 971.12 | 2277.10 | 21.89 |
| Example 79 | 0.52 | 0.21 | 1105.72 | 770.13 | 3450.68 | 27.12 |
| Example 96 | 0.55 | 0.36 | 1589.06 | 1580.79 | 1960.88 | 34.53 |
| Ibrutinib | 0.26 | 0.33 | 217.10 | 218.09 | 1200.00 | 2.67 |
| ACP-196 | 0.13 | 0.08 | 266.02 | 266.08 | 7489.19 | 19.75 |

It can be seen from the above druggability research data that the compounds of the present invention have significant inhibitory effects on BTK activity, and when compared with the drug already on the market, ibrutinib or the clinical phase III ACP-196, the compounds of the present invention have extremely small cardiotoxicities and obvious advantages from the pharmacokinetic aspect, can be used as BTK inhibitors and have broad application prospects against malignant tumor diseases or inflammatory diseases. The above description of the examples is merely to assist in understanding the method of the present invention and the core idea thereof. It should be noted that those skilled in the art can make various improvements and modifications to the present invention without departing from the principle of the present invention and such improvements and modifications are also within the protection scopes of the claims of the present invention.

The invention claimed is:

1. A compound, having the structure shown in formula (I) or an isomer, a pharmaceutically acceptable solvate or salt thereof:

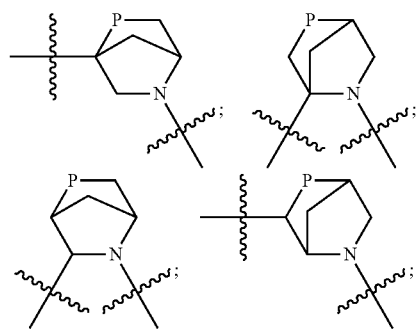

formula (I)

wherein Y is a substituted or unsubstituted aryl or heteroaryl;
R is a substituted or unsubstituted alkenyl or alkynyl;
M is

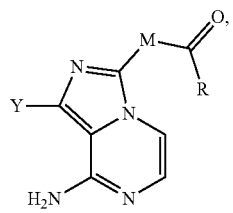

-continued

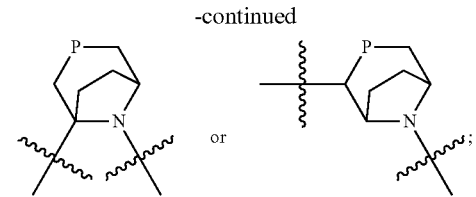

wherein P is $CR_5R_6$, $N-R_7$ or O;

$R_7$ is a substituted or unsubstituted C1-8 alkyl, a substituted or unsubstituted C1-8 heteroalkyl, a substituted or unsubstituted C3-8 cycloalkyl, a substituted or unsubstituted C3-8 heterocycloalkyl, or

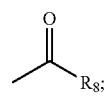

$R_5$, $R_6$ and $R_8$ are independently selected from the group consisting of substituted or unsubstituted C1-8 alkyls, substituted or unsubstituted C1-8 heteroalkyls, substituted or unsubstituted C3-8 cycloalkyls, and substituted or unsubstituted C3-8 heterocycloalkyls.

2. The compound according to claim 1, wherein the M is selected from the group consisting of:

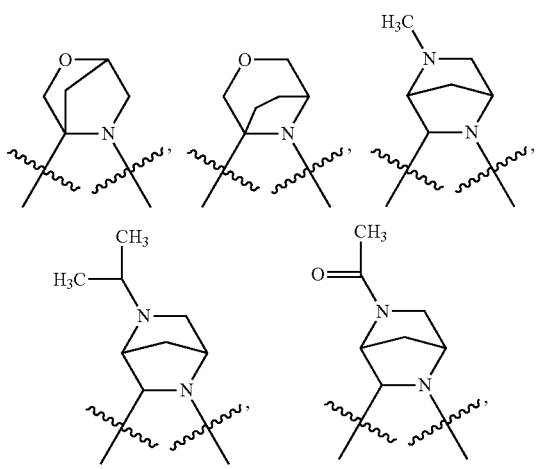

-continued

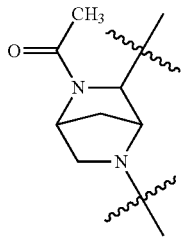 and 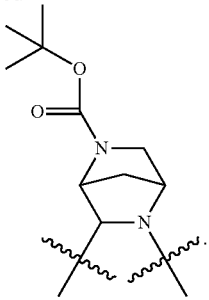

3. The compound according to claim 1, wherein the R is a substituted or unsubstituted alkenyl or alkynyl.

4. The compound according to claim 3, wherein the R is

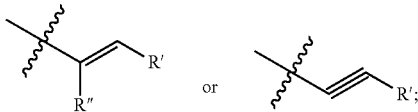

wherein R' is H, a substituted or unsubstituted C1-8 alkyl, a substituted or unsubstituted C1-8 heteroalkyl, a substituted or unsubstituted C1-8 cycloalkyl, or a substituted or unsubstituted C1-8 heterocycloalkyl;

R'' is H, nitro, halogen or cyano.

5. The compound according to claim 1, wherein the Y is a substituted or unsubstituted C5-10 aryl or heteroaryl.

6. The compound according to claim 1, wherein the Y is a substituted phenyl, the substituent of the phenyl is selected from the group consisting of substituted or unsubstituted amidos, substituted or unsubstituted alkyls, and substituted or unsubstituted ether groups.

7. The compound according to claim 6, wherein the Y is

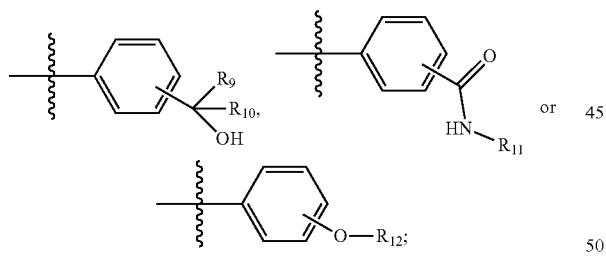

wherein $R_9$ is a trifluoromethyl or methyl;

$R_{10}$, $R_{11}$ and $R_{12}$ are independently a substituted or unsubstituted aryl or heteroaryl.

8. The compound according to claim 7, wherein the $R_{10}$, $R_{11}$ and $R_{12}$ are independently selected from the group consisting of substituted or unsubstituted phenyls, pyridyls, piperidinyls, piperazinyls and pyrimidinyls; the substituent of the above groups is selected from the group consisting of nitro, hydroxy, mercapto, fluorine, chlorine, bromine, iodine, cyano, substituted or unsubstituted C1-10 alkyls, substituted or unsubstituted C1-10 heteroalkyls, substituted or unsubstituted C3-10 cycloalkyls, and substituted or unsubstituted C3-10 heterocycloalkyls.

9. The compound according to claim 1, wherein the compound is selected from the group consisting of:

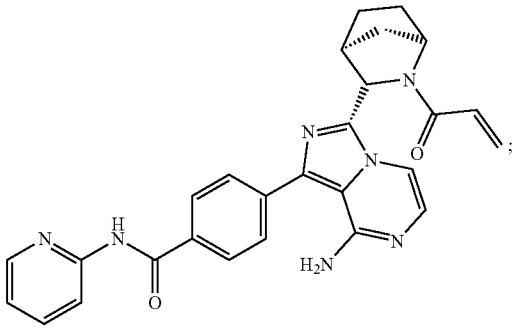

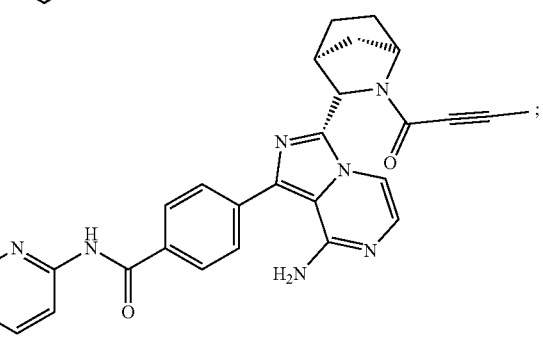

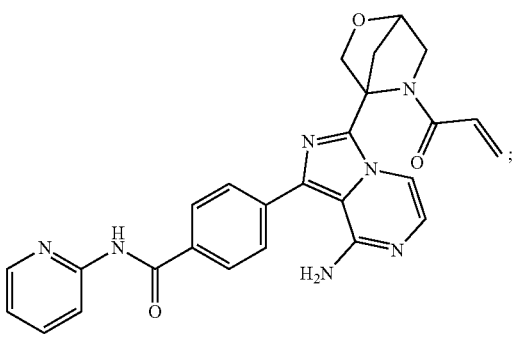

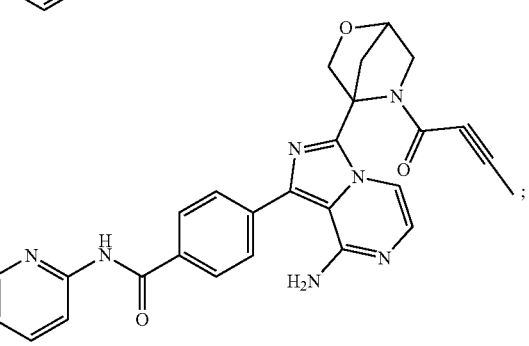

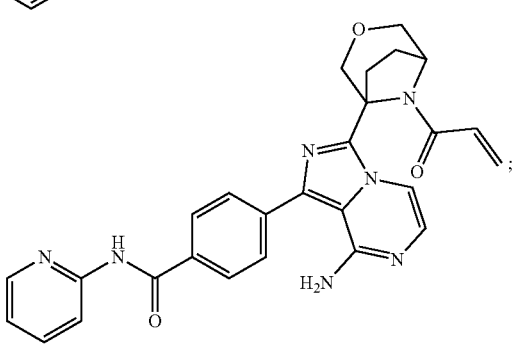

163
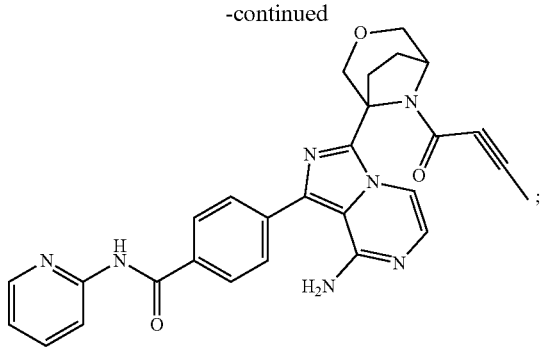
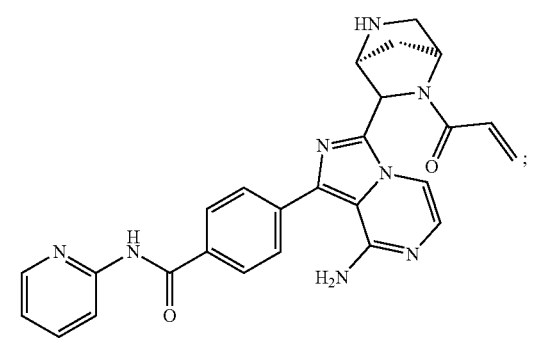
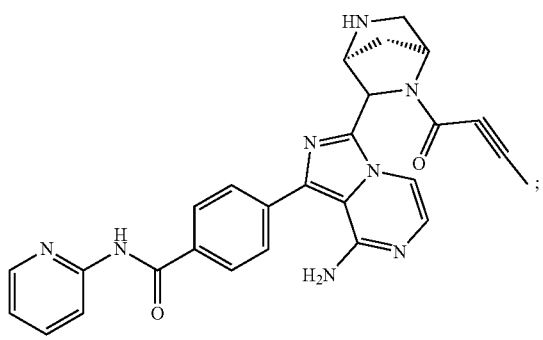
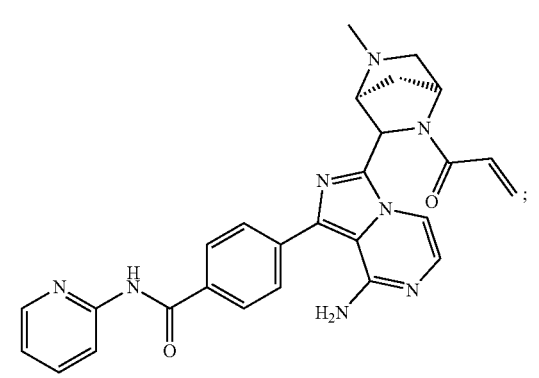
164
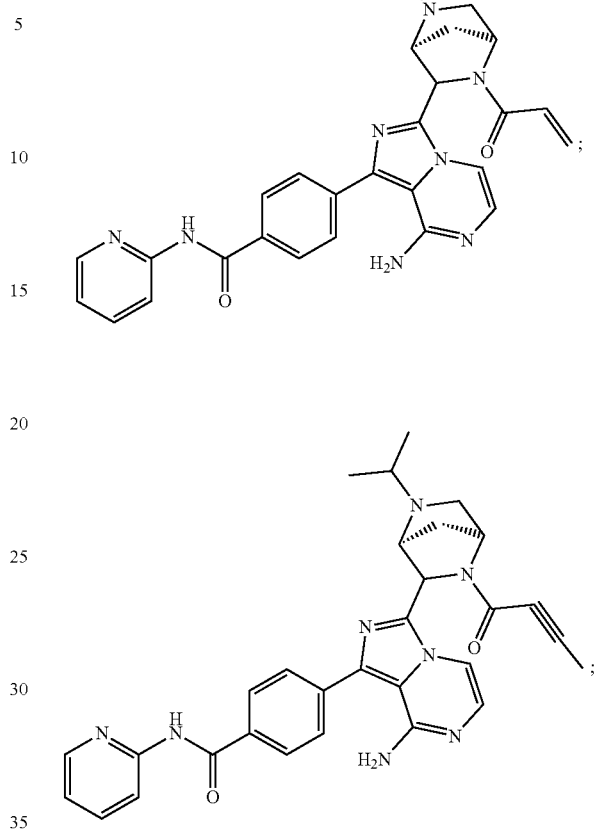
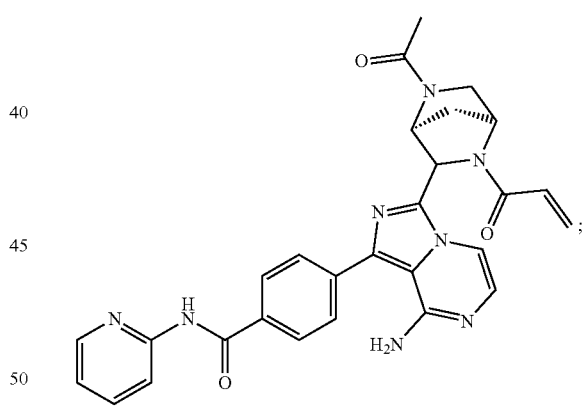
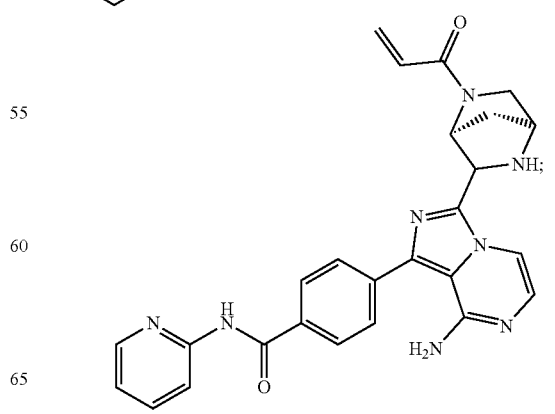

165
-continued
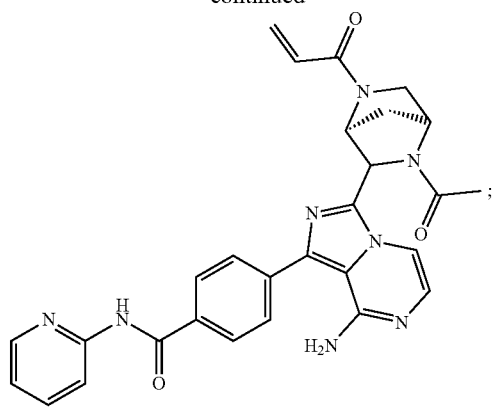
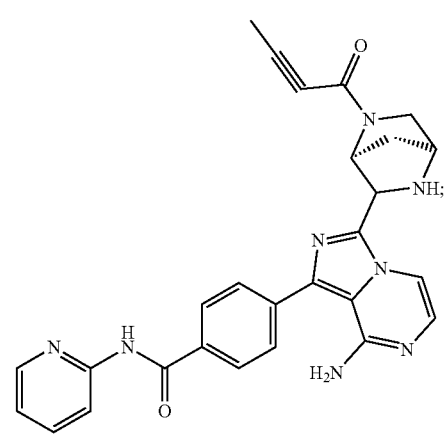
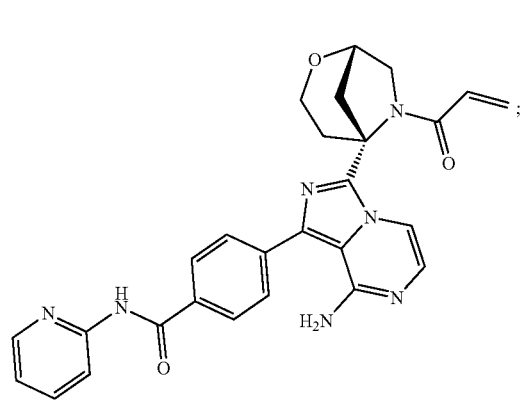
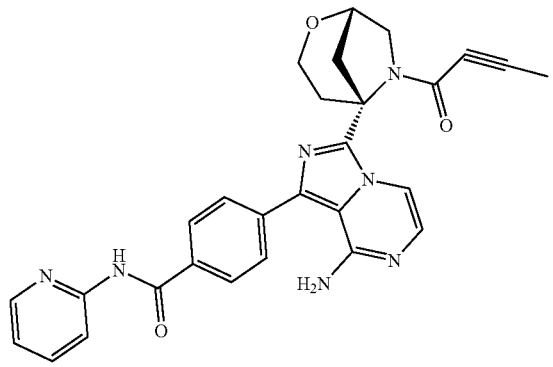
166
-continued
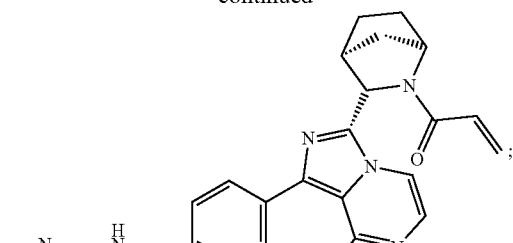
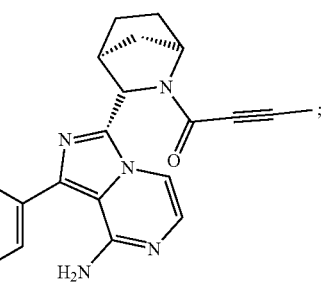
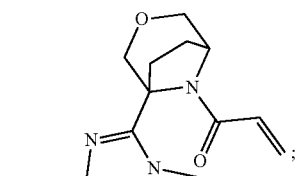
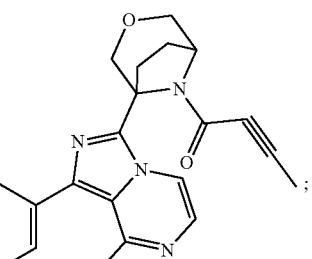

167
-continued

168
-continued

169
-continued
170
-continued
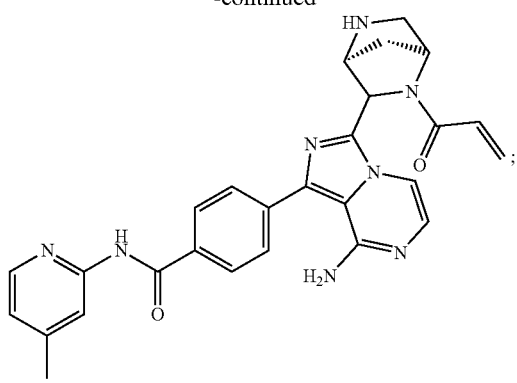
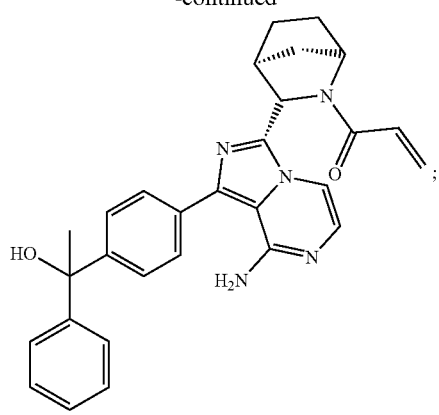
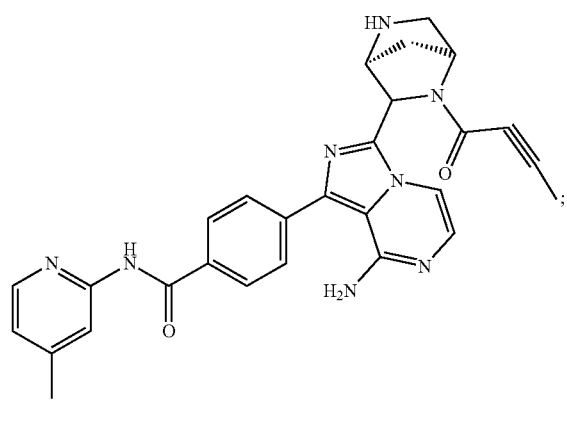
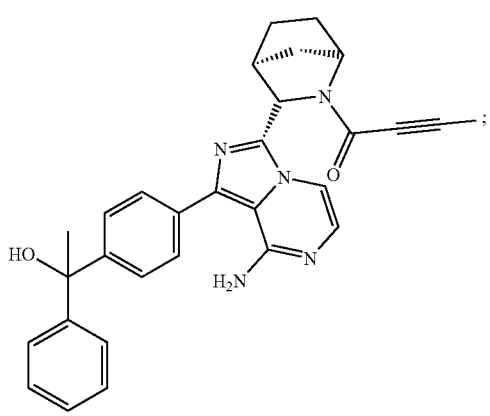
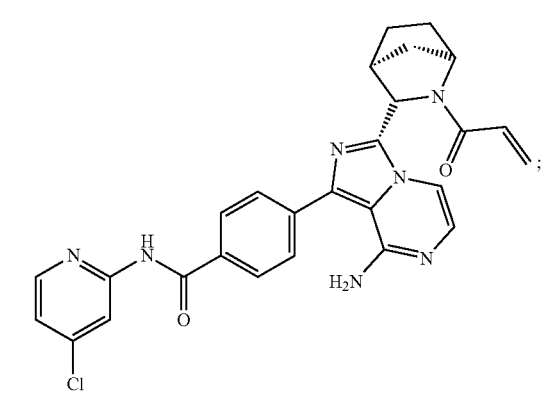
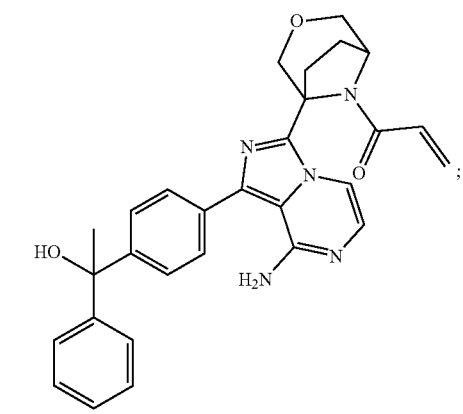
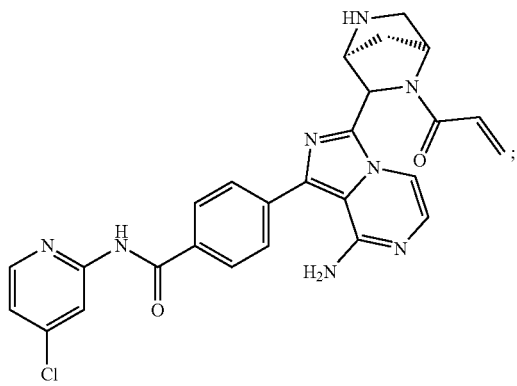
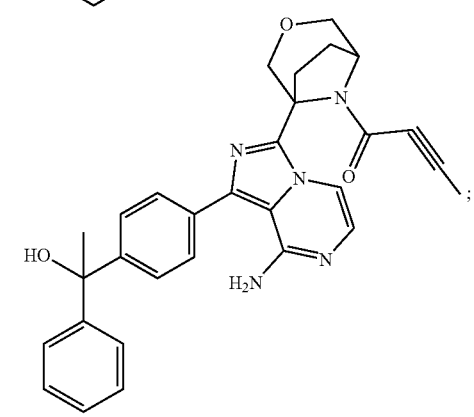

171
-continued
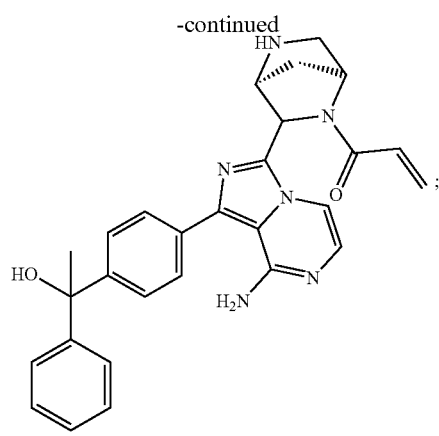
;
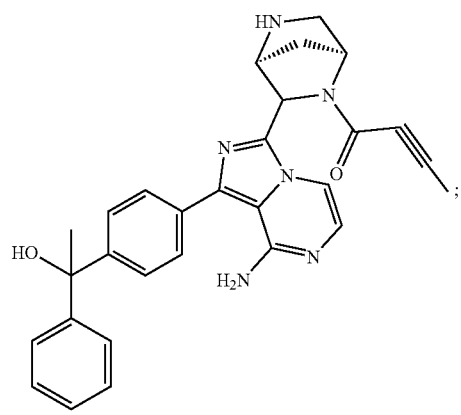
;
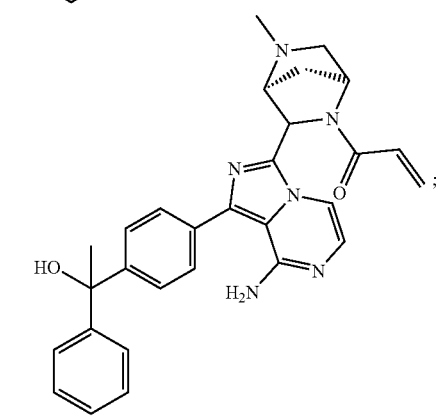
;
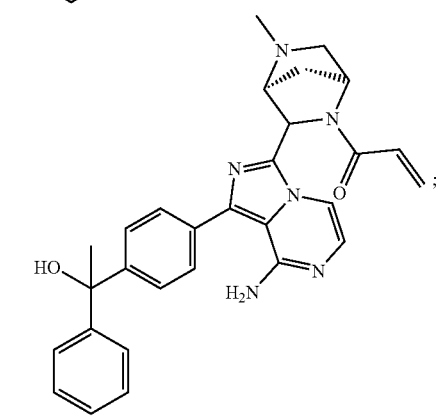
;
172
-continued
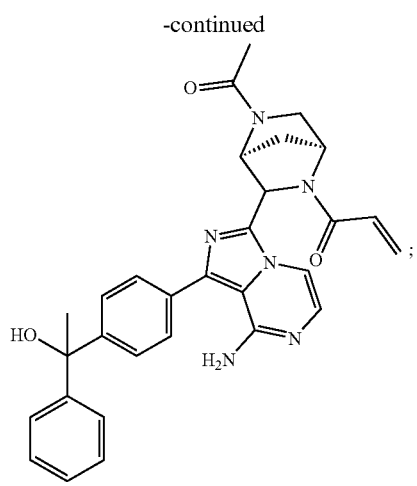
;
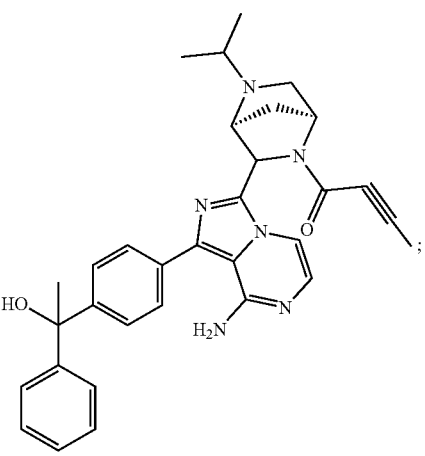 [SMILES: CC#CC(=O)N1C(c2nc(-c3ccc(C(C)(O)c4ccccc4)cc3)c3c(N)nccn23)[C@@H]2C[C@H]1CN2C(C)C]
;
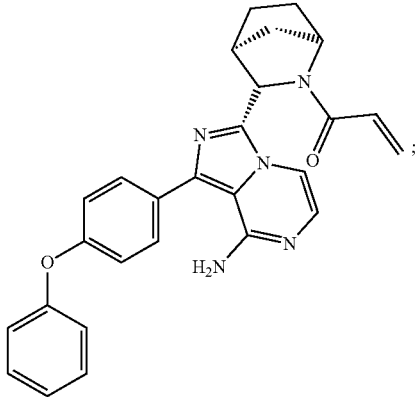
;
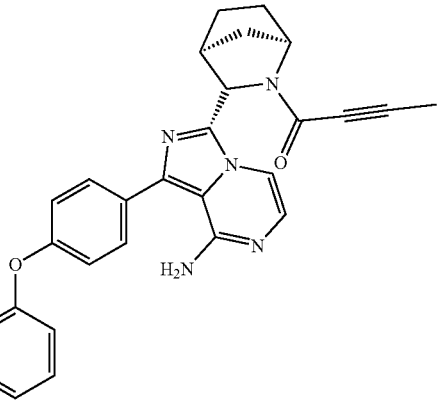
;

173
-continued
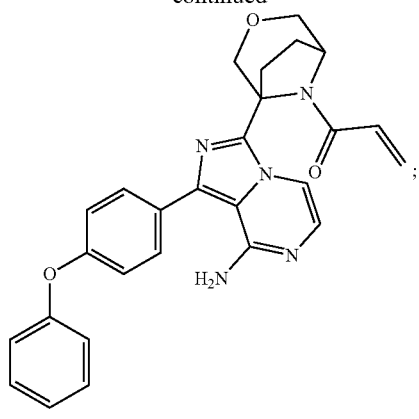
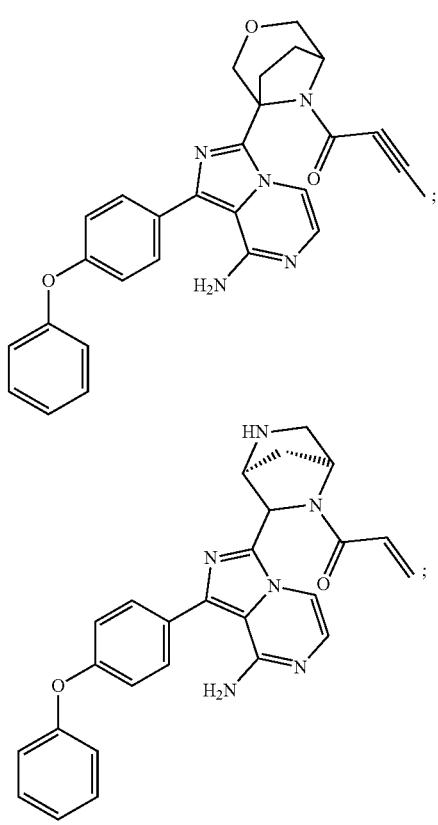
174
-continued
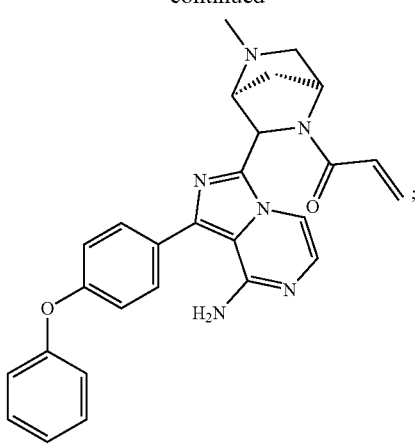
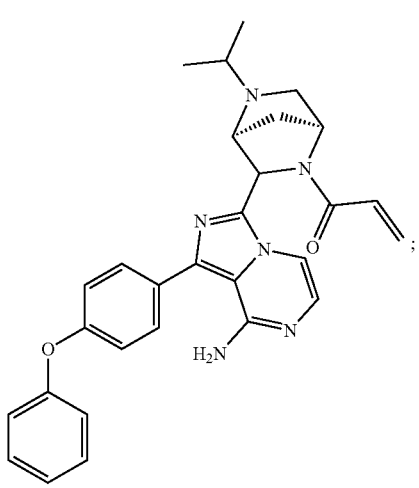
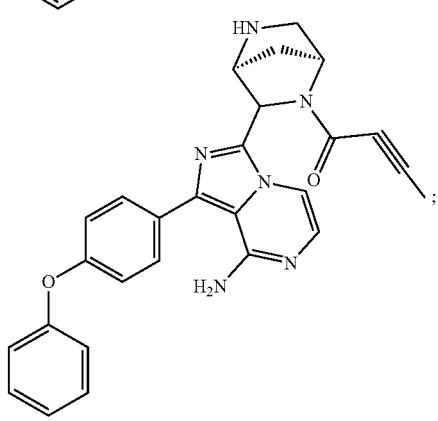
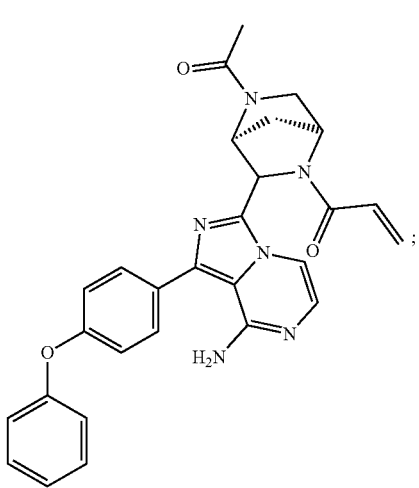

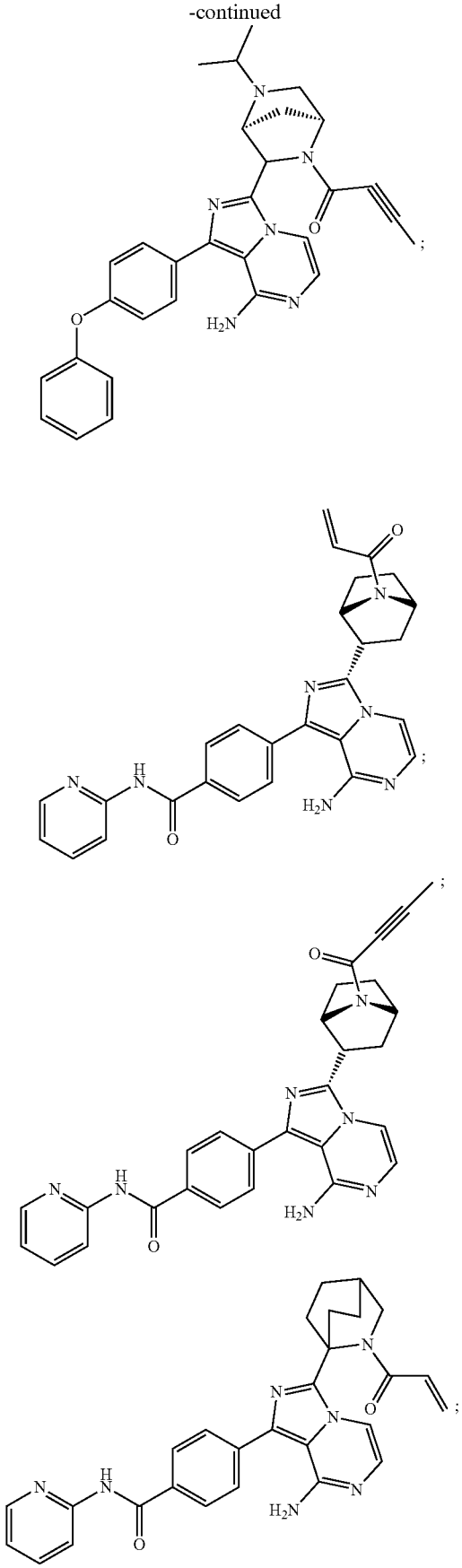
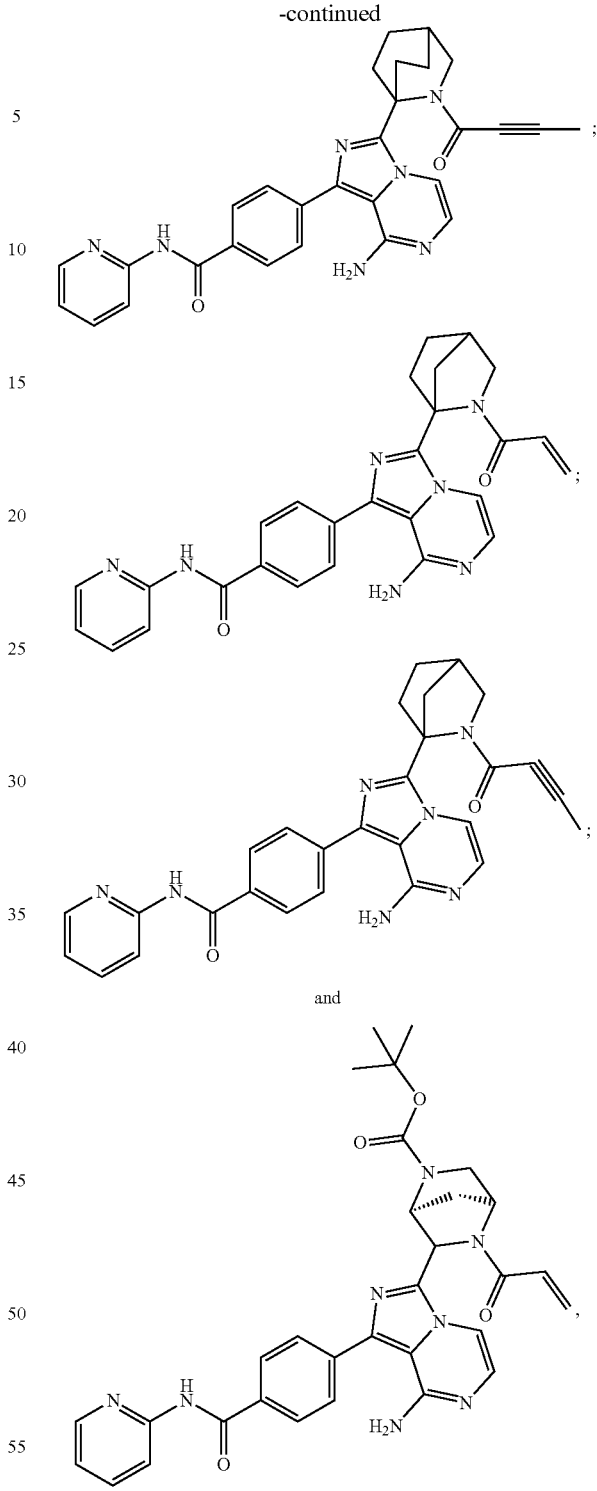
and
or a stereoisomer or cis-trans isomer thereof.
10. A method for preparing the compound according to claim 1, comprising the following steps:
1) using 2-chloropyrazine as a raw material, under the action of a basic compound, preparing (3-chloropyrazin-2-yl)methanol;
2) preparing (3-chloropyrazin-2-yl)methylamine by Gabriel synthesis from (3-chloropyrazin-2-yl)methanol;

3) reacting the (3-chloropyrazin-2-yl)methylamine with a spirocyclic carboxylic acid or a bridged-ring carboxylic acid shown in formula (III) to prepare an amide compound;

4) subjecting the amide compound to a ring-closure reaction under the action of phosphorus oxychloride, and then obtaining a compound shown in formula (IV) by NBS bromination;

5) subjecting the compound shown in above formula (IV) to an amination reaction under the action of alcohol and ammonia water;

6) subjecting the product obtained by the above amination reaction and the boronic acid shown in formula (V-1) or the boronic acid ester shown in formula (V-2) to a Suzuki coupling reaction to obtain a compound shown in formula (VI);

7) subjecting the compound shown in formula (VI) above and a substituted or unsubstituted 2-butynoic acid to a condensation reaction under the action of a condensing agent, to obtain a compound of formula (I-1);

alternatively, reacting the compound shown in formula (VI) above with 3-chloropropionyl chloride or acryloyl chloride under the action of a base by direct condensation or direct condensation followed by olefination by eliminating hydrogen chloride, to obtain the compound shown in formula (I-2);

alternatively, reacting the compound shown in formula (VI) above with the olefinic acid derivative shown in formula (VII) under the action of a condensing agent, to obtain a compound of the formula (I-3) or the formula (I-4), R" is H or fluorine, chlorine, bromine, iodine, respectively;

alternatively, reacting the compound shown in formula (VI) above and cyanoacetic acid or nitroacetic acid under the action of a condensing agent to obtain an amide compound, and then subjecting to Knoevenagel reaction with the aldehyde compound shown in formula (VIII) to obtain a compound shown in formula (I-4); R" is nitro or cyano;

M—COOH; (III)

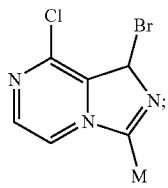
(IV)

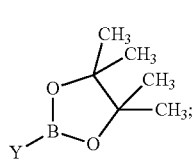
(V-1)

(V-2)

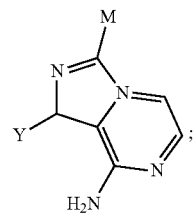
(VI)

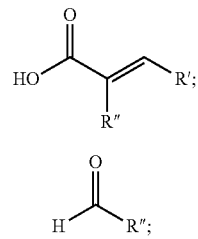
(VII)

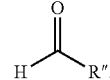
(VIII)

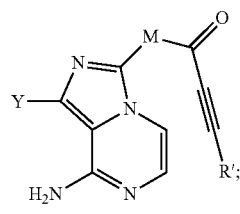
(I-1)

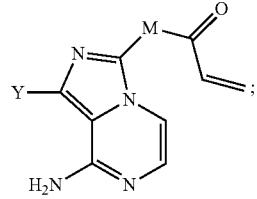
(I-2)

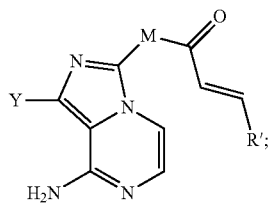
(I-3)

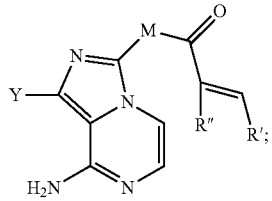
(I-4)

wherein Y is a substituted or unsubstituted aryl or heteroaryl;
M is

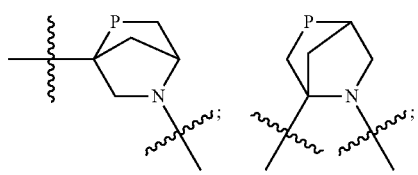

-continued

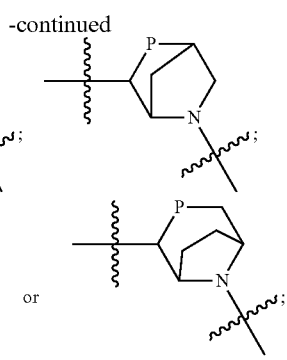

wherein P is $CR_5R_6$, N—$R_7$ or O;

$R_7$ is a substituted or unsubstituted C1-8 alkyl, a substituted or unsubstituted C1-8 heteroalkyl, a substituted or unsubstituted C3-8 cycloalkyl, a substituted or unsubstituted C3-8 heterocycloalkyl, or

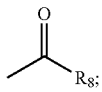

$R_5$, $R_6$ and $R_8$ are independently selected from the group consisting of substituted or unsubstituted C1-8 alkyls, substituted or unsubstituted C1-8 heteroalkyls, substituted or unsubstituted C3-8 cycloalkyls, and substituted or unsubstituted C3-8 heterocycloalkyls.

11. A pharmaceutical composition comprising the compound according to claim 1, and a pharmaceutically acceptable carrier, excipient, diluent, adjuvant, vehicle or combinations thereof.

12. A method for treating a disease in a patient in need thereof, comprising administering to the patient an effective amount of the compound of claim 1, wherein the disease selected from the group consisting of rheumatoid arthritis, infectious arthritis, teratogenic arthritis, gouty arthritis, spondylitis, pancreatitis, chronic bronchitis, acute bronchitis, allergic bronchitis, toxic bronchitis, allergic alveolitis, allergic or non-allergic rhinitis, chronic nasosinusitis, cystic fibrosis or mucous viscous disease, cough, emphysema, interstitial lung disease, alveolitis, lupus erythematosus, systemic scleroderma, sarcoidosis, subtypes of diffuse large B-cell lymphoma, mantle cell lymphoma (MCL), chronic lymphocytic lymphoma, extranodal marginal zone B-cell lymphoma, B-cell chronic lymphocytic leukemia (CLL), B-cell prolymphocytic leukemia, mature B-cell acute lymphoblastic leukemia, 17p-deletion chronic lymphocytic leukemia, Waldenström macroglobulinemia, lymphoplasmacytic lymphoma, splenic marginal zone lymphoma, plasma cell myeloma, plasmacytoma, intranodal marginal zone B-cell lymphoma, mantle cell lymphoma, intravascular large B-cell lymphoma, and primary effusion lymphoma, or a combination thereof.

13. The method of claim 12, wherein the patient has diffuse large B-cell lymphoma.

* * * * *